US010570184B2

(12) United States Patent
Sensfuss et al.

(10) Patent No.: US 10,570,184 B2
(45) Date of Patent: Feb. 25, 2020

(54) GLP-1/GLUCAGON RECEPTOR CO-AGONISTS FOR MEDICAL USE

(71) Applicant: Novo Nordisk A/S, Bagsvaerd (DK)

(72) Inventors: Ulrich Sensfuss, Vanloese (DK); Jesper F. Lau, Farum (DK); Thomas Kruse, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/315,985

(22) PCT Filed: Jun. 3, 2015

(86) PCT No.: PCT/EP2015/062401
§ 371 (c)(1),
(2) Date: Dec. 2, 2016

(87) PCT Pub. No.: WO2015/185640
PCT Pub. Date: Dec. 10, 2015

(65) Prior Publication Data
US 2017/0101454 A1 Apr. 13, 2017

(30) Foreign Application Priority Data
Jun. 4, 2014 (EP) ..................... 14171105

(51) Int. Cl.
A61K 38/26 (2006.01)
A61K 47/54 (2017.01)
A61K 47/56 (2017.01)
A61K 47/64 (2017.01)
C07K 14/605 (2006.01)
A61K 38/00 (2006.01)
A61K 38/28 (2006.01)

(52) U.S. Cl.
CPC ............ C07K 14/605 (2013.01); A61K 38/26 (2013.01); A61K 47/542 (2017.08); A61K 47/56 (2017.08); A61K 47/645 (2017.08); A61K 38/00 (2013.01); A61K 38/28 (2013.01)

(58) Field of Classification Search
CPC ...... A61K 38/26; A61K 47/542; A61K 47/56; A61K 47/645; C07K 14/605
See application file for complete search history.

(56) References Cited

U.S. PATENT DOCUMENTS

| | | | |
|---|---|---|---|
| 4,356,170 A | 10/1982 | Jennings et al. | |
| 5,408,037 A | 4/1995 | Smith et al. | |
| 5,424,286 A | 6/1995 | Eng | |
| 5,932,462 A | 8/1999 | Harris et al. | |
| 6,268,343 B1 | 7/2001 | Knudsen et al. | |
| 6,953,787 B2 | 10/2005 | Smith et al. | |
| 7,157,277 B2 | 1/2007 | DeFrees et al. | |
| 7,314,859 B2 | 1/2008 | Green et al. | |
| 8,129,343 B2 | 3/2012 | Lau et al. | |
| 2002/0049153 A1 | 4/2002 | Bridon et al. | |
| 2005/0027978 A1 | 2/2005 | Neuman et al. | |
| 2007/0105755 A1 | 5/2007 | DeFrees et al. | |
| 2007/0203058 A1 | 8/2007 | Lau et al. | |
| 2009/0062192 A1 | 3/2009 | Christensen et al. | |
| 2009/0137456 A1 | 5/2009 | Dimarchi et al. | |
| 2013/0157953 A1 | 6/2013 | Petersen et al. | |
| 2013/0288958 A1 | 10/2013 | Lau et al. | |
| 2015/0182594 A1 | 7/2015 | Lau et al. | |
| 2015/0274801 A1 | 10/2015 | Lau et al. | |
| 2015/0374794 A1 | 12/2015 | Sensfuss et al. | |
| 2016/0002311 A1 | 1/2016 | Lau et al. | |
| 2016/0271263 A1 | 9/2016 | Lau et al. | |
| 2016/0347812 A1 | 12/2016 | Lau et al. | |
| 2016/0355562 A1 | 12/2016 | Sensfuss et al. | |
| 2017/0051034 A1 | 2/2017 | Lau et al. | |
| 2017/0101454 A1 | 4/2017 | Sensfuss et al. | |
| 2017/0114115 A1 | 4/2017 | Alsina-Fernandez et al. | |
| 2017/0190757 A1 | 7/2017 | Lau et al. | |
| 2018/0044394 A1 | 2/2018 | Sensfuss et al. | |

FOREIGN PATENT DOCUMENTS

| | | |
|---|---|---|
| AU | 732957 C | 3/1998 |
| AU | 2011231503 A1 | 9/2012 |
| AU | 2013200675 A1 | 2/2013 |
| CN | 1867360 A | 11/2006 |
| EP | 1695983 A2 | 8/2006 |
| JP | H03254692 A | 11/1991 |
| JP | H09-510438 A | 10/1997 |
| JP | 2007-505840 A | 3/2007 |
| JP | 2011-524419 A | 9/2011 |
| JP | 2014-510739 A | 5/2014 |
| RU | 2401276 C2 | 10/2010 |
| RU | 2434019 C2 | 11/2011 |
| WO | 96/29342 | 9/1996 |
| WO | 97/09040 A1 | 3/1997 |
| WO | 97/26265 A1 | 7/1997 |

(Continued)

OTHER PUBLICATIONS

Pedersen et al., "N- and C-Terminal Hydrophobic Patches Are Involved in Fibrillation of Glucagon +," Biochemistry, 2006, vol. 45, No. 48, pp. 14503-14512.

(Continued)

Primary Examiner — Jeffrey E. Russel
(74) Attorney, Agent, or Firm — Leon Y. Lum

(57) ABSTRACT

The present invention relates to novel glucagon derivatives which are GLP-1/glucagon receptor co-agonists, and to the use of the glucagon derivatives in medicine, such as in the treatment of diabetes, obesity and related diseases and conditions.

19 Claims, 1 Drawing Sheet
Specification includes a Sequence Listing.

(56) References Cited

FOREIGN PATENT DOCUMENTS

| | | |
|---|---|---|
| WO | 97/41097 A2 | 11/1997 |
| WO | 97/41119 A1 | 11/1997 |
| WO | 97/41120 A1 | 11/1997 |
| WO | 9808871 A1 | 3/1998 |
| WO | 98/45292 A1 | 10/1998 |
| WO | 99/01423 A1 | 1/1999 |
| WO | 99/03861 A1 | 1/1999 |
| WO | 99/19313 A1 | 4/1999 |
| WO | 00/23415 A1 | 4/2000 |
| WO | 00/23416 A1 | 4/2000 |
| WO | 00/23417 A1 | 4/2000 |
| WO | 00/23425 A1 | 4/2000 |
| WO | 00/23445 A1 | 4/2000 |
| WO | 00/23451 A1 | 4/2000 |
| WO | 00/37474 A1 | 6/2000 |
| WO | 00/39088 A1 | 7/2000 |
| WO | 00/41121 A1 | 7/2000 |
| WO | 00/42023 A1 | 7/2000 |
| WO | 00/42026 A1 | 7/2000 |
| WO | 00/50414 A1 | 8/2000 |
| WO | 00/63153 A1 | 10/2000 |
| WO | 00/63189 A1 | 10/2000 |
| WO | 00/63190 A1 | 10/2000 |
| WO | 00/63191 A1 | 10/2000 |
| WO | 00/63192 A1 | 10/2000 |
| WO | 00/63193 A1 | 10/2000 |
| WO | 00/63196 A1 | 10/2000 |
| WO | 00/63208 A1 | 10/2000 |
| WO | 00/63209 A1 | 10/2000 |
| WO | 00/64884 A1 | 11/2000 |
| WO | 00/69900 A2 | 11/2000 |
| WO | 02/08209 | 1/2002 |
| WO | 03/022304 A1 | 3/2003 |
| WO | 2003/031464 A2 | 4/2003 |
| WO | 2003/062290 A1 | 7/2003 |
| WO | 2004/062685 A2 | 7/2004 |
| WO | 2005/012347 A2 | 2/2005 |
| WO | 2005/016974 A1 | 2/2005 |
| WO | 2005/027978 A2 | 3/2005 |
| WO | 2006/053299 A2 | 5/2006 |
| WO | 2006/090119 A1 | 8/2006 |
| WO | 2006/097537 A2 | 9/2006 |
| WO | 2006097536 A2 | 9/2006 |
| WO | 2006/103298 A2 | 10/2006 |
| WO | 2006/134148 A2 | 12/2006 |
| WO | 2006/134340 A2 | 12/2006 |
| WO | 2007056362 A2 | 5/2007 |
| WO | 2007/087711 A1 | 8/2007 |
| WO | 2007/100535 A2 | 9/2007 |
| WO | 2007/126808 A1 | 11/2007 |
| WO | 2008/011633 A2 | 1/2008 |
| WO | 2008/071972 A1 | 6/2008 |
| WO | 2008/074032 A1 | 6/2008 |
| WO | 2008086086 A2 | 7/2008 |
| WO | 2008101017 A2 | 8/2008 |
| WO | 2008/151258 | 12/2008 |
| WO | 2008/151448 A1 | 12/2008 |
| WO | 2008152403 A1 | 12/2008 |
| WO | 2009/030771 A1 | 3/2009 |
| WO | 2009030738 A1 | 3/2009 |
| WO | 2009033738 A2 | 3/2009 |
| WO | 2009/062100 A1 | 5/2009 |
| WO | 2009/083549 A1 | 7/2009 |
| WO | 2009/089396 | 7/2009 |
| WO | 2009099763 A1 | 8/2009 |
| WO | 2009/108806 A1 | 9/2009 |
| WO | 2009155257 A1 | 12/2009 |
| WO | 2009155258 A2 | 12/2009 |
| WO | 2010011439 A2 | 1/2010 |
| WO | 2010/014708 A2 | 2/2010 |
| WO | 2010016940 A2 | 2/2010 |
| WO | 2010/045568 A1 | 4/2010 |
| WO | 2010 070251 A1 | 6/2010 |
| WO | 2010 070252 A1 | 6/2010 |
| WO | 2010070253 A1 | 6/2010 |
| WO | 2010070255 A1 | 6/2010 |
| WO | 2010/102886 A1 | 9/2010 |
| WO | 2010148089 A1 | 12/2010 |
| WO | 2011006497 A1 | 1/2011 |
| WO | 2011038900 A2 | 4/2011 |
| WO | 2011075393 A2 | 6/2011 |
| WO | 2011/117416 A1 | 9/2011 |
| WO | 2011117415 A1 | 9/2011 |
| WO | 2011117417 A1 | 9/2011 |
| WO | 2011119657 A1 | 9/2011 |
| WO | 2011119675 A1 | 9/2011 |
| WO | 2011160630 A2 | 12/2011 |
| WO | 2011160633 A1 | 12/2011 |
| WO | 2011163473 A1 | 12/2011 |
| WO | 2012088116 A2 | 6/2012 |
| WO | 2012088117 A1 | 6/2012 |
| WO | 2012088379 A2 | 6/2012 |
| WO | 2012098462 A1 | 7/2012 |
| WO | 2012130866 A1 | 10/2012 |
| WO | 2012138941 A1 | 10/2012 |
| WO | 2012150503 A2 | 11/2012 |
| WO | 2012158962 A2 | 11/2012 |
| WO | 2012158965 A2 | 11/2012 |
| WO | 2012169798 A2 | 12/2012 |
| WO | 2012177443 A2 | 12/2012 |
| WO | 2012177444 A2 | 12/2012 |
| WO | 2013004983 A1 | 1/2013 |
| WO | 2013041678 A1 | 3/2013 |
| WO | 2014016300 A1 | 1/2014 |
| WO | 2014170496 A1 | 10/2014 |
| WO | 2015086733 A1 | 6/2015 |
| WO | 2017003191 A1 | 1/2017 |
| WO | 2017074798 A2 | 5/2017 |

OTHER PUBLICATIONS

Karin Julenius et al., Glycobiology, "Prediction, Conservation Analysis, and Structural Characterization of Mammalian Mucin-Type O-Glycosylation Sites", 2004, vol. 15, No. 2, pp. 153-164.

Kiely et al., Journal of Biological Chemistry, "Studies on the Attachement of Carbohydrate to Ovalbumin Nascent Chains in Hen Oviduct", 1976, vol. 251, No. 18, pp. 5490-5495.

Kojima et al., FEBS Letters, "A Developmentally Regulated Member of the Sialyltransferase Family (ST8SIA II, STX) is a Polysialic Acid Synthase", 1995, vol. 373, No. 2, pp. 119-122.

"Kunou M. et al., Biomacromolecules., "Synthesis of Sulfated Colominic Acids and Their Interaction With Fibroblast Growth Factors", 2000, vol. 1, No. 3, pp. 451-458".

"Nakayama et al., Proceedings of the National Academy of Sciences of The USA, "Expression Cloning of a Human Polysialyltransferase That Forms the Polysialylated Neural Cell Adhesion Molecule Present in Embryonic Brain", 1995, vol. 92, No. 15, pp. 7031-7035".

P. J. Lenting et al., Haemophilia, "Factor VIII and Von Willebrand Factor—Too Sweet for Own Good", 2010, vol. 16, No. 5, pp. 194-199.

Saenko E L et al, Haemophilia, "Strategles Towards a Longer Acting Factor VIII", 2006, vol. 12, No. 3, pp. 42-51.

"Scheidegger et al., Journal of Biological Chemistry, "A Human STX CDNA Confers Polysialic Acid Expression in Mammalian Cells", 1995, vol. 270, No. 39, pp. 22685-22688".

Thim L, et al., Haemophilia, "Purification and Characterization of a New Recombinant Factor VIII(N8)", 2010, vol. 16, No. 2, pp. 349-359.

Urlaub G. et al, Somatic Cell and Molecular Genetics, "Effect of Gamma Rays at the Dihydrofolate Reductase Locus: Deletions and Inversions", 1986, vol. 12, No. 6, pp. 555-566.

Urlaub et al, Proceedings of the National Academy of Sciences of the USA, "Isolation of Chinese Hamster Cell Mutants Deficient in Dihydrofolate Reductase Activity", 1980, vol. 77, No. 7, pp. 4216-4220.

"Urlaub, Gail et al., Cell, "Deletion of the Diploid Dihydrofolate Reductase Locus From Cultured Mammalian Cells", 1983, vol. 33, No. 2, pp. 405-412".

(56) References Cited

OTHER PUBLICATIONS

Veronese et al, Journal of Bioactive and Compatible Polymers, "Branched and Linear Poly(Ethylene Glycol): Influence of the Polymer Structure on Enzymological, Pharmacokinetic, and Immunological Properties of Protein Conjugates", 1997, vol. 12, No. 3, pp. 196-207.
Veronese et al., Advanced Drug Delivery Reviews, "I Ntroduction and Overview of Peptide and Protein Pegylation", 2002, vol. 54, pp. 453-456.
Waechter et al, Proceedings of the National Academy of Sciences of the USA, "Effect of Methylation on Expression of Microinjected Genes", 1982, vol. 79, pp. 1106-1110.
Willis et al., Glycobiology, "Characterization of the ¿-2,8-Polysialyltransferase From Neisseria Meningitidis With Synthetic Acceptors, and the Development of a Self-Priming Polysialyltransferase Fusion Enzyme", 2008, vol. 18, No. 2, pp. 177-186.
Haack et al., "Analysis of Expression Kinetics and Activity of a New B-Domain Truncated and Full-Lenth FVIII Protein in Three Different Cell Lines," Ann Hematol, 1999, vol. 78, pp. 111-116.
Nakayama et al., "Expression Cloning of a Human Polysialyltransferase That Forms the Polysialylated Neural Cell Adhesion Molecule Present in Embryonic Brain," PNAS, 1995, vol. 92, No. 15, pp. 7031-7035.
Harduin-Lepers A et al. Biochemistry. "The Human Sialyltransferase Family" 2001. vol. 83(8) pp. 727-737.
Dakin C. L. et al., Oxyntomodulin Inhibits Food Intake in the Rat, Endocrinology, 2001, vol. 142, No. 10, pp. 4244-4250.
Cho Min Y. et al., Targeting the glucagon receptor family for diabetes and obesity therapy, Pharmacology & Therapeutics, 2012, vol. 135, No. 3, pp. 247-278.
Dan Donnelly, The structure and function of the glucagon-like peptide-1 receptor and Its ligands, British Journal of Pharmacology, 2012, vol. 166, No. 1, pp. 27-41.
Hongxiang H. et al., Structure and function studies of glucagon-like peptide-1 (GLP-1): the designing of a novel pharmacological agent for the treatment of diabetes, Diabetes/Metabolism Research and Reviews, Wiley, London, GB, 2005, vol. 21, No. 4, pp. 313-331.
Cegla J. et al., Energy intake following infusion of glucagon and GLP-1: a double-blind crossover study, Endocrine Abstracts, 2013, 1 page.
Day J. W. et al., Optimization of Co-Agonism at GLP-1 and Glucagon Receptors to Safely Maximize Weight Reduction in DIO-Rodents, PeptideScience, 2012, vol. 98, No. 5, pp. 443-450.
Jiang G. et al., Glucagon and regulation of glucose metabolism, American Journal of Physiology,Endocrinology and Metabolism, 2003, vol. 284, pp. E671-E678.
Moran T. H. et al., Gut peptides in the control of food intake, International Journal of Obesity, 2009, vol. 33, pp. S7-S10.
Pocai A., Unraveling oxyntomodulin, GLP1's enigmatic brother, Journal of Endocrinology, 2012, vol. 215, pp. 335-346.
Sherwin R. S. et al., Hyperglucagonemia and blood glucose regulation in normal, obese and diabetic subjects, The New England Journal of Medicine, 1976, vol. 294, No. 9, pp. 455-461.
Tan T. M. et al., Coadministration of Glucagon-Like Peptide-1 During Glucagon Infusion in Humans Results in Increased Energy Expenditure and Amelioration of Hyperglycemia, Diabetes, 2013, vol. 62, pp. 1131-1138.
Schulman et al., "Effect of Glucagon on Food Intake and Body Weight in Man", Journal of Applied Physiology, 1957, vol. 11, pp. 419-421.
Carpenter et al., "Modes of Stabilization of a Protein by Organic Solutes During Desiccation", Cryobiology, 1988, vol. 25, pp. 459-470.
Cohen et al., "Oxyntomodulin Suppresses Appetite and Reduces Food Intake in Humans", Journal of Clinical Endocrinology and Metabolism, 2003, vol. 88, No. 10, pp. 4696-4701.
Geary, "Effects of Glucagon, Insulin, Amylin and CGRP on Feeding", Neuropeptides, 1999, vol. 33, No. 5, pp. 400-405.
Hippen et al., "Alleviation of Fatty Liver in Dairy Cows With 14-Day Intravenous Infusions of Glucagon", Journal of Dairy Science, 1999, vol. 82, No. 6, pp. 1139-1152.
Mumenthaler et al., "Feasibility Study on Spray-Drying Protein Pharmaceuticals: Recombinant Human Growth Hormone and Tissue-Type Plasminogen Activator", Pharmaceutical Research, 1994, vol. 11, No. 1, pp. 12-20.
Pocai et al., "Glucagon-Like Peptideiiglucagon Receptor Dual Agonism Reverses Obesity in Mice", Diabetes, 2009, vol. 58, pp. 2258-2266.
Roser, "Trehalose Drying: A Novel Replacement for Freeze Drying", Biopharmaceutical, 1991, vol. 4, pp. 47-53.
Williams et al., "The Lyophilization of Pharmaceuticals: A Literature Review", Journal of Parenteral Science and Technology, 1984, vol. 38, No. 2, pp. 48-59.
Wynne et al., "Subcutaneous Oxyntomodulin Reduces Body Weight in Overweight and Obese Subjects: A Double-Blind, Randomized, Controlled Trial", Diabetes, 2005, vol. 54, pp. 2390-2395.
Krstenansky, John L et al. J. Am. Chem. Soc. "Conformation considerations in the design of a glucagon analogue with increased receptor binding and adenylate cyclase potencies." 1986. vol. 108 p. 1696-1698.
Scrocchi et al., "Elimination of Glucgon-Like Peptide 1R Signaling Does Not Modify Weight Gain and Islet Adaptation in Mice With Combined Disruption of Leptin and GLP-1 Action", Diabetes, 2000, vol. 49, No. 9, pp. 1552-1560.
Batterham et al., "Gut Hormone PYY3-36 Physiologically Inhibits Food Intake", Nature, 2002, vol. 418, pp. 650-654.
Broadhead et al., The Spray Dying of Pharmaceuticals, Drug Development and Industrial Pharmacy, 1992, vol. 18, No. 11-12, pp. 1169-1206.
Day et al., "A New Glucagon and GLP-1 Co-Agonists Eliminates Obesity in Rodents", Nature Chemical Biology, 2009, vol. 5, No. 10, pp. 749-757.
Druce and Ghatei, "Oxyntomodulin", Current Opinion in Endocrinology, 2006, vol. 13, No. 1, pp. 49-55.
Geary et al., "Individual, But Not Simultaneous Glucagon and Cholecystokinin Infusions Inhibit Feeding in Men", American Journal of Physiology, 1992, vol. 262, pp. R975-R980.
Zhang et l., "Polyethylene Glycol Positioning Modification of Glucagon-Like Peptide", The Chinese Journal of Process Engineering, 2009, vol. 9, No. 6, pp. 1169-1173.
John Wilding. BMJ. "Science, Medecine and the Future Obesity Treatment." 1997. vol. 315. pp. 997-1000.
Bray et al. Nature. "Medicinal Strategies in the Treatment of Obesity." 2000. vol. 404. pp. 672-677.
Habegger et al. Natural Reviews of Endocrinology. "The Metabolic Actions of Glucagon Revisited." 2010. vol. 6. pp. 689-697.
Nielsen et al. Biochemistry. "Effect of Environmental Factors on the Kinetics of Insulin Fibril Formation:¿ Elucidation of the Molecular Mechanism." 2001. vol. 40(20). pp. 6036-6046.
LeVine III, Harry. Methods in Enzymology. "Quantification of B-Sheet Amyloid Fibril Structures With Thioflavin T." 1999. vol. 309. pp. 274-284.
Naiki et al. Analytical Biochemistry. "Fluorometric Determination of Amyloid Fibrils In Vitro Using the Fluorescent Dye, Thioflavine T." 1989. vol. 177(2). pp. 244-249.
Remington's Pharmaceutical Sciences: The Science and Practice of Pharmacy, 19th Edition. 1995.
Berge et al. Journal of Pharmceutical Sciences. "Pharmaceutical Salts." 1977. vol. 66(1). pp. 1-19.
Beaven et al. European Journal of Biochemistry. "Formation and Structure of Gels and Fibrils From Glucagon." 1969. vol. 11(1). pp. 37-42.
Schade & Eaton. Acta Diabetologica. "Modulation of the Catabolic Activity of Glucagon by Endogenous Insulin Secretion in Obese Man." 1977. vol. 14. pp. 62-72.
Groner et al., Journal of Thrombosis and Haemostasis, "Abstracts From XXII ISTH Congress", 2009, vol. 7, No. SUPPL2, pp. 508-517.
Angata et al., Journal of Biological Chemistry, "ST8SIA II and ST8SIA IV Polysialyltransferases Exhibit Marked Differences in

(56) References Cited

OTHER PUBLICATIONS

Utilizing Various Acceptors Containing Oligosialic Acid and Short Polysialic Acid", 2002, vol. 277, No. 39, pp. 36808-36817.

Bonora et al., Post-translational Modification of Protein Biopharmaceuticals, "Engineering in a PTM: Pegylation.", 2009, pp. 341-357.

"Cho, JW. et al., Proceedings of the National Academy of Sciences of the United Sta, "Polysialic Acid Engineering: Synthesis of Polysialylated Neoglycosphingolipids by Using the Polysialyltransferase From Neuroinvasive *Escherichia coli* K1", 1994, vol. 91, No. 24, pp. 11427-11431".

Eckhardt et al., Nature, "Molecular Characterization of Eukaryotic Polysialyltransferase-1", 1995, vol. 373, pp. 715-718.

"Fernandes et al., Biochimica Et Biophysica Acta, "Synthesis, Characterization and Properties of Sialylated Catalase Synthesis, Characterization and Properties of Sialylated Catalase", 1996, vol. 1293, pp. 90-96".

Fontana et al., Advanced Drug Delivery Reviews, "Site-Specific Modification and Pegylation of Pharmaceutical Proteins Mediated by Transglutaminase", 2008, vol. 60, No. 1, pp. 13-28.

Gilbert et al., Journal of Biological Chemistry, "The Genetic Bases for the Variation in the Lipo-Oligosaccharide of the Mucosal Pathogen, Campylobacter Jejuni", 2002, vol. 277, No. 1, pp. 327-337.

Glabe et al., Journal of Biological Chemistry, "Glycosylation of Ovalbumin Nascent Chains", 1980, vol. 255, No. 19, pp. 9236-9242.

Graham et al, Journal of General Virology, "Characteristics of a Human Cell Line Transformed by DNA From Human Adenovirus Type 5", 1977, vol. 36, pp. 59-72.

Gregoriadis et al., S.T.P. Pharma Sciences, "Polysialylated Proteins: An Approach to Improve Enzyme Stability and Half-Life in the Blood Circulation", 1999, vol. 9, No. 1, pp. 61-66.

Higuchi et al., Genomics, "Characterization of Mutations in the Factor VIII Gene by Direct Sequencing of Amplified Genomic DNA", 1990, vol. 6, No. 1, pp. 65-71.

Jain S et al, BBA—General Subjects, Elsevier Science Publishers, NL, "Polysialylated Insulin: Synthesis, Characterization and Biological Activity In Vivo", 2003, vol. 1622, No. 1, pp. 42-49.

Jennings and Lugowski, Journal of Immunology, "Immunochemistry of Groups A, B, and C Meningococcal Polysaccharide—Tetanus Toxoid Conjugates", 1981, vol. 127, No. 3, pp. 1011-1018.

Julenius, K. et al., Bioinformatics for Glycobiology and Glycomics:, "Prediction of Glycosylation Sites in Proteins", 2009, pp. 163-185.

Seghieri et al., "Future Perspectives on GLP-1 Receptor Agonists and GLP-1/glucagon Receptor Co-agonists in the Treatment of NAFLD." Frontiers in Endocrinology, 2018, vol. 9, Article 649, pp. 1-10.

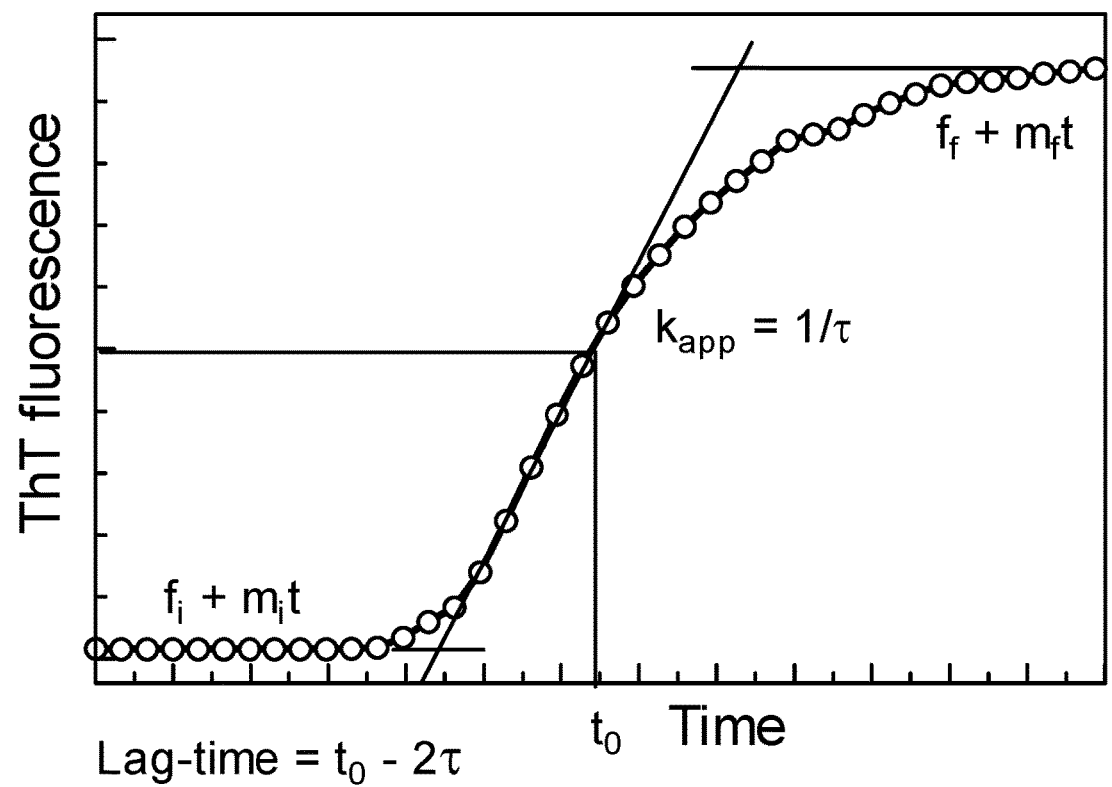

GLP-1/GLUCAGON RECEPTOR CO-AGONISTS FOR MEDICAL USE

CROSS-REFERENCE TO RELATED APPLICATIONS

This application is a 35 U.S.C. § 371 National Stage application of International Application PCT/EP2015/062401 (WO2015/185640), filed Jun. 3, 2015, which claims priority to European Patent Application 14171105.1, filed Jun. 4, 2014.

SEQUENCE LISTING

In accordance with 37 C.F.R. § 1.52(e)(5), Applicants enclose herewith the Sequence Listing for the above-captioned application entitled "130034US01_SeqListing_new_ST25", created on Nov. 16, 2016 and modified on Nov. 30, 2016, Jan. 26, 2018, and Feb. 13, 2019. The Sequence Listing is made up of 33 kilobytes, and the information contained in the attached "SEQUENCE LISTING" is identical to the information in the specification as originally filed. No new matter is added.

TECHNICAL FIELD

The present invention relates to novel glucagon derivatives which are GLP-1/glucagon receptor co-agonists and their use in medicine.

BACKGROUND OF THE INVENTION

The increase in obesity incidence has reached epidemic proportions in the western world, and more recently also in developing countries. Obesity is associated with significant co-morbidities such as cardiovascular diseases and type 2 diabetes. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Numerous gastro-intestinal peptide hormones are allegedly involved in the regulation of food intake, being either anorexigenic (e.g. CCK, GLP-1, PYY, secretin) or orexigenic (e.g. ghrelin). Recently, oxyntomodulin, a product from the proglucagon gene in intestinal L-cells was shown to induce satiety and reduce body weight in both rodents and humans [Cohen M A et al: Oxyntomodulin suppresses appetite and reduces food intake in humans; *J. Clin. Endocrinol. Metab.* 2003 88 4696-4701; Dakin C L et al: Oxyntomodulin inhibits food intake in the rat; *Endocrinology* 2001 142 4244-4250]. Oxyntomodulin is a dual agonist activating both GLP-1 and glucagon receptors, albeit with reduced potency compared to GLP-1 and glucagon, respectively. The anorexigenic effect of oxyntomodulin was previously speculated to be mediated by the GLP-1 receptor, although numerous older studies indicated the involvement of pancreatic glucagon in the control of bodyweight. Two recent papers allegedly show glucagon as an attractive target, and demonstrated the power of simultaneous GLP-1/glucagon receptor-targeting by constructing dual agonists, and comparing the weight lowering effect in knock-out models [Pocai et al; Glucagon-Like Peptide 1/Glucagon Receptor Dual Agonism Reverses Obesity in Mice; *Diabetes,* 2009, 58, 2258-2266; Day J W et al: A new GLP-1 co-agonist eliminates obesity in rodents; *Nat. Chem. Biol.* 2009 5 749-757].

One physiological effect of glucagon is to increase blood glucose levels in hypoglycaemic conditions by stimulating glycogenolysis and gluconeogenesis. However, the acute effect of glucagon on blood glucose levels seems to be modest when glucagon is infused at near-physiological levels [Sherwin R S et al: Hyperglucaonemia and blood glucose regulation in normal, obese and diabetic subjects; *N. Engl. J. Med.* 1976 294 455-461]. Glucagon receptor activation has also been shown to increase energy expenditure, and to decrease food intake in both rodents and humans [Habegger K M et al: The metabolic actions of glucagon revisited; *Nat. Rev. Endocrinol.* 2010 6 689-697], and these effects are robust and sustained in rodents.

The risk of increased blood glucose levels due to glucagon agonism may be counter-acted by appropriate levels of GLP-1 agonism. Accordingly, GLP-1/glucagon receptor co-agonists with a balanced effect on the two receptors are desired since they may give rise to an improved weight loss compared to a pure GLP-1 agonist without compromising the glucose tolerance. However, there are several obstacles in developing such a co-agonist to a pharmaceutical product, in particular relating to half-life, stability, solubility and receptor activity. For example, if glucagon is used as a starting point for such a co-agonist, the GLP-1 receptor activity needs to be established without destroying the activity at the glucagon receptor. Furthermore, since glucagon is inherently insoluble at neutral pH, it is chemically and physically unstable and its half-life in vivo is only a few minutes.

Several patent applications disclosing different GLP-1/glucagon receptor co-agonists are known in the art, such as e.g. those disclosed in WO 2007/056362, WO 2008/101017, WO 2010/070255, WO 2012/150503, and WO 2012/169798.

SUMMARY OF THE INVENTION

In some embodiments the present invention relates to glucagon derivatives comprising an amino acid sequence of Formula I (SEQ ID NO: 2):

$$X^1\text{-}X^2\text{-}X^3\text{-}Gly\text{-}Thr\text{-}Phe\text{-}Thr\text{-}Ser\text{-}Asp\text{-}X^{10}\text{-}Ser\text{-}X^{12}\text{-}\\Tyr\text{-}Leu\text{-}X^{15}\text{-}X^{16}\text{-}X^{17}\text{-}X^{18}\text{-}Ala\text{-}X^{20}\text{-}X^{21}\text{-}Phe\text{-}\\Val\text{-}X^{24}\text{-}Trp\text{-}Leu\text{-}Ile\text{-}X^{28}\text{-}X^{29}\text{-}X^{30} \quad (I)$$

wherein
$X^1$ represents His or Imp;
$X^2$ represents Aib or Acb;
$X^3$ represents Gln or His;
$X^{10}$ represents Tyr, Leu, Ile or Val;
$X^{12}$ represents Lys or Arg;
$X^{15}$ represents Asp or Glu;
$X^{16}$ represents Ser, Ala, Leu, Thr, Glu, Aib, Ile, Val or Lys;
$X^{17}$ represents Arg, Lys or Gln;
$X^{18}$ represents Arg, Ala or Lys;
$X^{20}$ represents Gln, Arg or Lys;
$X^{21}$ represents Asp, Glu or Lys;
$X^{24}$ represents Gln, Ala, Arg, Glu or Lys;
$X^{28}$ represents Asn, Ser, Thr, Gln, Ala, Gly, Glu or Lys;
$X^{29}$ represents Thr, Gly, Ser, Gln, Ala, Glu or Lys; and
$X^{30}$ is absent or represents Lys;
wherein said amino acid sequence of Formula I comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, and wherein said substituent is attached at the epsilon position of a lysine residue in one of the amino acid positions 16, 17, 18, 20, 21, 24, 28, 29 or 30; and wherein said glucagon derivative is a C-terminal amide; or a pharmaceutically acceptable salt thereof.

In some embodiments the invention relates to the use of a glucagon derivative as defined herein for use in medicine.

BRIEF DESCRIPTION OF THE DRAWING

FIG. 1 depicts the time course for fibril formation.

DETAILED DESCRIPTION OF THE INVENTION

The present invention relates to novel glucagon derivatives which are GLP-1/glucagon receptor co-agonists, i.e. glucagon derivatives having a dual biological activity on the GLP-1/glucagon receptors, and to the use of said glucagon derivatives in medicine, such as in the treatment of diabetes, obesity and related diseases and conditions.

The glucagon derivatives of the present invention activate both the GLP-1 and the glucagon receptor and comprise i) a combination of amino acid modifications, and ii) a substituent with negatively charged moieties. Specifically, the glucagon derivatives of the invention comprise the amino acid substitution isoleucine in position 27 compared to human glucagon. The glucagon derivatives of the invention further comprise a substituent having 3-10 negatively charged moieties, wherein said substituent is covalently attached to the side chain of an amino acid, such as the nitrogen atom of the side chain of a lysine.

The inventors surprisingly found that the glucagon derivatives of the present invention show reduced glucagon receptor binding and at the same time improved the GLP-1 receptor binding, e.g. compared to an identical compound with leucine in position 27. Therefore, the novel amino acid modifications of glucagon derivatives of the invention can be used as a tool for adjusting the ratio between glucagon and GLP-1 affinity, which is pivotal for obtaining the desired effect on body weight and maintain blood glucose levels.

Furthermore, the inventors have found that the glucagon derivatives of the present invention may be physically stable, i.e. the glucagon derivatives show none or delayed fibrillation in an assay used to assess physical stability, and the recovery of the compounds were improved. The inventors have found that the glucagon derivatives of the present invention may have adequate aqueous solubility at neutral pH or slightly basic pH and with improved chemical stability, i.e. the chemical degradation of the glucagon derivatives is reduced. The inventors have found that the glucagon derivatives of the present invention may have improved pharmacokinetic properties, i.e., they have prolonged half-life in vivo, e.g. compared to human glucagon. Furthermore, the glucagon derivatives of the present invention may induce a significant reduction in body weight after s.c. administration. Assay (I) and (II) as described herein may be used to measure the activity and affinity, respectively, of the glucagon derivatives of the invention on the glucagon and GLP-1 receptors. The solubility of the glucagon derivatives of the invention at different pH values may be measured as described herein, see e.g. the Functional Properties section. The physical stability of the glucagon derivatives of the invention may be measured by the method as described in Assay (III) herein. The chemical stability the glucagon derivatives of the invention may be measured as described in Assay (V) herein. The half-life of the glucagon derivatives may be determined in a pharmacokinetic study in species, such as mice (e.g., using the method described in Assay (IV) herein), rats or in minipigs. The reduction in body weight caused by the glucagon derivatives of the invention may be measured by administration to DIO mice of the glucagon derivative of the invention and comparing its effect on body weight to administration of vehicle alone.

In some embodiments the invention relates to glucagon derivatives comprising an amino acid sequence of Formula I (SEQ ID NO: 2):

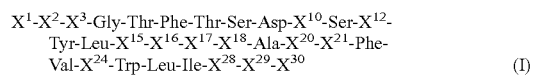

$X^1$-$X^2$-$X^3$-Gly-Thr-Phe-Thr-Ser-Asp-$X^{10}$-Ser-$X^{12}$-Tyr-Leu-$X^{15}$-$X^{16}$-$X^{17}$-$X^{18}$-Ala-$X^{20}$-$X^{21}$-Phe-Val-$X^{24}$-Trp-Leu-Ile-$X^{28}$-$X^{29}$-$X^{30}$ (I)

wherein
$X^1$ represents His or Imp;
$X^2$ represents Aib or Acb;
$X^3$ represents Gln or His;
$X^{10}$ represents Tyr, Leu, Ile or Val;
$X^{12}$ represents Lys or Arg;
$X^{15}$ represents Asp or Glu;
$X^{16}$ represents Ser, Ala, Leu, Thr, Glu, Aib, Ile, Val or Lys;
$X^{17}$ represents Arg, Lys or Gln;
$X^{18}$ represents Arg, Ala or Lys;
$X^{20}$ represents Gln, Arg or Lys;
$X^{21}$ represents Asp, Glu or Lys;
$X^{24}$ represents Gln, Ala, Arg, Glu or Lys;
$X^{28}$ represents Asn, Ser, Thr, Gln, Ala, Gly, Glu or Lys;
$X^{29}$ represents Thr, Gly, Ser, Gln, Ala, Glu or Lys; and
$X^{30}$ is absent or represents Lys;

wherein said amino acid sequence of Formula I comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, and wherein said substituent is attached at the epsilon position of a lysine residue in one of the amino acid positions 16, 17, 18, 20, 21, 24, 28, 29 or 30;

and wherein said glucagon derivative is a C-terminal amide;

or a pharmaceutically acceptable salt thereof.
Glucagon Peptides and Analogues

The term "glucagon peptide" as used herein refers to human glucagon, the sequence of which is included in the sequence listing as SEQ ID NO: 1 or an analogue thereof. The peptide having the sequence of SEQ ID NO: 1 may also simply be referred to as "glucagon" herein. In some embodiments as used herein the terms "human glucagon" and "glucagon" refers to His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1).

The term "glucagon analogue" as used herein refers to a peptide or a compound, which is a variant of glucagon (SEQ ID NO: 1). The amino acid sequence of Formula I herein is an example of a glucagon analogue. In some embodiments the glucagon derivative comprises an amino acid sequence of Formula I (SEQ ID NO: 2):

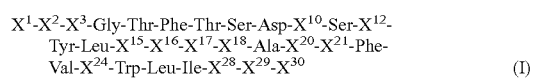

$X^1$-$X^2$-$X^3$-Gly-Thr-Phe-Thr-Ser-Asp-$X^{10}$-Ser-$X^{12}$-Tyr-Leu-$X^{15}$-$X^{16}$-$X^{17}$-$X^{18}$-Ala-$X^{20}$-$X^{21}$-Phe-Val-$X^{24}$-Trp-Leu-Ile-$X^{28}$-$X^{29}$-$X^{30}$ (I)

wherein
X$^1$ represents His or Imp;
X$^2$ represents Aib or Acb;
X$^3$ represents Gln or His;
X$^{10}$ represents Tyr, Leu, Ile or Val;
X$^{12}$ represents Lys or Arg;
X$^{15}$ represents Asp or Glu;
X$^{16}$ represents Ser, Ala, Leu, Thr, Glu, Aib, Ile, Val or Lys;
X$^{17}$ represents Arg, Lys or Gln;
X$^{18}$ represents Arg, Ala or Lys;
X$^{20}$ represents Gln, Arg or Lys;
X$^{21}$ represents Asp, Glu or Lys;
X$^{24}$ represents Gln, Ala, Arg, Glu or Lys;
X$^{28}$ represents Asn, Ser, Thr, Gln, Ala, Gly, Glu or Lys;
X$^{29}$ represents Thr, Gly, Ser, Gln, Ala, Glu or Lys; and
X$^{30}$ is absent or represents Lys;
wherein said amino acid sequence of Formula I comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, and wherein said substituent is attached at the epsilon position of a lysine residue in one of the amino acid positions 16, 17, 18, 20, 21, 24, 28, 29 or 30; and wherein said glucagon derivative is a C-terminal amide; or a pharmaceutically acceptable salt thereof.

Glucagon analogues of the derivatives of the invention may be described by reference to i) the number of the amino acid residue in human glucagon (SEQ ID NO: 1) which corresponds to the amino acid residue which is modified (i.e. the corresponding position in glucagon (SEQ ID NO: 1)), and to ii) the actual modification. The following are non-limiting examples of suitable analogue nomenclature.

In other words, the glucagon analogue is a glucagon peptide which a number of modifications of amino acid residues when compared to human glucagon (SEQ ID NO: 1). These modifications may represent, independently, one or more amino acid substitutions, additions, and/or deletions. For example, "[Imp1,His3,Glu15,Lys24,Leu27,Ser28]-Glucagon" designates glucagon (SEQ ID NO: 1), wherein the amino acid in position 1 has been substituted with Imp, the amino acid in position 3 has been substituted with His, the amino acid in position 15 has been substituted with Glu, the amino acid in position 24 has been substituted with Lys, the amino acid in position 27 has been substituted with Leu, and the amino acid in position 28 has been substituted with Ser.

Analogues "comprising" certain specified changes may comprise further changes, when compared to SEQ ID NO: 1. In a particular embodiment, the analogue "consists of" or "has" the specified changes.

As is apparent from the above examples, amino acid residues may be identified by their full name, their one-letter code, and/or their three-letter code. These three ways are fully equivalent. In some embodiments glucagon analogues and glucagon derivatives are drawn using standard one-letter or three-letter codes according to IUPAC-IUB nomenclature.

The expressions "position" or "corresponding position" may be used to characterise the site of change in a glucagon analogue sequence by reference to glucagon (SEQ ID NO: 1). The position, as well as the number of changes, are easily deduced, e.g. by simple handwriting and eyeballing.

The term "peptide", as e.g. used in the context of the glucagon analogues of the derivatives of the invention, refers to a compound which comprises a series of amino acids interconnected by amide (or peptide) bonds. The glucagon derivatives of the invention comprise at least five constituent amino acids connected by peptide bonds. In particular embodiments, the peptide a) comprises or b) consists of i) 29 or ii) 30 amino acids. In a still further particular embodiment the peptide consists of amino acids interconnected by peptide bonds.

Amino acids are molecules containing an amino group and a carboxylic acid group, and, optionally, one or more additional groups, often referred to as a side chain. The term "amino acid" as used herein includes coded amino acids (amongst those the 20 standard amino acids), as well as non-coded amino acids. Coded amino acids are those which are encoded by the genetic code (IUPAC Table 1 section 3AA-1, chem.qmul.ac.uk/iupac/AminoAcid/AA1n2.html#AA1). Non-coded amino acids are either not found in native (e.g. human) peptides and/or proteins or not produced by standard cellular machinery (e.g., they may have been subject to post-translational modification). Non-limiting examples of non-coded amino acids are Aib (alpha-aminoisobutyric acid), des-amino-histidine (3-(imidazol-4-yl)propionic acid, alternative name imidazopropionic acid, abbreviated Imp), as well as the D-isomers of the coded amino acids. Herein, Imp is defined as an amino acid although it does not contain an amino group.

In what follows, all amino acids of the peptide (e.g. the glucagon analogue or glucagon derivative) for which the optical isomer is not stated are to be understood to mean the L-isomer (unless otherwise specified).

The glucagon derivative may comprise a total of up to 15 amino acid modifications (for example one or more additions, one or more deletions and/or one or more substitutions) in the amino acid sequence of Formula I as compared to human glucagon (SEQ ID NO: 1). In some embodiments the glucagon derivative comprises an amino acid sequence of Formula I having 3-15 amino acid residue modifications, such as substitutions or additions, as compared to human glucagon (SEQ ID NO: 1). In some embodiments the glucagon derivative comprises an amino acid sequence of Formula I having up to 14, such as up to 13 or up to 12, amino acid residue modifications, such as substitutions or additions, as compared to human glucagon (SEQ ID NO: 1). In some embodiments the glucagon derivative comprises an amino acid sequence of Formula I having up to 11, such as up to 10 or up to 9, amino acid residue modifications, such as substitutions or additions, as compared to human glucagon (SEQ ID NO: 1). In some embodiments the glucagon derivative comprises an amino acid sequence of Formula I having up to 8, such as up to 7 or up to 6, amino acid residue modifications, such as substitutions or additions, as compared to human glucagon (SEQ ID NO: 1). In some embodiments the glucagon derivative comprises an amino acid sequence of Formula I having up to 5, such as up to 4 or up to 3, amino acid residue modifications, such as substitutions or additions, as compared to human glucagon (SEQ ID NO: 1).

In some embodiments the glucagon derivative comprises an amino acid sequence of Formula I as defined herein, wherein
X$^1$ represents His or Imp1;
X$^2$ represents Aib or Acb;
X$^3$ represents Gln;
X$^{10}$ represents Tyr, Leu, Ile or Val;
X$^{12}$ represents Lys or Arg;
X$^{15}$ represents Asp or Glu;
X$^{16}$ represents Ser, Ala, Leu or Val;
X$^{17}$ represents Arg or Lys;

$X^{18}$ represents Arg;
$X^{20}$ represents Gln or Arg;
$X^{21}$ represents Asp or Glu;
$X^{24}$ represents Gln, Ala or Lys;
$X^{28}$ represents Asn, Ser or Lys;
$X^{29}$ represents Thr or Lys; and
$X^{30}$ is absent.

In some embodiments the glucagon derivative comprises an amino acid sequence of Formula I, wherein
$X^1$ represents His or Imp1;
$X^2$ represents Aib or Acb;
$X^3$ represents Gln;
$X^{10}$ represents Tyr or Leu;
$X^{12}$ represents Lys or Arg;
$X^{15}$ represents Asp or Glu;
$X^{16}$ represents Ser, Ala or Leu;
$X^{17}$ represents Arg;
$X^{18}$ represents Arg;
$X^{20}$ represents Gln or Arg;
$X^{21}$ represents Asp or Glu;
$X^{24}$ represents Gln, Ala or Lys;
$X^{28}$ represents Ser or Lys;
$X^{29}$ represents Thr or Lys; and
$X^{30}$ is absent.

In some embodiments $X^1$ represents His or Imp1.
In some embodiments $X^2$ represents Aib or Acb.
In some embodiments $X^3$ represents Gln or His.
In some embodiments $X^3$ represents Gln.
In some embodiments $X^{10}$ represents Tyr, Leu, Ile or Val.
In some embodiments $X^{10}$ represents Tyr, Leu, or Val.
In some embodiments $X^{10}$ represents Tyr or Leu.
In some embodiments $X^{12}$ represents Lys or Arg.
In some embodiments $X^{15}$ represents Asp or Glu.
In some embodiments $X^{16}$ represents Ser, Ala, Leu, Thr, Glu, Aib, Ile, Val or Lys.
In some embodiments $X^{16}$ represents Ser, Ala, Leu or Val.
In some embodiments $X^{16}$ represents Ser, Ala or Leu.
In some embodiments $X^{17}$ represents Arg, Lys or Gln.
In some embodiments $X^{17}$ represents Arg or Lys.
In some embodiments $X^{17}$ represents Arg.
In some embodiments $X^{18}$ represents Arg, Ala or Lys.
In some embodiments $X^{18}$ represents Arg.
In some embodiments $X^{20}$ represents Gln, Arg or Lys.
In some embodiments $X^{20}$ represents Gln or Arg.
In some embodiments $X^{21}$ represents Asp, Glu or Lys.
In some embodiments $X^{21}$ represents Asp or Glu.
In some embodiments $X^{24}$ represents Gln, Ala, Arg, Glu or Lys.
In some embodiments $X^{24}$ represents Gln, Ala or Lys.
In some embodiments $X^{24}$ represents Gln or Lys.
In some embodiments $X^{28}$ represents Asn, Ser, Thr, Gln, Ala, Gly, Glu or Lys.
In some embodiments $X^{28}$ represents Asn, Ser or Lys.
In some embodiments $X^{28}$ represents Ser or Lys.
In some embodiments $X^{29}$ represents Thr, Gly, Ser, Gln, Ala, Glu or Lys.
In some embodiments $X^{29}$ represents Thr or Lys.
In some embodiments $X^{30}$ is absent or represents Lys.
In some embodiments $X^{30}$ is absent.

In some embodiments the glucagon analogue or derivative comprises no amino acid residues added to the C-terminal of $X_{30}$.

In some embodiments the glucagon derivative comprises the amino acid sequence selected from the group consisting of:

[Aib2,Ala16,Arg20,Lys24,Ile27,Ser28]-Glucagon amide;
[Aib2,Ala16,Lys17,Arg20,Glu21,Lys24,Ile27,Ser28]-Glucagon amide;
[Aib2,Leu10,Glu15,Arg20,Ile27,Lys28]-Glucagon amide;
[Aib2,Ala16,Arg20,Glu21,Lys24,Ile27,Ser28]-Glucagon amide;
[Aib2,Leu10,Ala16,Arg20,Ile27,Lys28]-Glucagon amide;
[Aib2,Leu10,Ala16,Arg20,Glu21,Ile27,Lys28]-Glucagon amide;
[Aib2,Leu10,Ala16,Ile27,Lys28]-Glucagon amide;
[Aib2,Leu10,Glu15,Ile27,Lys28]-Glucagon amide;
[Aib2,Leu10,Leu16,Ile27,Lys28]-Glucagon amide;
[Aib2,Val10,Glu15,Ile27,Lys28]-Glucagon amide;
[Aib2,Glu15,Arg20,Lys24,Ile27,Ser28]-Glucagon amide;
[Aib2,Leu16,Arg20,Lys24,Ile27,Ser28]-Glucagon amide;
[Acb2,Leu10,Glu15,Arg20,Glu21,Ile27,Lys28]-Glucagon amide;
[Aib2,Leu10,Arg2,Ala16,Arg20,Ile27,Lys28]-Glucagon amide;
[Acb2,Leu10,Glu15,Arg20,Glu21,Ile27,Lys28]-Glucagon amide;
[Acb2,Leu10,Arg12,Glu15,Arg20,Glu21,Ile27,Lys28]-Glucagon amide;
[Acb2,Leu10,Glu15,Arg20,Glu21,Ile27,Lys28]-Glucagon amide;
[Acb2,Val10,Glu15,Arg20,Glu21,Ile27,Lys28]-Glucagon amide;
[Aib2,Leu10,Ala16,Arg20,Ile27,Lys29]-Glucagon amide;
[Aib2,Leu10,Ala16,Arg20,Glu21,Ile27,Lys29]-Glucagon amide;
[Aib2,Leu10,Leu16,Arg20,Glu21,Ile27,Lys29]-Glucagon amide;
[Aib2,Leu10,Leu16,Arg20,Ile27,Lys29]-Glucago amide;
[Aib2,Leu10,Leu16,Arg20,Ala24,Ile27,Lys29]-Glucagon amide;
[Aib2,Leu10,Glu15,Arg20,Glu21,Ile27,Lys28]-Glucagon amide;
[Acb2,Leu10,Glu15,Arg20,Glu21,Ile27,Lys28]-Glucagon amide;
[Aib2,Leu10,Ala16,Arg20,Ile27,Ser28,Lys29]-Glucagon amide;
[Aib2,Leu10,Ala16,Arg20,Glu21,Ile27,Ser28,Lys29]-Glucagon amide;
[Aib2,Leu10,Leu16,Arg20,Ile27,Ser28,Lys29]-Glucagon amide;
[Aib2,Leu10,Leu16,Arg20,Glu21,Ile27,Ser28,Lys29]-Glucagon amide;
[Aib2,Leu10,Leu16,Arg20,Ala24,Ile27,Ser28,Lys29]-Glucagon amide;
[Aib2,Ala16,Arg20,Ala24,Ile27,Lys28]-Glucagon amide;
[Aib2,Leu16,Arg20,Ala24,Ile27,Lys28]-Glucagon amide;
[Aib2,Glu15,Ala24,Ile27,Lys28]-Glucagon amide;
[Aib2,Glu15,Ala24,Ile27,Ser28,Lys29]-Glucagon amide;
[Acb2,Arg12,Glu15,Arg20,Ile27,Lys28]-Glucagon amide;
[Aib2,Arg12,Glu15,Arg20,Ile27,Lys28]-Glucagon amide;
[Acb2,Leu10,Glu15,Glu21,Ile27,Lys28]-Glucagon amide;
[Aib2,Val10,Ala16,Ile27,Lys28]-Glucagon amide; and
[Aib2,Leu10,Val16,Ile27,Lys28]-Glucagon amide.

The amino acid abbreviations used in the present context have the following meanings:

| Amino acid (Three-letter code) | Amino acid (One-letter code) | Description |
|---|---|---|
| Acb | n/a[1] | 1-Aminocyclobutancarboxylic acid |
| Acpr | n/a | 1-Aminocyclopropanecarboxylic acid |
| Ado | n/a | 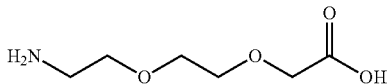 |
| Aib | n/a | 2-Aminoisobutyric acid |
| Ala | A | Alanine |
| Asn | N | Asparagine |
| Asp | D | Aspartic acid |
| Arg | R | Arginine |
| Cit | n/a | Citrulline |
| Cys | C | Cysteine |
| Gln | Q | Glutamine |
| Glu | E | Glutamic acid |
| γ-Glu | n/a | 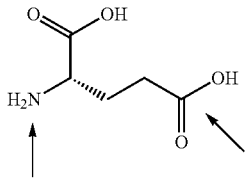 wherein the alpha-nitrogen (a-nitrogen) and the gamma-carboxy (g-carboxy) group form the amide bonds to the two neighbouring residues. Here, γ-Glu is also referred to as "gamma-Glu" or "gGlu". |
| Gly | G | Glycine |
| His | H | Histidine |
| Hyp | n/a | 4-hydroxyproline |
| Ile | I | Isoleucine |
| Leu | L | Leucine |
| Lys | K | Lysine |
| Met | M | Methionine |
| Orn | n/a | Ornithine |
| Phe | F | Phenylalanine |
| Pro | P | Proline |
| Ser | S | Serine |
| Thr | T | Threonine |
| Tyr | Y | Tyrosine |
| Trp | W | Tryptophan |
| Val | V | Valine |

[1]"n/a" is not available

Amino acid abbreviations beginning with D- followed by a three letter code, such as D-Ser, D-His and so on, refer to the D-enantiomer of the corresponding amino acid, for example D-serine, D-histidine and so on.

Glucagon Derivatives

The invention relates to glucagon derivatives which are derivatives of glucagon analogues. The term "derivative" as used herein in the context of a glucagon peptide, such as a glucagon analogue, means a chemically modified glucagon peptide in which one or more substituents have been covalently attached to the glucagon peptide. The term "substituent" as used herein, means a chemical moiety or group replacing a hydrogen atom. The derivative may comprise one or more modifications selected from amides, carbohydrates, alkyl groups, acyl groups, esters and the like.

In some embodiments the glucagon derivative comprises a substituent comprising a lipophilic moiety and at least three negatively charged moieties, wherein one of said negatively charged moieties is distal of a lipophilic moiety, and wherein said substituent is attached at the epsilon position of a lysine residue in one of the amino acid positions 16, 17, 18, 20, 21, 24, 28, 29 or 30 of Formula I. In some embodiments the term "distal" when used referring to a negatively charged moiety in the substituent refers to the end of the substituent situated away from the point of attachment to the amino acid sequence (e.g. Formula I) of the glucagon derivative. In some embodiments the glucagon derivative comprises a substituent comprising a lipophilic moiety and at least three negatively charged moieties, wherein at least one of said negatively charged moieties is distal of a lipophilic moiety, and wherein said substituent is attached at the epsilon position of a lysine residue in one of the amino acid positions 16, 17, 18, 20, 21, 24, 28, 29 or 30 of Formula I.

The term "lipophilic moiety" as used herein, means an aliphatic or cyclic hydrocarbon moiety with more than 6 and less than 30 carbon atoms, wherein said hydrocarbon moiety may contain additional substituents.

The term "negatively charged moiety" as used herein, means a negatively chargeable chemical moiety, such as, but not limited to an amino acid moiety (e.g. Glu, gamma-Glu, Asp or beta-Asp, a carboxylic acid, sulphonic acid or a tetrazole moiety). The number of negatively charged moieties may be determined at physiological pH (pH 7.4). The negatively charged moiety may be a carboxylic acid group.

In some embodiments the substituent is attached at the epsilon position of a lysine residue at one of positions 16, 17, 18, 20, 21, 24, 28, 29, or 30 of Formula I. In some embodiments the substituent is attached at the epsilon position of a lysine residue at one of positions 24, 28 or 29 of Formula I. In some embodiments the substituent is attached at the epsilon position of a lysine residue at position 24 of Formula I. In some embodiments the substituent is attached at the epsilon position of a lysine residue at position 28 of Formula I. In some embodiments the substituent is attached at the epsilon position of a lysine residue at position 29 of Formula I.

In some embodiments the substituent comprises three, four or five negatively charged moieties. In some embodiments the substituent comprises three or four negatively charged moieties. In some embodiments the substituent comprises three negatively charged moieties.

In some embodiments the substituent binds non-covalently to albumin.

In some embodiments the substituent is negatively charged at physiological pH.

In some embodiments the substituent comprises a lipophilic moiety and at least three negatively charged moieties and is a substituent represented by Formula II:

$$Z^1-Z^2-Z^3-Z^4-Z^5-Z^6-Z^7-Z^8-Z^9-Z^{10}- \quad (II)$$

wherein, $Z^1$ represents a structure according to the Formula IIa:

wherein
n is 6-20;
the symbol * represents the attachment point to the nitrogen of the neighbouring group; and $Z^2$-$Z^3$-$Z^4$-$Z^5$-$Z^6$-$Z^7$-$Z^8$-$Z^9$-$Z^{10}$- represents a linker, wherein each of $Z^2$ to $Z^{10}$ individually are represented by any one of the following amino acid residues: Glu, gamma-Glu (gGlu), Gly, Ser, Ala, Thr and/or Ado; or one or more of residues $Z^2$ to $Z^{10}$ are absent; provided, however, that at least two of residues $Z^2$ to $Z^{10}$ are present;

wherein $Z^1$-$Z^2$-$Z^3$-$Z^4$-$Z^5$-$Z^6$-$Z^7$-$Z^8$-$Z^9$-$Z^{10}$- together contains at least three negatively charged moieties; and wherein said substituent is attached at the epsilon position of a Lys in the amino acid sequence of Formula I.

In some embodiments $Z_1$ represents a fatty di-acid of Formula IIa;

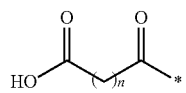

(IIa)

wherein n represents an integer in the range of from 12 to 18. In some embodiments n in Formula IIa represents 12, 14, 16 or 18. In some embodiments n in Formula IIa is 16 (i.e. $Z^1$ represents 17-carboxyheptadecanoyl).

In some embodiments, in Formula II, $Z^2$-$Z^3$-$Z^4$-$Z^5$-$Z^6$-$Z^7$-$Z^8$-$Z^9$-$Z^{10}$- represents a linker, wherein each of $Z^2$ to $Z^{10}$ individually are represented by any one of the following amino acid residues: Glu, gGlu, Gly, Ser, Ala, Thr and/or Ado; or one or more of residues $Z^2$ to $Z^{10}$ are absent; provided, however, that at least two of residues $Z^2$ to $Z^{10}$ are present; and wherein $Z^1$-$Z^2$-$Z^3$-$Z^4$-$Z^5$-$Z^6$-$Z^7$-$Z^8$-$Z^9$-$Z^{10}$- together contains at least three negatively charged moieties.

In some embodiments $Z^2$, $Z^3$, $Z^4$, $Z^5$, $Z^6$, $Z^7$, $Z^8$, $Z^9$ and $Z^{10}$ individually are represented by any one of the following amino acid residues: Glu, gGlu, Gly, Ser, and/or Ado; or one or more of residues $Z^2$ to $Z^{10}$ are absent; provided, however, that at least two of residues $Z^2$ to $Z^{10}$ are present. In some embodiments $Z^2$, $Z^3$, $Z^4$, $Z^5$, $Z^6$, $Z^7$, $Z^8$, $Z^9$ and $Z^{10}$ individually are represented by any one of the following amino acid residues: gGlu and/or Ado; or one or more of residues $Z^2$ to $Z^{10}$ are absent; provided, however, that at least two of residues $Z^2$ to $Z^{10}$ are present. In some embodiments at least three of residues $Z^2$ to $Z^{10}$ are present. In some embodiments at least four of residues $Z^2$ to $Z^{10}$ are present. In some embodiments at least five of residues $Z^2$ to $Z^{10}$ are present. In some embodiments at least six of residues $Z^2$ to $Z^{10}$ are present.

In some embodiments $Z^2$-$Z^3$-$Z^4$-$Z^5$-$Z^6$-$Z^7$-$Z^8$-$Z^9$-$Z^{10}$- represents a linker selected from the group consisting of
gGlu-Ado-gGlu-;
gGlu-Ado-2xgGlu- (SEQ ID NO: 51);
gGlu-2xAdo-2xgGlu- (SEQ ID NO:52);
2xgGlu-;
2xgGlu-Ado-;
2xgGlu-Ado-gGlu- (SEQ ID NO:53);
2xgGlu-Ado-gGlu-Ado- (SEQ ID NO:54);
2xgGlu-Ado-2xgGlu- (SEQ ID NO:55);
2xgGlu-2xAdo- (SEQ ID NO:56);
2xgGlu-2xAdo-gGlu- (SEQ ID NO:57);
2xgGlu-2xAdo-2xgGlu- (SEQ ID NO:58);
2xgGlu-Ser-Gly-Glu-Ser- (SEQ ID NO:49);
2xgGlu-Ser-Gly-Glu-Ser-Gly- (SEQ ID NO:50);
3xgGlu-;
3xgGlu-Ado- (SEQ ID NO:61);
3xgGlu-2xAdo- (SEQ ID NO:59); and
2xgGlu-Ado-gGlu-Ado-gGlu-Ado-gGlu- (SEQ ID NO:60).

In some embodiments the $Z^2$-$Z^3$-$Z^4$-$Z^5$-$Z^6$-$Z^7$-$Z^8$-$Z^9$-$Z^{10}$- represents a linker selected from the group consisting of
2xgGlu-2xAdo-gGlu- (SEQ ID NO:57);
gGlu-2xAdo-2xgGlu- (SEQ ID NO:52);
2xgGlu-2xAdo- (SEQ ID NO:56);
2xgGlu-2xAdo-2xgGlu- (SEQ ID NO:58);
2xgGlu-Ser-Gly-Glu-Ser-Gly (SEQ ID NO:50);
3xgGlu-;
3xgGlu-2xAdo- (SEQ ID NO:59); and
2xgGlu-Ado-gGlu-Ado-gGlu-Ado-gGlu- (SEQ ID NO:60). In some embodiments $Z^2$-$Z^3$-$Z^4$-$Z^5$-$Z^6$-$Z^7$-$Z^8$-$Z^9$-$Z^{10}$- represents the linker 2xgGlu-2xAdo-gGlu- (SEQ ID NO:57). In some embodiments $Z^2$-$Z^3$-$Z^4$-$Z^5$-$Z^6$-$Z^7$-$Z^8$-$Z^9$-$Z^{10}$- represents the linker gGlu-2xAdo-2xgGlu- (SEQ ID NO:52). In some embodiments $Z^2$-$Z^3$-$Z^4$-$Z^5$-$Z^6$-$Z^7$-$Z^8$-$Z^9$-$Z^{10}$- represents the linker 2xgGlu-2xAdo-(SEQ ID NO:56). In some embodiments $Z^2$-$Z^3$-$Z^4$-$Z^5$-$Z^6$-$Z^7$-$Z^8$-$Z^9$-$Z^{10}$- represents the linker 2xgGlu-2xAdo-2xgGlu- (SEQ ID NO:58). In some embodiments $Z^2$-$Z^3$-$Z^4$-$Z^5$-$Z^6$-$Z^7$-$Z^8$-$Z^9$-$Z^{10}$-represents the linker 2xgGlu-Ser-Gly-Glu-Ser-Gly- (SEQ ID NO:50). In some embodiments $Z^2$-$Z^3$-$Z^4$-$Z^5$-$Z^6$-$Z^7$-$Z^8$-$Z^9$-$Z^{10}$- represents the linker 3xgGlu-. In some embodiments $Z^2$-$Z^3$-$Z^4$-$Z^5$-$Z^6$-$Z^7$-$Z^8$-$Z^9$-$Z^{10}$- represents the linker 3xgGlu-2xAdo- (SEQ ID NO:59). In some embodiments $Z^2$-$Z^3$-$Z^4$-$Z^5$-$Z^6$-$Z^7$-$Z^8$-$Z^9$-$Z^{10}$- represents the linker 2xgGlu-Ado-gGlu-Ado-gGlu-Ado-gGlu- (SEQ ID NO:60).

In some embodiments the glucagon derivative comprises an amino acid sequence of Formula I, wherein
$X^1$ represents His or Imp;
$X^3$ represents Gln;
$X^{10}$ represents Tyr, Leu, Ile or Val;
$X^{16}$ represents Ser, Ala, Leu or Val;
$X^{17}$ represents Arg or Lys;
$X^{18}$ represents Arg;
$X^{20}$ represents Gln or Arg;
$X^{21}$ represents Asp or Glu;
$X^{24}$ represents Gln, Ala or Lys;
$X^{28}$ represents Asn, Ser or Lys;
$X^{29}$ represents Thr or Lys; and
$X^{30}$ is absent;
and wherein said substituent is attached at the epsilon position of a lysine residue in one of the amino acid positions 24, 28, and 29.

In some embodiments the glucagon derivative comprises an amino acid sequence of Formula I, wherein
$X^1$ represents His or Imp;
$X^3$ represents Gln;
$X^{10}$ represents Tyr or Leu;
$X^{16}$ represents Ser, Ala or Leu;
$X^{17}$ represents Arg;
$X^{18}$ represents Arg;
$X^{20}$ represents Gln or Arg;
$X^{21}$ represents Asp or Glu;
$X^{24}$ represents Gln, Ala or Lys;
$X^{28}$ represents Ser or Lys;
$X^{29}$ represents Thr or Lys; and
$X^{30}$ is absent;
and wherein said substituent is attached at the epsilon position of a lysine residue in one of the amino acid positions 24, 28, and 29.

In some embodiments the glucagon derivative comprises an amino acid sequence of Formula I, wherein $X^{24}$ represents Gln or Ala; $X^{28}$ represents Asn or Ser; $X^{29}$ represents Lys; and $X^{30}$ is absent; and wherein said substituent is attached at the epsilon position of a lysine residue in position 29. In some embodiments the glucagon derivative comprises an amino acid sequence of Formula I, wherein $X^{24}$ represents Gln or Ala; $X^{28}$ represents Lys; $X^{29}$ represents Thr; and $X^{30}$ is absent; and wherein said substituent is attached at the epsilon position of a lysine residue in position 28. In some embodiments the glucagon derivative comprises an amino acid sequence of Formula I, wherein $X^{24}$ represents Lys; $X^{28}$ represents Asn or Ser; $X^{29}$ represents Thr; and $X^{30}$ is absent; and wherein said substituent is attached at the epsilon position of a lysine residue in position 24.

In some embodiments the glucagon derivative is N$^{\varepsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Arg20,Lys24,Ile27,Ser28]-Glucagon amide Chem 1(SEQ ID NO: 3):

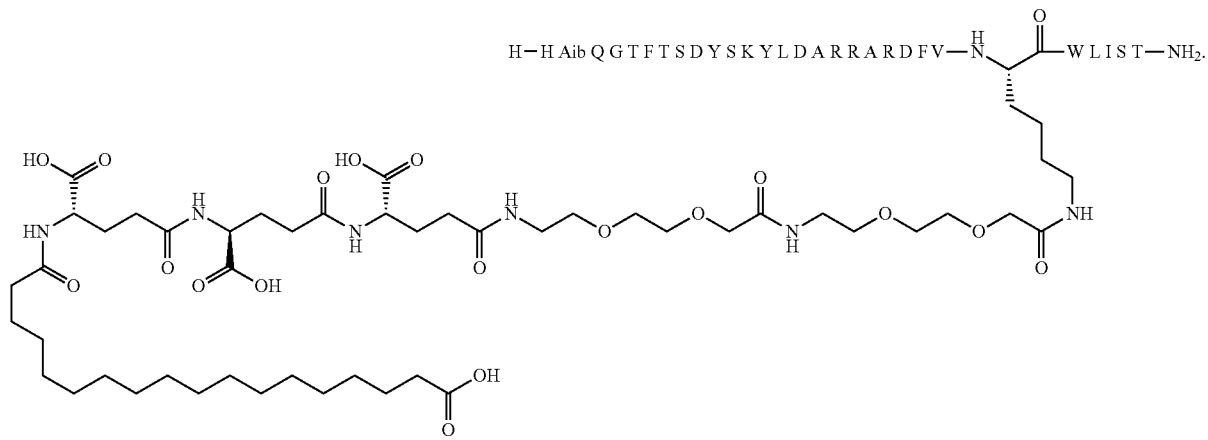

In some embodiments the glucagon derivative is N$^{\varepsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Lys17,Arg20,Glu21,Lys24,Ile27,Ser28]-Glucagon amide Chem 2(SEQ ID NO: 4):

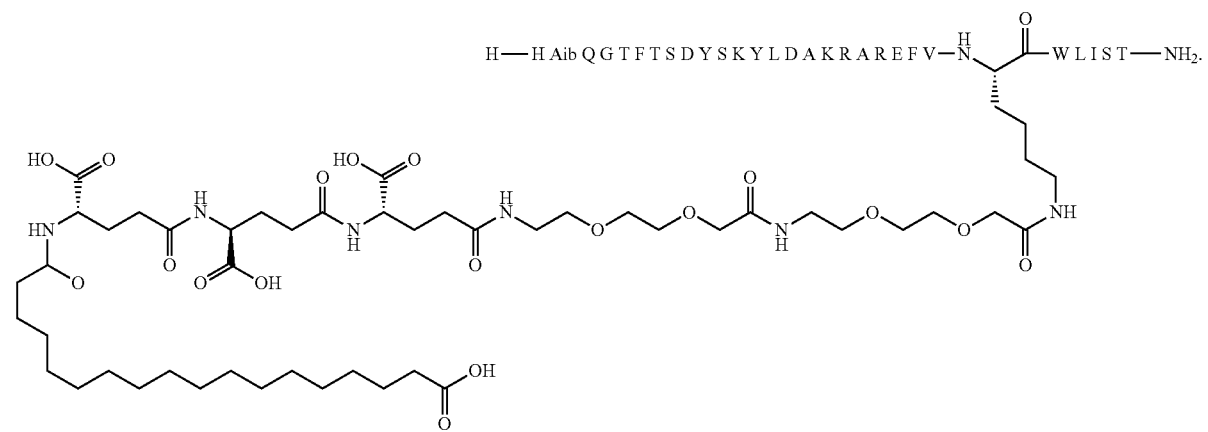

In some embodiments the glucagon derivative is N$^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Arg20,Ile27,Lys28]-Glucagon amide Chem 3(SEQ ID NO: 5):

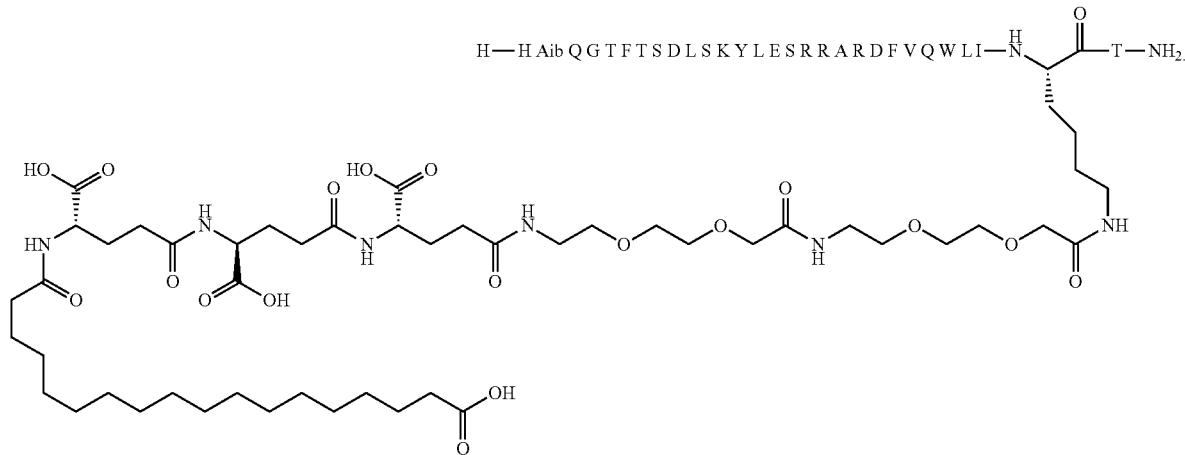

In some embodiments the glucagon derivative is $N^{\epsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Arg20,Glu21,Lys24,Ile27,Ser28]-Glucagon amide Chem 4(SEQ ID NO: 6):

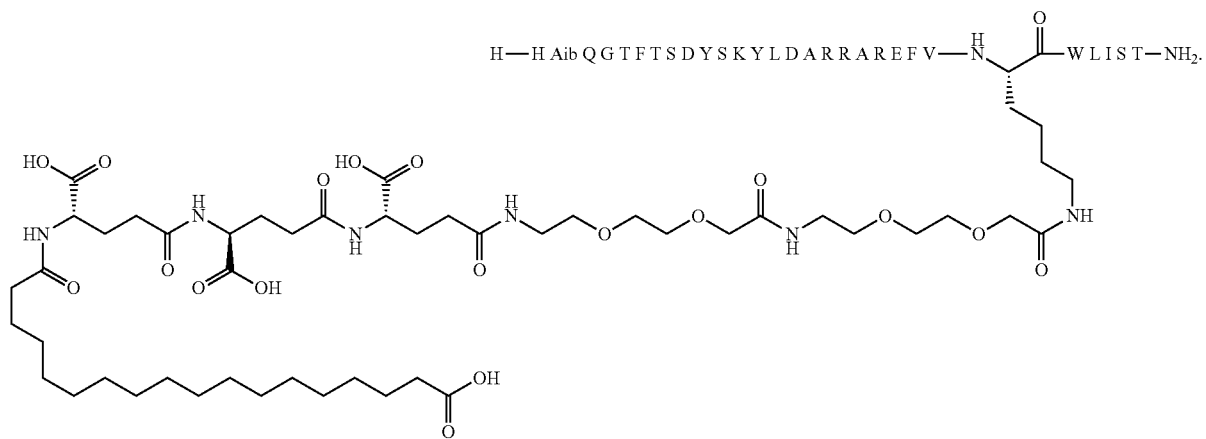

In some embodiments the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Ala16,Arg20,Glu21,Ile27,Lys28]-Glucagon amide Chem 5(SEQ ID NO: 7):

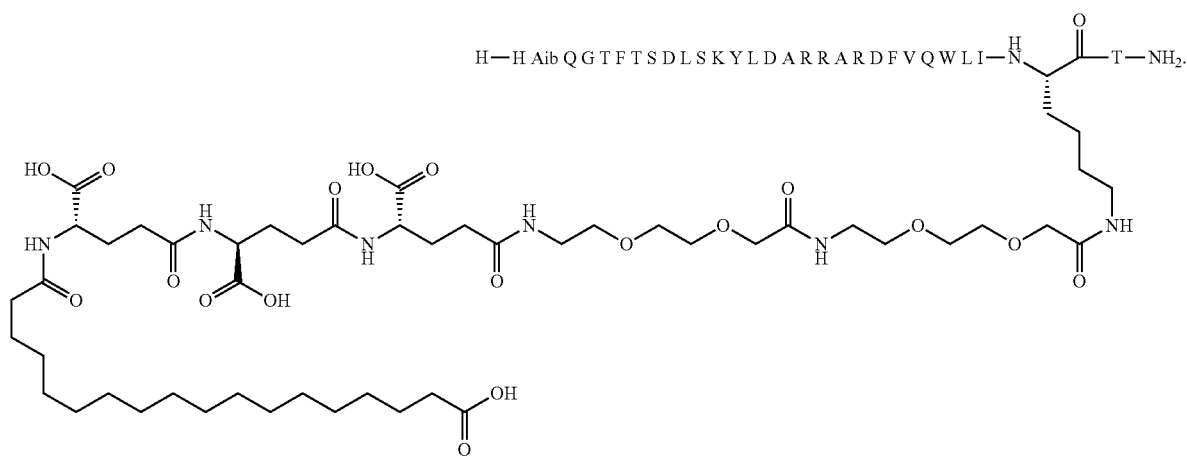

In some embodiments the glucagon derivative is $N^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Ala16,Arg20,Glu21,Ile27,Lys28]-Glucagon amide Chem 6(SEQ ID NO: 8):

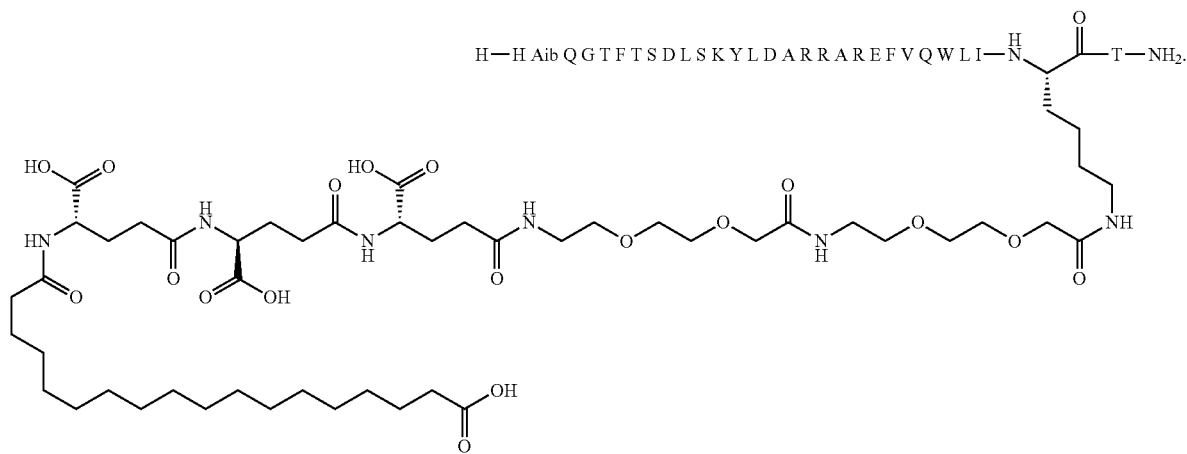

In some embodiments the glucagon derivative is $N^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Ile27,Lys28]-Glucagon amide Chem 7(SEQ ID NO: 9):

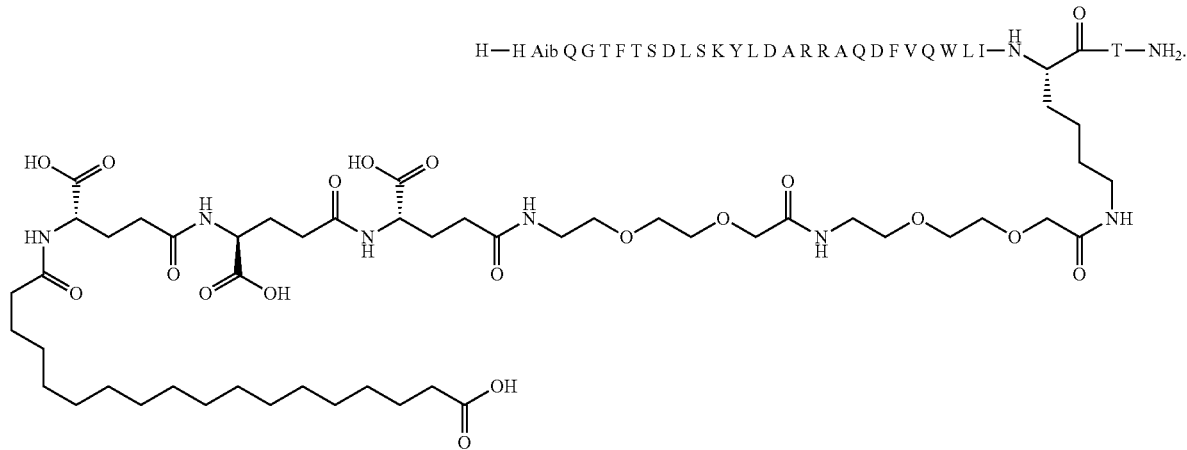

In some embodiments the glucagon derivative is $N^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Ile27,Lys28]-Glucagon amide Chem 8(SEQ ID NO: 10):

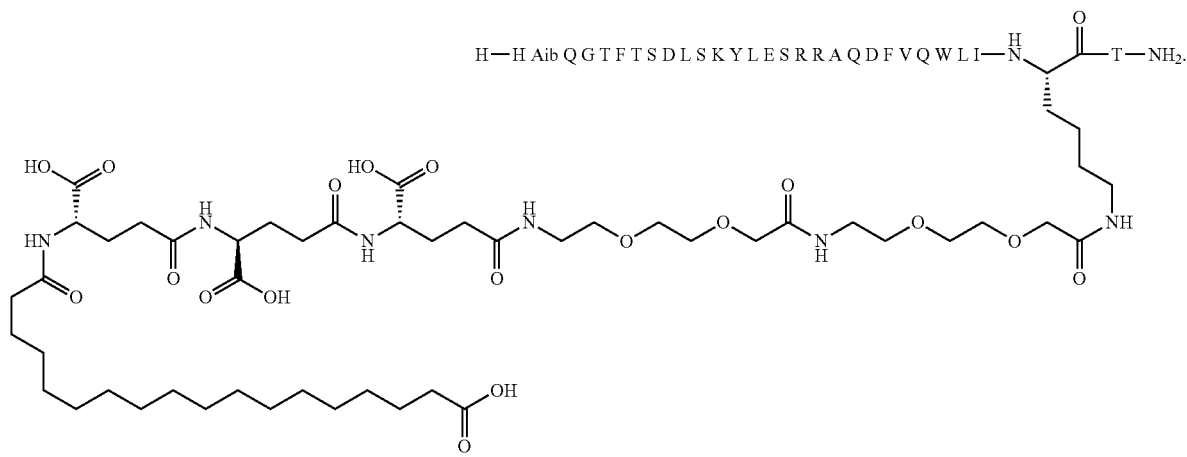

In some embodiments the glucagon derivative is $N^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Leu16,Ile27,Lys28]-Glucagon amide Chem 9(SEQ ID NO: 11):

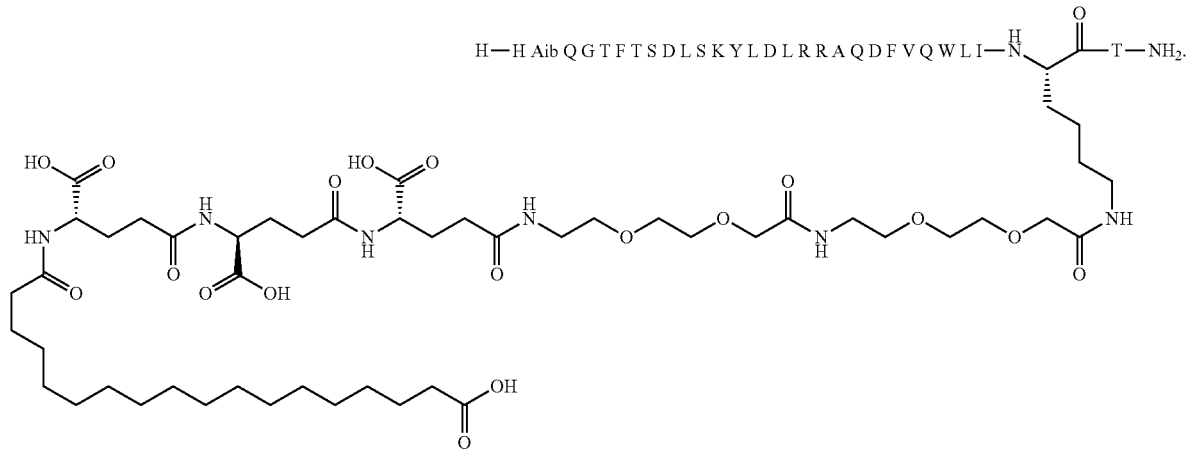

In some embodiments the glucagon derivative is N$^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Glu15,Ile27,Lys28]-Glucagon amide Chem 10(SEQ ID NO: 12):

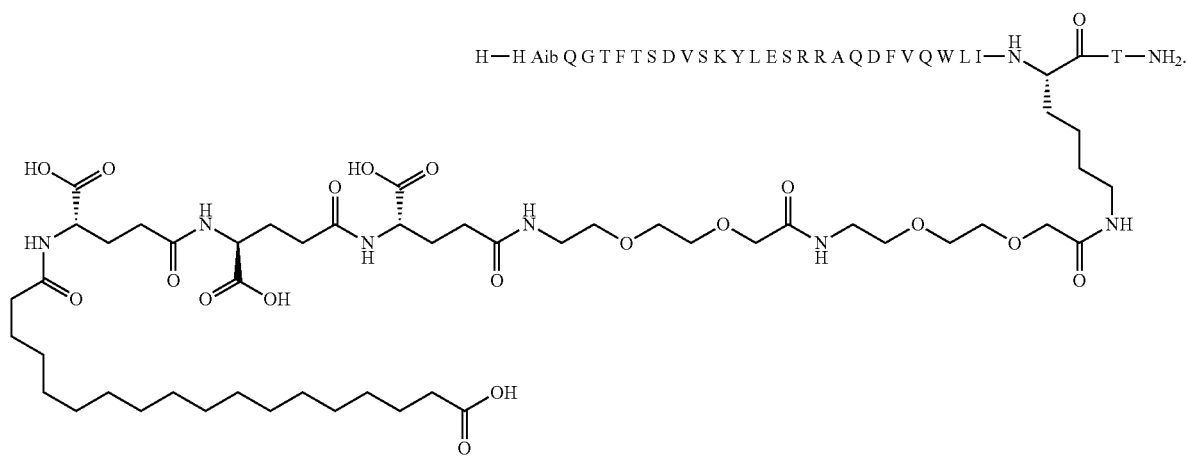

In some embodiments the glucagon derivative is N$^{\varepsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Glu15,Arg20,Lys24,Ile27,Ser28]-Glucagon amide Chem 11(SEQ ID NO: 13):

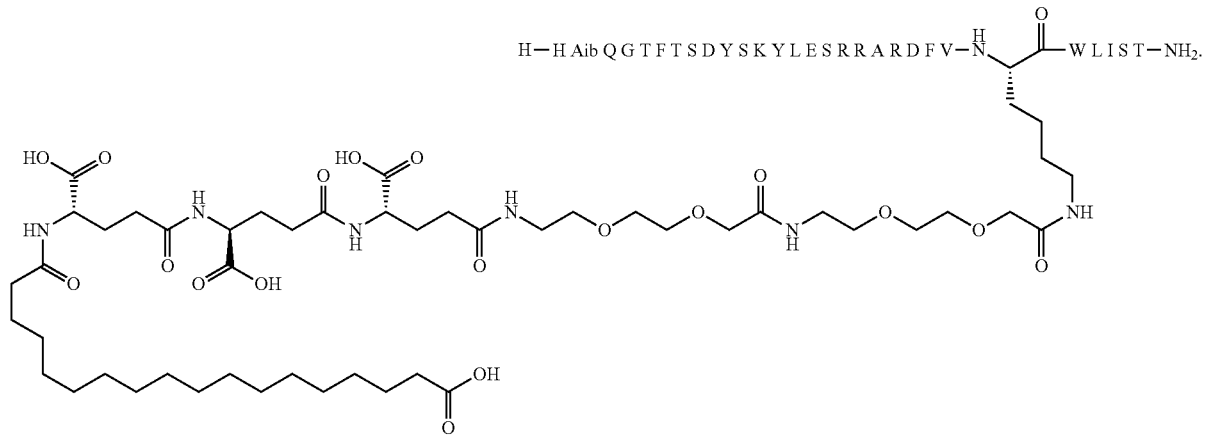

In some embodiments the glucagon derivative is $N^{\varepsilon24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu16,Arg20,Lys24,Ile27,Ser28]-Glucagon amide Chem 12(SEQ ID NO: 14):

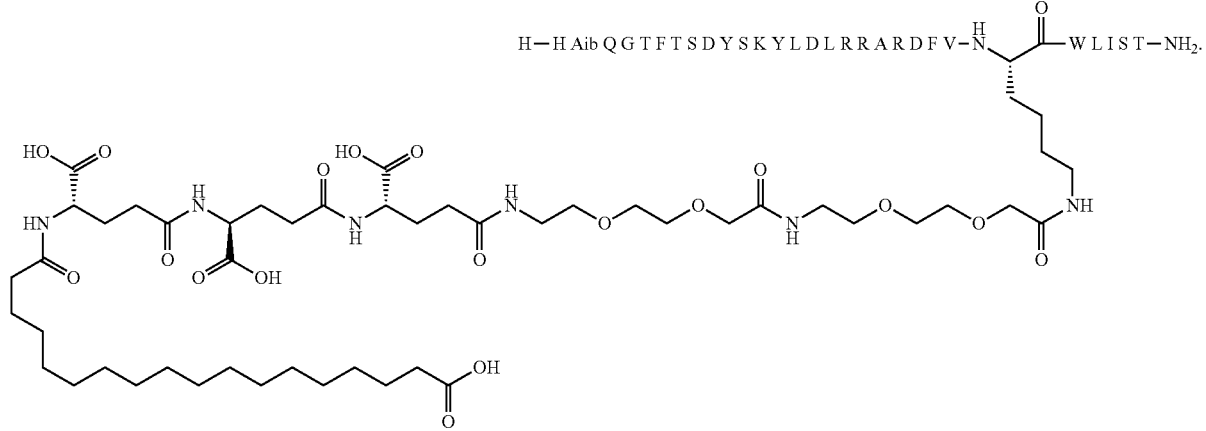

In some embodiments the glucagon derivative is $N^{\varepsilon28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Ile27,Lys28]-Glucagon amide Chem 13(SEQ ID NO: 15):

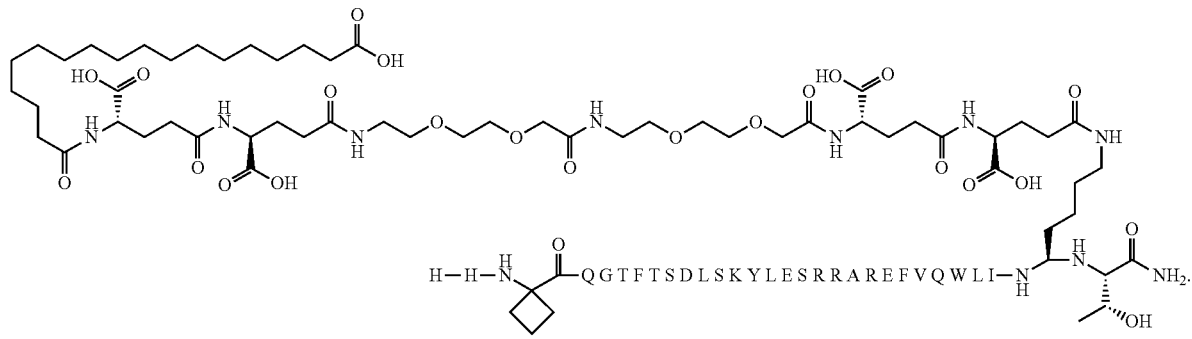

In some embodiments the glucagon derivative is $N^{\varepsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Arg12,Ala16,Arg20,Ile27,Lys28]-Glucagon amide
Chem 14(SEQ ID NO: 16):

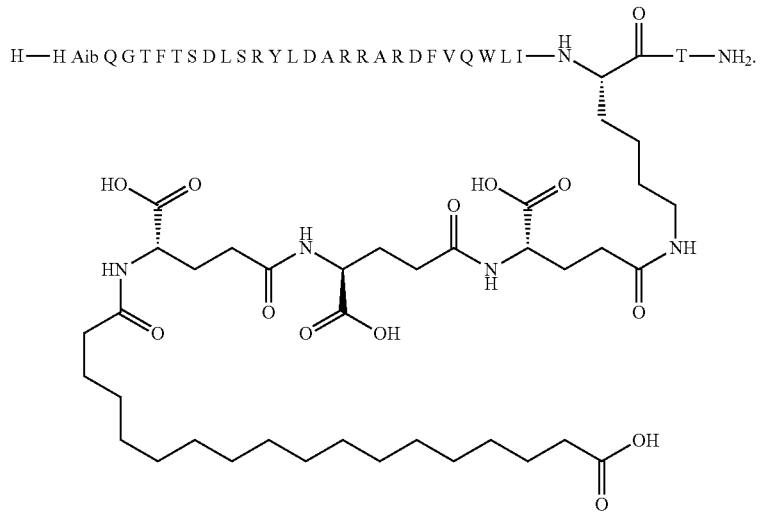

In some embodiments the glucagon derivative is $N^{\varepsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Ala16,Arg20,Ile27,Lys28]-Glucagon amide
Chem 15(SEQ ID NO: 17):

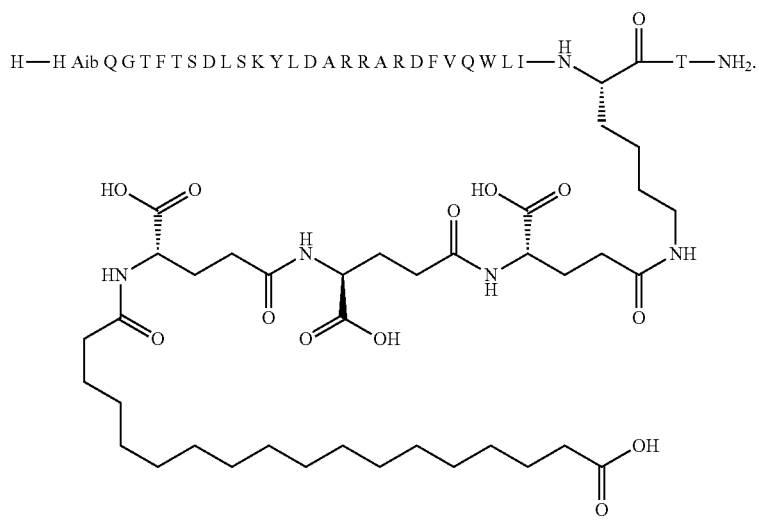

In some embodiments the glucagon derivative is $N^{\varepsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15,Arg20,Glu21,Ile27,Lys28]-Glucagon amide Chem 16(SEQ ID NO: 18):

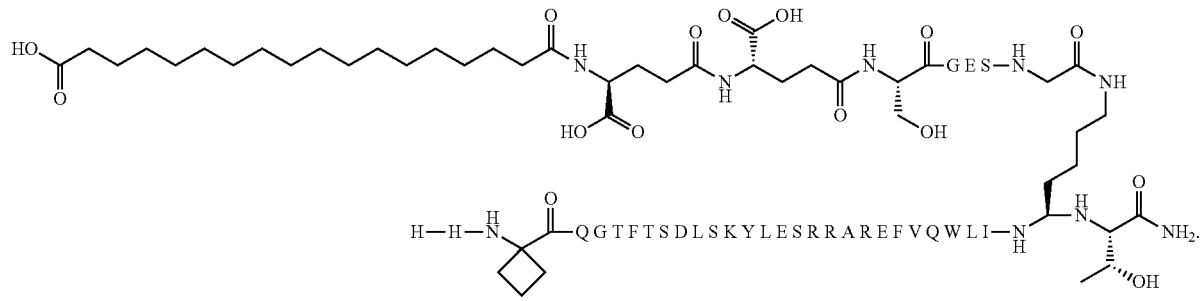

In some embodiments the glucagon derivative is N$^{\varepsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Glu15,Arg20,Glu21,Ile27,Lys28]-Glucagon amide Chem 17(SEQ ID NO: 19):

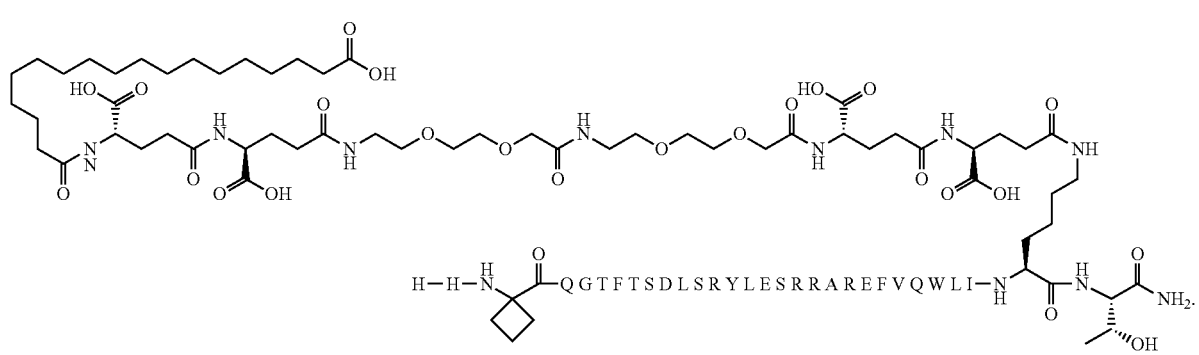

In some embodiments the glucagon derivative is N$^{\varepsilon 28}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Acb2,Leu10,Glu15,Arg20,Glu21,Ile27,Lys28]-Glucagon amide Chem 18(SEQ ID NO: 20):

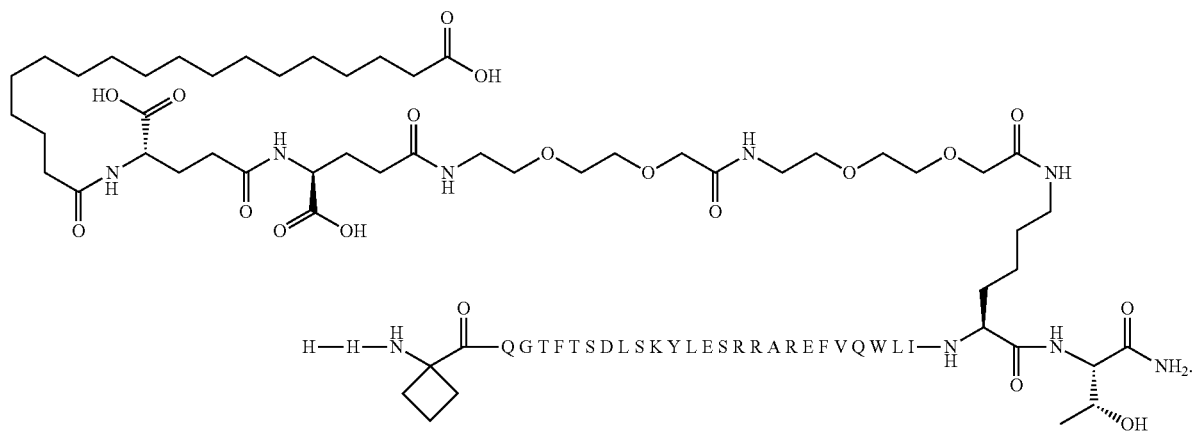

In some embodiments the glucagon derivative is $N^{\varepsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2 Val10,Glu15,Arg20,Glu21,Ile27,Lys28]-Glucagon amide
Chem 19(SEQ ID NO: 21):

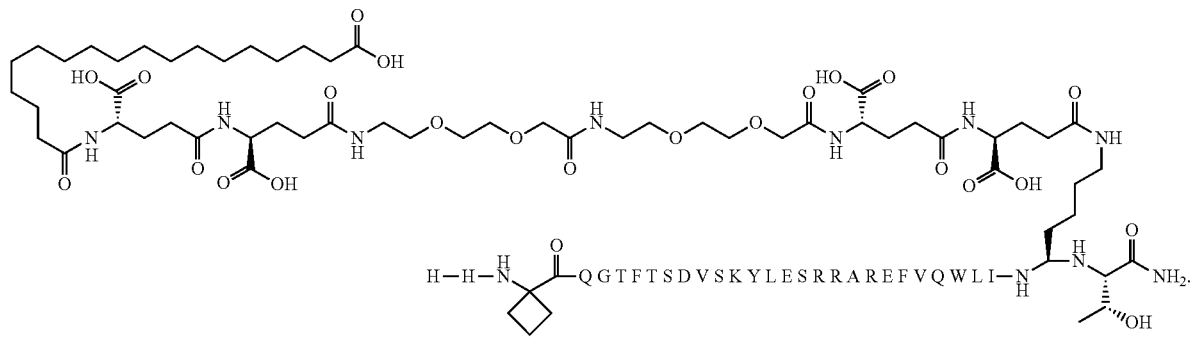

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Lys29]-Glucagon amide
Chem 20(SEQ ID NO: 22):

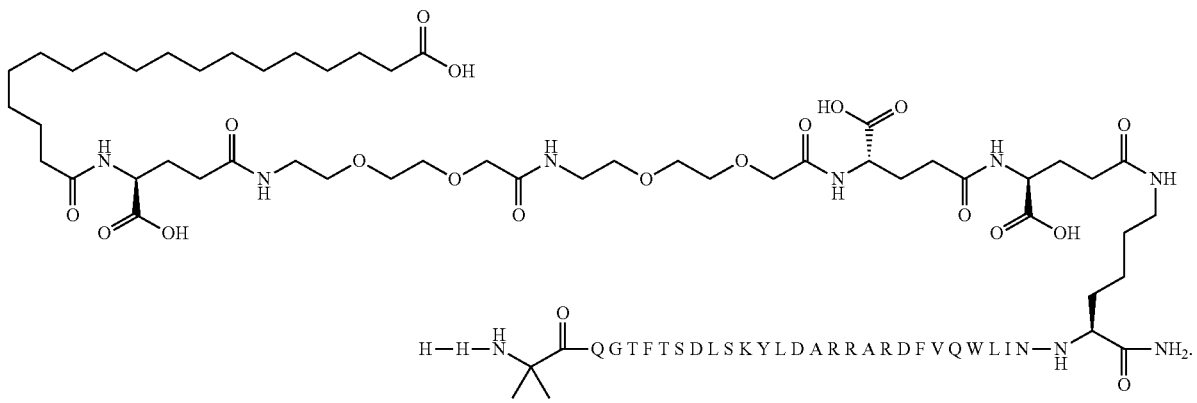

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Lys29]-Glucagon amide Chem 21(SEQ ID NO: 23):

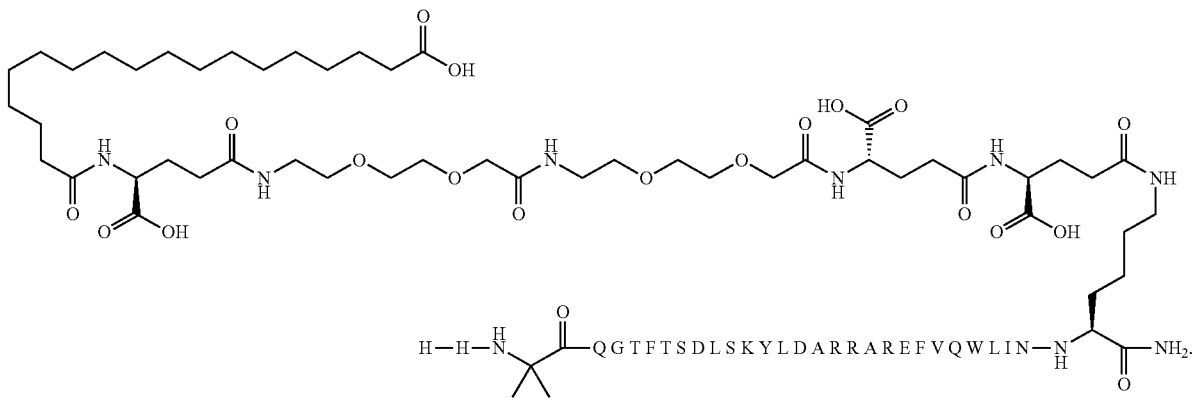

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Lys29]-Glucagon amide Chem 22(SEQ ID NO: 24):

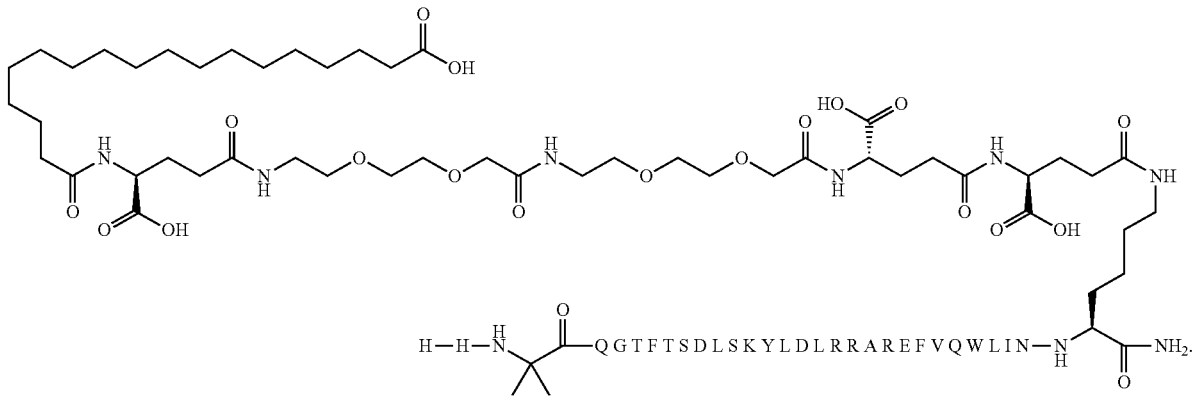

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Lys29]-Glucagon amide Chem 23(SEQ ID NO: 25):

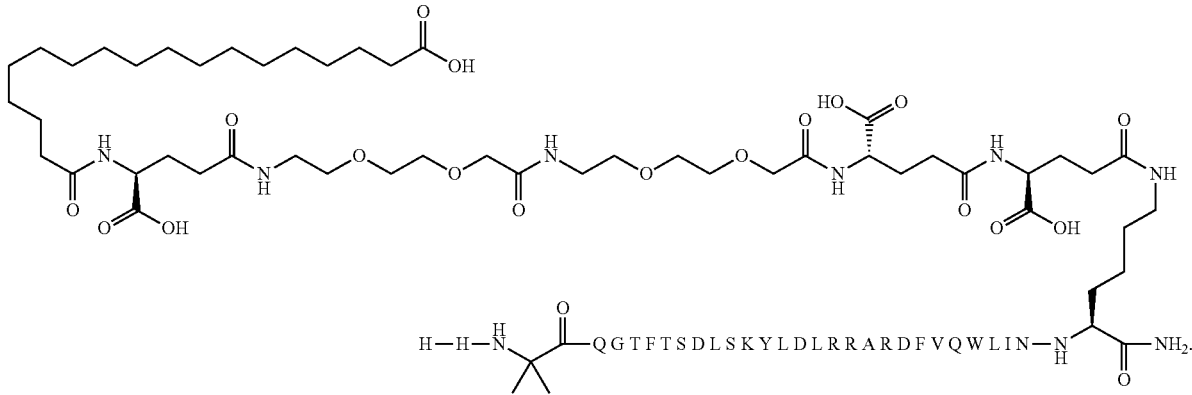

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Lys29]-Glucagon amide
Chem 24(SEQ ID NO: 26):

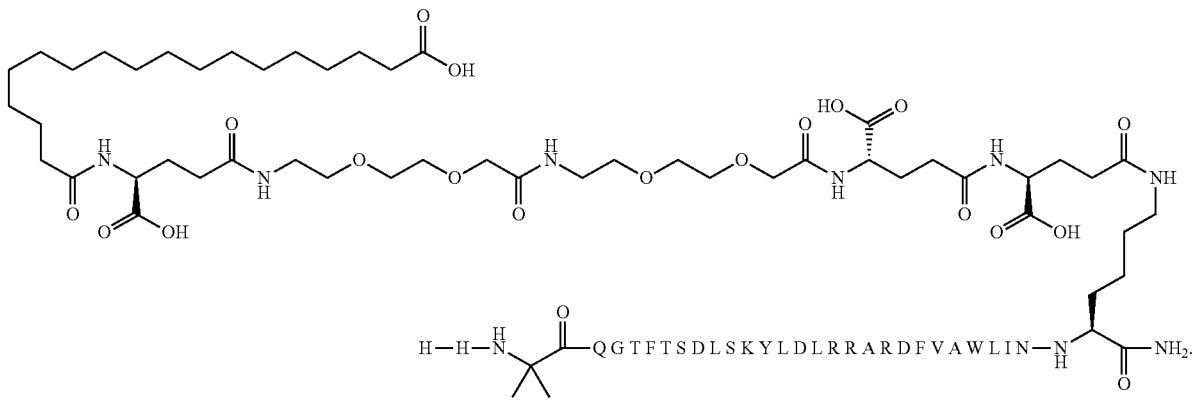

In some embodiments the glucagon derivative is $N^{\varepsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Aib2,Leu10,Glu15,Arg20, Glu21,Ile27,Lys28]-Glucagon amide
Chem 25(SEQ ID NO: 27):

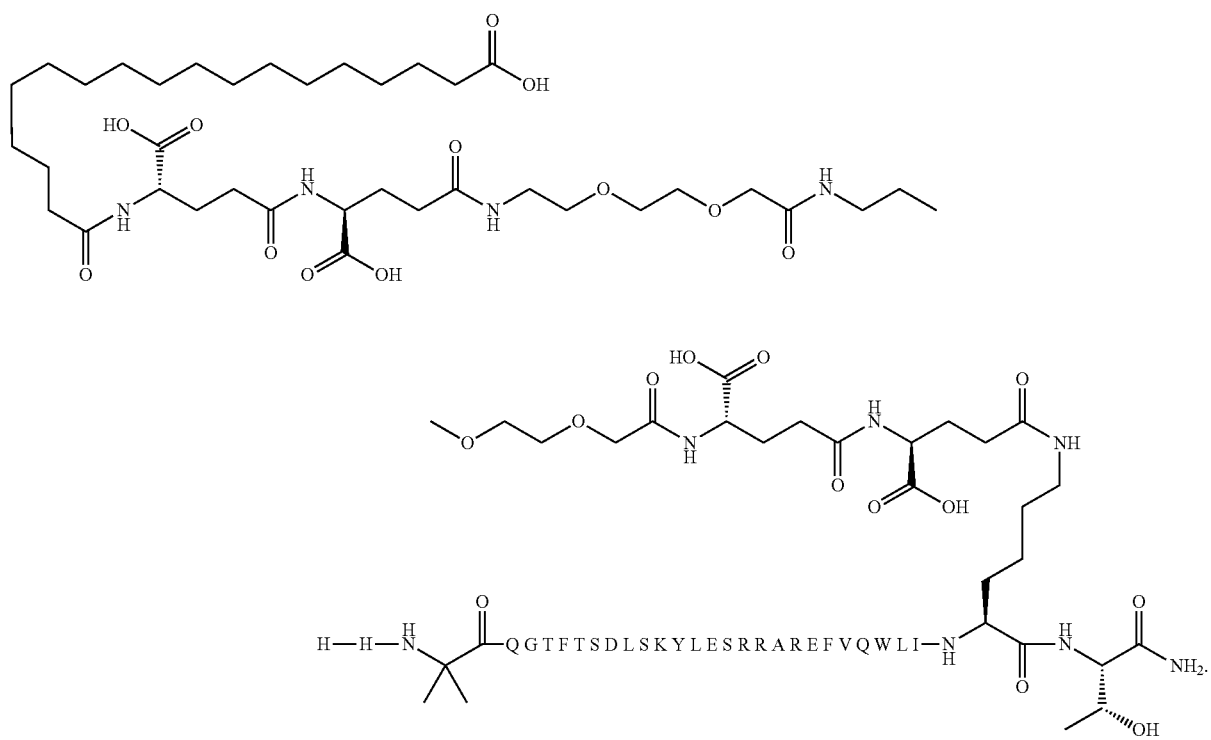

In some embodiments the glucagon derivative is $N^{\varepsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Ile10,Glu15,Arg20,Glu21,Ile27,Lys28]-Glucagon amide
Chem 26(SEQ ID NO: 28):

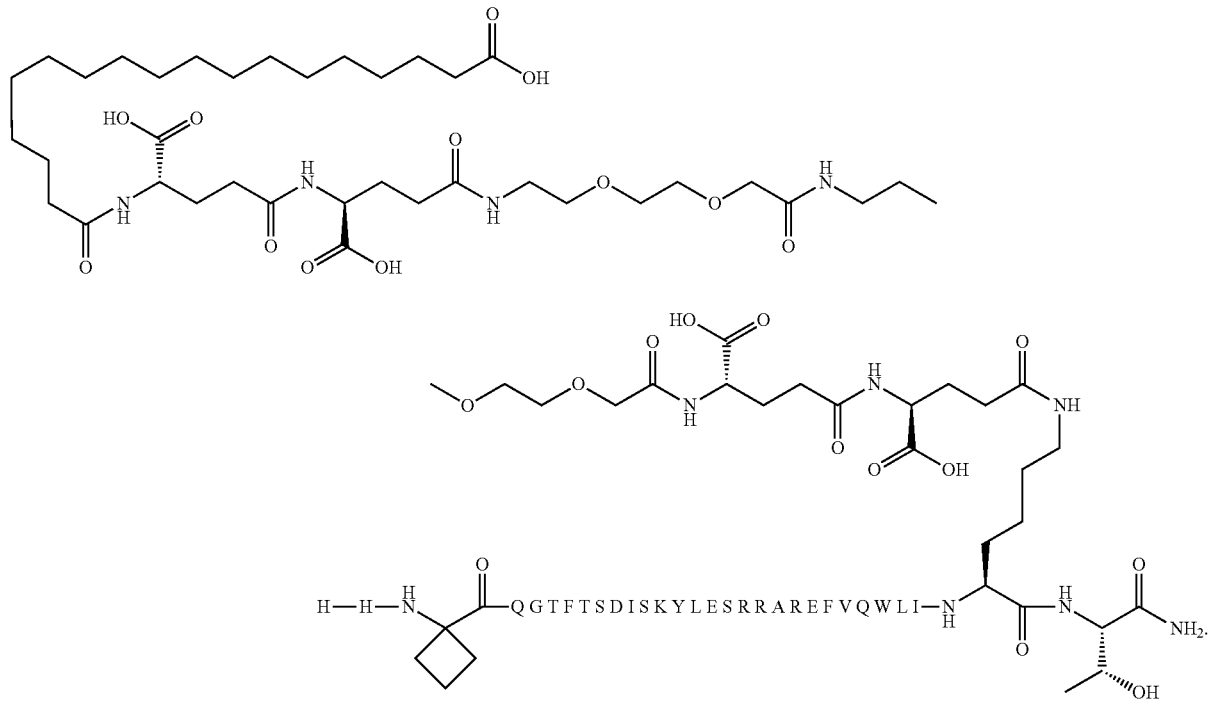

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Ser28,Lys29]-Glucagon amide
Chem 27(SEQ ID NO: 29):

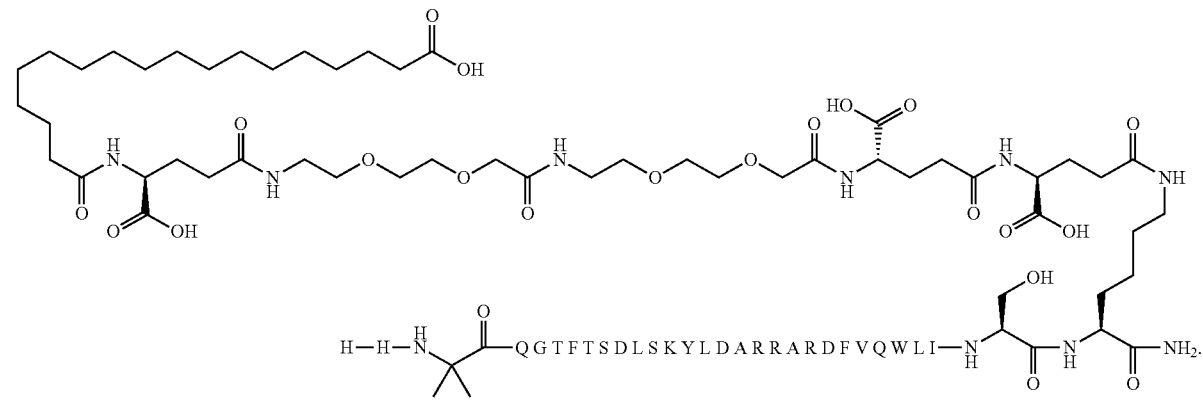

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Ser28,Lys29]-Glucagon amide Chem 28(SEQ ID NO: 30):

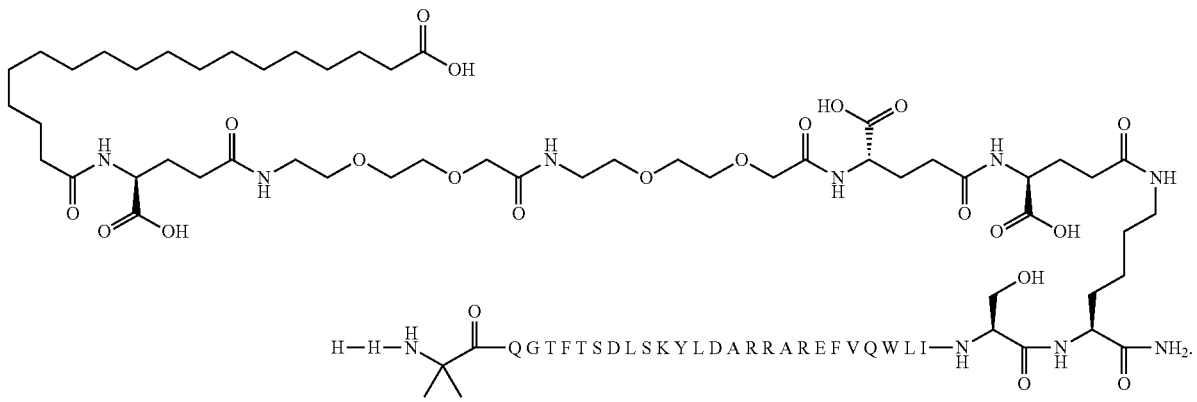

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Ser28,Lys29]-Glucagon amide Chem 29(SEQ ID NO: 31):

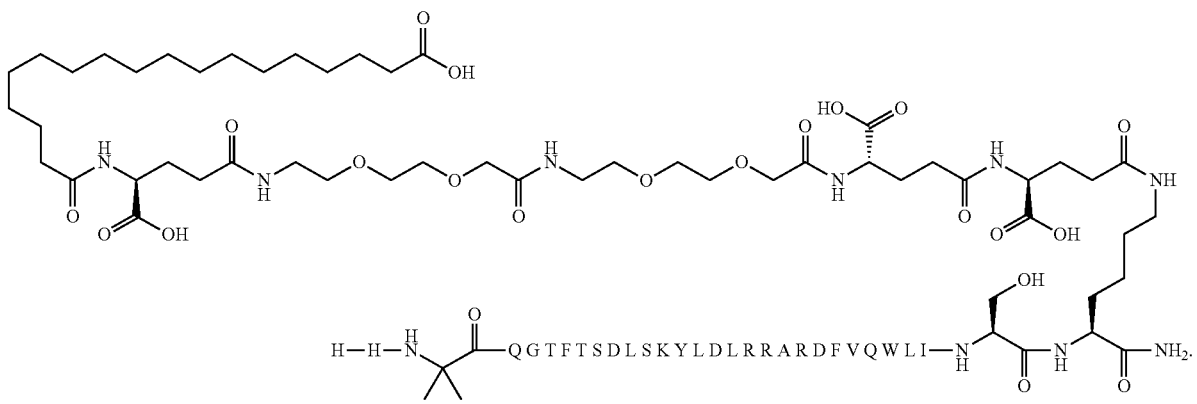

In some embodiments the glucagon derivative is $N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Ser28,Lys29]-Glucagon amide Chem 30(SEQ ID NO: 32):

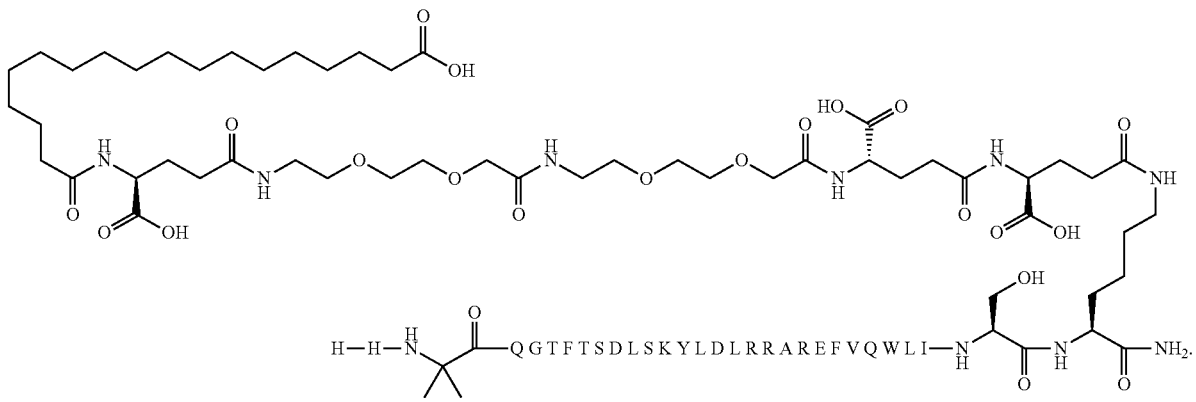

In some embodiments the glucagon derivative is N$^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Ser28,Lys29]-Glucagon amide Chem 31(SEQ ID NO: 33):

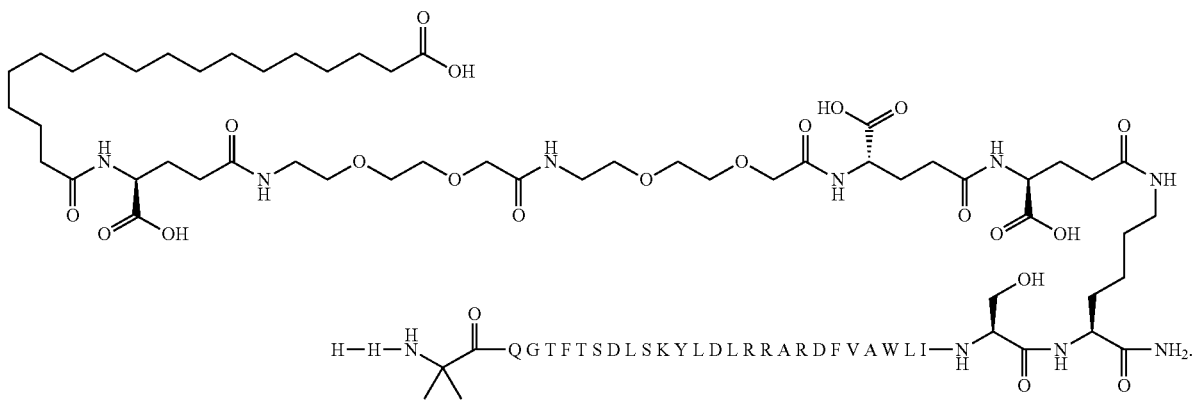

In some embodiments the glucagon derivative is N$^{\varepsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Ala16,Arg20,Ala24,Ile27,Lys28]-Glucagon amide Chem 32(SEQ ID NO: 34):

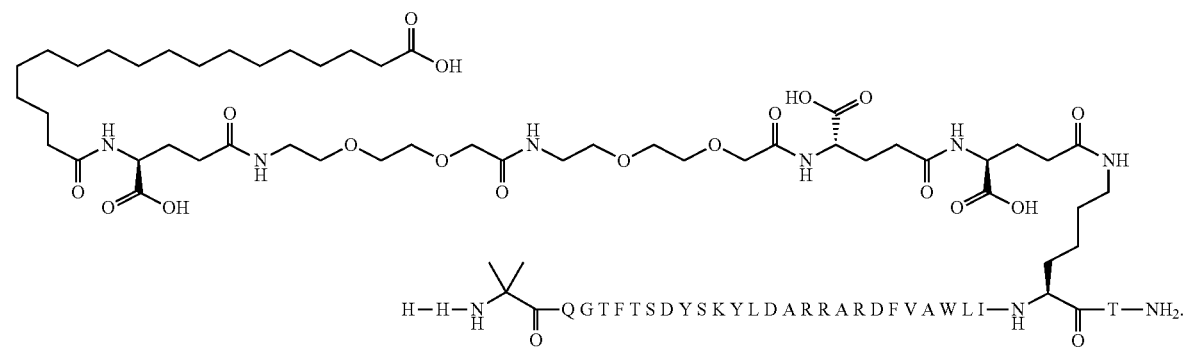

In some embodiments the glucagon derivative is N$^{\varepsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu16,Arg20,Ala24,Ile27,Lys28]-Glucagon amide
Chem 33(SEQ ID NO: 35):

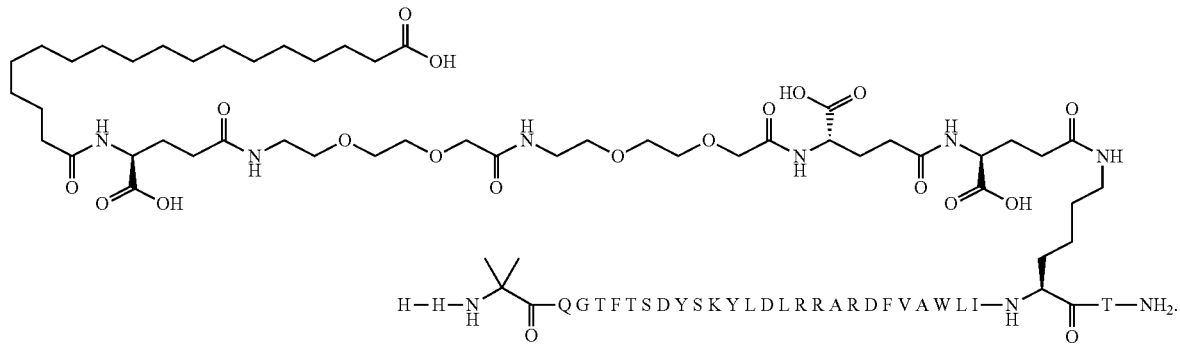

In some embodiments the glucagon derivative is N$^{\varepsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Lys28]-Glucagon amide
Chem 34(SEQ ID NO: 36):

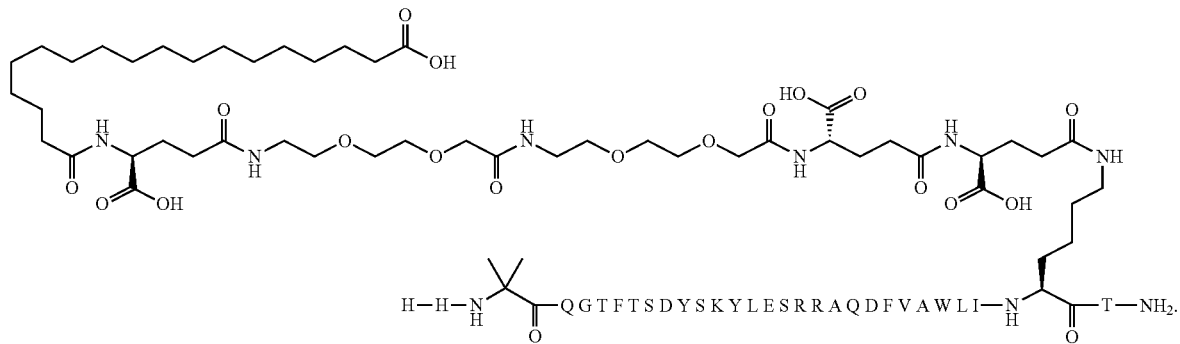

In some embodiments the glucagon derivative is N$^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Ser28,Lys29]-Glucagon amide
Chem 35(SEQ ID NO: 37):

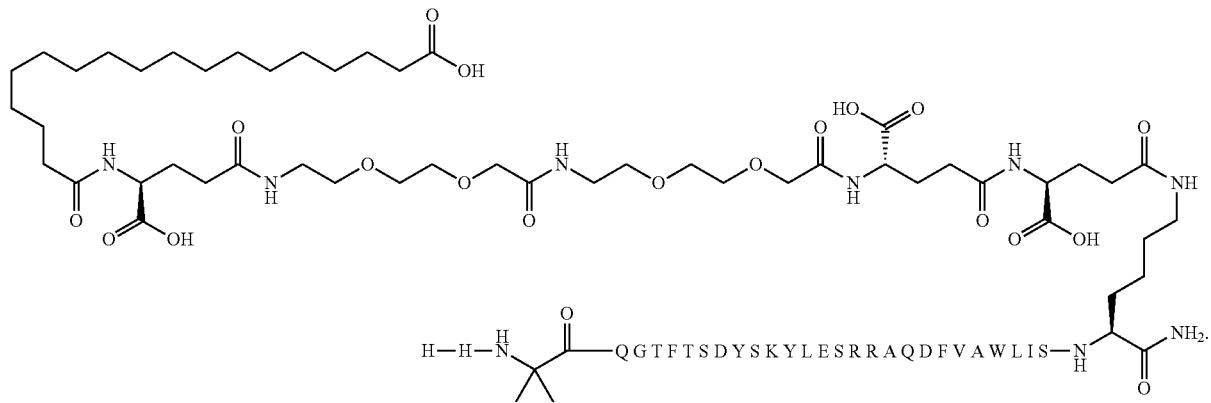

In some embodiments the glucagon derivative is $N^{\varepsilon 28}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Acb2,Arg12,Glu15,Arg20,Ile27,Lys28]-Glucagon amide
Chem 36(SEQ ID NO: 38):

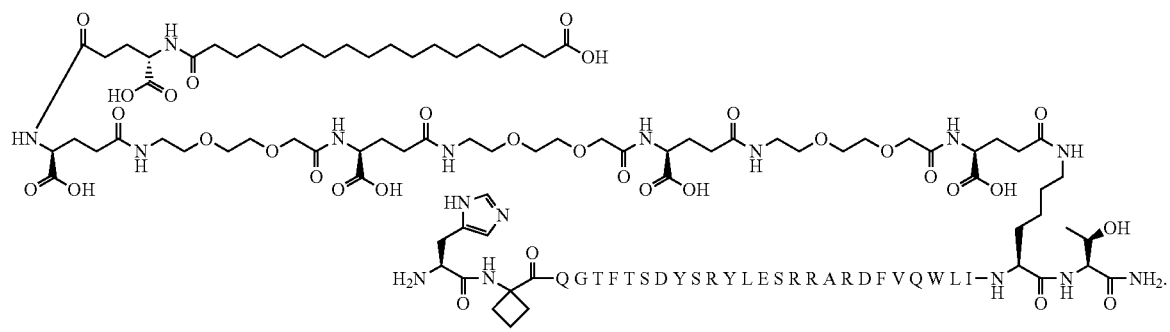

In some embodiments the glucagon derivative is $N^{\varepsilon 28}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Aib2,Arg12,Glu15,Arg20,Ile27,Lys28]-Glucagon amide
Chem 37(SEQ ID NO: 39):

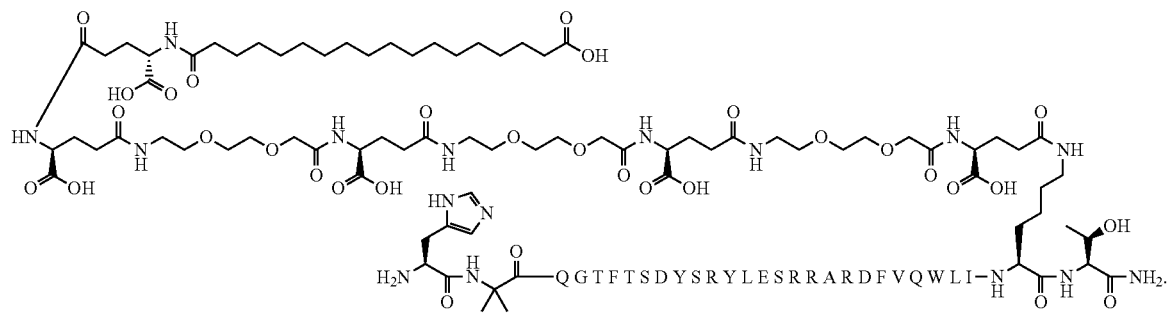

In some embodiments the glucagon derivative is $N^{\varepsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Acb2,Leu10,Glu15,Glu21,Ile27,Lys28]-Glucagon amide Chem 38(SEQ ID NO: 40):

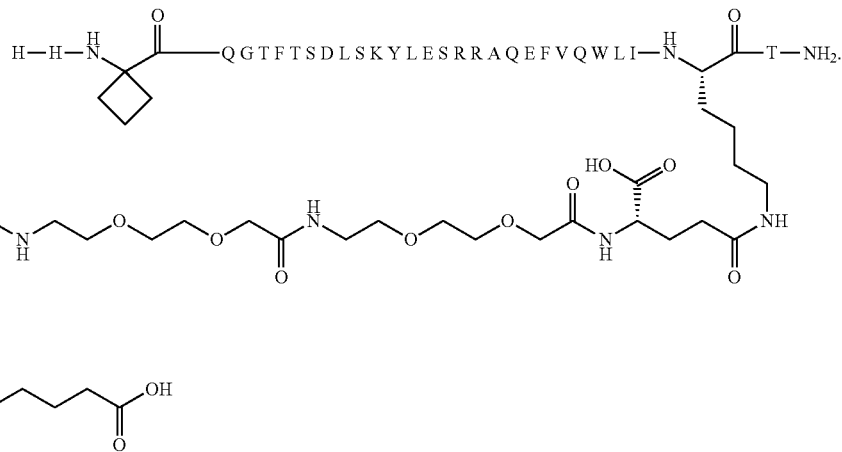

In some embodiments the glucagon derivative is $N^{\varepsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Val10,Ala16,Ile27,Lys28]-Glucagon amide Chem 39(SEQ ID NO: 41):

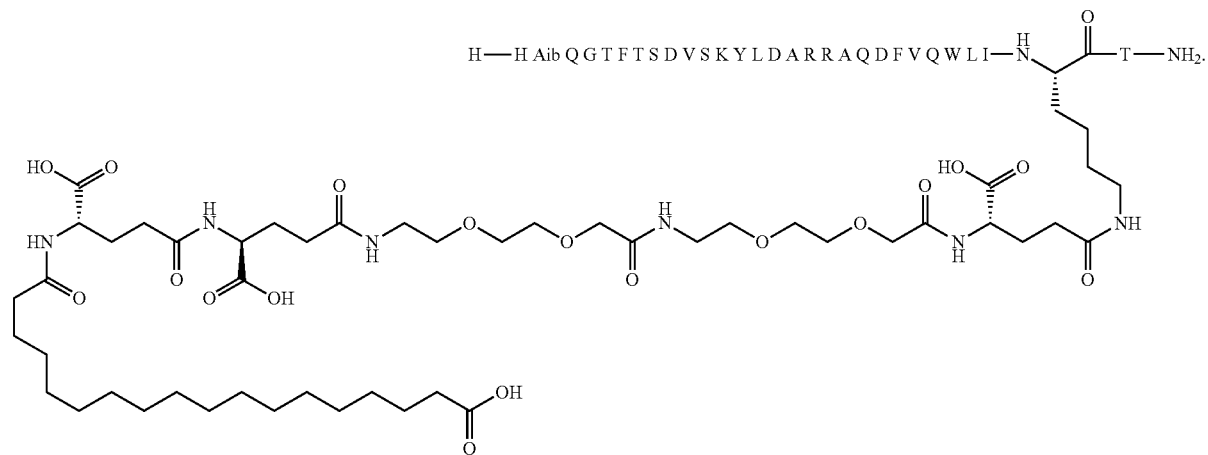

In some embodiments the glucagon derivative is $N^{\varepsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Val16,Ile27,Lys28]-Glucagon amide Chem 40(SEQ ID NO: 42):

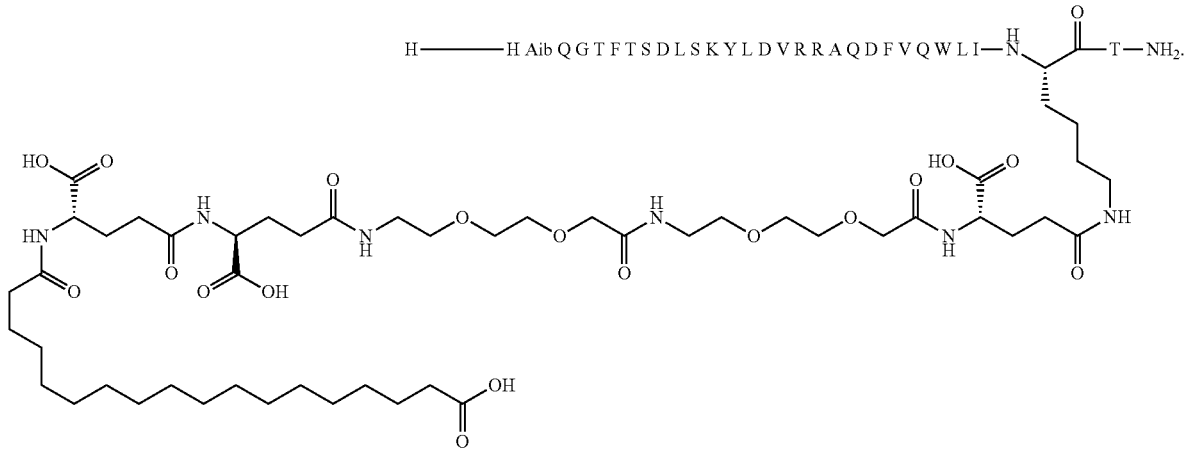

Preparation of Derivatives of Glucagon Peptides

The derivative of the invention may be prepared by the method described below.

SPPS General Methods

The Fmoc-protected amino acid derivatives to be used may be the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)—OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)—OH, Fmoc-Tyr(tBu)-OH, Fmoc-Val-OH and Fmoc-Lys(Mtt)-OH supplied from e.g. Anaspec, Bachem, Iris Biotech or NovabioChem. 3-(N-1-Trityl-imidazol-4-yl)-propionic acid is used for incorporating Imp.

SPPS may be performed using Fmoc based chemistry on a Prelude Solid Phase Peptide Synthesizer from Protein Technologies (Tucson, Ariz. 85714 U.S.A.). A suitable resin for the preparation of C-terminal carboxylic acids is a Wang resin preloaded with an amino acid such as Fmoc-Thr(tBu)-Wang resin (Low Load, 0.35 mmol/g). In cases where the substituent is attached to the C-terminal lysine, a suitable resin is a pre-loaded fmoc-Lys(Mtt)-Wang. A suitable resin for the preparation of C-terminal peptide amides is H-Rink Amide-ChemMatrix resin (loading e.g. 0.52 nmol/g) or Rink Amide AM polystyrene resin (Novabiochem, loading e.g. 0.62 mmol/g) or the like. Fmoc-deprotection is achieved with 20% piperidine in NMP. Peptide couplings are performed by using either DIC/HOAt/collidine or DIC/Oxyma Pure/collidine without preactivation. Amino acid/HOAt or amino acid/Oxyma Pure solutions (0.3 M/0.3 M in NMP at a molar excess of 3-10 fold) are added to the resin followed by the same molar equivalent of DIC (3 M in NMP) followed by collidine (3 M in NMP). For example, the following amounts of 0.3 M amino acid/HOAt solution can be used per coupling for the following scale reactions: Scale/mL, 0.05 mmol/1.5 mL, 0.10 mmol/3.0 mL, 0.25 mmol/7.5 mL. The Mtt group may be removed by washing the resin with HFIP/DCM (75:25) (2×2 min), washing with DCM and suspending the resin in HFIP/DCM (75:25)(2×20 min) and subsequently washed before the substituent can be introduced at the epsilon-position of the lysine moiety.

Attachment of the Substituent

The substituent can be introduced in a stepwise procedure by the Prelude peptide synthesizer as described above using suitably protected building blocks, such as the standard amino acids described above, Fmoc-8-amino-3,6-dioxaoctanoic acid and Fmoc-Glu-OtBu. Introduction of the fatty acid moiety can be achieved using a building block, such as, but not limited to, octadecanedioic acid mono-tert-butyl-ester. After each coupling step, unreacted peptide intermediate can be capped using acetic acid anhydride and collidine in excess (>10 eq.).

After each coupling step, unreacted peptide intermediate can be capped using acetic acid anhydride and collidine in excess (>10 eq.).

The introduction of a substituent on the epsilon-nitrogen of a lysine is achieved using a Lysine protected with Mtt (Fmoc-Lys(Mtt)-OH). Alternatively, the epsilon-nitrogen of a lysine could be protected with an ivDde group (Fmoc-Lys(ivDde)-OH). The incorporation of gamma-Glu moieties in the substituent may be achieved by coupling with the amino acid Fmoc-Glu-OtBu.

Introduction of each moiety in the substituent can be achieved using prolonged coupling time (1×6 hours) followed by capping with acetic anhydride or alternatively acetic acid/DIC/HOAt/collidine. Acetylation of the terminal nitrogen on the substituent is achieved using acetic anhydride (10 eq.) and collidine (20 eq.) in NMP.

Cleavage from the Resin

After synthesis the resin is washed with DCM, and the peptide is cleaved from the resin by a 2-3 hour treatment with TFA/TIS/water (95/2.5/2.5) followed by precipitation with diethylether. The precipitate is washed with diethylether.

Purification and Quantification

The crude peptide is dissolved in a suitable mixture of water and MeCN, such as water/MeCN (4:1), and purified by reversed-phase preparative HPLC (Waters Deltaprep 4000 or Gilson) on a column containing C18-silica gel. Elution is performed with an increasing gradient of MeCN in water containing 0.1% TFA. Relevant fractions are checked by analytical HPLC or UPLC. Fractions containing the pure target peptide are mixed and concentrated under reduced pressure. The resulting solution is analyzed (HPLC, LCMS) and the product (i.e. the derivative) is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

Intermediate Products

In some embodiments the invention relates to an intermediate product in the form of a glucagon analogue which comprises the following modifications as compared to human glucagon (SEQ ID NO: 1):
[Aib2,Ala16,Arg20,Lys24,Ile27,Ser28]-Glucagon amide;
[Aib2,Ala16,Lys17,Arg20,Glu21,Lys24,Ile27,Ser28]-Glucagon amide;
[Aib2,Leu10,Glu15,Arg20,Ile27,Lys28]-Glucagon amide;
[Aib2,Ala16,Arg20,Glu21,Lys24,Ile27,Ser28]-Glucagon amide;
[Aib2,Leu10,Ala16,Arg20,Ile27,Lys28]-Glucagon amide;
[Aib2,Leu10,Ala16,Arg20,Glu21,Ile27,Lys28]-Glucagon amide;
[Aib2,Leu10,Ala16,Ile27,Lys28]-Glucagon amide;
[Aib2,Leu10,Glu15,Ile27,Lys28]-Glucagon amide;
[Aib2,Leu10,Leu16,Ile27,Lys28]-Glucagon amide;
[Aib2,Val10,Glu15,Ile27,Lys28]-Glucagon amide;
[Aib2,Glu15,Arg20,Lys24,Ile27,Ser28]-Glucagon amide;
[Aib2,Leu16,Arg20,Lys24,Ile27,Ser28]-Glucagon amide;
[Acb2,Leu10,Glu15,Arg20,Glu21,Ile27,Lys28]-Glucagon amide;
[Aib2,Leu10,Arg12,Ala16,Arg20,Ile27,Lys28]-Glucagon amide;
[Acb2,Leu10,Glu15,Arg20,Glu21,Ile27,Lys28]-Glucagon amide;
[Acb2,Leu10,Arg12,Glu15,Arg20,Glu21,Ile27,Lys28]-Glucagon amide;
[Acb2,Leu10,Glu15,Arg20,Glu21,Ile27,Lys28]-Glucagon amide;
[Acb2,Val10,Glu15,Arg20,Glu21,Ile27,Lys28]-Glucagon amide;
[Aib2,Leu10,Ala16,Arg20,Ile27,Lys29]-Glucagon amide;
[Aib2,Leu110,Ala16,Arg20,Glu21,Ile27,Lys29]-Glucagon amide;
[Aib2,Leu10,Leu16,Arg20,Glu21,Ile27,Lys29]-Glucagon amide;
[Aib2,Leu10,Leu16,Arg20,Ile27,Lys29]-Glucago amide;
[Aib2,Leu10,Leu16,Arg20,Ala24,Ile27,Lys29]-Glucagon amide;
[Aib2,Leu10,Glu15,Arg20,Glu21,Ile27,Lys28]-Glucagon amide;
[Acb2,Ile10,Glu15,Arg20,Glu21,Ile27,Lys28]-Glucagon amide;
[Aib2,Leu10,Ala16,Arg20,Ile27,Ser28,Lys29]-Glucagon amide;
[Aib2,Leu10,Ala16,Arg20,Glu21,Ile27,Ser28,Lys29]-Glucagon amide;
[Aib2,Leu10,Leu16,Arg20,Ile27,Ser28,Lys29]-Glucagon amide;
[Aib2,Leu10,Leu16,Arg20,Glu21,Ile27,Ser28,Lys29]-Glucagon amide;
[Aib2,Leu10,Leu16,Arg20,Ala24,Ile27,Ser28,Lys29]-Glucagon amide;
[Aib2,Ala16,Arg20,Ala24,Ile27,Lys28]-Glucagon amide;
[Aib2,Leu16,Arg20,Ala24,Ile27,Lys28]-Glucagon amide;
[Aib2,Glu15,Ala24,Ile27,Lys28]-Glucagon amide;
[Aib2,Glu15,Ala24,Ile27,Ser28,Lys29]-Glucagon amide;
[Acb2,Arg12,Glu15,Arg20,Ile27,Lys28]-Glucagon amide;
[Aib2,Arg12,Glu15,Arg20,Ile27,Lys28]-Glucagon amide;
[Acb2,Leu10,Glu15,Glu21,Ile27,Lys28]-Glucagon amide;
[Aib2,Val10,Ala16,Ile27,Lys28]-Glucagon amide; and
[Aib2,Leu10,Val16,Ile27,Lys28]-Glucagon amide;
or a pharmaceutically acceptable salt thereof.

In some embodiments the invention relates to an intermediate product, wherein the glucagon analogue is selected from the following analogues of glucagon (SEQ ID NO: 1):
[Aib2,Ala16,Arg20,Lys24,Ile27,Ser28]-Glucagon amide;
[Aib2,Ala16,Lys17,Arg20,Glu21,Lys24,Ile27,Ser28]-Glucagon amide;
[Aib2,Leu10,Glu15,Arg20,Ile27,Lys28]-Glucagon amide;
[Aib2,Ala16,Arg20,Glu21,Lys24,Ile27,Ser28]-Glucagon amide;
[Aib2,Leu10,Ala16,Arg20,Ile27,Lys28]-Glucagon amide;
[Aib2,Leu10,Ala16,Arg20,Glu21,Ile27,Lys28]-Glucagon amide;
[Aib2,Leu10,Ala16,Ile27,Lys28]-Glucagon amide;
[Aib2,Leu10,Glu15,Ile27,Lys28]-Glucagon amide;
[Aib2,Leu10,Leu16,Ile27,Lys28]-Glucagon amide;
[Aib2,Val10,Glu15,Ile27,Lys28]-Glucagon amide;
[Aib2,Glu15,Arg20,Lys24,Ile27,Ser28]-Glucagon amide;
[Aib2,Leu16,Arg20,Lys24,Ile27,Ser28]-Glucagon amide;
[Acb2,Leu10,Glu15,Arg20,Glu21,Ile27,Lys28]-Glucagon amide;
[Aib2,Leu10,Arg12,Ala16,Arg20,Ile27,Lys28]-Glucagon amide;
[Acb2,Leu10,Glu15,Arg20,Glu21,Ile27,Lys28]-Glucagon amide;
[Acb2,Leu10,Arg12,Glu15,Arg20,Glu21,Ile27,Lys28]-Glucagon amide;
[Acb2,Leu10,Glu15,Arg20,Glu21,Ile27,Lys28]-Glucagon amide;
[Acb2,Val10,Glu15,Arg20,Glu21,Ile27,Lys28]-Glucagon amide;
[Aib2,Leu10,Ala16,Arg20,Ile27,Lys29]-Glucagon amide;
[Aib2,Leu10,Ala16,Arg20,Glu21,Ile27,Lys29]-Glucagon amide;
[Aib2,Leu10,Leu16,Arg20,Glu21,Ile27,Lys29]-Glucagon amide;
[Aib2,Leu10,Leu16,Arg20,Ile27,Lys29]-Glucago amide;
[Aib2,Leu10,Leu16,Arg20,Ala24,Ile27,Lys29]-Glucagon amide;
[Aib2,Leu10,Glu15,Arg20,Glu21,Ile27,Lys28]-Glucagon amide;
[Acb2,Leu10,Glu15,Arg20,Glu21,Ile27,Lys28]-Glucagon amide;
[Aib2,Leu10,Ala16,Arg20,Ile27,Ser28,Lys29]-Glucagon amide;
[Aib2,Leu10,Ala16,Arg20,Glu21,Ile27,Ser28,Lys29]-Glucagon amide;
[Aib2,Leu10,Leu16,Arg20,Ile27,Ser28,Lys29]-Glucagon amide;
[Aib2,Leu10,Leu16,Arg20,Glu21,Ile27,Ser28,Lys29]-Glucagon amide;
[Aib2,Leu10,Leu16,Arg20,Ala24,Ile27,Ser28,Lys29]-Glucagon amide;
[Aib2,Ala16,Arg20,Ala24,Ile27,Lys28]-Glucagon amide;
[Aib2,Leu16,Arg20,Ala24,Ile27,Lys28]-Glucagon amide;
[Aib2,Glu15,Ala24,Ile27,Lys28]-Glucagon amide;
[Aib2,Glu15,Ala24,Ile27,Ser28,Lys29]-Glucagon amide;
[Acb2,Arg12,Glu15,Arg20,Ile27,Lys28]-Glucagon amide;
[Aib2,Arg12,Glu15,Arg20,Ile27,Lys28]-Glucagon amide;
[Acb2,Leu10,Glu15,Glu21,Ile27,Lys28]-Glucagon amide;
[Aib2,Val10,Ala16,Ile27,Lys28]-Glucagon amide; and
[Aib2,Leu10,Val16,Ile27,Lys28]-Glucagon amide;
or a pharmaceutically acceptable salt thereof.

The glucagon derivatives of the invention may be prepared by the following a stepwise synthesis method comprising (i) preparation of the intermediate glucagon peptide followed by (ii) attachment of the substituent. Step (i) of this method can be achieved using standard solid phase synthesis as described in the experimental section using protected amino acids; after cleavage from the resin the glucagon peptide can be subjected to purification using preparative HPLC as described in the experimental section herein to give the intermediate product. Alternatively, step (i) of this method, preparation of the intermediate product, can be carried out using a semi-recombinant synthesis as described in WO2009/083549. Step (ii) of this method, i.e. the attachment of the substituent to the intermediate product leading to the final product, as well as preparation of the substituent itself can be achieved using methods described in WO2009/083549.

Pharmaceutically Acceptable Salt, Amide or Ester

The derivatives or intermediate products of the invention may be in the form of a pharmaceutically acceptable salt, amide or ester. Salts are e.g. formed by a chemical reaction between a base and an acid, e.g.: $2NH_3 + H_2SO_4 \rightarrow (NH_4)_2SO_4$. The salt may be a basic salt, an acid salt or it may be neither nor (i.e. a neutral salt). Basic salts produce hydroxide ions and acid salts hydronium ions in water.

The salts of the derivatives or intermediate products of the invention may be formed with added cations or anions between anionic or cationic groups, respectively. These groups may be situated in the peptide moiety, and/or in the side chain (e.g. the substituent) of the derivatives or intermediate products of the invention.

Non-limiting examples of anionic groups of the derivatives or intermediate products of the invention include free carboxylic groups in the side chain (e.g. the substituent), if any, as well as in the peptide moiety. The peptide moiety often includes free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives or intermediate products of the invention may, e.g., be formed by the reaction of a free carboxylic acid group with an alcohol or a phenol, which leads to replacement of at least one hydroxyl group by an alkoxy or aryloxy group. The ester formation may involve the free carboxylic group at the C-terminus of the peptide, and/or any free carboxylic group in the side chain (e.g. the substituent).

The amide of the analogues or derivatives of the invention may, e.g., be formed by the reaction of a free carboxylic acid group with an amine or a substituted amine or by reaction of a free or substituted amino group with a carboxylic acid.

The amide formation may involve the free carboxylic group at the C-terminus of the peptide, any free carboxylic group in the side chain (e.g. the substituent), the free amino group at the N-terminus of the peptide, and/or any free or substituted amino group of the peptide in the peptide and/or the side chain (e.g. the substituent).

In the present context, the term "pharmaceutically acceptable salt" is intended to indicate a salt which is not harmful to the patient. Such salts include pharmaceutically acceptable acid addition salts, pharmaceutically acceptable metal salts, ammonium and alkylated ammonium salts. Acid addition salts include salts of inorganic acids as well as organic acids.

In some embodiments, the peptide is in the form of a pharmaceutically acceptable salt. In some embodiments, the peptide is in the form of a pharmaceutically acceptable amide, preferably with an amide group at the C-terminus of the peptide. In some embodiments, the peptide is in the form a pharmaceutically acceptable ester.

Functional Properties

The glucagon derivatives of the invention are capable of binding to both the GLP-1 receptor and glucagon receptor with good affinity. In other words, the glucagon derivative of the invention is both an agonist of the glucagon receptor and an agonist of the GLP-1 receptor, also referred to herein as a "GLP-1/glucagon receptor co-agonist". In some embodiments, the glucagon derivatives of the invention are GLP-1 and glucagon receptor agonists, as is reflected by their potency on both receptors.

In some embodiments, the glucagon derivative has a lower $EC_{50}$ value on the GLP-1 receptor than on the glucagon receptor.

Also, or alternatively, in some embodiments the glucagon derivative has a good receptor binding and potency on the glucagon receptor, e.g. compared to human glucagon (SEQ ID NO: 1).

Also, or alternatively, in some embodiments the glucagon derivative has a good receptor binding and potency on the GLP-1 receptor, e.g. compared to human GLP-1 (SEQ ID NO: 1).

Also, or alternatively, in some embodiments, the glucagon derivatives have improved pharmacokinetic properties.

Also, or alternatively, in some embodiments the glucagon derivative is a protracted derivative, e.g. compared to human glucagon (SEQ ID NO: 1).

Also, or alternatively, in some embodiments the glucagon derivative is chemically stable, e.g. with an improved chemical stability compared to human glucagon (SEQ ID NO: 1).

Also, or alternatively, in some embodiments, the glucagon derivative is physically stable, e.g. with an improved physical stability compared to human glucagon (SEQ ID NO: 1).

Also, or alternatively, in some embodiments the glucagon derivative has a high solubility, e.g. compared to human glucagon (SEQ ID NO: 1).

Receptor Binding and Potency

The derivatives of the invention are GLP-1/glucagon receptor co-agonists, i.e. both GLP-1 receptor agonists and glucagon receptor agonists.

A receptor agonist may be defined as a peptide (e.g. a glucagon derivative) that binds to a receptor and elicits a response typical of the natural ligand. Thus, for example, a "GLP-1 receptor agonist" may be defined as a compound which is capable of binding to the human GLP-1 receptor and capable of fully or partially activating it. Similarly, the term "glucagon receptor agonist" as used herein may be defined as a compound which is capable of binding to the glucagon receptor and capable of fully or partially activating it. A response typical of the natural ligand may be activation of intracellular signal transduction pathways, such as activation of adenylate cyclase and increased levels of intracellular cAMP, mediating the physiological effects as is known in the art. For example, the term "GLP-1 receptor activity" refers to the ability to bind to the GLP-1 receptor and initiate a signal transduction pathway resulting in insulinotropic action or other physiological effects as is known in the art.

The derivatives or analogues of the invention may be tested for GLP-1 receptor activity using Assay (I)(a) or Assay (II)(a) described herein or for glucagon receptor activity using Assay (I)(b) or Assay (II)(b) described herein. In some embodiments the term "receptor activity" as used herein refers to the effect of a receptor agonist.

In some embodiments the term "glucagon receptor" as used herein means the human glucagon receptor. In some embodiments the term "GLP-1 receptor" as used herein means the human GLP-1 receptor.

Biological Activity—In Vitro Affinity and Potency

In some embodiments, the terms "affinity" or "receptor binding" as used herein refers to in vitro binding affinity, i.e. performance in a GLP-1 receptor binding affinity assay and in a glucagon receptor binding affinity assay, more in particular to the capability of binding the human GLP-1 receptor and to the human glucagon receptor. The binding affinity of the human GLP-1 receptor may be measured in a binding assay, e.g. in a stably transfected BHK cell line that expresses the human GLP-1 receptor. Radioactively labelled GLP-1 binds to the receptor and may be displaced competitively by a compound. Binding of radioligand may be determined by adding scintillation proximity assay (SPA) beads which binds to cell membranes and when radioactivity is close to the bead it produces light which is measured and is a measure of the in vitro binding affinity. One non-limiting example of an assay for determination of binding affinity is described in Assay (II) herein. The binding affinity of the human glucagon receptor may be measured in a binding affinity assay, e.g. in a stably transfected BHK cell line that expresses the human glucagon receptor. Radioactively-labelled glucagon binds to the receptor and may be displaced competitively by a compound. Binding of radioligand may be determined by adding scintillation proximity assay (SPA) beads which binds to cell membranes and when radioactivity is close to the bead it produces light which is measured and is a measure of the in vitro binding affinity.

The term half maximal inhibitory concentration ($IC_{50}$) generally refers to the concentration of competing compound which displaces 50% of the specific binding of the radioligand binding corresponding to halfway between the baseline and maximum, by reference to the dose response curve. $IC_{50}$ is used as a measure of the binding affinity of a compound and represents the concentration where 50% of its maximal binding is observed.

The in vitro binding of the glucagon derivatives of the invention may be determined as described above, and the $IC_{50}$ of the peptide in question determined. The lower the $IC_{50}$ value, the better the binding affinity.

In some embodiments, the glucagon derivative has an in vitro binding affinity on the GLP-1 receptor, determined using the method described in Assay (II)(a) herein, corresponding to an $IC_{50}$ at or below 100 nM, more preferably below 10 nM, even more preferably below 5 nM or most preferably below 1 nM.

The glucagon derivative may have an in vitro binding affinity on the glucagon receptor, determined using the method described in Assay (II)(b) herein, corresponding to an $IC_{50}$ at or below 100 nM or below 50 nM or below 10 nM.

In some embodiments, potency and/or activity refers to in vitro potency, i.e. performance in a functional GLP-1 receptor assay and glucagon receptor assay, more in particular to the capability of activating the human GLP-1 receptor and the human glucagon receptor. The response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase expression may be determined by adding luciferin, which by the enzyme is converted to oxyluciferin and produces bioluminescence, which is measured and is a measure of the in vitro potency. One non-limiting example of an assay for determination of receptor potency is described in Assay (I) herein. The response of the human glucagon receptor may be measured in a reporter gene assay, e.g. in a stably transfected BHK cell line that expresses the human glucagon receptor and contains the DNA for the cAMP response element (CRE) coupled to a promoter and the gene for firefly luciferase (CRE luciferase). When cAMP is produced as a result of activation of the glucagon receptor this in turn results in the luciferase being expressed. Luciferase expression may be determined by adding luciferin, which by the enzyme is converted to oxyluciferin and produces bioluminescence, which is measured and is a measure of the in vitro potency.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the glucagon derivatives of the invention may be determined as described above, and the $EC_{50}$ of the peptide in question determined. The lower the $EC_{50}$ value, the better the potency.

GLP-1/Glucagon Receptor Co-Agonists

A GLP-1/glucagon receptor co-agonist may be defined as a peptide that is able to activate both the GLP-1 receptor and the glucagon receptor. The derivative of the invention has an $EC_{50}$ below 1 nM on the GLP-1 receptor and an $EC_{50}$ below 10 nM on the glucagon receptor. In some embodiments derivative of the invention has an $EC_{50}$ below 100 pM on the GLP-1 receptor and has an $EC_{50}$ below 100 pM on the glucagon receptor; or has an $EC_{50}$ below 50 pM on the GLP-1 receptor and has an $EC_{50}$ below 100 pM on the glucagon receptor; or has an $EC_{50}$ below 10 pM on the GLP-1 receptor and has an $EC_{50}$ below 50 pM on the glucagon receptor. EC50 may be determined as described in Assay (I) herein.

In some embodiments the glucagon derivative has a lower $EC_{50}$ value on the GLP-1 receptor than on the glucagon receptor. In some embodiments the glucagon derivative has a ratio between its $EC_{50}$ value on the glucagon receptor and $EC_{50}$ on the GLP-1 receptor in the range of 100 to 250, such as in the range of 50 to 100, in the range of 20 to 50, in the range of 10 to 20, or in the range of 1 to 10. In some embodiments the glucagon derivative has a ratio between its $EC_{50}$ value on the glucagon receptor and $EC_{50}$ on the GLP-1 receptor in the range of 50 to 100. In some embodiments the glucagon derivative has a ratio between its $EC_{50}$ value on the glucagon receptor and $EC_{50}$ on the GLP-1 receptor in the range of 20 to 50. In some embodiments the glucagon derivative has a ratio between its $EC_{50}$ value on the glucagon receptor and $EC_{50}$ on the GLP-1 receptor in the range of 10 to 20. In some embodiments the glucagon derivative has a ratio between its $EC_{50}$ value on the glucagon receptor and $EC_{50}$ on the GLP-1 receptor in the range of 1 to 10. In some embodiments the $EC_{50}$ on the GLP-1 receptor is determined according to Assay (I)(a) described herein. In some embodiments the $EC_{50}$ on the glucagon receptor is determined according to Assay (I)(b) described herein.

The glucagon derivative may have a potency ($EC_{50}$) on the glucagon receptor below 10 nM or below 1 nM or 100 pM or below 10 pM. In some embodiments the glucagon derivative has an $EC_{50}$<10 nM on the glucagon receptor. In some embodiments the glucagon derivative has an $EC_{50}$<1 nM on the glucagon receptor. In some embodiments the glucagon derivative has an $EC_{50}$<100 pM on the glucagon receptor. In some embodiments the glucagon derivative has an $EC_{50}$<10 pM on the glucagon receptor.

The glucagon derivatives of the present invention may have an $EC_{50}$ on the GLP-1 receptor below 1 nM or below 100 pM or below 50 pM or below 10 pM. In some embodiments the glucagon derivative has an $EC_{50}$ below 100 pM on the GLP-1 receptor. In some embodiments the glucagon derivative has an $EC_{50}$ below 50 pM on the GLP-1 receptor. In some embodiments the glucagon derivative has an $EC_{50}$ below 10 pM on the GLP-1 receptor.

The potency, i.e. $EC_{50}$, on the GLP-1 receptor of a glucagon derivative of the invention may be determined according to Assay (I)(a) described herein. The potency, i.e. $EC_{50}$, on the glucagon receptor of a glucagon derivative of the invention may be determined according to Assay (I)(b) described herein.

Biological Activity—In Vivo Pharmacology

In some embodiments the glucagon derivatives of the invention are potent in vivo, which may be determined as is known in the art in any suitable animal model, as well as in clinical trials.

The diet-induced obese (DIO) mouse is one example of a suitable animal model and the effect on body weight, food intake and glucose tolerance can be assessed during sub-chronic dosing in this model. Effect on body weight and blood glucose may be determined in such mice in vivo. Food intake can be assessed by single housing animals and weighing food consumed per day. This model can also be used to evaluate effects on glucose tolerance by performing an oral or i.p. glucose tolerance test (OGTT or IPGTT). These tests are performed by administration of a glucose load orally or i.p. to semi-fasted animals and subsequent blood glucose measure for up to three hours.

Pharmacokinetics Profile

The glucagon derivatives of the invention may have improved pharmacokinetic properties such as increased terminal half-life, e.g. compared to human GLP-1 or human glucagon. Preferably the glucagon derivatives of the invention have pharmacokinetic properties suitable for once daily administration or less.

The pharmacokinetic properties of the glucagon derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog or pig, may be used to perform this characterisation. Any of these models can be used to test the pharmacokinetic properties of the glucagon derivatives of the invention.

In such studies, animals are typically administered with a single dose of the drug, either intravenously (i.v.), subcutaneously (s.c.) or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Rats

The pharmacokinetic properties of the glucagon derivatives may be determined as terminal half-life ($T_{1/2}$) in vivo in rats after i.v. and s.c. administration. In some embodiments, the terminal half-life of the glucagon derivatives is at least 1 hour, preferably at least 3 hours, preferably at least 4 hours, even more preferably at least 5 hours or most preferably at least 6 hours.

Pharmacokinetics Profile—Half Life In Vivo in Mice

The glucagon derivatives of the invention may have improved pharmacokinetic properties compared to human GLP-1 or human glucagon. Preferably the glucagon derivatives of the invention have pharmacokinetic properties suitable for once daily administration or less.

In some embodiments, the pharmacokinetic properties of the glucagon derivatives may be determined as terminal half-life ($T_{1/2}$) in vivo in mice after i.v. and s.c. administration. In some embodiments, the terminal half-life of the glucagon derivatives is at least 1 hour, preferably at least 3 hours, preferably at least 4 hours, even more preferably at least 5 hours or most preferably at least 6 hours. A suitable assay for determining terminal half-life of the glucagon derivatives in mice after s.c. administration is described in Assay (IV) herein.

Pharmacokinetics Profile—Half Life In Vivo in Minipigs

The glucagon derivatives of the invention may have improved pharmacokinetic properties compared to hGLP-1 and preferably suitable for once daily or once weekly administration. In some embodiments, the pharmacokinetic properties of the glucagon derivatives may be determined as terminal half-life ($T_{1/2}$) in vivo in minipigs after i.v. administration, e.g. as described below.

In some embodiments, the terminal half-life of the glucagon derivatives in minipigs is at least 5 hours, preferably at least 10 hours, even more preferably at least 15 hours or most preferably at least 20 hours.

The purpose of this study is to determine the pharmacokinetic properties in vivo of the glucagon derivatives after i.v. administration to minipigs. This is done in a pharmacokinetic (PK) study, where among other parameters the terminal half-life and the clearance of the derivative in question is determined. Increasing the terminal half-life and decreasing the clearance means that the compound of study is eliminated slower from the body. For glucagon derivatives this entails an extended duration of pharmacological effect.

Female Göttingen minipigs are obtained from Ellegaard Göttingen Minipigs (Dalmose, Denmark) approximately 7-14 months of age and weighing from approximately 16-35 kg are used in the studies. The minipigs are housed either individually (pigs with permanent catheters) or in a group, and are fed restrictedly once or twice daily with SDS minipig diet (Special Diets Services, Essex, UK).

In some studies two permanent central venous catheters are implanted in vena cava caudalis or cranialis in each animal after at least 2 weeks of acclimation. The animals are allowed 1 week recovery after the surgery, and are then used for repeated pharmacokinetic studies with a suitable wash-out period between successive glucagon derivative dosings. In other studies the animals are acclimatized for 1 week, after which they are used for repeated pharmacokinetic studies with a suitable wash-out period between successive glucagon derivative dosings. On each dosing occasion these pigs are instrumented with a venflon in one ear vein through which the derivatives were dosed. Blood sampling are performed by venipuncture in v. jugularis or v. cava cranialis.

The animals are either unfasted or fasted for approximately 18 h before dosing and from 0 to 4 h after dosing, but have ad libitum access to water during the whole period.

The glucagon derivatives are usually dissolved in 50 mM sodium phosphate, 145 mM sodium chloride, 0.05% tween 80, pH 7.4 to a concentration of usually from 20-60 nmol/ml. Intravenous injections (the volume corresponding to usually 2-3 nmol/kg, for example 0.1 ml/kg) of the compounds are given through one catheter or through the venflon, and blood are sampled at predefined time points for up till 13 days post dosing (preferably through the other catheter or by venipuncture). Blood samples (for example 0.8 ml) are collected in tubes with EDTA buffer (8 mM) (sometimes aprotinin 500 KIU/ml blood was added) and then centrifuged at 4° C. and 1942 G for 10 minutes. Plasma is pippetted into Micronic tubes on dry ice, and kept at −20° C. until analyzed for plasma concentration of the respective glucagon derivative using an appropriate quantitative assay like ELISA or LC-MS.

Based on these measurements, time-plasma concentration profiles for the compound of study are plotted and a so-called non-compartmental pharmacokinetic analysis of the data is performed in WinNonlin v. 5.0 or Phoenix v. 6.2 (Pharsight Inc., Mountain View, Calif., USA) or other relevant software for PK analysis. For most compounds, the terminal part of the plasma-concentration profiles will be linear when drawn in a semi-logarithmic plot, reflecting that after the initial distribution, drug is removed from the body at a constant fractional rate. The rate (lambda Z or $\lambda z$) is equal to minus the slope of the terminal part of the plot. From this rate, also the terminal half-life may be calculated, as $t\frac{1}{2}=\ln(2)/\lambda z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)). Clearance is defined as the dose (D) divided by area under the curve (AUC) on the plasma concentration versus time profile (Rowland, M and Tozer T N: Clinical Pharmacokinetics: Concepts and Applications, 3rd edition, 1995 Williams Wilkins).

Physical Stability

Peptides may undergo various changes of physical state. Peptides may precipitate due to lack of solubility at a certain set of conditions, e.g. due to neutralization of repulsing charges on amino acid side chains due to a change of pH. Another physical change is the formation of amyloid fibrils, which involves a conformational change into beta-sheet rich macromolecular fibre structures. Other macromolecular structures may be formed by less systematic structural repeats due to aggregation. In the two latter instances peptide substance may eventually be observed as a precipitate. In fact these physical changes may to some extent be interrelated, e.g. solubility versus pH and fibril formation is related [Schmittschmitt and Scholtz, Protein Science, 12, 10, 2374-2378, 2003]. Furthermore, it is very difficult to distinguish these phenomena by visual inspection only, therefore the result of these changes are often described by the general term "precipitate".

Other changes of physical state include adsorption to surfaces observed as a loss of content of peptide from solution, and the change from a liquid solution to a gel. Nevertheless, the observation of a precipitate regardless its nature or formation of a gel is a problem when in a pharmaceutical injectable during its storage and in-use time.

Glucagon has a very low aqueous solubility at neutral pH, which disables pharmaceutical composition at neutral pH. Even when dissolved at acidic pH, glucagon may undergo various phase transitions that depend on concentration and temperature and is thus very physically unstable. After dissolving samples of glucagon in hydrochloric acid a lag-phase may occur where the viscosity of the sample is low and the solution is fully transparent. After some hours the viscosity begins to increase—indicative of a gel formation (Beaven et al, European J. Biochem. 11 (1969) 37-42). After reaching a plateau viscosity may begin to fall again and at the same time fibrils may appear and precipitate out of solution. The process is seedable, addition of a small amount of pre-formed gel reduce the lag-phase. Formation of gels and fibrillation is highly dependent of physical stress, such as heating and shaking, both increasing the rate of the process.

The term "physical stability" of the derivative or composition as used herein refers to the tendency of the peptide and/or protein (i.e. herein the glucagon derivative) to form biologically inactive and/or insoluble aggregates of the peptide and/or protein as a result of exposure of the peptide and/or protein to thermo-mechanical stresses and/or interaction with interfaces and surfaces that are destabilizing, such as hydrophobic surfaces and interfaces. Physical stability of an aqueous peptide and/or protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition may be classified physical unstable with respect to protein aggregation, when it shows visual turbidity in daylight. Alternatively, the turbidity of the composition can be evaluated by simple turbidity measurements well-known to the skilled person. Physical stability of the aqueous peptide and/or protein compositions can also be evaluated by using a spectroscopic agent or probe of the conformational status of the peptide and/or protein. The probe is preferably a small molecule that preferentially binds to a non-native conformer of the peptide and/or protein. One example of a small molecular spectroscopic probe of peptide and/or protein structure is Thioflavin T. Thioflavin T is a fluorescent dye that has been widely used for the detection of amyloid fibrils. In the presence of fibrils, and perhaps other peptide and/or protein configurations as well, Thioflavin T gives rise to a new excitation maximum at about 450 nm and enhanced emission at about 482 nm when bound to a fibril peptide and/or protein form. Unbound Thioflavin T is essentially non-fluorescent at these wavelengths.

Other small molecules can be used as probes of the changes in peptide and/or protein structure from native to non-native states. For instance the "hydrophobic patch" probes that bind preferentially to exposed hydrophobic patches of a peptide and/or protein. The hydrophobic patches are generally buried within the tertiary structure of a peptide and/or protein in its native state, but become exposed as a peptide and/or protein begins to unfold or denature. Examples of these small molecular, spectroscopic probes are aromatic, hydrophobic dyes, such as antrhacene, acridine, phenanthroline or the like.

Physical stability of the derivative may be determined by the recovery and/or lag time in Assay (III) described herein, i.e. the ThT fibrillation assay. In some embodiments the physically stable derivative has more than 70% recovery and/or more than 7 hours lag time in Assay (III) described herein.

In some embodiments the derivative has more than 70% recovery in a ThT fibrillation assay, such as Assay (III) described herein. In some embodiments the derivative has more than 90%, such as more than 95% or more than 98%, recovery in a ThT fibrillation assay, such as Assay (III) described herein. In some embodiments the derivative has about 100% recovery in a ThT fibrillation assay, such as Assay (III) described herein.

In some embodiments the derivative has more than 7 hours, such as more than 20 hours or more than 45 hours, lag time in a ThT fibrillation assay, such as Assay (III) described herein.

In some embodiments the glucagon derivative has more than 70% recovery in the ThT fibrillation assay. In some embodiments the glucagon derivative has more than 90% recovery in the ThT fibrillation assay. In some embodiments the glucagon derivative has about 100% recovery in the ThT fibrillation assay. In some embodiments the glucagon derivative has more than 7 hours lag time in the ThT fibrillation assay. In some embodiments the glucagon derivative has more than 20 hours lag time in the ThT fibrillation assay. In some embodiments the glucagon derivative has 45 hours lag time or more in the ThT fibrillation assay. In some embodiments the ThT fibrillation assay is Assay (III) described herein.

Chemical Stability

The term "chemical stability" of the derivative or composition as used herein refers to chemical covalent changes in the peptide structure leading to formation of chemical degradation products with potential less biological potency and/or potential increased immunogenic properties compared to the native peptide (e.g. human glucagon) structure. Various chemical degradation products can be formed depending on the type and nature of the native peptide and the environment to which the peptide is exposed. Elimination of chemical degradation can most likely not be completely avoided and increasing amounts of chemical degradation products is often seen during prolonged storage. Most peptides are prone to deamidation, a process in which the side chain amide group in glutaminyl or asparaginyl residues is hydrolysed to form a free carboxylic acid. Other degradations pathways involves formation of high molecular weight transformation products where two or more peptide molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. Asparagine or aspartic acid containing peptides may be prone to isomerization via the formation of an intermediate aspartimide giving rise to the corresponding iso-aspartic acid isomer in where both the D- and L-isomer can be formed. The aspartimide intermediate may also lead to the formation of the D-aspartic acid isomer. (Formulation Consideration for Proteins Susceptible to Asparagine Deamidation and Aspartate Isomerization, Wakankar and Borchardt, Journal of Pharmaceutical Sciences, 2006, Vol. 95, no. 11, p 2321). Finally, peptides may also undergo hydrolytic cleavage in which peptide fragments or single amino acids are cleaved by hydrolysis of the peptide bond.

The chemical stability of the composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SE-HPLC and/or RP-UPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

Chemical stability of the derivative may be measured by determination of the chemical degradation in Assay (V) described herein. In some embodiments the derivative has less than 14% degradation in the chemical stability assay. In some embodiments the glucagon derivative has less than 13% degradation in the chemical stability assay. In some embodiments the glucagon derivative has less than 12% degradation in the chemical stability assay. In some embodiments the glucagon derivative has less than 10% degradation in the chemical stability assay. In some embodiments the glucagon derivative has less than 9% degradation in the chemical stability assay. In some embodiments the glucagon derivative has less than 7% degradation in the chemical stability assay. In some embodiments the glucagon derivative has less than 5% degradation in the chemical stability assay. In some embodiments the glucagon derivative has less than 3% degradation in the chemical stability assay. In some embodiments the glucagon derivative has less than 2% degradation in the chemical stability assay. In some embodiments the chemically stable derivative has a chemical degradation of less than 5%, such as less than 4%, less than 3% or less than 2%, wherein said chemical degradation may be determined by Assay (V) described herein.

Solubility

In the present context, if not stated otherwise, the terms "soluble", "solubility", "soluble in aqueous solution", "aqueous solubility", "water soluble", "water-soluble", "water solubility" and "water-solubility", refer to the solubility of a compound in water or in an aqueous salt or aqueous buffer solution, for example a 10 mM phosphate solution or in an aqueous solution containing other compounds. Solubility may be assessed using the following assay.

pH Dependent Solubility Assay

The solubility of peptides and proteins depends on the pH of the solution. Often a protein or peptide precipitates at or close to its isoelectric point (pI), at which its net charge is zero. At low pH (i.e. lower than the pI) proteins and peptides are typically positively charged, at pH higher than the pI they are negatively charged.

It is advantageous for a therapeutic peptide if it is soluble in a sufficient concentration at a given pH, which is suitable for both formulating a stable drug product and for administrating the drug product to the patient e.g. by subcutaneous injection.

Solubility versus pH curves are measured as described: a formulation or a peptide solution in water is prepared and aliquots are adjusted to pH values in the desired range by adding HCl and NaOH. These samples are left equilibrating at room temperature for 2-4 days. Then the samples are centrifuged. A small aliquot of each sample is withdrawn for reverse HPLC analysis for determination of the concentration of the proteins in solution. The pH of each sample is measured after the centrifugation, and the concentration of each protein is depicted versus the measured pH.

The compounds of the present invention may be a soluble glucagon/GLP-1 receptor co-agonist, for example with solubility of at least 0.1 mmol/l, 0.2 mmol/l, at least 0.5 mmol/l, at least 2 mmol/l, at least 4 mmol/l, at least 8 mmol/l, at least 10 mmol/l or at least 15 mmol/l.

DPP-IV Stability

In some embodiments the glucagon derivative is a DPPIV protected compound. In some embodiments the glucagon derivative is a DPPIV stabilised compound.

DPP-IV stability may be determined using the following assay: 10 μM of peptide is incubated with DPP-IV (2 μg/ml) in duplicate at 37° C. in a HEPES buffer to which 0.005% Tween20 is added. In the experiment human GLP-1 is used as a positive control. Aliquots of sample are taken at 3, 15, 30, 60, 120 and 240 min and three volumes of ethanol are added to stop the reaction. The samples are analysed by LC-MS for parent peptide. Data are plotted according to $1^{st}$ order kinetics, and the stability is reported as half-lives.

Combinations

In some embodiments the invention relates to the glucagon derivative of the invention in combination with one or more additional therapeutically active compounds, such as a GLP-1 compound or with an insulin compound. In some embodiments the glucagon derivative of the invention is in combination with a GLP-1 compound. In some embodiments the glucagon derivative of the invention is in combination with an insulin compound.

As used herein, a "GLP-1 compound" is a compound which is able to active the GLP-1 receptor and not e.g. on the glucagon receptor.

As used herein, an "insulin compound" is a compound which is able to active the insulin receptor.

In some embodiments the GLP-1 compound of the combination is selected from the group consisting of:
N-epsilon26-((S)-4-Carboxy-4-hexadecanoylamino-butyryl)[Arg34]GLP-1-(7-37)

(compound G1)(SEQ ID NO: 43)

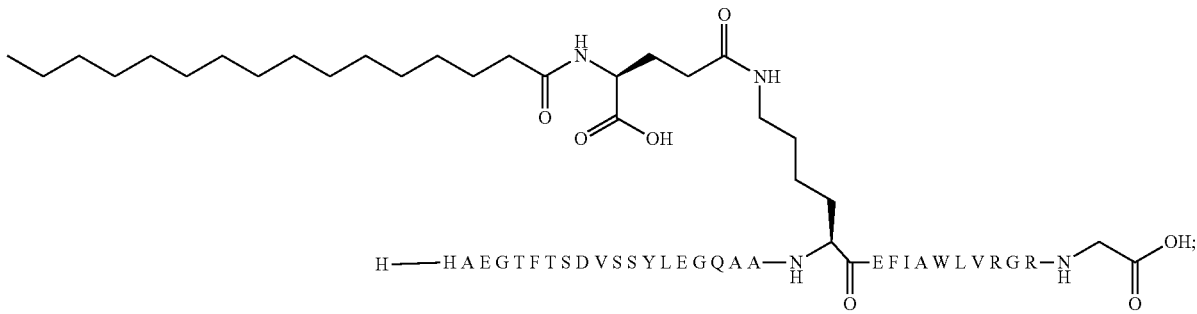

N-epsilon37-[2-(2-{2-[2-(2-{2-[(S)-4-Carboxy-4-({trans-4-[(19-carboxynonadecanoylamino)methyl]cyclohexanecarbonyl}amino) butyrylamino]ethoxy}ethoxy)acetylamino]ethoxy}ethoxy)acetyl][DesaminoHis7,Glu22,Arg26,Arg34,Lys37]GLP-1-(7-37)

(compound G2)(SEQ ID NO: 44)

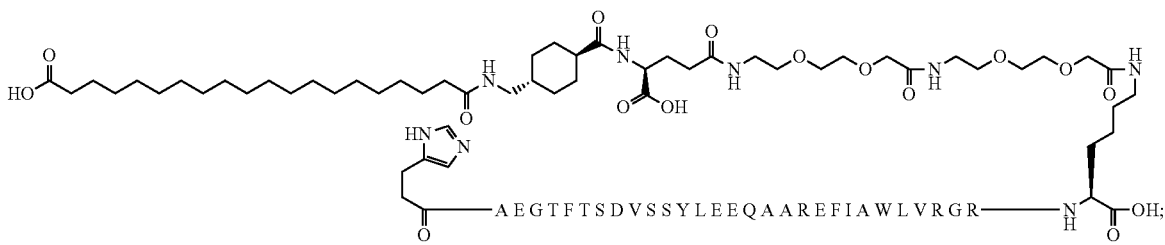

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37)

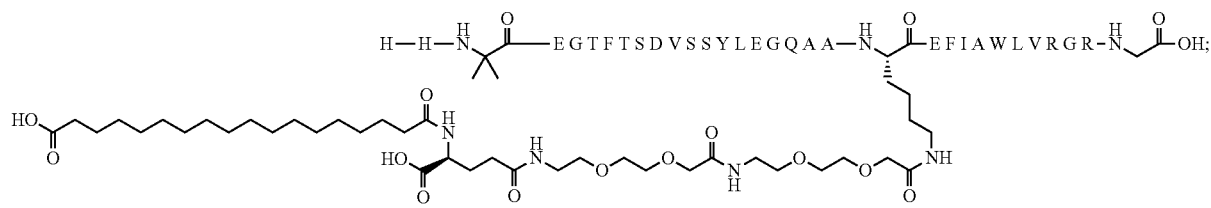
(compound G3)(SEQ ID NO: 45)

N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35, Lys37]GLP-1-(7-37)

or a stabilizer. Thus a pharmaceutical composition is also known in the art as a pharmaceutical formulation. The terms "pharmaceutical composition" and "composition" are used interchangeably herein.

(compound G4)(SEQ ID NO: 46)

and their pharmaceutically acceptable salts, amides, alkyls or esters.

In some embodiments the insulin compound of the combination is: N-epsilon-B29-[(S)-4-Carboxy-4-(15-carboxy-pentadecanoylamino)butyryl] desB30 human insulin

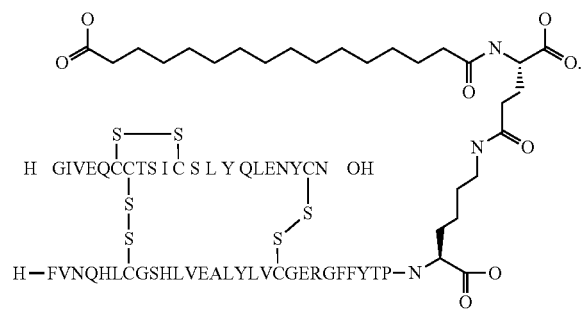
(compound G5)(SEQ ID NO: 47)(SEQ ID NO: 48)

Pharmaceutical Compositions

In some embodiments the invention relates to a pharmaceutical composition comprising the derivative of the invention and one or more pharmaceutically acceptable excipients. In some embodiments the composition is suited for parenteral administration, such as SC, IM or IV administration. The term "pharmaceutical composition" as used herein means a product comprising an active compound or a salt thereof together with pharmaceutical excipients such as buffer, preservative, and optionally a tonicity modifier and/

Pharmaceutical compositions containing a derivative of the invention may be prepared by conventional techniques, e.g. as described in Remington's Pharmaceutical Sciences, 1985 or in Remington: The Science and Practice of Pharmacy, 19th edition, 1995.

In some embodiments the invention relates to a pharmaceutical composition comprising a derivative of the invention, wherein said glucagon derivative is present in a concentration from about 0.01 mg/mL to about 25 mg/mL, such as from about 0.05 mg/mL to about 5 mg/mL and from about 0.1 mg/mL to about 2 mg/mL, and wherein said composition has a pH from 2.0 to 10.0. The pharmaceutical composition may comprise a derivative of the invention, wherein said glucagon derivative is present in a concentration from about 0.01 mg/mL to about 50 mg/mL, and wherein said composition has a pH from 2.0 to 10.0.

In some embodiments the pharmaceutical composition comprises an aqueous solution of a derivative of the invention, and a buffer, wherein said glucagon derivative is present in a concentration from 0.01 mg/mL or above, and wherein said composition has a pH from about 2.0 to about 10.0. In some embodiments the pharmaceutical composition comprises an aqueous solution of a derivative of the invention, and a buffer, wherein said glucagon derivative is present in a concentration from 0.01 mg/mL or above, and wherein said composition has a pH from about 6.5 to about 8.5.

In some embodiments the composition of the invention has a pH from about 2.0 to about 10.0. In some embodiments the composition has a pH from about 6.5 to about 8.5. In some embodiments the composition has a pH from about 7.0 to about 8.5, such as from about 7.2 to about 8.2.

The composition may further comprise a buffer system, preservative(s), isotonicity agent(s), chelating agent(s), stabilizers and surfactants. In some embodiments the pharmaceutical composition is an aqueous composition, i.e. a composition comprising water. Such composition is typically a solution or a suspension. In some embodiments of the invention the pharmaceutical composition is an aqueous solution. The term "aqueous composition" is defined as a composition comprising at least 50% w/w water. Likewise, the term "aqueous solution" is defined as a solution comprising at least 50% w/w water. In some embodiments the composition comprises a non-aqeuous organic solvent.

In some embodiments the pharmaceutical composition is a freeze-dried composition to which solvents and/or diluents are added prior to use, e.g. by the physician or the patient.

In some embodiments the pharmaceutical composition is a dried composition (e.g. freeze-dried or spray-dried) ready for use without any prior dissolution.

In some embodiments the invention relates to a composition comprising the derivative of the invention and one or more other active ingredients, such as GLP-1, insulin or analogues and/or derivatives thereof. In some embodiments the invention relates to a composition comprising the derivative of the invention and GLP-1 or analogues and/or derivatives thereof. In some embodiments the invention relates to a composition comprising the derivative of the invention and insulin or analogues and/or derivatives thereof. A composition comprising the derivative of the invention and one or more other active ingredients may be referred to as a "co-formulation". In some embodiments such co-formulations are physically stable and/or chemically stable compositions.

The fact that the derivatives of the invention may be soluble at neutral pH, may allow a co-formulation with insulin and allow for more stable blood glucose levels and a reduced number of hypoglycaemic episodes, as well as a reduced risk of diabetes related complications.

The term "excipient" as used herein means the chemical compounds which are normally added to pharmaceutical compositions, e.g. buffers, tonicity agents, preservatives and the like.

In some embodiments the pharmaceutical composition further comprises one or more additional therapeutically active compounds or substances. In some embodiments the additional therapeutically active compound is a GLP-1 compound or an insulin compound. In some embodiments the additional therapeutically active compound is a GLP-1 compound. In some embodiments the additional therapeutically active compound is an insulin compound. In some embodiments the GLP-1 compound is selected from the group consisting of:

N-epsilon26-((S)-4-Carboxy-4-hexadecanoylamino-butyryl)[Arg34]GLP-1-(7-37)
(Compound G1)(SEQ ID NO: 43):

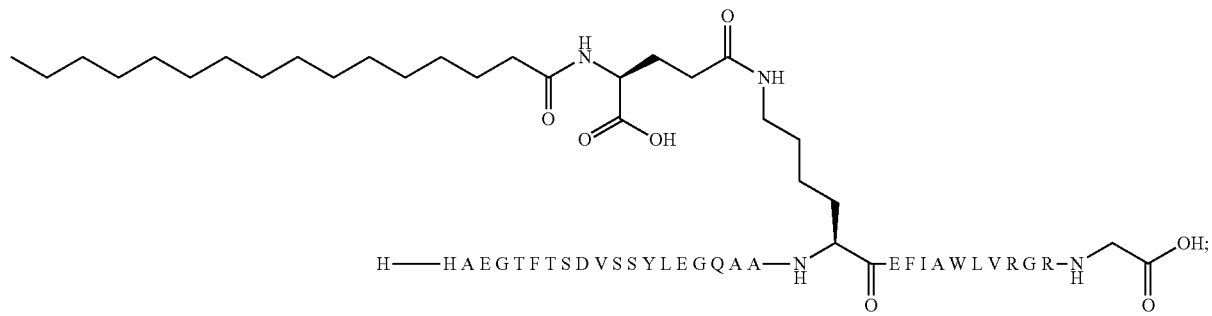

N-epsilon37-[2-(2-{2-[2-(2-{2-[(S)-4-Carboxy-4-({trans-4-[(19-carboxynonadecanoylamino)methyl]cyclohexanecarbonyl}amino) butyrylamino]ethoxy}ethoxy)acetylamino]ethoxy}ethoxy)acetyl][DesaminoHis7,Glu22,Arg26,Arg34,Lys37]GLP-1-(7-37)
(Compound G2)(SEQ ID NO: 44):

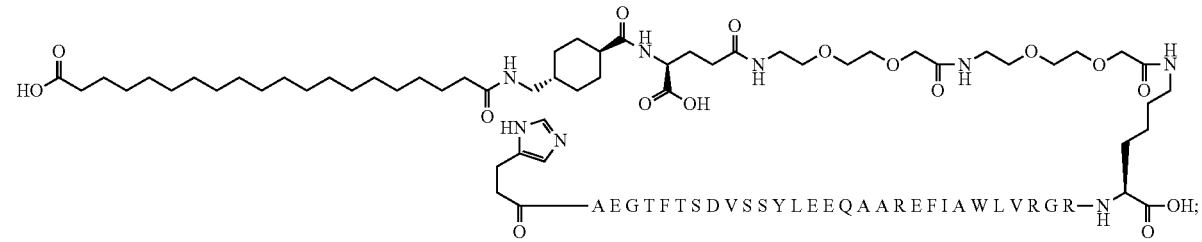

N-epsilon26-[2-(2-{2-[2-(2-{2-[(S)-4-Carboxy-4-(17-carboxyheptadecanoylamino) butyrylamino]ethoxy}ethoxy)acetylamino]ethoxy}ethoxy)acetyl][Aib 8,Arg34]GLP-1-(7-37)

(Compound G3)(SEQ ID NO: 45):

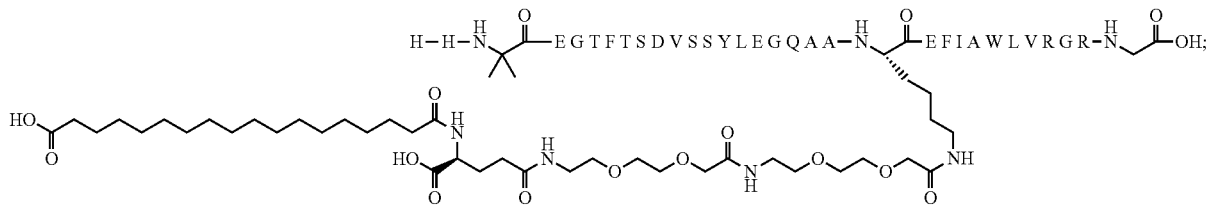

and
N-epsilon37-[2-(2-{2-[2-(2-{2-[(S)-4-carboxy-4-(15-carboxy-pentadecanoylamino)-butyrylamino]ethoxy}ethoxy)acetylamino]ethoxy}-ethoxy)-acetyl] [Aib22,35,Lys7]GLP-1-(7-37)
(Compound G4)(SEQ ID NO: 46):

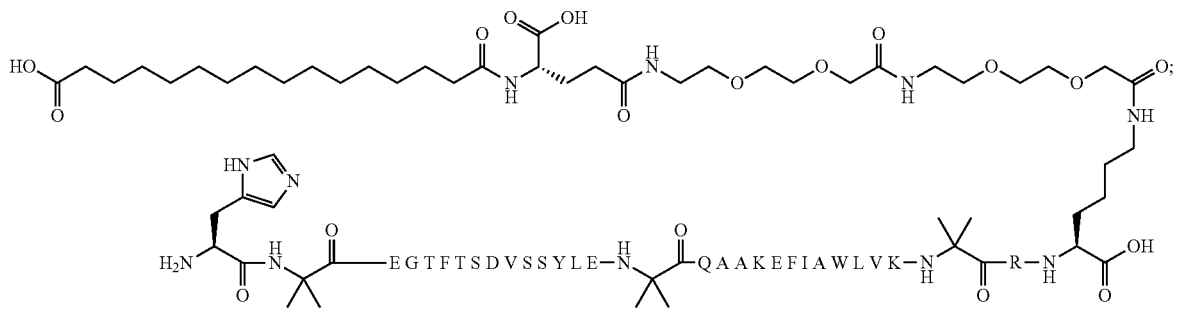

and their pharmaceutically acceptable salts, amides, alkyls or esters.

In some embodiments the insulin compound is N-epsilon-B29-[(S)-4-Carboxy-4-(15-carboxypentadecanoylamino) butyryl] desB30 human insulin
(Compound G5)(SEQ ID NO: 47)(SEQ ID NO: 48):

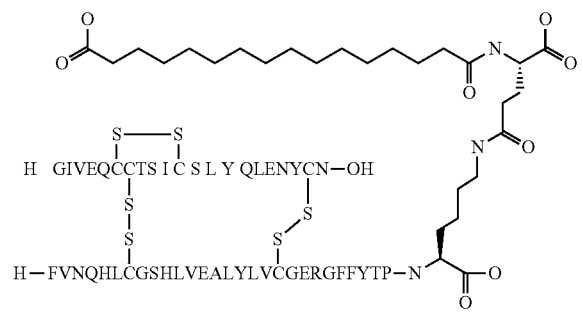

In some embodiments the pharmaceutical composition is in a unit dosage form comprising from about 0.01 mg to about 1000 mg, such as from about 0.1 mg to about 500 mg, from about 0.5 mg to about 5 mg, e.g. from about 0.5 mg to about 200 mg, of a glucagon derivative as defined in any one of the preceding embodiments.

In some embodiments the pharmaceutical composition is suited for parenteral administration.

Pharmaceutical Administration

The derivative of the invention may be administered parenterally to a patient. The route of administration of the derivative may be intramuscular (IM), subcutaneous (SC) or intravenous (IV). It is recommended that the dosage of the compositions comprising the derivative of this invention which is to be administered to the patient be selected by a physician.

Parenteral administration may be performed by subcutaneous, intramuscular, intraperitoneal or intravenous injection by means of a syringe, optionally a pen-like syringe. In some embodiments the compositions comprising the derivative of the invention can be used in ready to use pen devices for glucagon administration. Alternatively, parenteral administration can be performed by means of an infusion pump. In some embodiments the compositions comprising the derivative of the invention can be used in pumps for glucagon administration. Parenteral administration may be nasal administration. As a further option, the glucagon preparations containing the derivative of the invention can also be adapted to transdermal administration, e.g. by needle-free injection or from a patch, optionally an iontophoretic patch or transmucosal, e.g. buccal, administration.

A typical dosage of a derivative or composition of the invention when employed in a method according to the invention is in the range of from about 0.0001 to about 1 mg/kg body weight per day, preferably from about 0.001 to about 1 mg/kg body weight, more preferably from about 0.005 to about 0.02 mg/kg body. As described above, derivatives of the invention may be administered or applied in combination with one or more additional therapeutically active compounds or substances, and suitable additional compounds or substances may be selected, for example, from antidiabetic agents, antihyperlipidemic agents, antiobesity agents, antihypertensive agents and agents for the treatment of complications resulting from or associated with, diabetes.

Suitable antidiabetic agents include insulin, insulin derivatives or analogues, GLP-1 (glucagon like peptide-1)

derivatives or analogues [such as those disclosed in WO 98/08871 (Novo Nordisk A/S) or other GLP-1 analogues such as exenatide (Byetta, Eli Lilly/Amylin; AVE0010, Sanofi-Aventis), taspoglutide (Roche), albiglutide (Syncria, GlaxoSmithKline)], amylin, amylin analogues (e.g. Symlin/ Pramlintide) as well as orally active hypoglycemic agents.

In the case of administration of a glucagon derivative of the invention, optionally in combination with one or more additional therapeutically active compounds or substances as disclosed above, for a purpose related to treatment or prevention of obesity or overweight, i.e. related to reduction or prevention of excess adiposity, it may be of relevance to employ such administration in combination with surgical intervention for the purpose of achieving weight loss or preventing weight gain, e.g. in combination with bariatric surgical intervention. Examples of frequently used bariatric surgical techniques include, but are not limited to, the following: vertical banded gastroplasty (also known as "stomach stapling"), wherein a part of the stomach is stapled to create a smaller pre-stomach pouch which serves as a new stomach; gastric banding, e.g. using an adjustable gastric band system (such as the *Swedish Adjustable Gastric Band* (SAGB), the LAP-BAND™ or the MiDband™), wherein a small pre-stomach pouch which is to serve as a new stomach is created using an elastomeric (e.g. silicone) band which can be adjusted in size by the patient; and gastric bypass surgery, e.g. "Roux-en-Y" bypass wherein a small stomach pouch is created using a stapler device and is connected to the distal small intestine, the upper part of the small intestine being reattached in a Y-shaped configuration.

The administration of a glucagon derivative of the invention (optionally in combination with one or more additional therapeutically active compounds as disclosed above) may take place for a period prior to carrying out the bariatric surgical intervention in question and/or for a period of time subsequent thereto. In many cases it may be preferable to begin administration of a compound of the invention after bariatric surgical intervention has taken place.

The glucagon derivatives of the present invention and anti-obesity or anti-diabetic agents as defined herein, may be administered simultaneously or sequentially. The factors may be supplied in single-dosage form wherein the single-dosage form contains both compounds or in the form of a kit-of-parts comprising a preparation of a glucagon derivatives of the present invention as a first unit dosage form and a preparation of an anti-obesity or anti-diabetic agents as a second unit dosage form. Whenever a first or second or third, etc., unit dose is mentioned throughout this specification this does not indicate the preferred order of administration, but is merely done for convenience purposes.

By "simultaneous" dosing of a preparation of a glucagon derivatives of the present invention and a preparation of anti-obesity or anti-diabetic agents is meant administration of the compounds in single-dosage form or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

As already indicated, in all of the therapeutic methods or indications disclosed above, a glucagon derivative of the present invention may be administered alone. However, it may also be administered in combination with one or more additional therapeutically active compounds, either sequentially or concomitantly.

A typical dosage of a compound of the invention, e.g. a glucagon derivative, when employed in a method according to the present invention is in the range of from about 0.0001 to about 100 mg/kg body weight per day, preferably from about 0.001 to about 10 mg/kg body weight, more preferably from about 0.001 to about 5 mg/kg body weight per day, e.g. from about 0.001 to about 10 mg/kg body weight per day or from about 0.001 to about 5 mg/kg body weight per day administered in one or more doses, such as from 1 to 3 doses. The exact dosage will depend upon the frequency and mode of administration, the sex, age, weight and general condition of the subject treated, the nature and severity of the condition treated, any concomitant diseases to be treated and other factors evident to those skilled in the art.

Compounds of the invention comprise compounds that are believed to be well-suited to administration with longer intervals than, for example, once daily, thus, appropriately formulated compounds of the invention may be suitable for, e.g., twice-weekly or once-weekly administration by a suitable route of administration, such as one of the routes disclosed herein.

As described above, compounds of the present invention may be administered or applied in combination with one or more additional therapeutically active compounds or substances, and suitable additional compounds or substances may be selected, for example, from antidiabetic agents, antihyperlipidemic agents, antiobesity agents, antihypertensive agents and agents for the treatment of complications resulting from or associated with, diabetes.

Pharmaceutical Indications

In some embodiments the invention relates to the glucagon derivative as defined herein for use in medicine, optionally in combination with one or more additional therapeutically active compounds.

As use herein, the term "therapeutically effective amount" of a compound, e.g. a glucagon derivative, refers to an amount sufficient to cure, alleviate or partially arrest the clinical manifestations of a given disease and/or its complications. An amount adequate to accomplish this is defined as a "therapeutically effective amount". Effective amounts for each purpose will depend on the severity of the disease or injury, as well as on the weight and general state of the subject. It will be understood that determination of an appropriate dosage may be achieved using routine experimentation, by constructing a matrix of values and testing different points in the matrix, all of which is within the level of ordinary skill of a trained physician or veterinarian.

The terms "treatment", "treating" and other variants thereof as used herein refer to the management and care of a patient for the purpose of combating a condition, such as a disease or a disorder. The terms are intended to include the full spectrum of treatments for a given condition from which the patient is suffering, such as administration of the active compound(s) in question to alleviate symptoms or complications thereof, to delay the progression of the disease, disorder or condition, to cure or eliminate the disease, disorder or condition, and/or to prevent the condition, in that prevention is to be understood as the management and care of a patient for the purpose of combating the disease, condition or disorder, and includes the administration of the active compound(s) in question to prevent the onset of symptoms or complications. The patient to be treated is preferably a mammal, in particular a human being, but treatment of other animals, such as dogs, cats, cows, horses, sheep, goats or pigs, is within the scope of the invention.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by beta-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

The term "euglycaemia" as used herein means normal concentration of glucose in the blood. Also called normoglycaemia.

The term "obesity" implies an excess of adipose tissue. When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity. In this context, obesity is best viewed as any degree of excess adipose tissue that imparts a health risk. The distinction between normal and obese individuals can only be approximated, but the health risk imparted by obesity is probably a continuum with increasing adipose tissue. However, in the context of the present invention, individuals with a body mass index (BMI=body weight in kilograms divided by the square of the height in meters) above 25 are to be regarded as obese.

In some embodiments the invention relates to a glucagon derivative as defined herein for use treating obesity or preventing overweight. In some embodiments the invention relates to a glucagon derivative as defined herein for use in for decreasing food intake. In some embodiments the invention relates to a glucagon derivative as defined herein for use in increasing energy expenditure. In some embodiments the invention relates to a glucagon derivative as defined herein for use in reducing body weight. In some embodiments the invention relates to a glucagon derivative as defined herein for use regulating appetite. In some embodiments the invention relates to a glucagon derivative as defined herein for use inducing satiety. In some embodiments the invention relates to a glucagon derivative as defined herein for use in preventing weight regain after successful weight loss. In some embodiments the invention relates to a glucagon derivative as defined herein for use in treating a disease or state related to overweight or obesity. In some embodiments the invention relates to a glucagon derivative as defined herein for use in treating bulimia. In some embodiments the invention relates to a glucagon derivative as defined herein for use in treating binge-eating.

In some embodiments the invention relates to a glucagon derivative as defined herein for use in treating atherosclerosis. In some embodiments the invention relates to a glucagon derivative as defined herein for use in treating hypertension. In some embodiments the invention relates to a glucagon derivative as defined herein for use in treating dyslipidaemia. In some embodiments the invention relates to a glucagon derivative as defined herein for use in treating coronary heart disease. In some embodiments the invention relates to a glucagon derivative as defined herein for use in treating hepatic steatosis.

In some embodiments the invention relates to a glucagon derivative as defined herein for use in treating type 2 diabetes. In some embodiments the invention relates to a glucagon derivative as defined herein for use in treating impaired glucose tolerance. In some embodiments the invention relates to a glucagon derivative as defined herein for use in delaying or preventing disease progression in type 2 diabetes. In some embodiments the invention relates to a glucagon derivative as defined herein for use in delaying the progression from impaired glucose tolerance (IGT) to type 2 diabetes. In some embodiments the invention relates to a glucagon derivative as defined herein for use in delaying the progression from type 2 diabetes to insulin-requiring diabetes.

In some embodiments the invention relates to a method for treating obesity, preventing overweight, decreasing food intake, increasing energy expenditure, reducing body weight, regulating appetite, inducing satiety, preventing weight regain after successful weight loss, treating a disease or state related to overweight or obesity, treating bulimia, or treating binge-eating comprising administering to a patient in need thereof, an effective amount of a glucagon derivative as defined herein, optionally in combination with one or more additional therapeutically active compounds.

In some embodiments the invention relates to a method for treating atherosclerosis, hypertension, dyslipidaemia, coronary heart disease, or hepatic steatosis comprising administering to a patient in need thereof, an effective amount of a glucagon derivative as defined herein, optionally in combination with one or more additional therapeutically active compounds.

In some embodiments the invention relates to a method for treating type 2 diabetes, treating impaired glucose tolerance, delaying the progression from impaired glucose tolerance (IGT) to type 2 diabetes, delaying the progression from type 2 diabetes to insulin-requiring diabetes comprising administering to a patient in need thereof, an effective amount of a glucagon derivative as defined herein, optionally in combination with one or more additional therapeutically active compounds.

In some embodiments the invention relates to a use of a glucagon derivative as defined herein for the preparation of a medicament. In some embodiments the invention relates to use of a glucagon derivative as defined in any one of the preceding embodiments, for the preparation of a medicament for the treatment or prevention of obesity, hyperglycaemia, type 2 diabetes, impaired glucose tolerance, and type 1 diabetes.

Embodiments of the Invention

The invention may be further described by the following non-limiting embodiments:

1. A glucagon derivative comprising an amino acid sequence of Formula I (SEQ ID NO: 2):

$X^1$-$X^2$-$X^3$-Gly-Thr-Phe-Thr-Ser-Asp-$X^{10}$-Ser-$X^{12}$-Tyr-Leu-$X^{15}$-$X^{16}$-$X^{17}$-$X^{18}$-Ala-$X^{20}$-$X^{21}$-Phe-Val-$X^{24}$-Trp-Leu-Ile-$X^{28}$-$X^{29}$-$X^{30}$    (I)

wherein $X^1$ represents His or Imp;

$X^2$ represents Aib or Acb;

$X^3$ represents Gln or His;

$X^{10}$ represents Tyr, Leu, Ile or Val;

$X^{12}$ represents Lys or Arg;
$X^{15}$ represents Asp or Glu;
$X^{16}$ represents Ser, Ala, Leu, Thr, Glu, Aib, Ile, Val or Lys;
$X^{17}$ represents Arg, Lys or Gln;
$X^{18}$ represents Arg, Ala or Lys;
$X^{20}$ represents Gln, Arg or Lys;
$X^{21}$ represents Asp, Glu or Lys;
$X^{24}$ represents Gln, Ala, Arg, Glu or Lys;
$X^{28}$ represents Asn, Ser, Thr, Gln, Ala, Gly, Glu or Lys;
$X^{29}$ represents Thr, Gly, Ser, Gln, Ala, Glu or Lys; and
$X^{30}$ is absent or represents Lys;
wherein said amino acid sequence of Formula I comprises a lysine residue at one or more of positions 12, 16, 17, 18, 20, 21, 24, 28, 29, and/or 30; and
wherein said glucagon derivative comprises a substituent comprising a lipophilic moiety and at least three negatively charged moieties, wherein one of said negatively charged moieties is distal of a lipophilic moiety, and wherein said substituent is attached at the epsilon position of a lysine residue in one of the amino acid positions 16, 17, 18, 20, 21, 24, 28, 29 or 30;
and wherein said glucagon derivative is a C-terminal amide;
or a pharmaceutically acceptable salt thereof.

2. The glucagon derivative according to any one of the preceding embodiments, wherein
$X^1$ represents His or Imp1;
$X^2$ represents Aib or Acb;
$X^3$ represents Gln;
$X^{10}$ represents Tyr, Leu, Ile or Val;
$X^{12}$ represents Lys or Arg;
$X^{15}$ represents Asp or Glu;
$X^{16}$ represents Ser, Ala, Leu or Val;
$X^{17}$ represents Arg or Lys;
$X^{18}$ represents Arg;
$X^{20}$ represents Gln or Arg;
$X^{21}$ represents Asp or Glu;
$X^{24}$ represents Gln, Ala or Lys;
$X^{28}$ represents Asn, Ser or Lys;
$X^{29}$ represents Thr or Lys; and
$X^{30}$ is absent.

3. The glucagon derivative according to any one of the preceding embodiments, wherein
$X^1$ represents His or Imp1;
$X^2$ represents Aib or Acb;
$X^3$ represents Gln;
$X^{10}$ represents Tyr or Leu;
$X^{12}$ represents Lys or Arg;
$X^{15}$ represents Asp or Glu;
$X^{16}$ represents Ser, Ala or Leu;
$X^{17}$ represents Arg;
$X^{18}$ represents Arg;
$X^{20}$ represents Gln or Arg;
$X^{21}$ represents Asp or Glu;
$X^{24}$ represents Gln, Ala or Lys;
$X^{28}$ represents Ser or Lys;
$X^{29}$ represents Thr or Lys; and
$X^{30}$ is absent.

4. The glucagon derivative according to any one of the preceding embodiments, wherein
$X^1$ represents His or Imp;
$X^3$ represents Gln;
$X^{10}$ represents Tyr, Leu, Ile or Val;
$X^{16}$ represents Ser, Ala, Leu or Val;
$X^{17}$ represents Arg or Lys;
$X^{18}$ represents Arg;
$X^{20}$ represents Gln or Arg;
$X^{21}$ represents Asp or Glu;
$X^{24}$ represents Gln, Ala or Lys;
$X^{28}$ represents Asn, Ser or Lys;
$X^{29}$ represents Thr or Lys; and
$X^{30}$ is absent;
and wherein said substituent is attached at the epsilon position of a lysine residue in one of the amino acid positions 24, 28, and 29.

5. The glucagon derivative according to any one of the preceding embodiments, wherein
$X^1$ represents His or Imp;
$X^3$ represents Gln;
$X^{10}$ represents Tyr or Leu;
$X^{16}$ represents Ser, Ala or Leu;
$X^{17}$ represents Arg;
$X^{18}$ represents Arg;
$X^{20}$ represents Gln or Arg;
$X^{21}$ represents Asp or Glu;
$X^{24}$ represents Gln, Ala or Lys;
$X^{28}$ represents Ser or Lys;
$X^{29}$ represents Thr or Lys; and
$X^{30}$ is absent;
and wherein said substituent is attached at the epsilon position of a lysine residue in one of the amino acid positions 24, 28, and 29.

6. The glucagon derivative according to any one of the preceding embodiments, wherein
$X^{24}$ represents Gln or Ala;
$X^{28}$ represents Asn or Ser;
$X^{29}$ represents Lys; and
$X^{30}$ is absent;
and wherein said substituent is attached at the epsilon position of a lysine residue in position 29.

7. The glucagon derivative according to any one of the preceding embodiments, wherein
$X^{24}$ represents Gln or Ala;
$X^{28}$ represents Lys;
$X^{29}$ represents Thr; and
$X^{30}$ is absent;
and wherein said substituent is attached at the epsilon position of a lysine residue in position 28.

8. The glucagon derivative according to any one of the preceding embodiments, wherein
$X^{24}$ represents Lys;
$X^{28}$ represents Asn or Ser;
$X^{29}$ represents Thr; and
$X^{30}$ is absent;
and wherein said substituent is attached at the epsilon position of a lysine residue in position 24.

9. The glucagon derivative according to any one of the preceding embodiments, wherein said amino acid sequence of Formula I has 3-15 amino acid residue modifications, such as substitutions or additions, as compared to human glucagon (SEQ ID NO: 1).

10. The glucagon derivative according to any one of the preceding embodiments, wherein said amino acid sequence of Formula I has up to 14, such as up to 13 or up to 12, amino acid residue modifications, such as substitutions or additions, as compared to human glucagon (SEQ ID NO: 1).

11. The glucagon derivative according to any one of the preceding embodiments, wherein said amino acid sequence of Formula I has up to 11, such as up to 10 or up to 9, amino acid residue modifications, such as substitutions or additions, as compared to human glucagon (SEQ ID NO: 1).

12. The glucagon derivative according to any one of the preceding embodiments, wherein said amino acid sequence of Formula I has up to 8, such as up to 7 or up to 6, amino acid residue modifications, such as substitutions or additions, as compared to human glucagon (SEQ ID NO: 1).

13. The glucagon derivative according to any one of the preceding embodiments, wherein said glucagon derivative comprises up to 5 amino acid residue modifications, such as substitutions or additions, in said amino acid sequence of Formula I as compared to human glucagon (SEQ ID NO: 1).

14. The glucagon derivative according to any one of the preceding embodiments, wherein $X^1$ represents His or Imp1.

15. The glucagon derivative according to any one of the preceding embodiments, wherein $X^2$ represents Aib or Acb.

16. The glucagon derivative according to any one of the preceding embodiments, wherein $X^3$ represents Gln or His.

17. The glucagon derivative according to any one of the preceding embodiments, wherein $X^3$ represents Gln.

18. The glucagon derivative according to any one of the preceding embodiments, wherein $X^{10}$ represents Tyr, Leu, Ile or Val.

19. The glucagon derivative according to any one of the preceding embodiments, wherein $X^{10}$ represents Tyr.

20. The glucagon derivative according to any one of the preceding embodiments, wherein $X^{10}$ represents Leu.

21. The glucagon derivative according to any one of the preceding embodiments, wherein $X^{10}$ represents Val.

22. The glucagon derivative according to any one of the preceding embodiments, wherein $X^{12}$ represents Lys or Arg.

23. The glucagon derivative according to any one of the preceding embodiments, wherein $X^{15}$ represents Asp or Glu.

24. The glucagon derivative according to any one of the preceding embodiments, wherein $X^{16}$ represents Ser, Ala, Leu, Thr, Glu, Aib, Ile, Val or Lys.

25. The glucagon derivative according to any one of the preceding embodiments, wherein $X^{16}$ represents Ser, Ala, Leu or Val.

26. The glucagon derivative according to any one of the preceding embodiments, wherein $X^{16}$ represents Ser, Ala or Leu.

27. The glucagon derivative according to any one of the preceding embodiments, wherein $X^{17}$ represents Arg, Lys or Gln.

28. The glucagon derivative according to any one of the preceding embodiments, wherein $X^{17}$ represents Arg or Lys.

29. The glucagon derivative according to any one of the preceding embodiments, wherein $X^{17}$ represents Arg.

30. The glucagon derivative according to any one of the preceding embodiments, wherein $X^{18}$ represents Arg, Ala or Lys.

31. The glucagon derivative according to any one of the preceding embodiments, wherein $X^{18}$ represents Arg.

32. The glucagon derivative according to any one of the preceding embodiments, wherein $X^{20}$ represents Gln, Arg or Lys.

33. The glucagon derivative according to any one of the preceding embodiments, wherein $X^{20}$ represents Gln or Arg.

34. The glucagon derivative according to any one of the preceding embodiments, wherein $X^{21}$ represents Asp, Glu or Lys.

35. The glucagon derivative according to any one of the preceding embodiments, wherein $X^{21}$ represents Asp or Glu.

36. The glucagon derivative according to any one of the preceding embodiments, wherein $X^{24}$ represents Gln, Ala, Arg, Glu or Lys.

37. The glucagon derivative according to any one of the preceding embodiments, wherein $X^{24}$ represents Gln, Ala or Lys.

38. The glucagon derivative according to any one of the preceding embodiments, wherein $X^{24}$ represents Gln.

39. The glucagon derivative according to any one of the preceding embodiments, wherein $X^{24}$ represents Ala.

40. The glucagon derivative according to any one of the preceding embodiments, wherein $X^{24}$ represents Lys.

41. The glucagon derivative according to any one of the preceding embodiments, wherein $X^{28}$ represents Asn, Ser, Thr, Gln, Ala, Gly, Glu or Lys.

42. The glucagon derivative according to any one of the preceding embodiments, wherein $X^{28}$ represents Asn.

43. The glucagon derivative according to any one of the preceding embodiments, wherein $X^{28}$ represents Ser.

44. The glucagon derivative according to any one of the preceding embodiments, wherein $X^{28}$ represents Lys.

45. The glucagon derivative according to any one of the preceding embodiments, wherein $X^{28}$ represents Ser or Lys.

46. The glucagon derivative according to any one of the preceding embodiments, wherein $X^{29}$ represents Thr, Gly, Ser, Gln, Ala, Glu or Lys.

47. The glucagon derivative according to any one of the preceding embodiments, wherein $X^{29}$ represents Thr.

48. The glucagon derivative according to any one of the preceding embodiments, wherein $X^{29}$ represents Lys.

49. The glucagon derivative according to any one of the preceding embodiments, wherein $X^{30}$ is absent or represents Lys.

50. The glucagon derivative according to any one of the preceding embodiments, wherein $X^{30}$ is absent.

51. The glucagon derivative according to any one of the preceding embodiments, wherein said glucagon derivative comprises the amino acid sequence selected from the group consisting of:
[Aib2,Ala16,Arg20,Lys24,Ile27,Ser28]-Glucagon amide;
[Aib2,Ala16,Lys17,Arg20,Glu21,Lys24,Ile27,Ser28]-Glucagon amide;
[Aib2,Leu10,Glu15,Arg20,Ile27,Lys28]-Glucagon amide;
[Aib2,Ala16,Arg20,Glu21,Lys24,Ile27,Ser28]-Glucagon amide;
[Aib2,Leu10,Ala16,Arg20,Ile27,Lys28]-Glucagon amide;
[Aib2,Leu10,Ala16,Arg20,Glu21,Ile27,Lys28]-Glucagon amide;
[Aib2,Leu10,Ala16,Ile27,Lys28]-Glucagon amide;
[Aib2,Leu10,Glu15,Ile27,Lys28]-Glucagon amide;
[Aib2,Leu10,Leu16,Ile27,Lys28]-Glucagon amide;
[Aib2,Val10,Glu15,Ile27,Lys28]-Glucagon amide;
[Aib2,Glu15,Arg20,Lys24,Ile27,Ser28]-Glucagon amide;
[Aib2,Leu16,Arg20,Lys24,Ile27,Ser28]-Glucagon amide;
[Acb2,Leu10,Glu15,Arg20,Glu21,Ile27,Lys28]-Glucagon amide;
[Aib2,Leu10,Arg12,Ala16,Arg20,Ile27,Lys28]-Glucagon amide;
[Acb2,Leu10,Glu15,Arg20,Glu21,Ile27,Lys28]-Glucagon amide;
[Acb2,Leu10,Arg12,Glu15,Arg20,Glu21,Ile27,Lys28]-Glucagon amide;
[Acb2,Leu10,Glu15,Arg20,Glu21,Ile27,Lys28]-Glucagon amide;
[Acb2,Val10,Glu15,Arg20,Glu21,Ile27,Lys28]-Glucagon amide;
[Aib2,Leu10,Ala16,Arg20,Ile27,Lys29]-Glucagon amide;
[Aib2,Leu10,Ala16,Arg20,Glu21,Ile27,Lys29]-Glucagon amide;
[Aib2,Leu10,Leu16,Arg20,Glu21,Ile27,Lys29]-Glucagon amide;
[Aib2,Leu10,Leu16,Arg20,Ile27,Lys29]-Glucago amide;
[Aib2,Leu10,Leu16,Arg20,Ala24,Ile27,Lys29]-Glucagon amide;

[Aib2,Leu10,Glu15,Arg20,Glu21,Ile27,Lys28]-Glucagon amide;
[Acb2,Ile10,Glu15,Arg20,Glu21,Ile27,Lys28]-Glucagon amide;
[Aib2,Leu10,Ala16,Arg20,Ile27,Ser28,Lys29]-Glucagon amide;
[Aib2,Leu10,Ala16,Arg20,Glu21,Ile27,Ser28,Lys29]-Glucagon amide;
[Aib2,Leu10,Leu16,Arg20,Ile27,Ser28,Lys29]-Glucagon amide;
[Aib2,Leu10,Leu16,Arg20,Glu21,Ile27,Ser28,Lys29]-Glucagon amide;
[Aib2,Leu10,Leu16,Arg20,Ala24,Ile27,Ser28,Lys29]-Glucagon amide;
[Aib2,Ala16,Arg20,Ala24,Ile27,Lys28]-Glucagon amide;
[Aib2,Leu16,Arg20,Ala24,Ile27,Lys28]-Glucagon amide;
[Aib2,Glu15,Ala24,Ile27,Lys28]-Glucagon amide;
[Aib2,Glu15,Ala24,Ile27,Ser28,Lys29]-Glucagon amide;
[Acb2,Arg12,Glu15,Arg20,Ile27,Lys28]-Glucagon amide;
[Aib2,Arg12,Glu15,Arg20,Ile27,Lys28]-Glucagon amide;
[Acb2,Leu10,Glu15,Glu21,Ile27,Lys28]-Glucagon amide;
[Aib2,Val10,Ala16,Ile27,Lys28]-Glucagon amide; and
[Aib2,Leu10,Val16,Ile27,Lys28]-Glucagon amide.

52. The glucagon derivative according to any one of the preceding embodiments, wherein said substituent is attached at the epsilon position of a lysine residue at one of positions 16, 17, 18, 20, 21, 24, 28, 29, or 30.

53. The glucagon derivative according to any one of the preceding embodiments, wherein said substituent is attached at the epsilon position of a lysine residue at one of positions 24, 28 or 29.

54. The glucagon derivative according to any one of the preceding embodiments, wherein said substituent is attached at the epsilon position of a lysine residue at position 24.

55. The glucagon derivative according to any one of the preceding embodiments, wherein $X^{24}$ represents Lys; and wherein said substituent is attached at the epsilon position of a lysine residue at position 24.

56. The glucagon derivative according to any one of the preceding embodiments, wherein $X^{28}$ represents Lys; and wherein said substituent is attached at the epsilon position of a lysine residue at position 28.

57. The glucagon derivative according to any one of the preceding embodiments, wherein $X^{29}$ represents Lys; and wherein said substituent is attached at the epsilon position of a lysine residue at position 29.

58. The glucagon derivative according to any one of the preceding embodiments, wherein said substituent comprises three, four or five negatively charged moieties.

59. The glucagon derivative according to any one of the preceding embodiments, wherein said substituent comprises three or four negatively charged moieties.

60. The glucagon derivative according to any one of the preceding embodiments, wherein said substituent comprises three negatively charged moieties.

61. The glucagon derivative according to any one of the preceding embodiments, wherein said substituent binds non-covalently to albumin.

62. The glucagon derivative according to any one of the preceding embodiments, wherein said substituent is negatively charged at physiological pH.

63. The glucagon derivative according to any one of the preceding embodiments, wherein said substituent comprising a lipophilic moiety and at least three negatively charged moieties is a substituent represented by Formula II:

$$Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-} \quad (II)$$

wherein,
$Z^1$ represents a structure according to the Formula IIa:

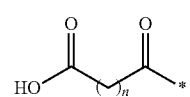

(IIa)

wherein
n is 6-20;
the symbol * represents the attachment point to the nitrogen of the neighbouring group; and
$Z^2\text{-}Z^3\text{-}Z^4\text{-}Z^5\text{-}Z^6\text{-}Z^7\text{-}Z^8\text{-}Z^9\text{-}Z^{10}\text{-}$ represents a linker, wherein each of $Z^2$ to $Z^{10}$ individually are represented by any one of the following amino acid residues: Glu, gamma-Glu (gGlu), Gly, Ser, Ala, Thr and/or Ado; or one or more of residues $Z^2$ to $Z^{10}$ are absent; provided, however, that at least two of residues $Z^2$ to $Z^{10}$ are present;
wherein $Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}$ together contains at least three negatively charged moieties; and
wherein said substituent is attached at the epsilon position of a Lys in the amino acid sequence of Formula I.

64. The glucagon derivative according to any one of the preceding embodiments, wherein $Z_1$ represents a fatty di-acid of Formula IIa;

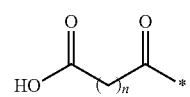

(IIa)

wherein n represents an integer in the range of from 12 to 18.

65. The glucagon derivative according to any one of the preceding embodiments, wherein n in Formula IIa represents 12, 14, 16 or 18.

66. The glucagon derivative according to any one of the preceding embodiments, wherein n in Formula IIa is 16 (i.e. $Z^1$ represents 17-carboxyheptadecanoyl).

67. The glucagon derivative according to any one of the preceding embodiments, wherein in Formula II $Z^2\text{-}Z^3\text{-}Z^4\text{-}Z^5\text{-}Z^6\text{-}Z^7\text{-}Z^8\text{-}Z^9\text{-}Z^{10}\text{-}$ represents a linker, wherein each of $Z^2$ to $Z^{10}$ individually are represented by any one of the following amino acid residues: Glu, gGlu, Gly, Ser, Ala, Thr and/or Ado; or one or more of residues $Z^2$ to $Z^{10}$ are absent; provided, however, that at least two of residues $Z^2$ to $Z^{10}$ are present; and wherein $Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}$together contains at least three negatively charged moieties.

68. The glucagon derivative according to any one of the preceding embodiments, wherein $Z^2$, $Z^3$, $Z^4$, $Z^5$, $Z^6$, $Z^7$, $Z^8$, $Z^9$ and $Z^{10}$ individually are represented by any one of the following amino acid residues: Glu, gGlu, Gly, Ser, and/or Ado; or one or more of residues $Z^2$ to $Z^{10}$ are absent; provided, however, that at least two of residues $Z^2$ to $Z^{10}$ are present.

69. The glucagon derivative according to any one of the preceding embodiments, wherein $Z^2$, $Z^3$, $Z^4$, $Z^5$, $Z^6$, $Z^7$, $Z^8$, $Z^9$ and $Z^{10}$ individually are represented by any one of the following amino acid residues: gGlu and/or Ado; or one or more of residues $Z^2$ to $Z^{10}$ are absent; provided, however, that at least two of residues $Z^2$ to $Z^{10}$ are present.

70. The glucagon derivative according to any one of the preceding embodiments, wherein at least three of residues $Z^2$ to $Z^{10}$ are present.

71. The glucagon derivative according to any one of the preceding embodiments, wherein at least four of residues $Z^2$ to $Z^{10}$ are present.

72. The glucagon derivative according to any one of the preceding embodiments, wherein at least five of residues $Z^2$ to $Z^{10}$ are present.

73. The glucagon derivative according to any one of the preceding embodiments, wherein at least six of residues $Z^2$ to $Z^{10}$ are present.

74. The glucagon derivative according to any one of the preceding embodiments, wherein $Z^2-Z^3-Z^4-Z^5-Z^6-Z^7-Z^8-Z^9-Z^{10}$- represents a linker selected from the group consisting of
gGlu-Ado-gGlu-;
gGlu-Ado-2xgGlu- (SEQ ID NO:51);
gGlu-2xAdo-2xgGlu- (SEQ ID NO:52);
2xgGlu-;
2xgGlu-Ado-;
2xgGlu-Ado-gGlu- (SEQ ID NO:53);
2xgGlu-Ado-gGlu-Ado- (SEQ ID NO:54);
2xgGlu-Ado-2xgGlu- (SEQ ID NO:55);
2xgGlu-2xAdo- (SEQ ID NO:56);
2xgGlu-2xAdo-gGlu (SEQ ID NO:57);
2xgGlu-2xAdo-2xgGlu- (SEQ ID NO:58);
2xgGlu-Ser-Gly-Glu-Ser- (SEQ ID NO:49);
2xgGlu-Ser-Gly-Glu-Ser-Gly- (SEQ ID NO:50);
3xgGlu-;
3xgGlu-Ado- (SEQ ID NO:61);
3xgGlu-2xAdo- (SEQ ID NO:59); and
2xgGlu-Ado-gGlu-Ado-gGlu-Ado-gGlu- (SEQ ID NO:60).

75. The glucagon derivative according to any one of the preceding embodiments, wherein $Z^2-Z^3-Z^4-Z^5-Z^6-Z^7-Z^8-Z^9-Z^{10}$- represents a linker selected from the group consisting of
2xgGlu-2xAdo-gGlu- (SEQ ID NO:57);
gGlu-2xAdo-2xgGlu- (SEQ ID NO:52);
2xgGlu-2xAdo- (SEQ ID NO:56);
2xgGlu-2xAdo-2xgGlu- (SEQ ID NO:58);
2xgGlu-Ser-Gly-Glu-Ser-Gly- (SEQ ID NO:50);
3xgGlu-;
3xgGlu-2xAdo- (SEQ ID NO:59); and
2xgGlu-Ado-gGlu-Ado-gGlu-Ado-gGlu- (SEQ ID NO:60).

76. The glucagon derivative according to any one of the preceding embodiments, wherein $Z^2-Z^3-Z^4-Z^5-Z^6-Z^7-Z^8-Z^9-Z^{10}$- represents the linker 2xgGlu-2xAdo-gGlu- (SEQ ID NO:57).

77. The glucagon derivative according to any one of the preceding embodiments, wherein $Z^2-Z^3-Z^4-Z^5-Z^6-Z^7-Z^8-Z^9-Z^{10}$- represents the linker gGlu-2xAdo-2xgGlu- (SEQ ID NO:52).

78. The glucagon derivative according to any one of the preceding embodiments, wherein $Z^2-Z^3-Z^4-Z^5-Z^6-Z^7-Z^8-Z^9-Z^{10}$- represents the linker 2xgGlu-2xAdo- (SEQ ID NO:56).

79. The glucagon derivative according to any one of the preceding embodiments, wherein $Z^2-Z^3-Z^4-Z^5-Z^6-Z^7-Z^8-Z^9-Z^{10}$- represents the linker 2xgGlu-2xAdo-2xgGlu- (SEQ ID NO: 58).

80. The glucagon derivative according to any one of the preceding embodiments, wherein $Z^2-Z^3-Z^4-Z^5-Z^6-Z^7-Z^8-Z^9-Z^{10}$- represents the linker 2xgGlu-Ser-Gly-Glu-Ser-Gly- (SEQ ID NO:50).

81. The glucagon derivative according to any one of the preceding embodiments, wherein $Z^2-Z^3-Z^4-Z^5-Z^6-Z^7-Z^8-Z^9-Z^{10}$- represents the linker 3xgGlu-.

82. The glucagon derivative according to any one of the preceding embodiments, wherein $Z^2-Z^3-Z^4-Z^5-Z^6-Z^7-Z^8-Z^9-Z^{10}$- represents the linker 3xgGlu-2xAdo- (SEQ ID NO:59).

83. The glucagon derivative according to any one of the preceding embodiments, wherein $Z^2-Z^3-Z^4-Z^5-Z^6-Z^7-Z^8-Z^9-Z^{10}$- represents the linker 2xgGlu-Ado-gGlu-Ado-gGlu-Ado-gGlu-(SEQ ID NO:60).

84. The glucagon derivative according to any one of the preceding embodiments, wherein said glucagon derivative is selected from the group consisting of:
$N^{\varepsilon 24}$-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]ethoxy]ethoxy]acetyl]amino]ethoxy]ethoxy]acetyl]-[Aib2,Ala16,Arg20,Lys24,Ile27,Ser28]-Glucagon amide
Chem 1(SEQ ID NO: 3):

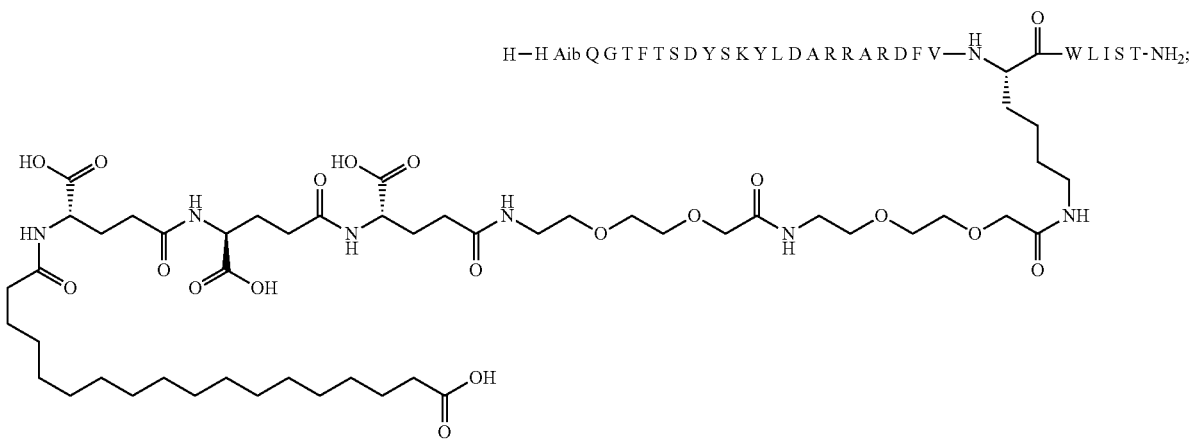

N^ε24-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Lys17,Arg20,Glu21,Lys24,Ile27,Ser28]-Glucagon amide Chem 2 (SEQ ID NO: 4):

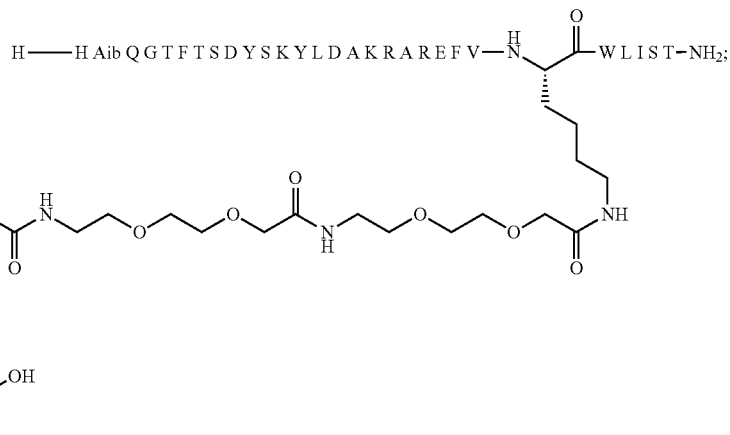

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Glu15,Arg20,Ile27,Lys28]-Glucagon amide Chem 3 (SEQ ID NO: 5):

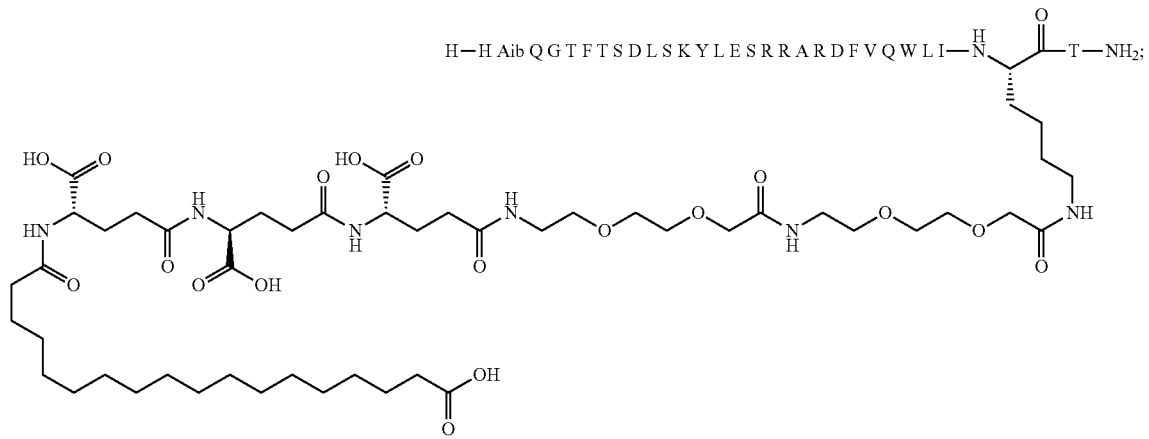

N^ε24-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Arg20,Glu21,Lys24,Ile27,Ser28]-Glucagon amide Chem 4 (SEQ ID NO: 6):

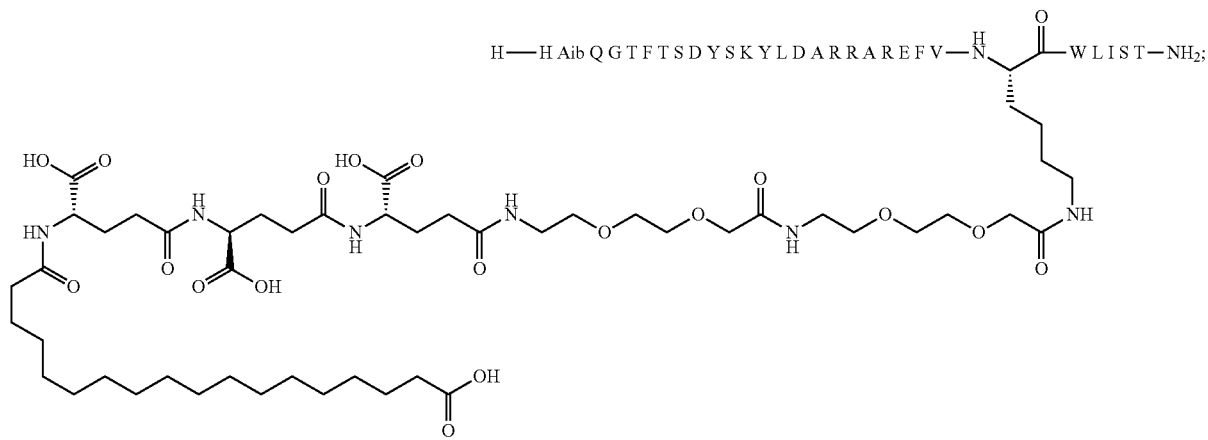

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Arg20,Ile27,Lys28]-Glucagon amide Chem 5 (SEQ ID NO: 7):

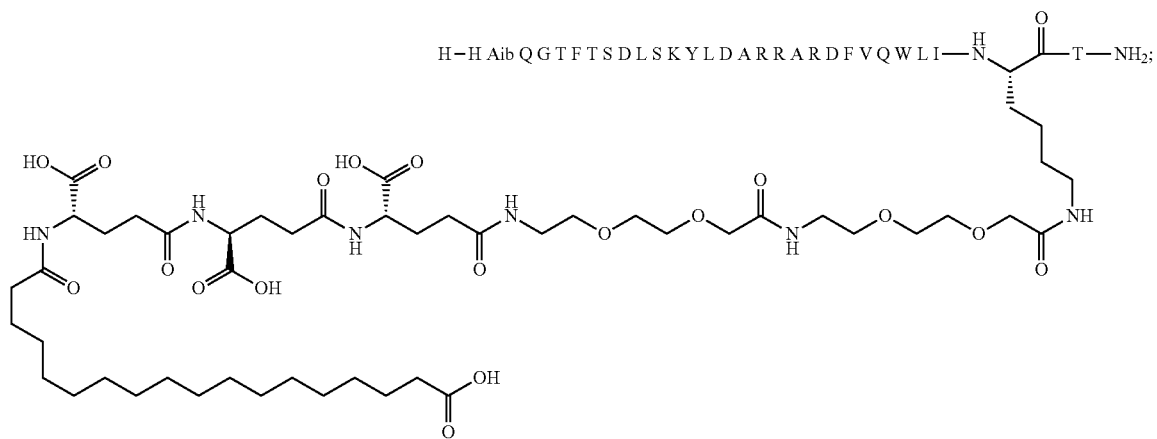

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Arg20,Glu21,Ile27,Lys28]-Glucagon amide Chem 6 (SEQ ID NO: 8):

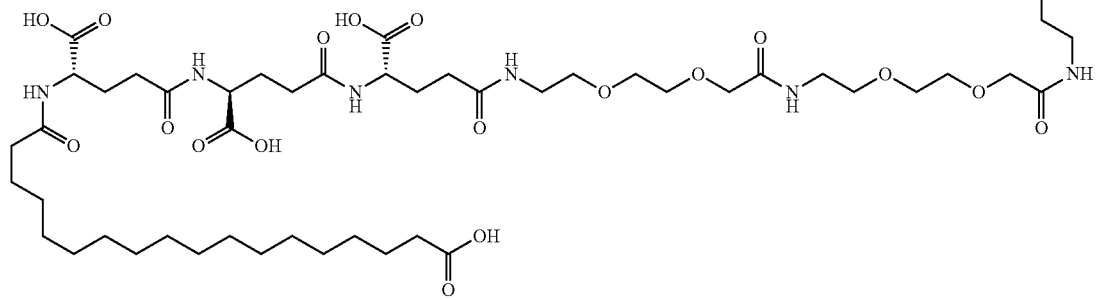

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2, Leu10,Ala16,Ile27,Lys28]-Glucagon amide Chem 7 (SEQ ID NO: 9):

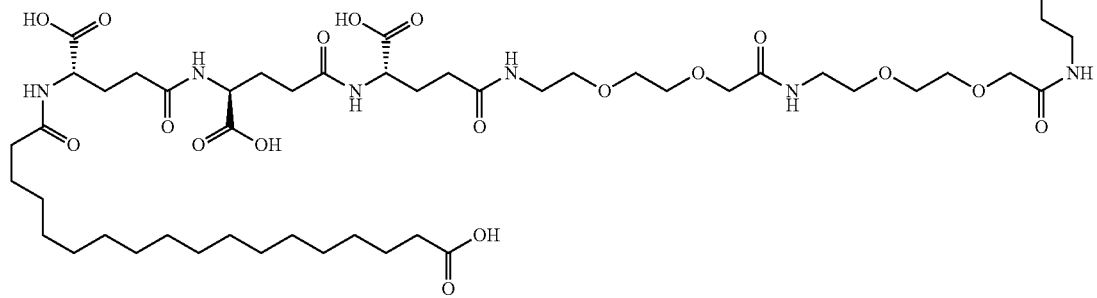

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2, Leu10,Glu15,Ile27,Lys28]-Glucagon amide Chem 8 (SEQ ID NO: 10):

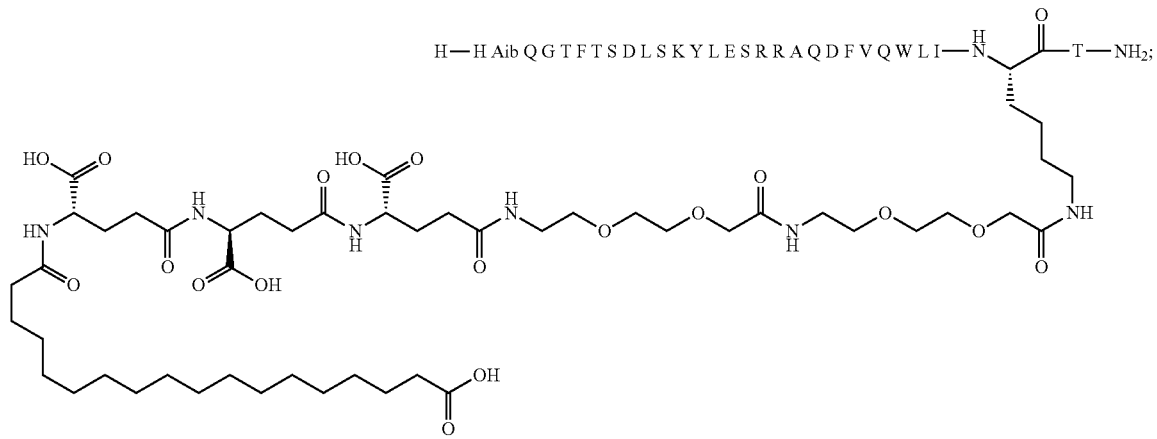

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Leu16,Ile27,Lys28]-Glucagon amide Chem 9 (SEQ ID NO: 11):

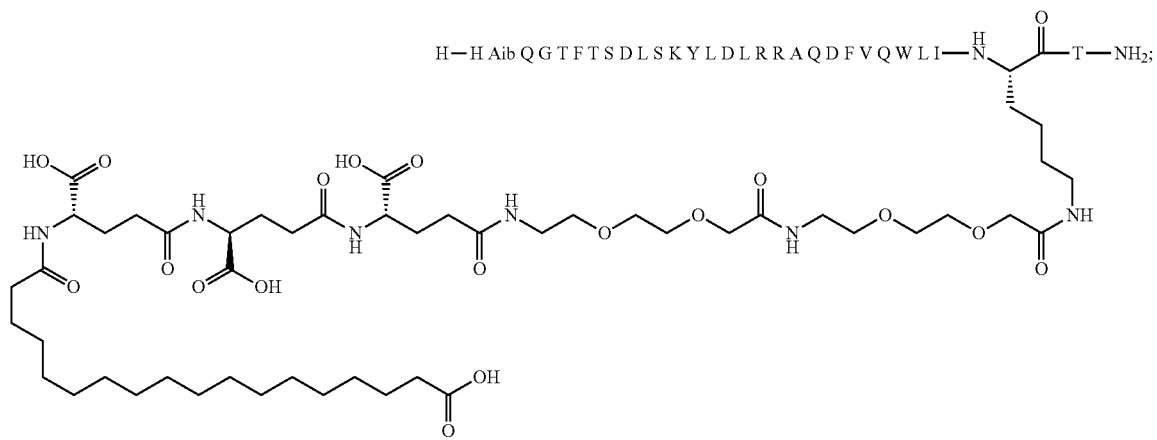

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Glu5,Ile27,Lys28]-Glucagon amide Chem 10 (SEQ ID NO: 12):

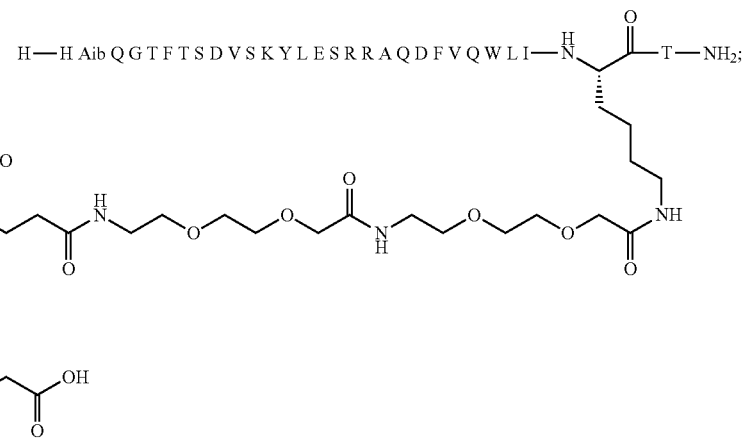

N^ε24-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2, Glu15,Arg20,Lys24,Ile27,Ser28]-Glucagon amide Chem 11 (SEQ ID NO: 13):

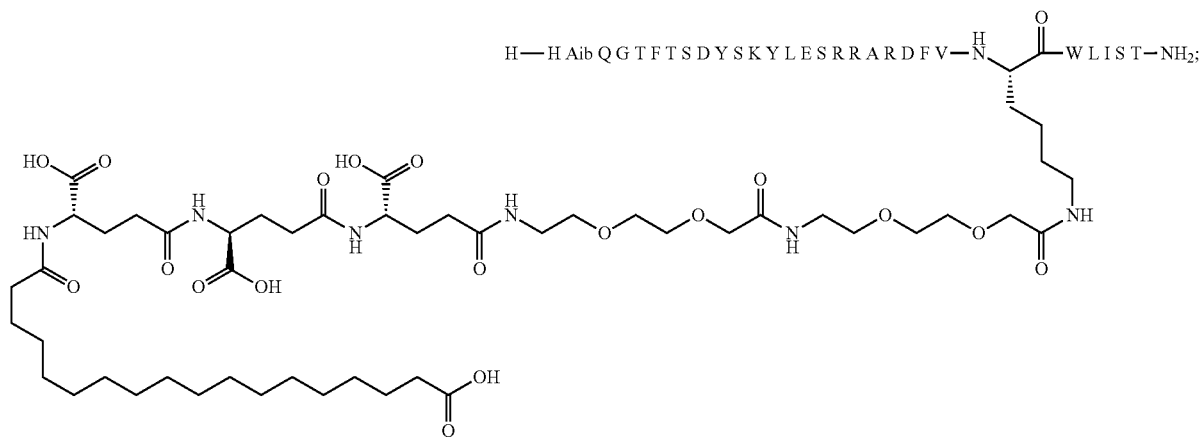

N^ε24-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2, Leu16,Arg20,Lys24,Ile27,Ser28]-Glucagon amide Chem 12 (SEQ ID NO: 14):

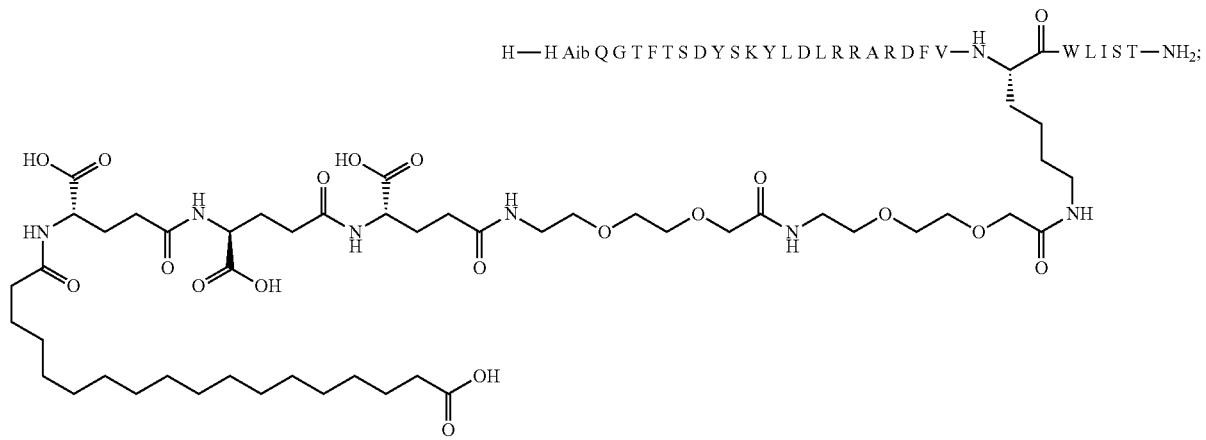

N$^{\varepsilon 28}$-[(4S)-4-carboxy-4-[[(4S)-4-carboxy-4-[[2-[2-[2-[[2-[2-[2-[[(4S)-4- carboxy-4-[[(4S)-4-carboxy-4-(17-carboxy-heptadecanoylamino)butanoyl]amino]butanoyl]amino] ethoxy]ethoxy]acetyl]amino]ethoxy]ethoxy]acetyl]amino] butanoyl]amino]butanoyl]-[Acb2,Leu10,Glu15,Arg20, Glu21,Ile27,Lys28]-Glucagon amide Chem 13 (SEQ ID NO: 15):

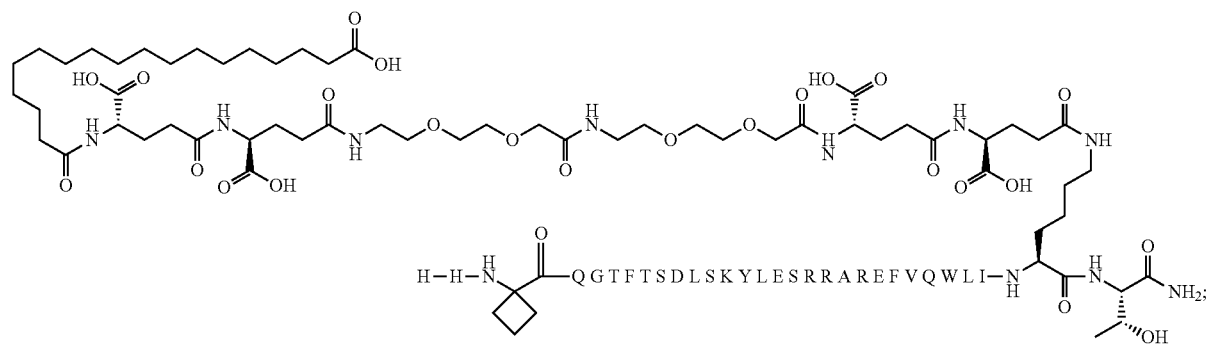

N$^{\varepsilon 28}$-[(4S)-4-carboxy-4-[[(4S)-4-carboxy-4-[[(4S)-4-car-boxy-4-(17-carboxyheptadecanoylamino)butanoyl]amino] butanoyl]amino]butanoyl]-[Aib2,Leu10,Arg12,Ala16, Arg20,Ile27,Lys28]-Glucagon amide Chem 14 (SEQ ID NO: 16):

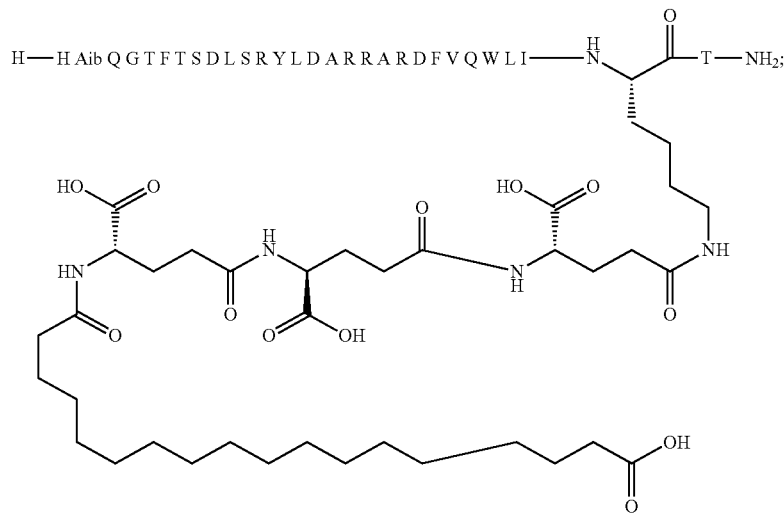

$N^{\varepsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Ala16,Arg20,Ile27,Lys28]-Glucagon amide Chem 15 (SEQ ID NO: 17):

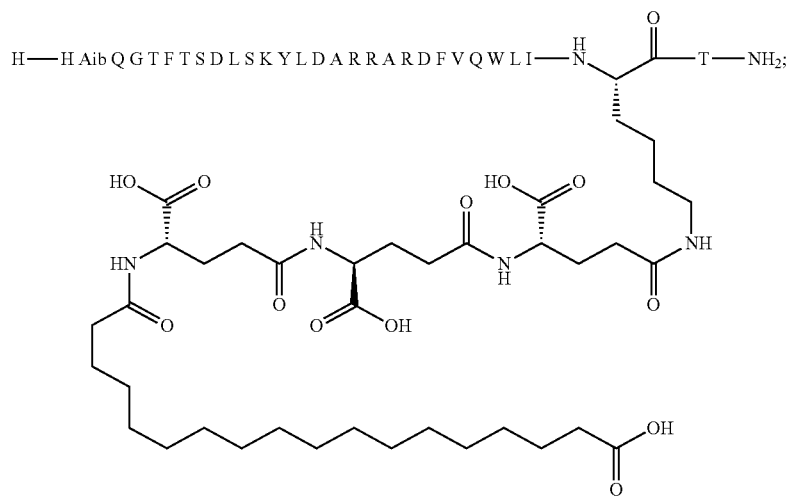

$N^{\varepsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15,Arg20,Glu21,Ile27,Lys28]-Glucagon amide Chem 16 (SEQ ID NO: 18):

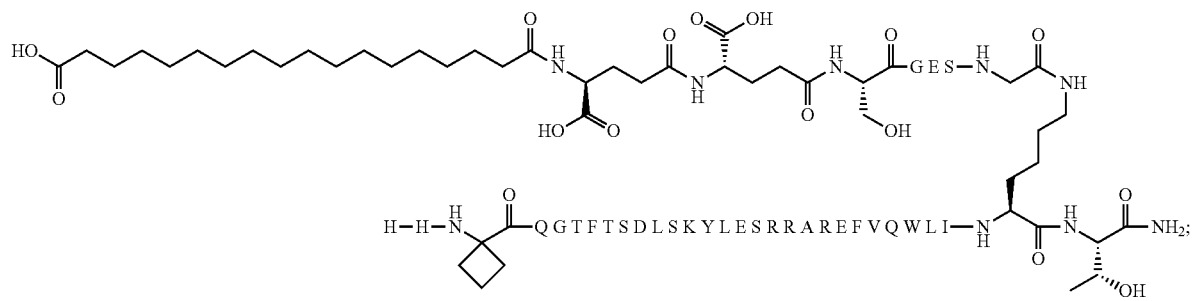

N^ε28 [(4S)-4-carboxy-4-[[(4S)-4-carboxy-4-[[2-[2-[2-[[2-[2-[2-[[(4S)-4-carboxy-4-[[(4S)-4-carboxy-4-(17-carboxy-heptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Glu15,Arg20,Glu21,Ile27,Lys28]-Glucagon amide Chem 17 (SEQ ID NO: 19):

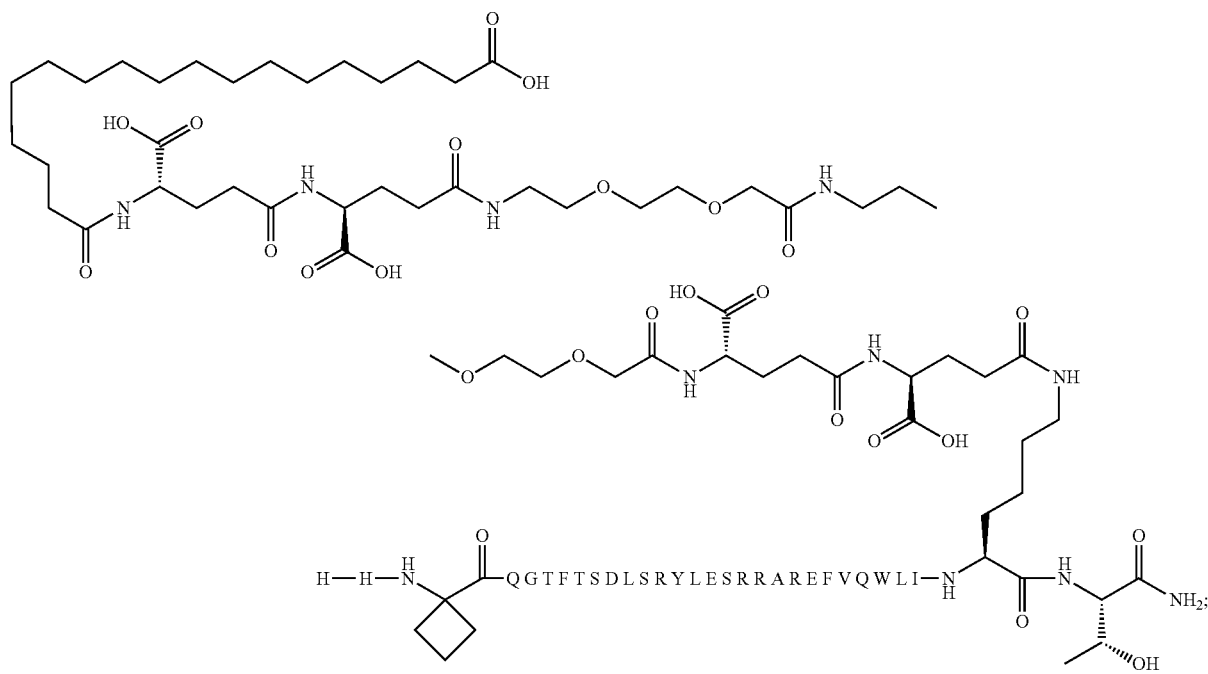

N^ε28-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Acb2,Leu10,Glu15,Arg20,Glu21,Ile27,Lys28]-Glucagon amide Chem 18 (SEQ ID NO: 20)

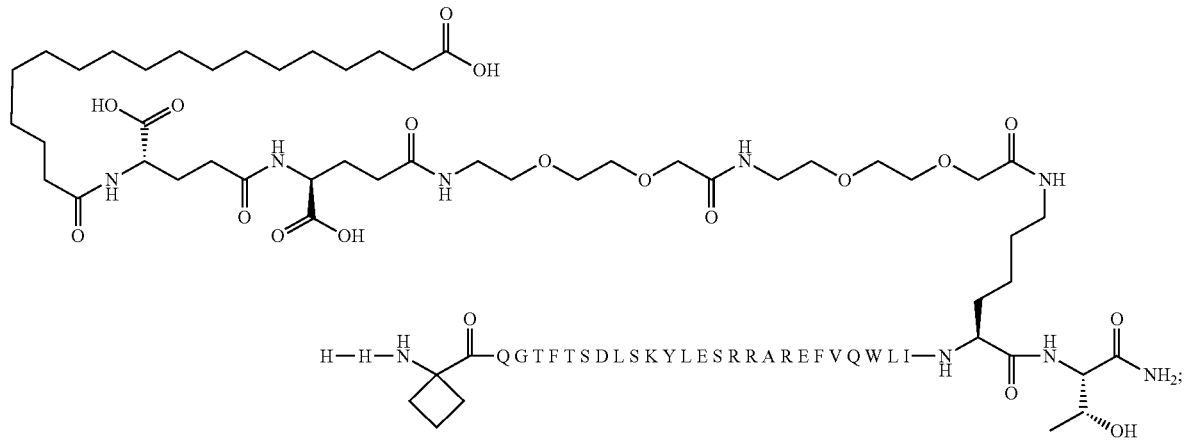

N^ε28-[(4S)-4-carboxy-4-[[(4S)-4-carboxy-4-[[2-[2-[2-[[2-[2-[2-[[(4S)-4- carboxy-4-[[(4S)-4-carboxy-4-(17-carboxy-heptadecanoylamino)butanoyl]amino]butanoyl]amino] ethoxy]ethoxy]acetyl]amino]ethoxy]ethoxy]acetyl]amino] butanoyl]amino]butanoyl]-[Acb2,Val10,Glu15,Arg20, Glu21,Ile27,Lys28]-Glucagon amide Chem 19 (SEQ ID NO: 21):

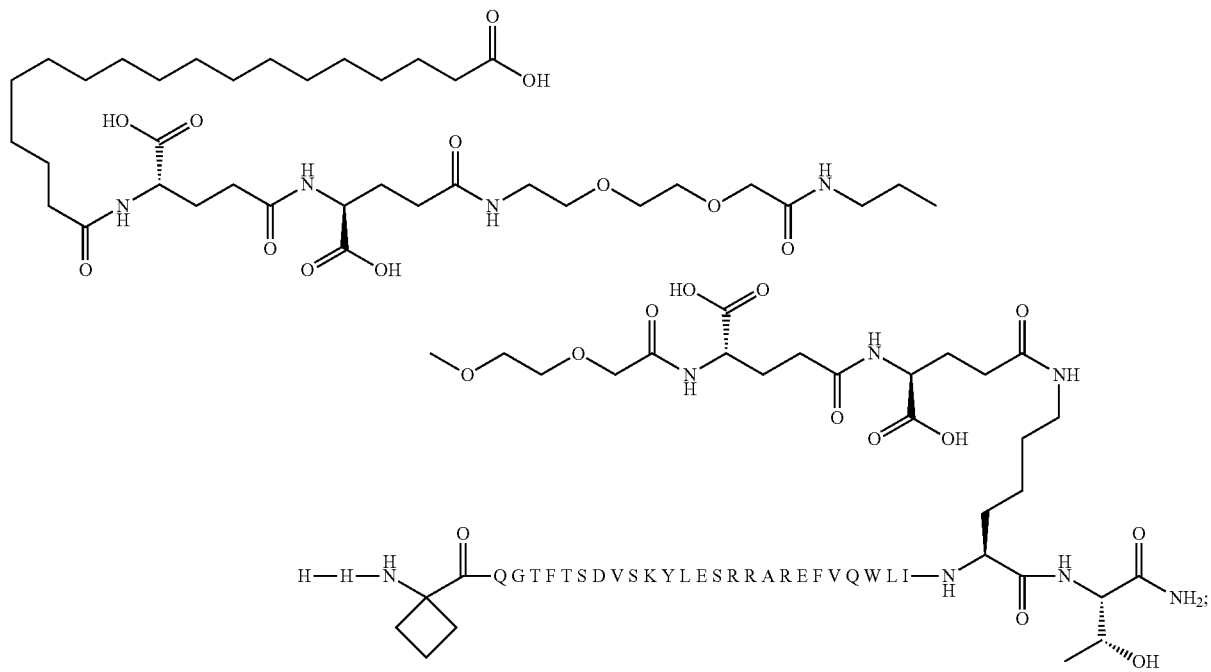

N^ε29-[(4S)-4-carboxy-4-[[(4S)-4-carboxy-4-[[2-[2-[2-[[2-[2-[2-[[(4S)-4- carboxy-4-(17-carboxyheptadecanoylamino) butanoyl]amino]ethoxy]ethoxy]acetyl]amino]ethoxy] ethoxy]acetyl]amino]butanoyl]amino]butanoyl]-[Aib2, Leu10,Ala16,Arg20,Ile27,Lys29]-Glucagon amide Chem 20 (SEQ ID NO: 22):

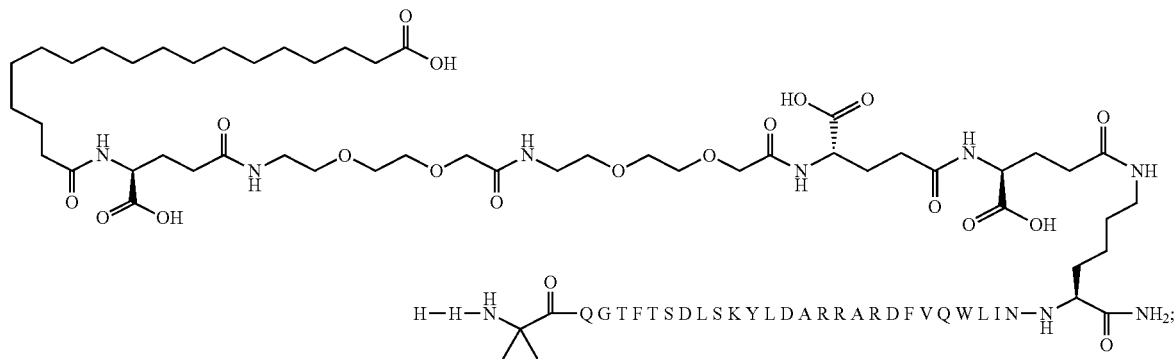

$N^{\epsilon 29}$-[(4S)-4-carboxy-4-[[(4S)-4-carboxy-4-[[2-[2-[2-[[2-[2-[2-[[(4S)-4- carboxy-4-(17-carboxyheptadecanoylamino) butanoyl]amino]ethoxy]ethoxy]acetyl]amino]ethoxy] ethoxy]acetyl]amino]butanoyl]amino]butanoyl]-[Aib2, Leu10,Ala16,Arg20,Glu21,Ile27,Lys29]-Glucagon amide Chem 21 (SEQ ID NO: 23):

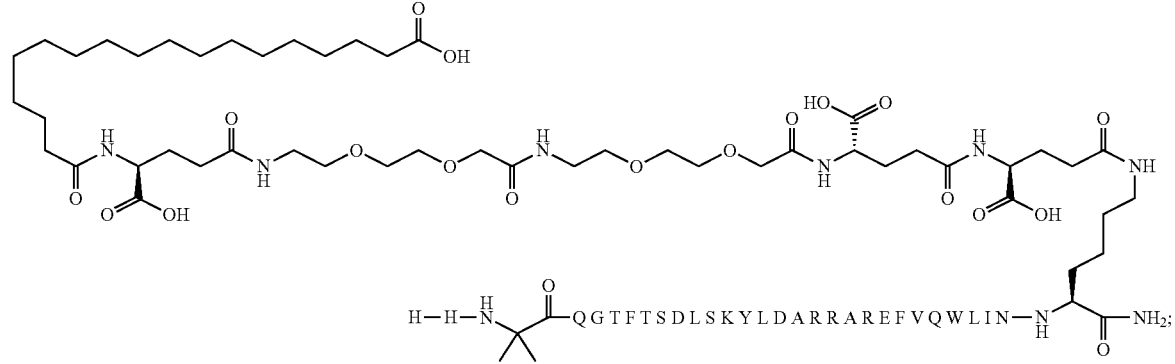

$N^{\epsilon 29}$-[(4S)-4-carboxy-4-[[(4S)-4-carboxy-4-[[2-[2-[2-[[2-[2-[2-[[(4S)-4- carboxy-4-(17-carboxyheptadecanoylamino) butanoyl]amino]ethoxy]ethoxy]acetyl]amino]ethoxy] ethoxy]acetyl]amino]butanoyl]amino]butanoyl]-[Aib2, Leu10,Leu16,Arg20,Glu21,Ile27,Lys29]-Glucagon amide Chem 22 (SEQ ID NO: 24):

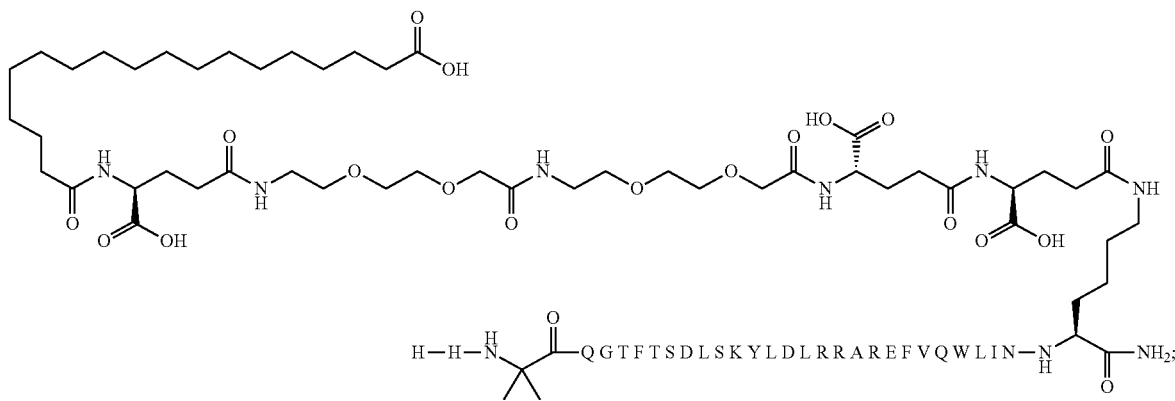

N^ε29-[(4S)-4-carboxy-4-[[(4S)-4-carboxy-4-[[2-[2-[2-[[2-[2-[2-[[(4S)-4- carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Lys29]-Glucagon amide
Chem 23 (SEQ ID NO: 25):

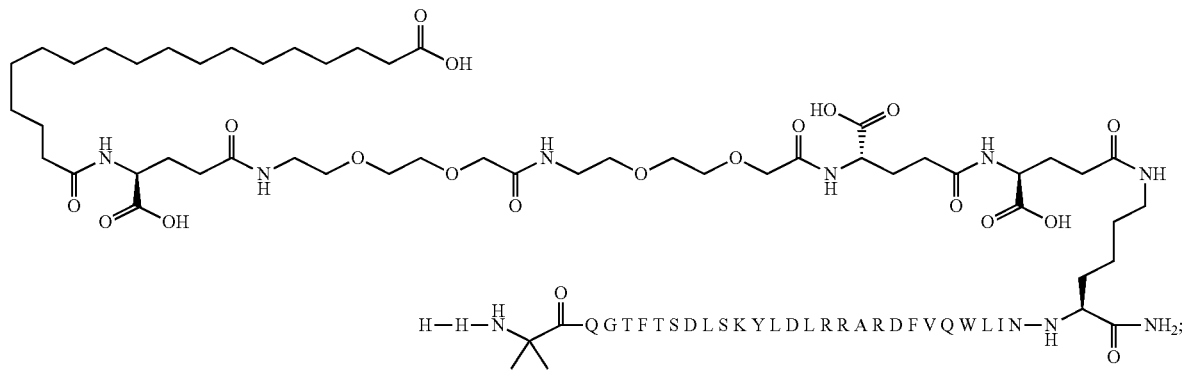

N^ε29-[(4S)-4-carboxy-4-[[(4S)-4-carboxy-4-[[2-[2-[2-[[2-[2-[2-[[(4S)-4- carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Lys29]-Glucagon amide
Chem 24 (SEQ ID NO: 26):

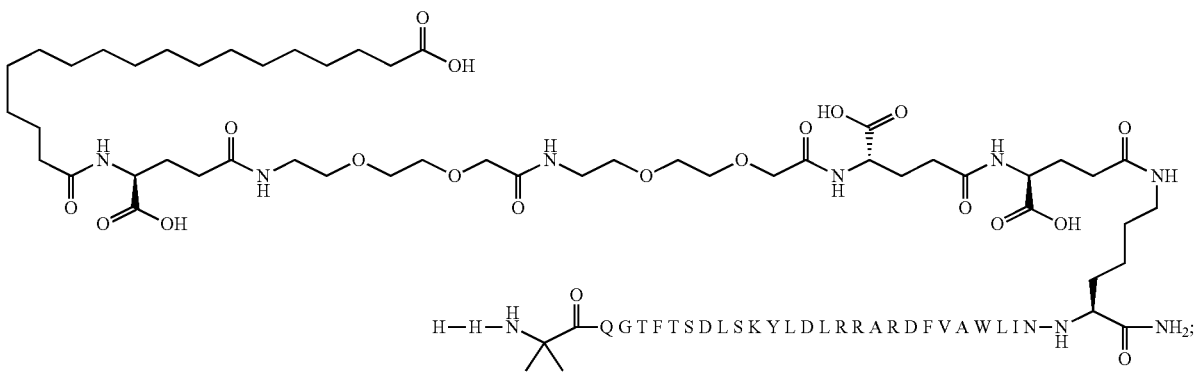

N^ε28-[(4S)-4-carboxy-4-[[(4S)-4-carboxy-4-[[2-[2-[2-[[2-[2-[2-[[(4S)-4- carboxy-4-[[(4S)-4-carboxy-4-(17-carboxy-heptadecanoylamino)butanoyl]amino]butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Ile27,Lys28]-Glucagon amide Chem 25 (SEQ ID NO: 27):
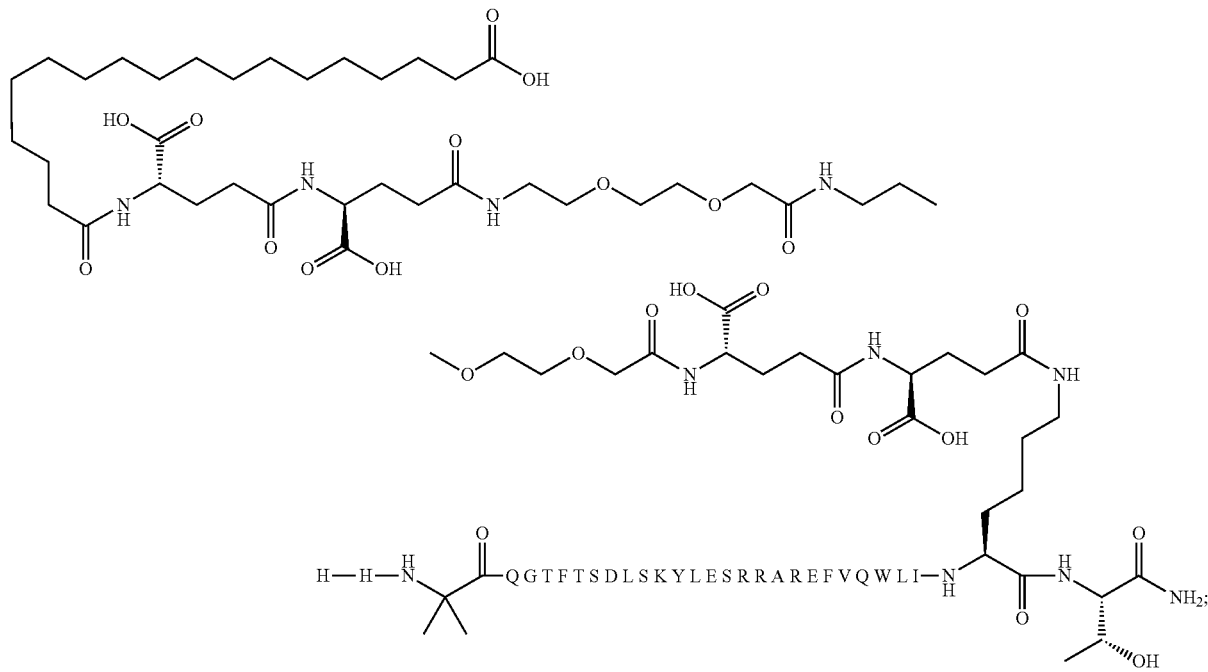
N$^{\epsilon 28}$-[(4S)-4-carboxy-4-[[(4S)-4-carboxy-4-[[2-[2 [2-[[2-[2-[2-[[(4S)-4- carboxy-4-[[(4S)-4-carboxy-4-(17-carboxy-heptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Ile10,Glu15,Arg20, Glu21,Ile27,Lys28]-Glucagon amide
Chem 26 (SEQ ID NO: 28):
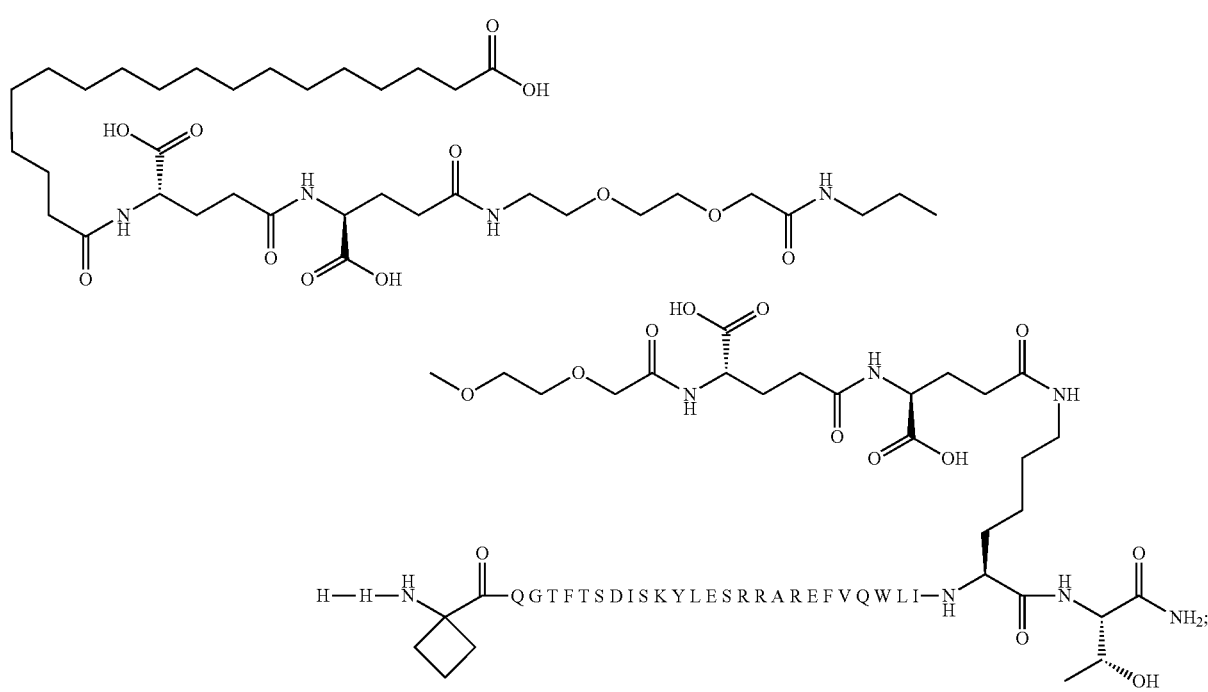

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Ser28,Lys29]-Glucagon amide Chem 27 (SEQ ID NO: 29):

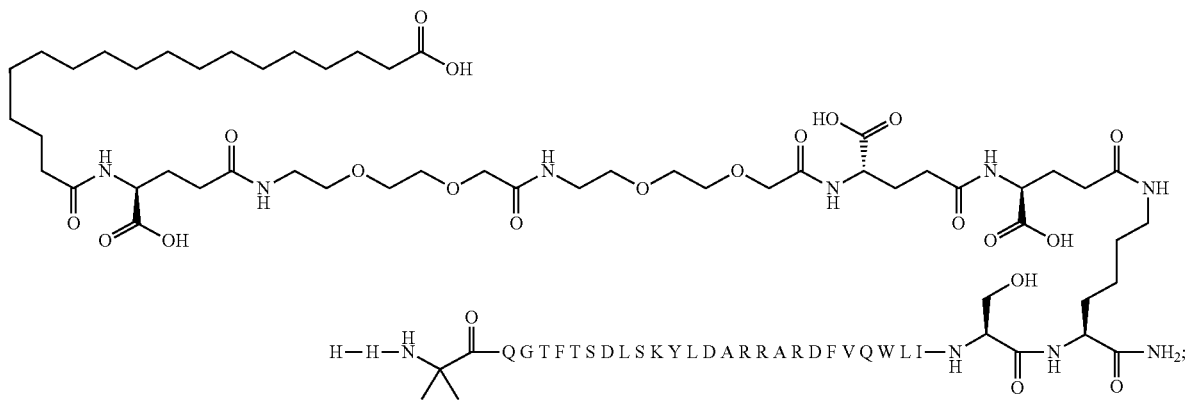

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Ser28,Lys29]-Glucagon amide Chem 28 (SEQ ID NO: 30):

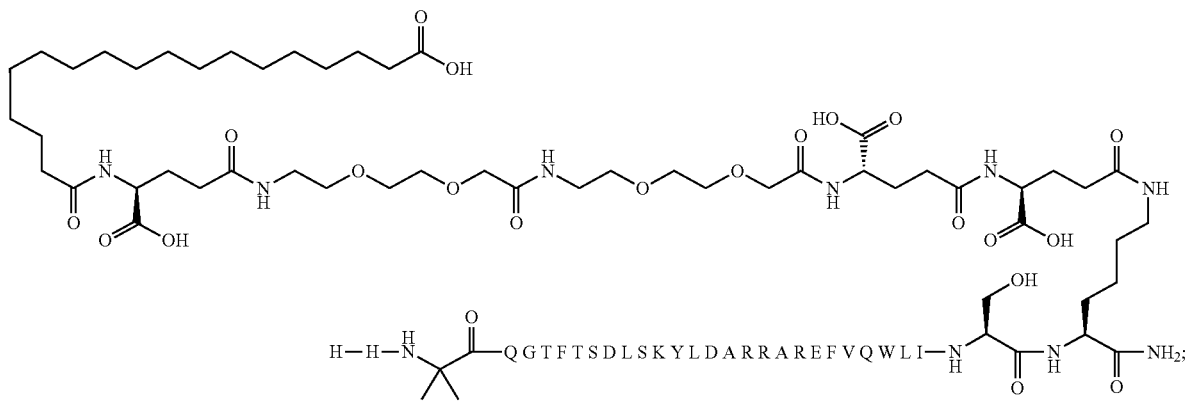

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Ser28,Lys29]-Glucagon amide Chem 29 (SEQ ID NO: 31):

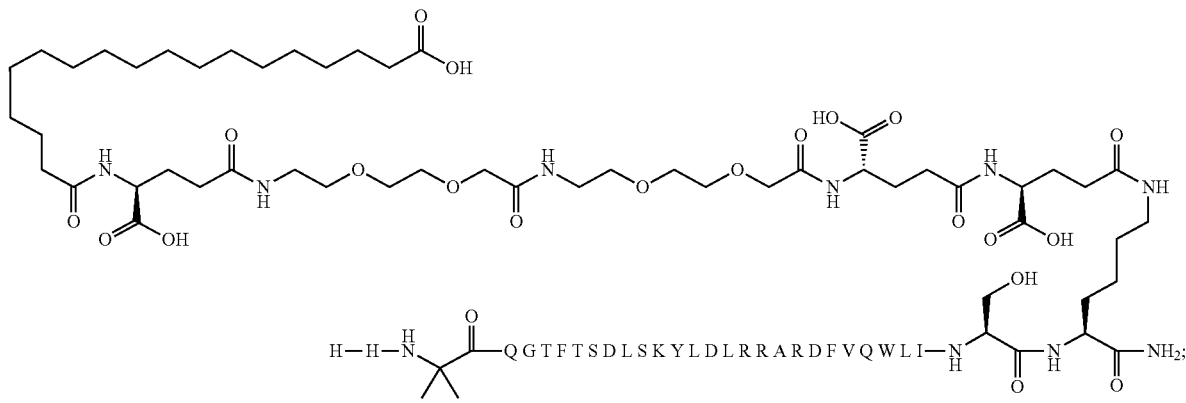

$N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Ser28,Lys29]-Glucagon amide Chem 30 (SEQ ID NO: 32):

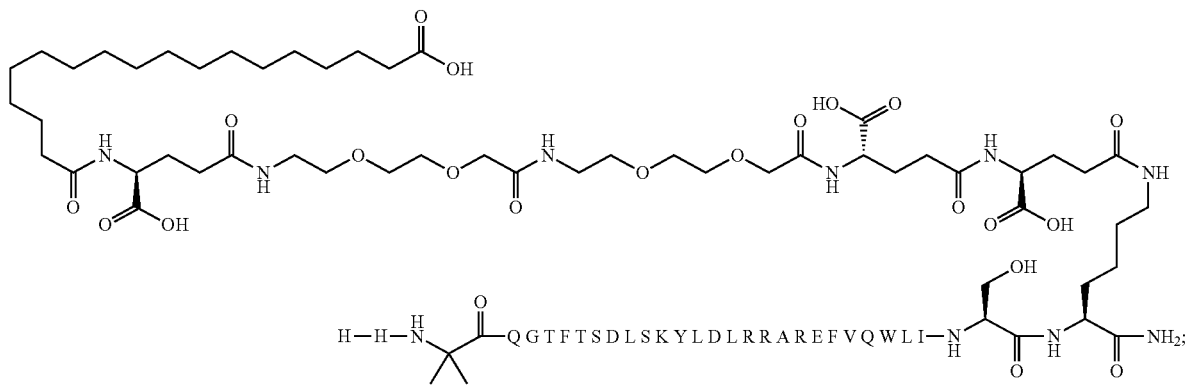

$N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Ser28,Lys29]-Glucagon amide Chem 31 (SEQ ID NO: 33):

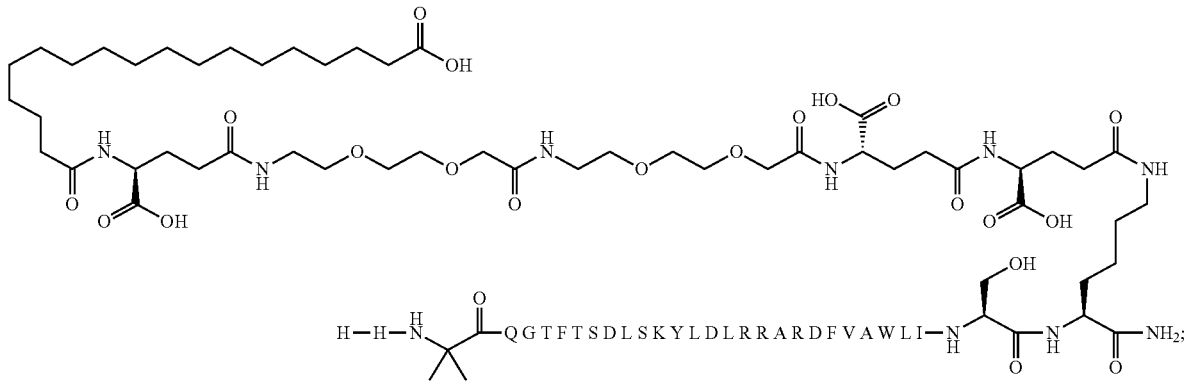

N^ε28-[(4S)-4-carboxy-4-[[(4S)-4-carboxy-4-[[2-[2-[2-[[2-[2-[2-[[(4S)-4- carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Ala16,Arg20,Ala24,Ile27,Lys28]-Glucagon amide Chem 32 (SEQ ID NO: 34):

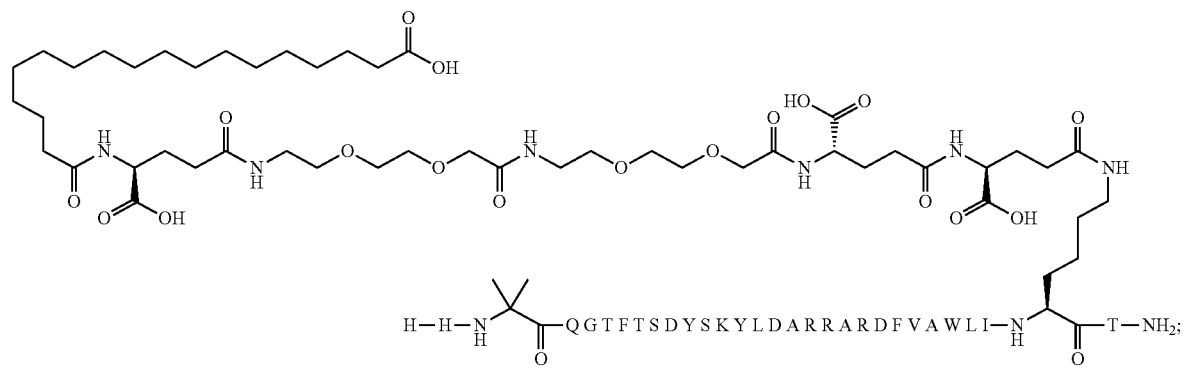

N^ε28-[(4S)-4-carboxy-4-[[(4S)-4-carboxy-4-[[2-[2-[2-[[2-[2-[2-[[(4S)-4- carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu6,Arg20,Ala24,Ile27,Lys28]-Glucagon amide Chem 33 (SEQ ID NO: 35):

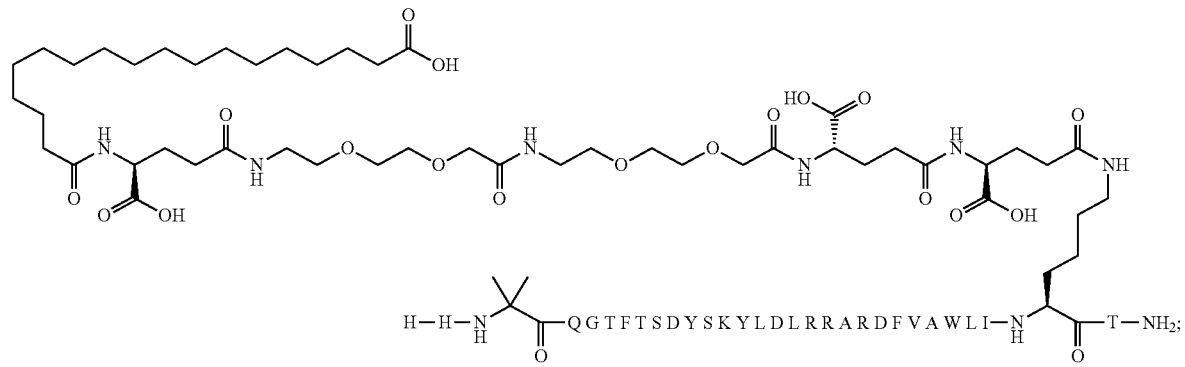

N^ε28-[(4S)-4-carboxy-4-[[(4S)-4-carboxy-4-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy]acetyl]amino]butanoyl]amino]butanoyl]-[Aib2,Glu15,Ala24,Ile27,Lys28]-Glucagon amide
Chem 34 (SEQ ID NO: 36):

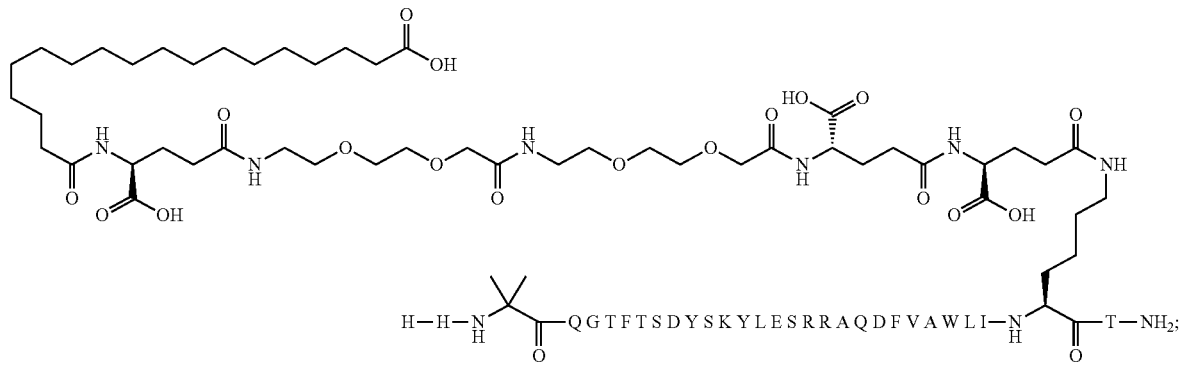

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Ser28,Lys29]-Glucagon amide
Chem 35 (SEQ ID NO: 37):

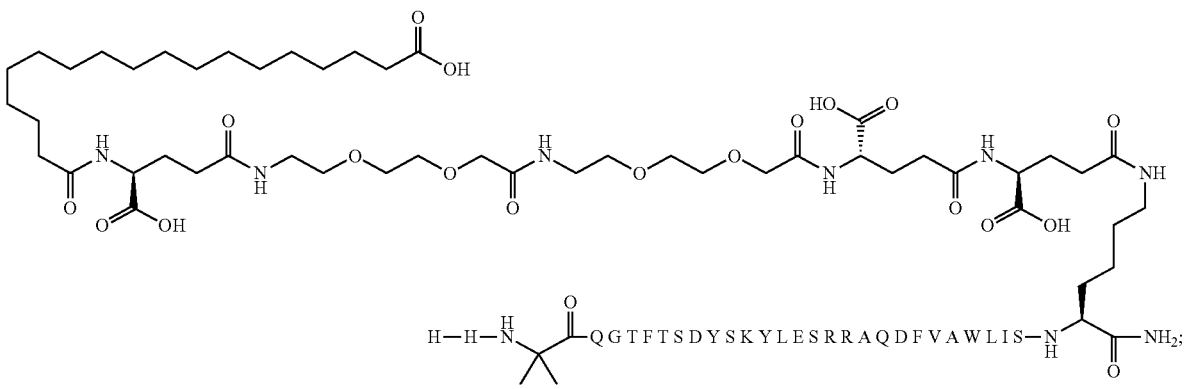

N^ε28-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Acb2,Arg12,Glu15,Arg20,Ile27,Lys28]-Glucagon amide
Chem 36 (SEQ ID NO: 38):

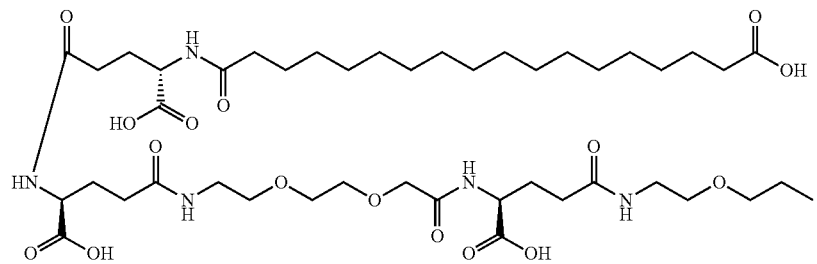

-continued

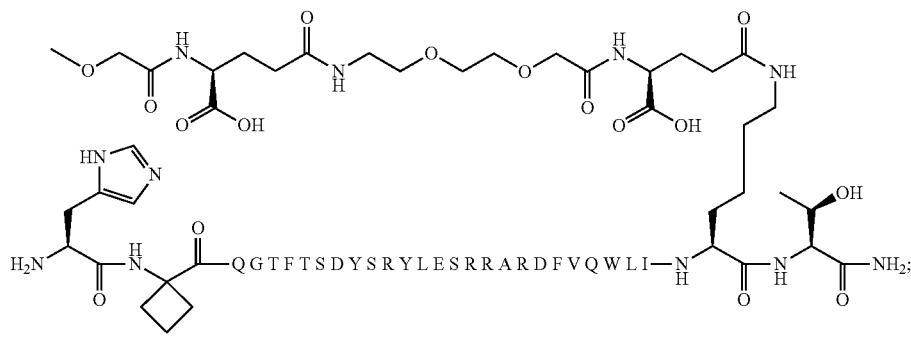

N$^{\varepsilon 28}$-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Aib2,Arg12,Glu15,Arg20,Ile27,Lys28]-Glucagon amide Chem 37 (SEQ ID NO: 39):

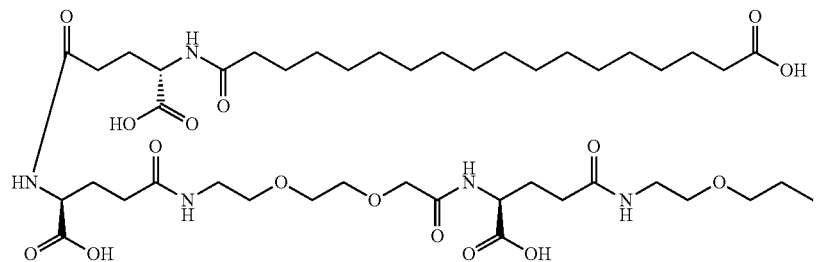

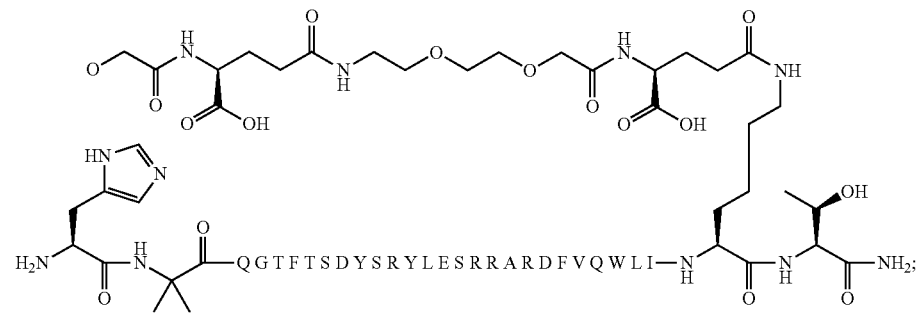

N$^{\varepsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Acb2,Leu10,Glu15,Glu21,Ile27,Lys28]-Glucagon amide Chem 38 (SEQ ID NO: 40):

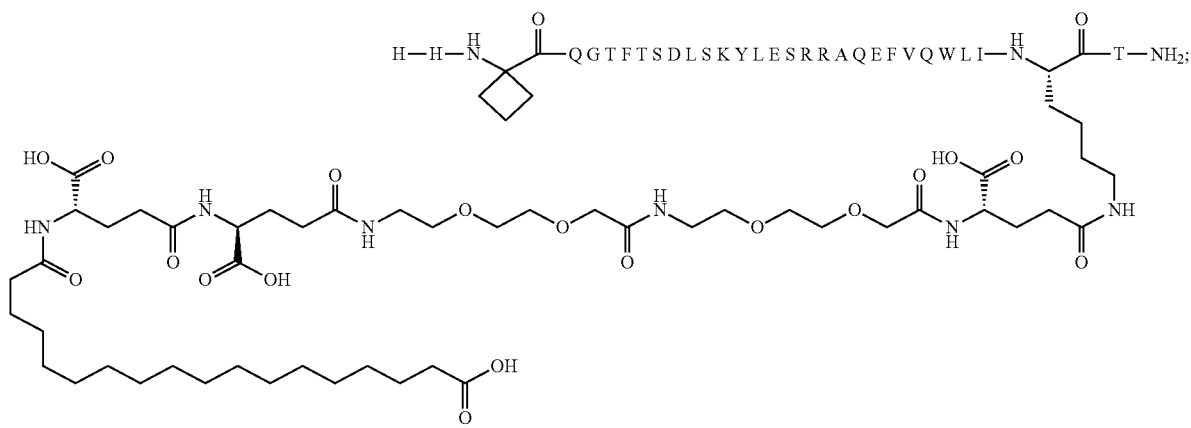

$N^{\varepsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Val10,Ala16,Ile27,Lys28]-Glucagon amide Chem 39 (SEQ ID NO: 41):

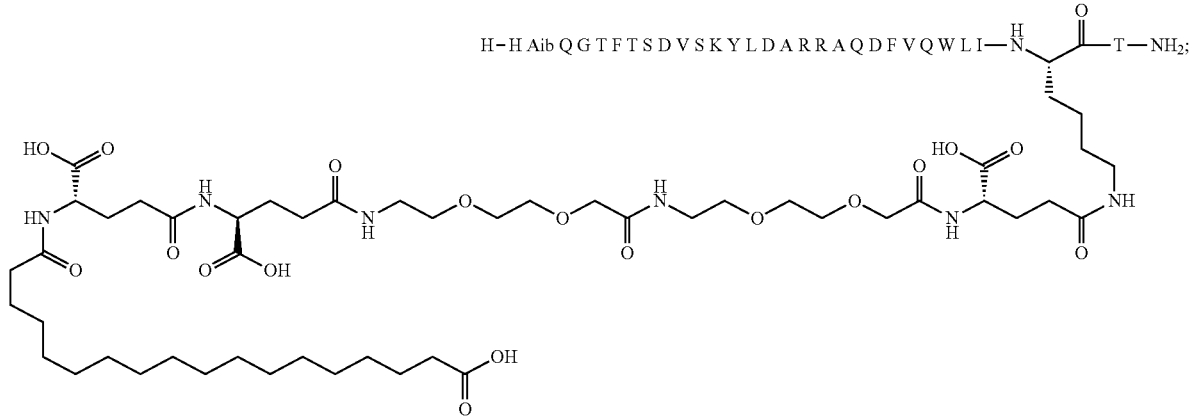

and $N^{\varepsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Val16,Ile27,Lys28]-Glucagon amide Chem 40 (SEQ ID NO: 42):

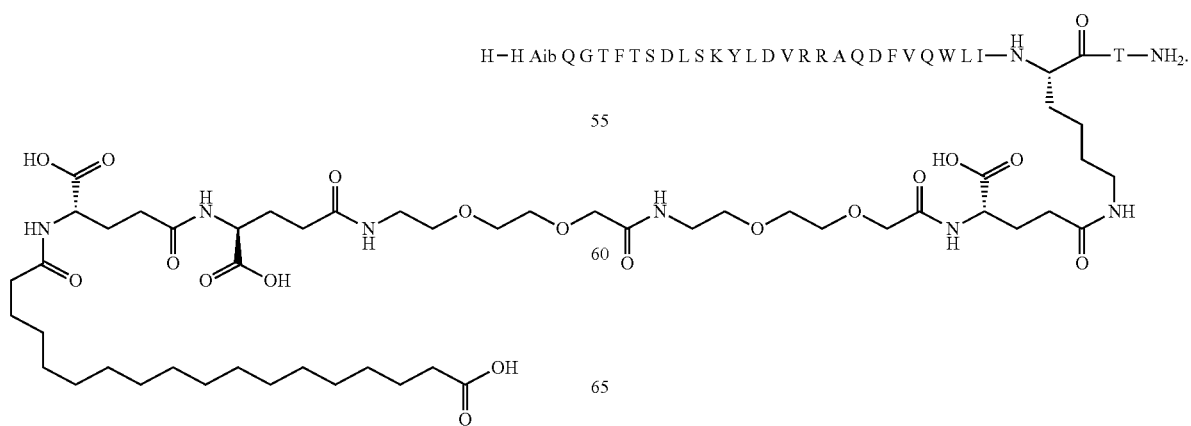

85. The glucagon derivative according to any one of the preceding embodiments, wherein said glucagon derivative is an agonist of the glucagon receptor and an agonist of the GLP-1 receptor.

86. The glucagon derivative according to any one of the preceding embodiments, wherein said glucagon derivative has a ratio between its $EC_{50}$ value on the glucagon receptor and $EC_{50}$ on the GLP-1 receptor in the range of 100 to 250, such as in the range of 50 to 100, in the range of 20 to 50, in the range of 10 to 20, or in the range of 1 to 10.

87. The glucagon derivative according to any one of the preceding embodiments, wherein said glucagon derivative has a ratio between its $EC_{50}$ value on the glucagon receptor and $EC_{50}$ on the GLP-1 receptor in the range of 50 to 100.

88. The glucagon derivative according to any one of the preceding embodiments, wherein said glucagon derivative has a ratio between its $EC_{50}$ value on the glucagon receptor and $EC_{50}$ on the GLP-1 receptor in the range of 20 to 50.

89. The glucagon derivative according to any one of the preceding embodiments, wherein said glucagon derivative has a ratio between its $EC_{50}$ value on the glucagon receptor and $EC_{50}$ on the GLP-1 receptor in the range of 10 to 20.

90. The glucagon derivative according to any one of the preceding embodiments, wherein said glucagon derivative has a ratio between its $EC_{50}$ value on the glucagon receptor and $EC_{50}$ on the GLP-1 receptor in the range of 1 to 10.

91. The glucagon derivative according to any one of the preceding embodiments, wherein said glucagon derivative has a ratio between its $EC_{50}$ value on the glucagon receptor and $EC_{50}$ on the GLP-1 receptor in the range of 1 to 10.

92. The glucagon derivative according to any one of the preceding embodiments, wherein said glucagon derivative has an $EC_{50}<10$ nM on the glucagon receptor.

93. The glucagon derivative according to any one of the preceding embodiments, wherein said glucagon derivative has an $EC_{50}<1$ nM on the glucagon receptor.

94. The glucagon derivative according to any one of the preceding embodiments, wherein said glucagon derivative has an $EC_{50}<100$ μM on the glucagon receptor.

95. The glucagon derivative according to any one of the preceding embodiments, wherein said glucagon derivative has an $EC_{50}<10$ μM on the glucagon receptor.

96. The glucagon derivative according to any one of the preceding embodiments, wherein said glucagon derivative has an $EC_{50}<100$ μM on the GLP-1 receptor.

97. The glucagon derivative according to any one of the preceding embodiments, wherein said glucagon derivative has an $EC_{50}<50$ μM on the GLP-1 receptor.

98. The glucagon derivative according to any one of the preceding embodiments, wherein said glucagon derivative has an $EC_{50}<10$ μM on the GLP-1 receptor.

99. The glucagon derivative according to any one of the preceding embodiments, wherein said glucagon derivative has a lower $EC_{50}$ value on the GLP-1 receptor than on the glucagon receptor.

100. The glucagon derivative according to any one of the preceding embodiments, wherein said $EC_{50}$ on the GLP-1 receptor is determined according to Assay (I)(a) described herein.

101. The glucagon derivative according to any one of the preceding embodiments, wherein said $EC_{50}$ on the glucagon receptor is determined according to Assay (I)(b) described herein.

102. The glucagon derivative according to any one of the preceding embodiments, wherein said glucagon derivative has more than 70% recovery in the ThT fibrillation assay.

103. The glucagon derivative according to any one of the preceding embodiments, wherein said glucagon derivative has more than 90% recovery in the ThT fibrillation assay.

104. The glucagon derivative according to any one of the preceding embodiments, wherein said glucagon derivative has about 100% recovery in the ThT fibrillation assay.

105. The glucagon derivative according to any one of the preceding embodiments, wherein said glucagon derivative has more than 7 hours lag time in the ThT fibrillation assay.

106. The glucagon derivative according to any one of the preceding embodiments, wherein said glucagon derivative has more than 20 hours lag time in the ThT fibrillation assay.

107. The glucagon derivative according to any one of the preceding embodiments, wherein said glucagon derivative has 45 hours lag time or more in the ThT fibrillation assay.

108. The glucagon derivative according to any one of the preceding embodiments, wherein said ThT fibrillation assay is Assay (Ill) described herein.

109. The glucagon derivative according to any one of the preceding embodiments, wherein said glucagon derivative has less than 14% degradation in the chemical stability assay.

110. The glucagon derivative according to any one of the preceding embodiments, wherein said glucagon derivative has less than 13% degradation in the chemical stability assay.

111. The glucagon derivative according to any one of the preceding embodiments, wherein said glucagon derivative has less than 12% degradation in the chemical stability assay.

112. The glucagon derivative according to any one of the preceding embodiments, wherein said glucagon derivative has less than 10% degradation in the chemical stability assay.

113. The glucagon derivative according to any one of the preceding embodiments, wherein said glucagon derivative has less than 9% degradation in the chemical stability assay.

114. The glucagon derivative according to any one of the preceding embodiments, wherein said glucagon derivative has less than 7% degradation in the chemical stability assay.

115. The glucagon derivative according to any one of the preceding embodiments, wherein said glucagon derivative has less than 5% degradation in the chemical stability assay.

116. The glucagon derivative according to any one of the preceding embodiments, wherein said glucagon derivative has less than 3% degradation in the chemical stability assay.

117. The glucagon derivative according to any one of the preceding embodiments, wherein said glucagon derivative has less than 2% degradation in the chemical stability assay.

118. The glucagon derivative according to any one of the preceding embodiments, wherein said chemical stability assay is Assay (V) described herein.

119. The glucagon derivative according to any one of the preceding embodiments, wherein said glucagon derivative is a DPPIV protected compound.

120. The glucagon derivative according to any one of the preceding embodiments, wherein said glucagon derivative is a DPPIV stabilised compound.

121. The glucagon derivative according to any one of the preceding embodiments, in combination with one or more additional therapeutically active compounds, such as a GLP-1 compound or with an insulin compound.

122. The glucagon derivative according to any one of the preceding embodiments, in combination with a GLP-1 compound.

123. The glucagon derivative according to any one of the preceding embodiments, in combination with an insulin compound.

124. The glucagon derivative according to any one of the preceding embodiments, wherein the GLP-1 compound is selected from the group consisting of:

N-epsilon26-((S)-4-Carboxy-4-hexadecanoylamino-butyryl)[Arg34]GLP-1-(7-37):

(compound G1)(SEQ ID NO: 43)

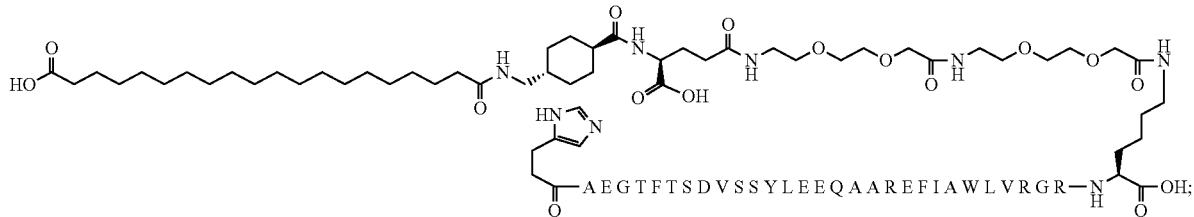

N-epsilon37-[2-(2-{2-[2-(2-{2-[(S)-4-Carboxy-4-({trans-4-[(19-carboxynonadecanoylamino)methyl]cyclohexanecarbonyl}amino) butyrylamino]ethoxy}ethoxy)acetylamino]ethoxy}ethoxy)acetyl][DesaminoHis7,Glu22,Arg26,Arg34,Lys37]GLP-1-(7-37):

(compound G2)

N-epsilon26-[2-(2-{2-[2-(2-{2-[(S)-4-Carboxy-4-(17-carboxyheptadecanoylamino) butyrylamino]ethoxy}ethoxy)acetylamino]ethoxy}ethoxy)acetyl][Aib 8,Arg34]GLP-1-(7-37):

(compound G3)(SEQ ID NO: 45)

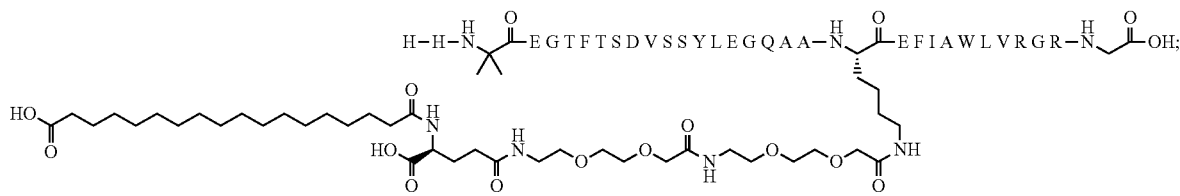

N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35,Lys37]GLP-1-(7-37):

(compound G4)(SEQ ID NO: 46)

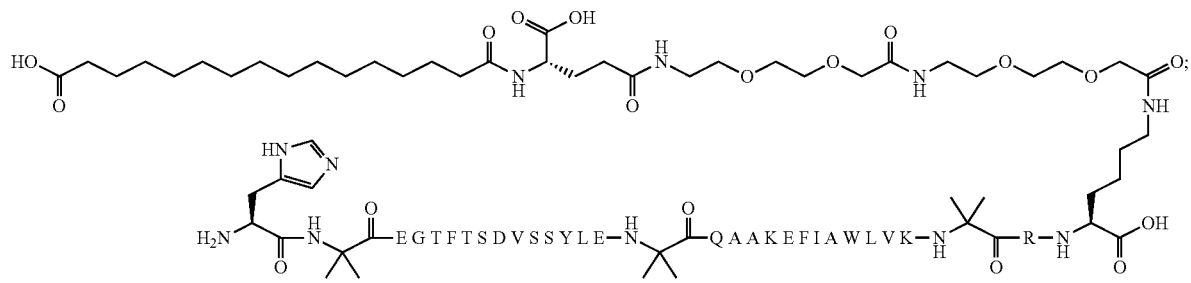

and their pharmaceutically acceptable salts, amides, alkyls or esters.

125. The glucagon derivative according any one of the preceding embodiments, wherein the insulin compound is: N-epsilon-B29-[(S)-4-Carboxy-4-(15-carboxypentadecanoylamino)butyryl] desB30 human insulin (compound G5)(SEQ ID NO: 47)(SEQ ID NO: 48)

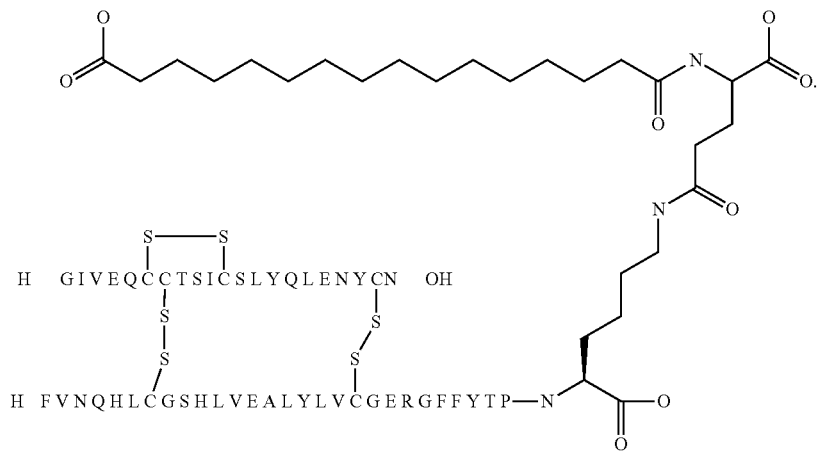

126. A pharmaceutical composition comprising the glucagon derivative as defined in any one of the preceding embodiments and one or more pharmaceutically acceptable excipients.

127. The pharmaceutical composition as defined in any one of the preceding embodiments, further comprising one or more additional therapeutically active compounds or substances.

128. The pharmaceutical composition as defined in any one of the preceding embodiments, wherein said additional therapeutically active compound is a GLP-1 compound or an insulin compound.

129. The pharmaceutical composition as defined in any one of the preceding embodiments, wherein said additional therapeutically active compound is a GLP-1 compound.

130. The pharmaceutical composition as defined in any one of the preceding embodiments, wherein said additional therapeutically active compound is an insulin compound.

131. The pharmaceutical composition as defined in any one of the preceding embodiments, wherein the GLP-1 compound is selected from the group consisting of:

N-epsilon26-((S)-4-Carboxy-4-hexadecanoylamino-butyryl)[Arg34]GLP-1-(7-37)
(Compound G1)(SEQ ID NO: 43):

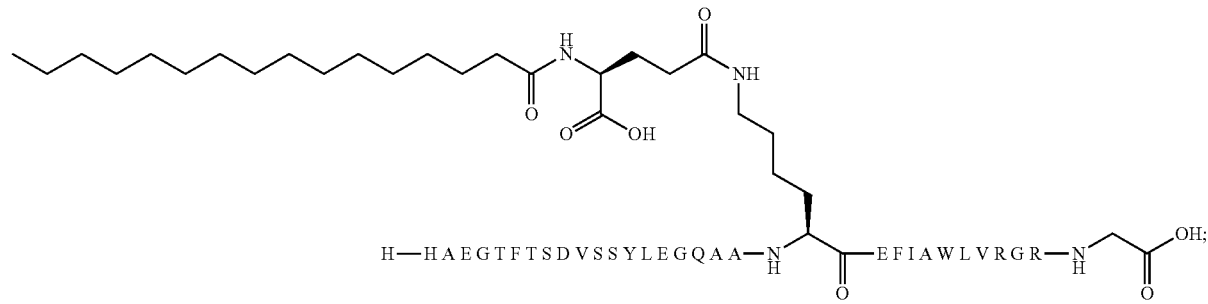

N-epsilon37-[2-(2-{2-[2-(2-{2-[(S)-4-Carboxy-4-({trans-4-[(19-carboxynonadecanoylamino)methyl]cyclohexanecarbonyl}amino) butyrylamino]ethoxy}ethoxy) acetylamino]ethoxy}ethoxy)acetyl][DesaminoHis7,Glu22,Arg26,Arg34,Lys37]GLP-1-(7-37)
(Compound G2)(SEQ ID NO: 44):

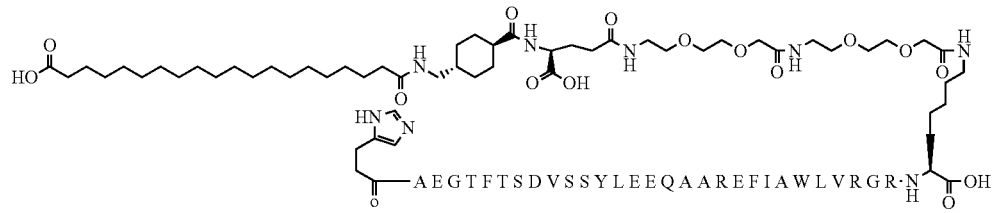

N-epsilon26-[2-(2-{2-[2-(2-{2-[(S)-4-Carboxy-4-(17-carboxyheptadecanoylamino) butyrylamino]ethoxy}ethoxy) acetylamino]ethoxy}ethoxy)acetyl][Aib 8,Arg34]GLP-1-(7-37)
(Compound G3)(SEQ ID NO: 45):

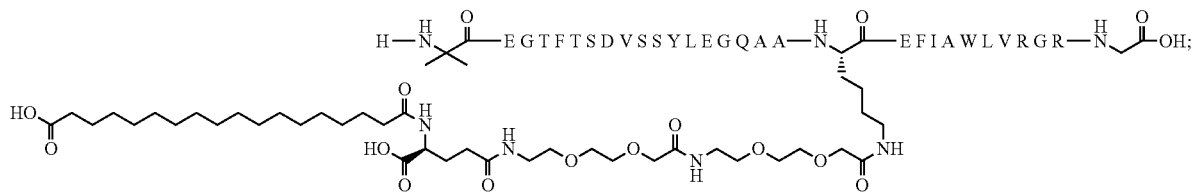

and
N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35, Lys37]GLP-1-(7-37)

(Compound G4)(SEQ ID NO: 46):

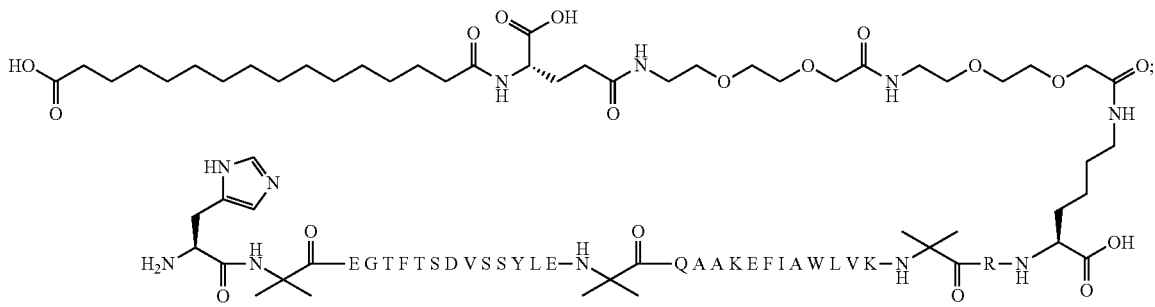

and their pharmaceutically acceptable salts, amides, alkyls or esters.

132. The pharmaceutical composition as defined in any one of the preceding embodiments, wherein the insulin compound is N-epsilon-B29-[(S)-4-Carboxy-4-(15-carboxypentadecanoylamino)butyryl] desB30 human insulin (Compound G5)(SEQ ID NO: 47)(SEQ ID NO: 48):

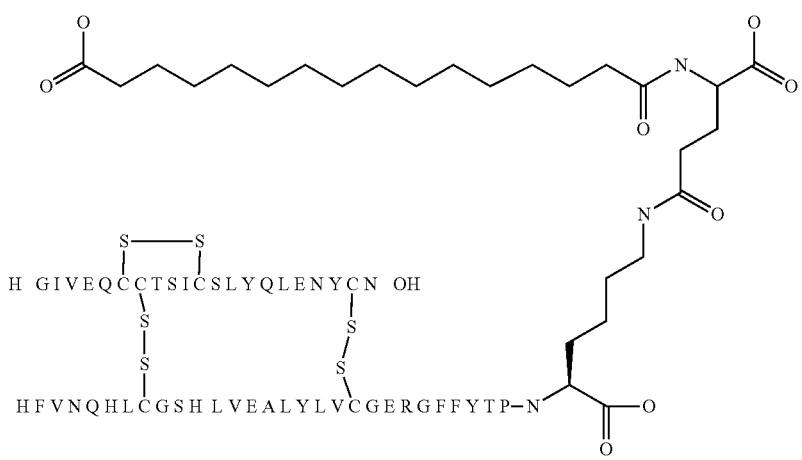

133. The pharmaceutical composition as defined in any one of the preceding embodiments, in unit dosage form comprising from about 0.01 mg to about 1000 mg, such as from about 0.1 mg to about 500 mg, from about 0.5 mg to about 5 mg, e.g. from about 0.5 mg to about 200 mg, of a glucagon derivative as defined in any one of the preceding embodiments.

134. The pharmaceutical composition as defined in any one of the preceding embodiments, which is suited for parenteral administration.

135. The glucagon derivative as defined in any one of the preceding embodiments, optionally in combination with one or more additional therapeutically active compounds, for use in medicine.

136. The glucagon derivative as defined in any one of the preceding embodiments for use in the treatment or prevention of obesity, hyperglycaemia, type 2 diabetes, impaired glucose tolerance, and/or type 1 diabetes.

137. The glucagon derivative as defined in any one of the preceding embodiments for use in the treatment or prevention of obesity.

138. The glucagon derivative as defined in any one of the preceding embodiments for use in the treatment or prevention of hyperglycaemia, type 2 diabetes, impaired glucose tolerance, and/or type 1 diabetes.

139. The glucagon derivative as defined in any one of the preceding embodiments for use in the treatment or prevention of obesity or preventing overweight, decreasing food intake, increasing energy expenditure, regulating appetite, inducing satiety, preventing weight regain after successful weight loss, treating a disease or state related to overweight or obesity, treating bulimia, and/or treating binge-eating.

140. The glucagon derivative as defined in any one of the preceding embodiments for use in the treatment or prevention of type 2 diabetes, treating impaired glucose tolerance, delaying or preventing disease progression in type 2 diabetes, delaying the progression from impaired glucose tolerance (IGT) to type 2 diabetes, and/or delaying the progression from type 2 diabetes to insulin-requiring diabetes.

141. The glucagon derivative as defined in any one of the preceding embodiments for use in the treatment or prevention of atherosclerosis, hypertension, dyslipidaemia, coronary heart disease and/or hepatic steatosis.

142. A method for treating obesity or preventing overweight comprising administering to a patient in need thereof, an effective amount of a glucagon derivative as defined in any one of the preceding embodiments, optionally in combination with one or more additional therapeutically active compounds.

143. A method for treating obesity or preventing overweight, decreasing food intake, increasing energy expenditure, reducing body weight, regulating appetite, inducing satiety, preventing weight regain after successful weight loss, treating a disease or state related to overweight or obesity, treating bulimia, and/or treating binge-eating, comprising administering to a patient in need thereof, an effective amount of a glucagon derivative as defined in any one of the preceding embodiments, optionally in combination with one or more additional therapeutically active compounds.

144. A method for the treatment or prevention of type 2 diabetes, impaired glucose tolerance, delaying or preventing disease progression in type 2 diabetes, delaying the progression from impaired glucose tolerance (IGT) to type 2 diabetes, and/or delaying the progression from type 2 diabetes to insulin-requiring diabetes, comprising administering to a patient in need thereof, an effective amount of a glucagon derivative as defined in any one of the preceding embodiments, optionally in combination with one or more additional therapeutically active compounds.

145. A method for the treatment or prevention of atherosclerosis, treating hypertension, treating dyslipidaemia, treating coronary heart disease, and/or treating hepatic steatosis, comprising administering to a patient in need thereof, an effective amount of a glucagon derivative as defined in any one of the preceding embodiments, optionally in combination with one or more additional therapeutically active compounds.

146. Use of a glucagon derivative as defined in any one of the preceding embodiments for the preparation of a medicament.

147. Use of a glucagon derivative as defined in any one of the preceding embodiments, for the preparation of a medicament for the treatment or prevention of obesity, hyperglycaemia, type 2 diabetes, impaired glucose tolerance, and type 1 diabetes.

EXAMPLES

The invention is further illustrated with reference to the following examples, which are not intended to be in any way limiting to the scope of the invention as claimed.

List of Abbreviations
  BOC: tert-Butyl oxycarbonyl
  DCM: Dichloromethane
  DIC: Diisopropylcarbodiimide
  Fmoc: 9-fluorenylmethyloxycarbonyl
  HOAt: 1-hydroxy-7-azabenzotriazole
  HPLC: High Performance Liquid Chromatography
  LCMS: Liquid Chromatography Mass Spectroscopy
  MeCN: Acetonitrile
  Mtt: 4-Methyltrityl
  NMP: N-methyl pyrrolidone
  Oxyma Pure: Cyano-hydroxyimino-acetic acid ethyl ester
  RP: Reverse Phase
  RP-HPLC: Reverse Phase High Performance Liquid Chromatography
  RT: Room Temperature
  Rt: Retention time
  SPPS: Solid Phase Peptide Synthesis
  TFA: Trifluoroacetic acid
  TIPS: Triisopropylsilane
  UPLC: Ultra Performance Liquid Chromatography
  10EE: 10 to the power (e.g. "10EE(X)" refers to the number 10 to the power (X), or simply the number $10^{(X)}$, i.e. $5 \times 10EE3$ is $5 \times 10^3$)

General Methods

This section relates to methods for synthesising resin bound peptide (SPPS methods, including methods for de-protection of amino acids, methods for cleaving the peptide from the resin, and for its purification), as well as methods for detecting and characterising the resulting peptide (LCMS and UPLC methods).

SPPS General Methods

The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)—OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)—OH, Fmoc-Tyr(tBu)-OH, Fmoc-Val-OH and Fmoc-Lys(Mtt)-OH supplied from e.g. Anaspec, Bachem, Iris Biotech or NovabioChem.

SPPS were performed using Fmoc based chemistry on a Prelude Solid Phase Peptide Synthesizer from Protein Technologies (Tucson, Ariz. 85714 U.S.A.). A suitable resin for the preparation of C-terminal peptide amides is H-Rink Amide-ChemMatrix resin (loading e.g. 0.52 nmol/g) or Rink Amide AM polystyrene resin (Novabiochem: loading eg 0.62 mmol/g) or the like. The N-terminal alpha amino group was protected with Boc.

Fmoc-deprotection was achieved with 20% piperidine in NMP. Peptide couplings were performed by using either DIC/HOAt/collidine or DIC/Oxyma Pure/collidine without preactivation. Amino acid/HOAt or amino acid/Oxyma Pure solutions (0.3 M/0.3 M in NMP at a molar excess of 3-10 fold) were added to the resin followed by the same molar equivalent of DIC (3 M in NMP) followed by collidine (3 M in NMP). For example, the following amounts of 0.3 M amino acid/HOAt solution can be used per coupling for the following scale reactions: Scale/ml, 0.05 mmol/1.5 mL, 0.10 mmol/3.0 mL, 0.25 mmol/7.5 mL. The Mtt group is removed by washing the resin with HFIP/DCM (75:25) (2×2 min), washed with DCM and suspending the resin in HFIP/DCM (75:25)(2×20 min) and subsequently washed in sequence with Piperidine/NMP (20:80), DCM(1×), NMP(1×), DCM(1×), NMP(1×).

The introduction of a substituent on the epsilon-nitrogen of a lysine is achieved using a Lysine protected with Mtt (Fmoc-Lys(Mtt)-OH). Likewise when the side-chain was present on an ornithine sidechain the delta amino group of the ornithine to be acylated was protected with Mtt (e.g. Fmoc-Orn(Mtt)-OH). Alternatively the epsilon-nitrogen of a lysine could be protected with an ivDde group (Fmoc-Lys(ivDde)-OH). The delta amino group of an ornithine could likewise be protected with an ivDde group (Fmoc-Orn(ivDde)-OH). The incorporation of gamma-Glu moieties in the side-chain were achieved by coupling with the amino acid Fmoc-Glu-OtBu.

Introduction of each moiety in the side-chain can be achieved using prolonged coupling time (1×6 hours) followed by capping with acetic anhydride or alternatively acetic acid/DIC/HOAt/collidine. Acetylation of the terminal nitrogen on the substituent is achieved using acetic anhydride (10 eq.) and collidine (20 eq.) in NMP.

Attachment of the Substituent

The substituent can be introduced in a stepwise procedure by the Prelude peptide synthesizer as described above using suitably protected building blocks, with the modification that the amino acids and fatty acid derivatives including Fmoc-Ado-OH, Fmoc-Glu-OtBu, and octadecanedioic acid mono-tert-butyl ester (or the analogous C8, C10, C12-, C14-C16-, C20-diacid mono tert-butyl esters). After each coupling step, unreacted peptide intermediate can be capped using acetic acid anhydride and collidine in excess (>10 eq.).

Cleavage from the Resin

After synthesis the resin was washed with DCM, and the peptide was cleaved from the resin by a 2-3 hour treatment with TFA/TIS/water (95/2.5/2.5) followed by precipitation with diethylether. The precipitate was washed with diethylether.

Purification and Quantification

The crude peptide is dissolved in a suitable mixture of water and MeCN such as water/MeCN (4:1) and purified by reversed-phase preparative HPLC (Waters Deltaprep 4000 or Gilson) on a column containing C18-silica gel. Elution is performed with an increasing gradient of MeCN in water containing 0.1% TFA. Relevant fractions are checked by analytical HPLC or UPLC. Fractions containing the pure target peptide are mixed and concentrated under reduced pressure. The resulting solution is analyzed (HPLC, LCMS) and the product is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

Methods for Detection and Characterization

LCMS Methods

Method: LCMS01v01

| System | LC-system: Waters Acquity UPLC<br>Column:: Waters Acquity UPLC BEH, C-18, 1.7 μm, 2.1 mm × 50 mm<br>Detector:: Waters (Micromass) LCT Premier XE |
|---|---|
| Detector setup | Ionisation method: ES<br>Scanning range: 500-2000 amu<br>Operating mode: W mode<br>positive/negative: positive mode<br>Cone Voltage: 50 V<br>Scantime 1.0 s |
| Conditions | Linear gradient: 5% to 95% B<br>Gradient run-time: 4.0 minutes<br>Total run-time: 7.0 minutes<br>Flow rate: 0.4 ml/min<br>Column temperature: 40° C. |
| Eluents | Solvent A: 99.90% MQ-water, 0.1% formic acid<br>Solvent B: 99.90% acetonitrile, 0.1% formic acid<br>Solvent C: NA |
| Results specification and validation | Mass found is the mass found of the compound<br>M/z found is the molecular ion found ((M + z)/z) of the compound<br>Calculated Mass is the molecular weight of the desired compound<br>Calculated M/z is the molecular weight (M + z)/z of the desired compound |

Method: LCMS13v01

| System | System: Waters Acquity UPLC SQD 2000<br>Column: Acquity UPLC BEH 1.7 μ C18 100 Å 2.1 × 100 mm<br>Detector: UV: PDA, SQD 2000 |
|---|---|
| Detector setup | Ionisation method: ES+<br>Scanning range: 500-2000<br>Cone Voltage: 60 V<br>Scantime 0.5 s |
| Conditions | Linear gradient: 10% to 90% B<br>Gradient run-time: 3 min<br>Total run-time: 4 min<br>low rate: 0.3 ml/min<br>Column temperature: 40° C.<br>PDA: 210-400 nm |
| Eluents | Solvent A: 99.90% H2O, 0.1% TFA<br>Solvent B: 99.90% CH3CN, 0.1% TFA<br>Solvent C: NA |
| Results specification and validation | Mass found is the mass found of the compound<br>M/z found is the molecular ion found ((M + z)/z) of the compound<br>Calculated Mass is the molecular weight of the desired compound<br>Calculated M/z is the molecular weight (M + z)/z of the desired compound |

UPLC Methods

Method: UPLC01v01

| System | System: Waters Acquity UPLC system<br>Column: ACQUITY UPLC BEH C18, 1.7 um, 2.1 mm × 150 mm column<br>Detectors: Waters Acquity TUV Detector |
|---|---|
| Detector setup | 214 nm and 254 nm |
| Conditions | Linear gradient: 5% to 60% B<br>Gradient run-time: 16 minutes<br>Total run-time: 20 minutes<br>Flow rate: 0.40 ml/min fixed<br>Column temperature: 40° C. |
| Eluents | Solvent A: 99.95% Water, 0.05% Trifluoroacetic acid<br>Solvent B: 99.95% Acetonitrile, 0.05% Trifluoroacetic acid |

Method: UPLC2v01

| System | System: Waters Acquity UPLC system<br>Column: ACQUITY UPLC BEH C18, 1.7 um, 2.1 mm × 150 mm column<br>Detectors: Waters Acquity TUV Detector |
|---|---|
| Detector setup | 214 nm and 254 nm |
| Conditions | Linear gradient: 5% to 95% B<br>Gradient run-time: 16 minutes<br>Flow rate: 0.40 ml/min fixed<br>Column temperature: 40° C. |
| Eluents | Solvent A: 99.95% Water, 0.05% Trifluoroacetic acid<br>Solvent B: 99.95% Acetonitrile, 0.05% Trifluoroacetic acid |

Example 1

N^ε24-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Ala16,Arg20,Lys24,Ile27,Ser28]-Glucagon amide Chem. 1 (SEQ ID NO: 3):

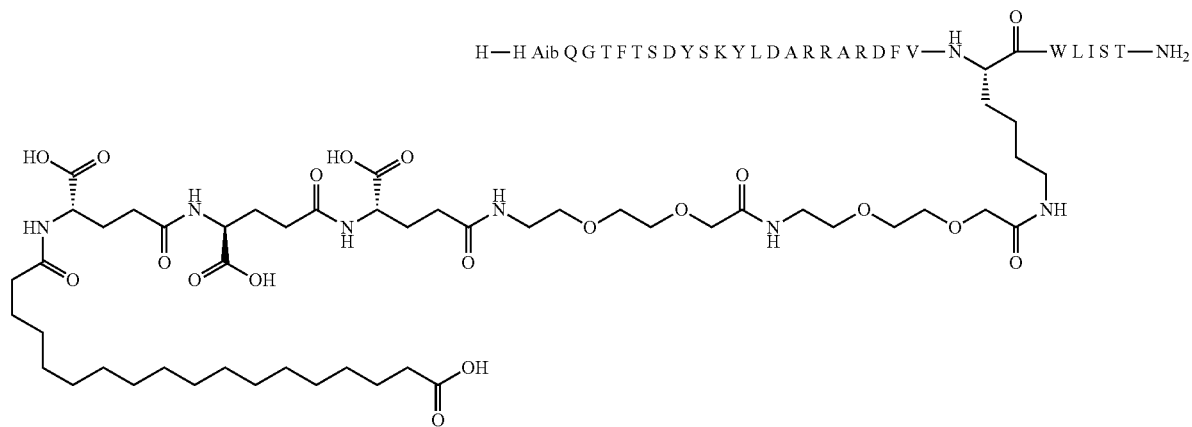

UPLC02v01: Rt=8.0 min
LCMS13v01: RT=2.2 min; m/3=1474; m/4=1106

Example 2

N^ε24-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Ala16,Lys17,Arg20,Glu21,Lys24,Ile27,Ser28]-Glucagon amide Chem. 2 (SEQ ID NO: 4):

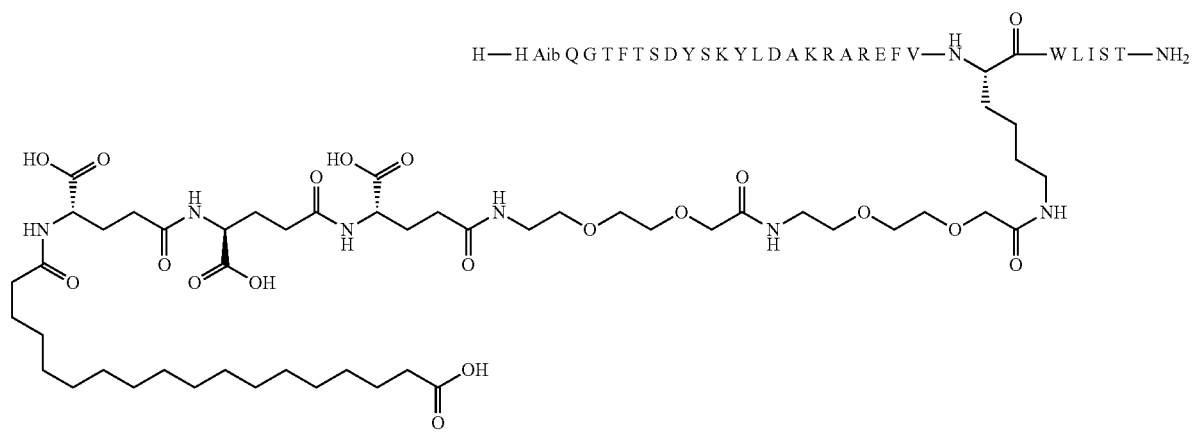

UPLC02v01: Rt=7.9 min
LCMS13v01: Rt=2.2 min; m/3=1469.6; m/4=1102.8

Example 3

$N^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Glu15,Arg20,Ile27,Lys28]-Glucagon amide Chem. 3 (SEQ ID NO: 5):

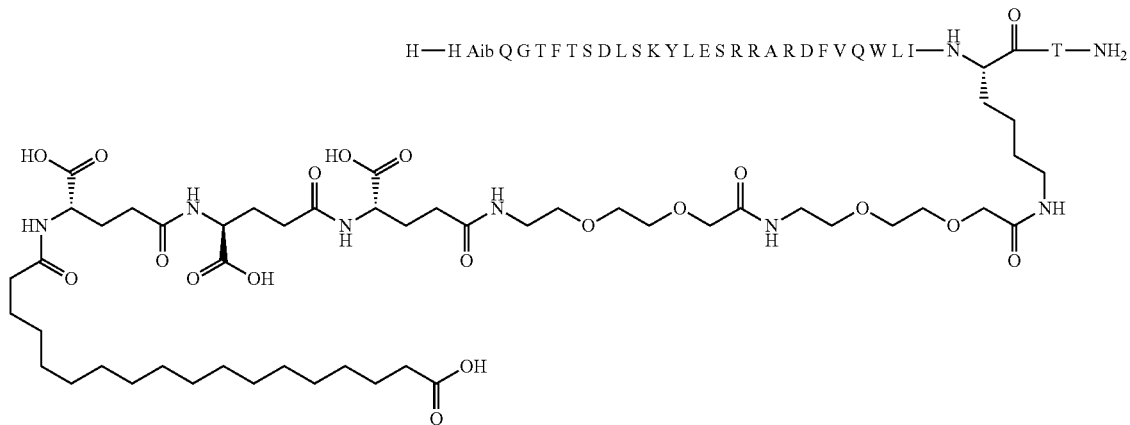

UPLC02v01: Rt=8.0 min
LCMS13v01: Rt=2.2 min; m/3=1481; m/4=1111

Example 4

$N^{\varepsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Ala16,Arg20,Glu21,Lys24,Ile27,Ser28]-Glucagon amide Chem. 4 (SEQ ID NO: 6):

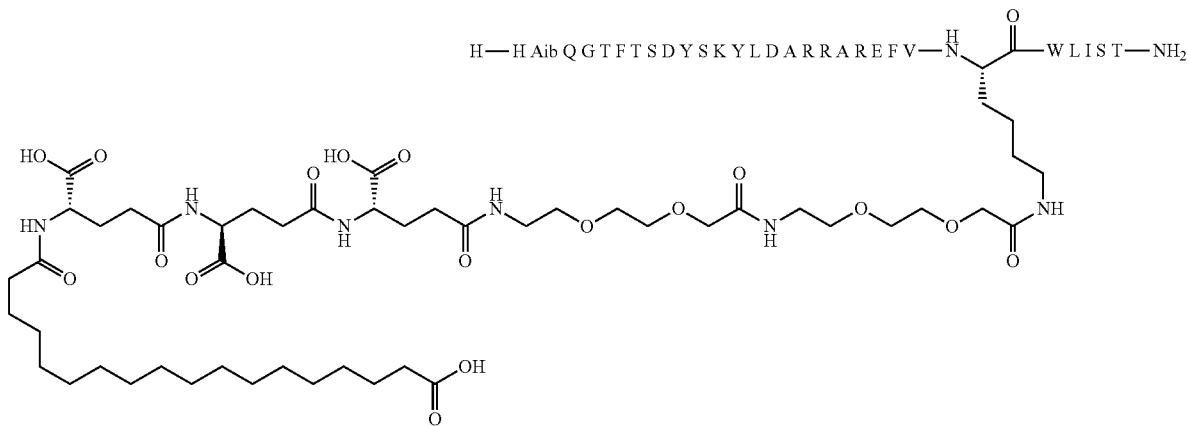

UPLC02v01: Rt=7.9 min
LCMS13v01: Rt=2.2 min; m/3=1479; m/4=1109

Example 5

N^ε28-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Arg20,Ile27,Lys28]-Glucagon amide Chem. 5 (SEQ ID NO: 7):

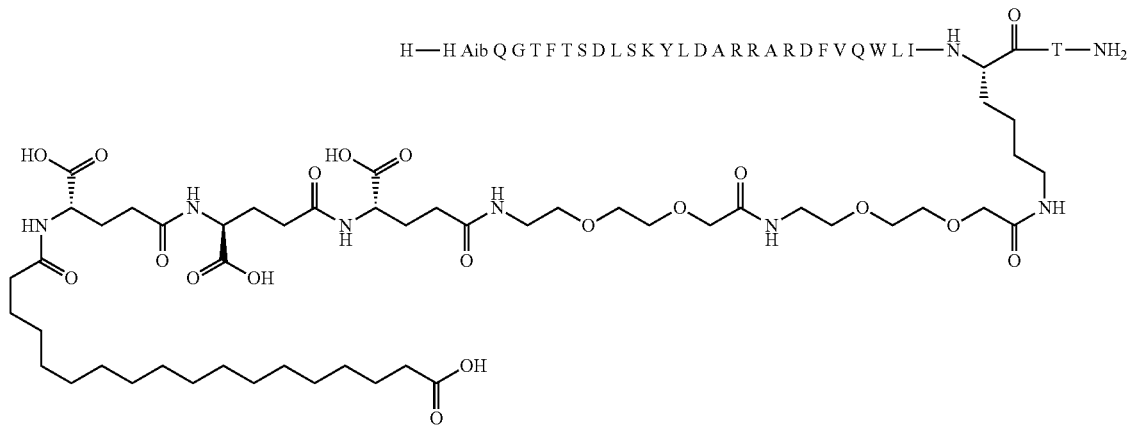

UPLC02v01: Rt=8.4 min
LCMS13v01: Rt=2.2 min; m/3=1471; m/4=1104

Example 6

N^ε28-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Arg20,Glu21,Ile27,Lys28]-Glucagon amide Chem. 6 (SEQ ID NO: 8):

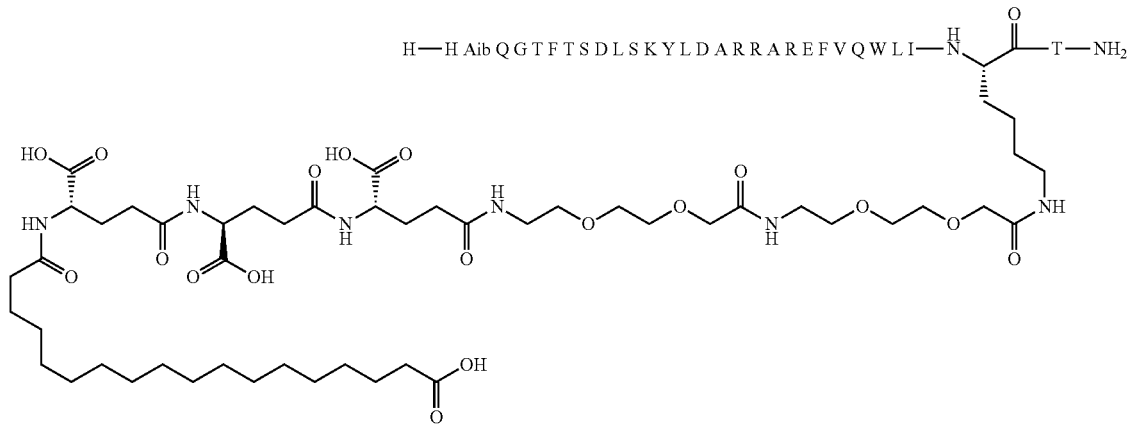

UPLC02v01: Rt=8.4 min
LCMS13v01: Rt=2.1 min; m/3=1476; m/4=1107

Example 7

N$^{\varepsilon 28}$-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Ile27,Lys28]-Glucagon amide Chem. 7 (SEQ ID NO: 9):

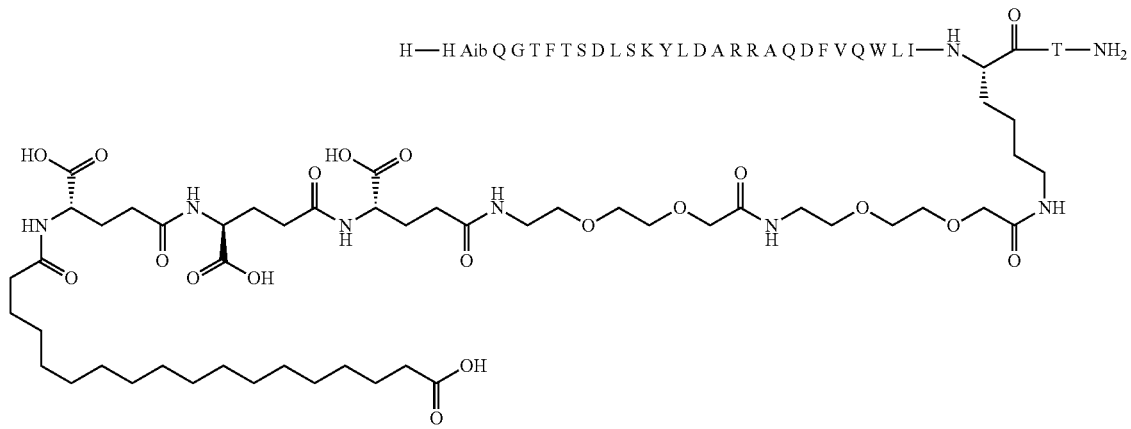

UPLC02v01: Rt=8.6 min
LCMS13v01: Rt=2.2 min; m/3=1462; m/4=1097

Example 8

N$^{\varepsilon 28}$-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Glu15,Ile27,Lys28]-Glucagon amide Chem. 8 (SEQ ID NO: 10):

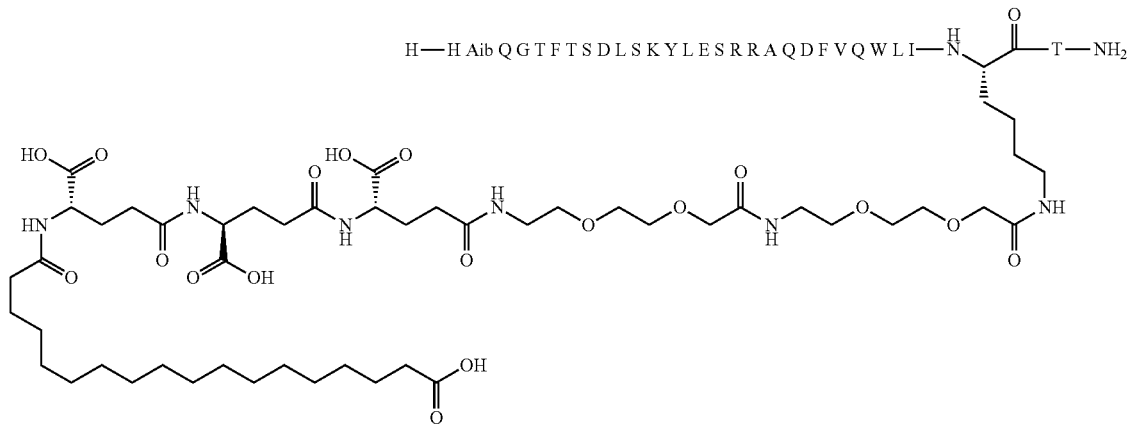

UPLC02v01: Rt=8.4 min
LCMS13v01: Rt=2.2 min; m/3=1472; m/4=1104

Example 9

$N^{\varepsilon 28}$-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Leu16,Ile27,Lys28]-Glucagon amide Chem. 9 (SEQ ID NO: 11):

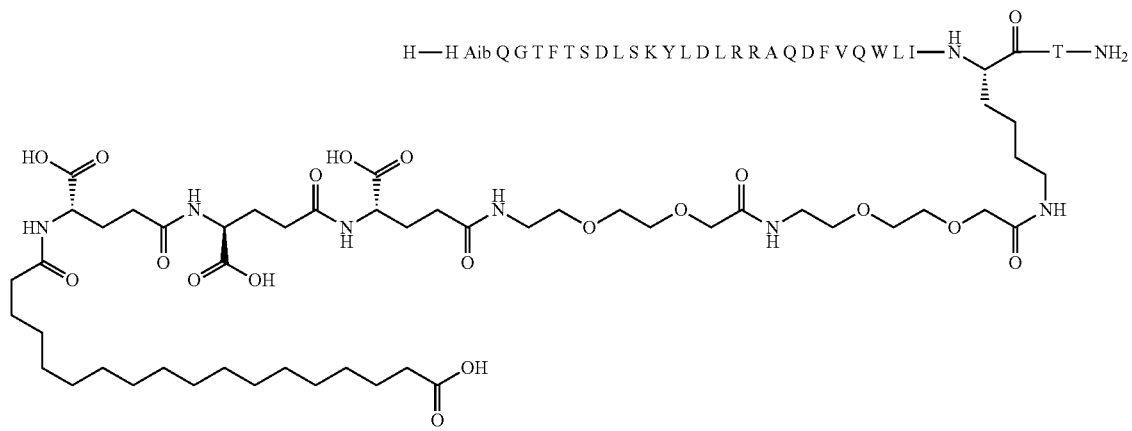

UPLC02v01: Rt=8.6 min
LCMS13v01: Rt=2.2 min; m/3=1476; m/4=1107

Example 10

$N^{\varepsilon 28}$-[2-[2-[2-[[2-[2-[2-[[(4S)-4-carboxy-4-[[(4S)-4-carboxy-4-[[(4S)-4- carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Val10,Glu15,Ile27,Lys28]-Glucagon amide Chem. 10 (SEQ ID NO: 12):

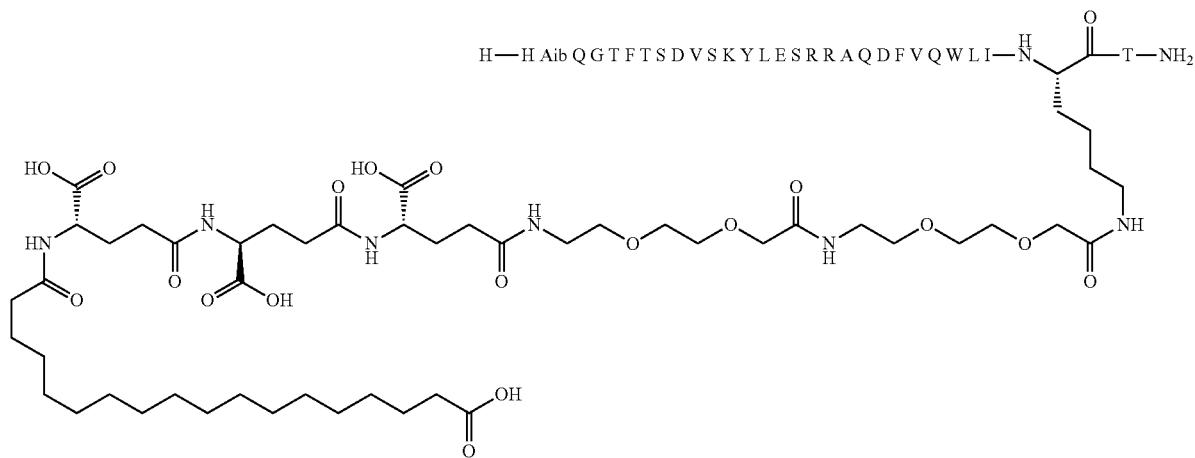

UPLC02v01: Rt=8.5 min
LCMS13v01: Rt=2.2 min; m/3=1467; m/4=1101

Example 11

$N^{\epsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Glu15,Arg20,Lys24,Ile27,Ser28]-Glucagon amide Chem. 11 (SEQ ID NO: 13):

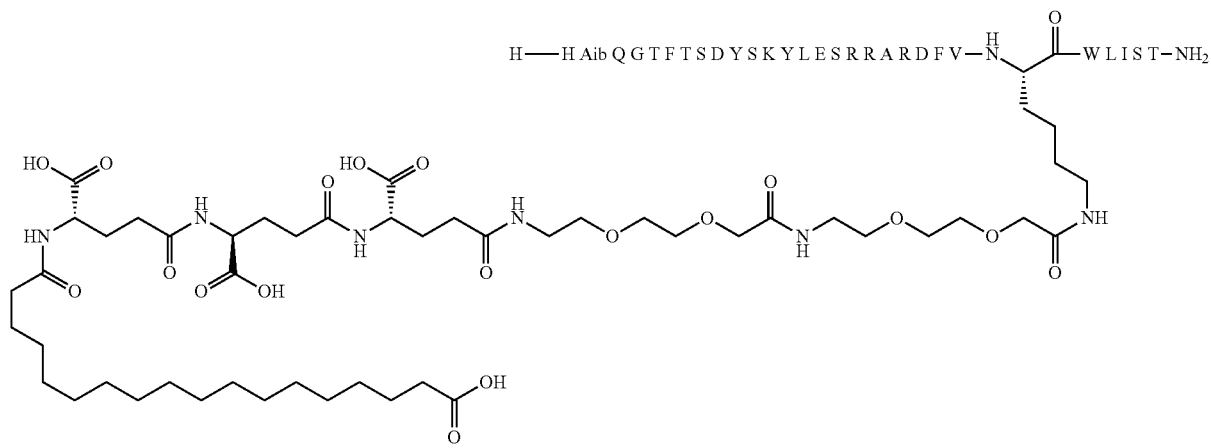

UPLC02v01: RT=8.1 min
LCMS13v01: Rt=2.1 min; m/3=1484; m/4=1114

Example 12

$N^{\epsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu16,Arg20,Lys24,Ile27,Ser28]-Glucagon amide Chem. 12 (SEQ ID NO: 14):

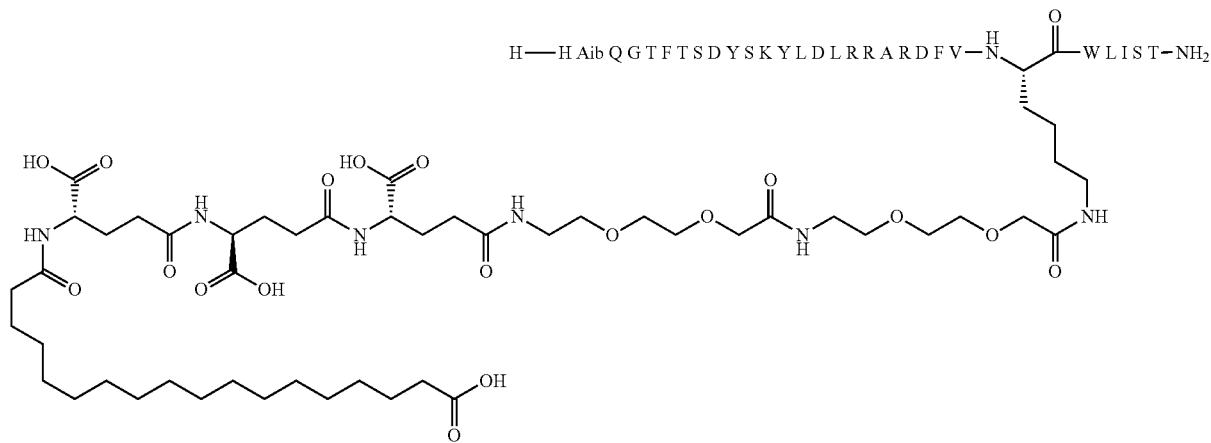

UPLC02v01: Rt=8.4 min
LCMS13v01: Rt=2.2 min; m/3=1488; m/4=1117
Example 13
N^ε28-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Ile27,Lys28]-Glucagon amide
Chem. 13 (SEQ ID NO: 15):
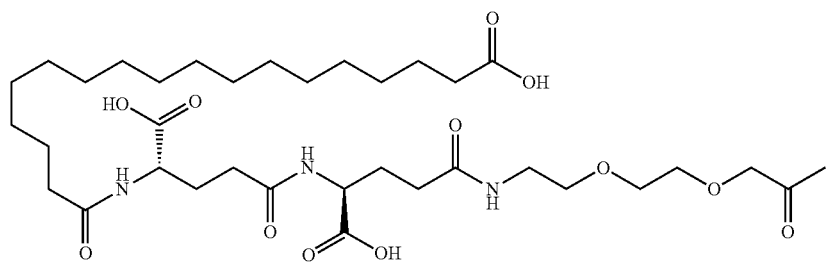
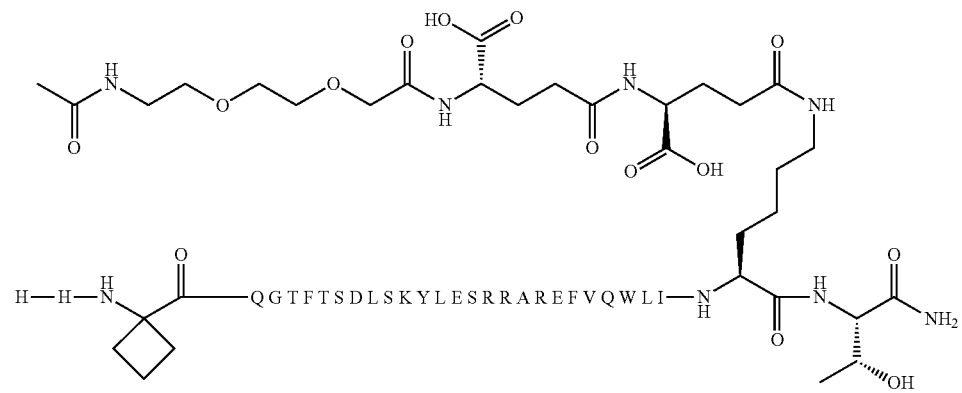

UPLC02v01: Rt=8.1 min
LCMS01v01: Rt=2.1 min; m/4=1150; m/5=920; m/5=767

Example 14

N^{ε28}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Arg12,Ala16,Arg20,Ile27,Lys28]-Glucagon amide Chem. 14 (SEQ ID NO: 16):

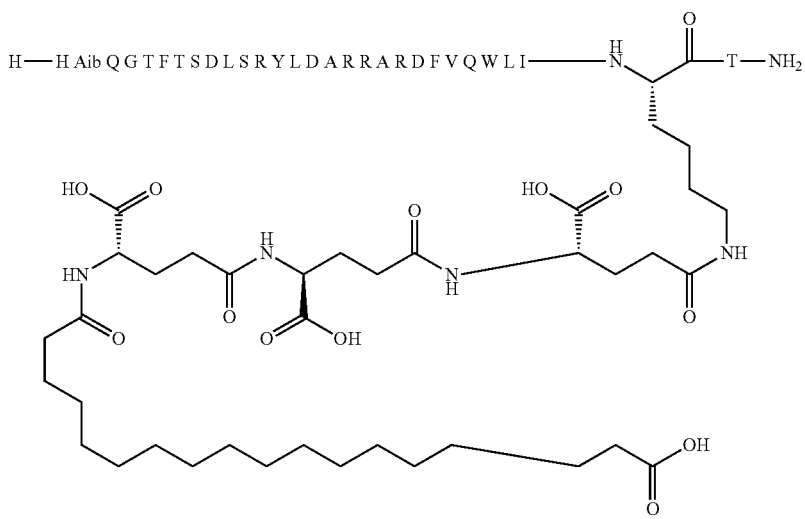

UPLC02v01: Rt=8.1 min
LCMS13v01: Rt=2.2 min; m/3=1384; m/4=1038

Example 15

N^{ε28}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Ala16,Arg20,Ile27,Lys28]-Glucagon amide Chem. 15 (SEQ ID NO: 17):

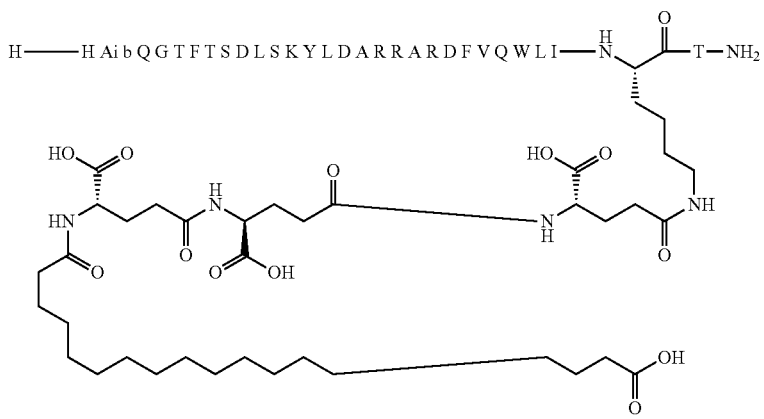

UPLC02v01: Rt=8.1 min
LCMS13v01: Rt=2.3 min; m/3=1374; m/4=1031

Example 16

$N^{\varepsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15,Arg20,Glu21,Ile27,Lys28]-Glucagon amide Chem. 16 (SEQ ID NO: 18):

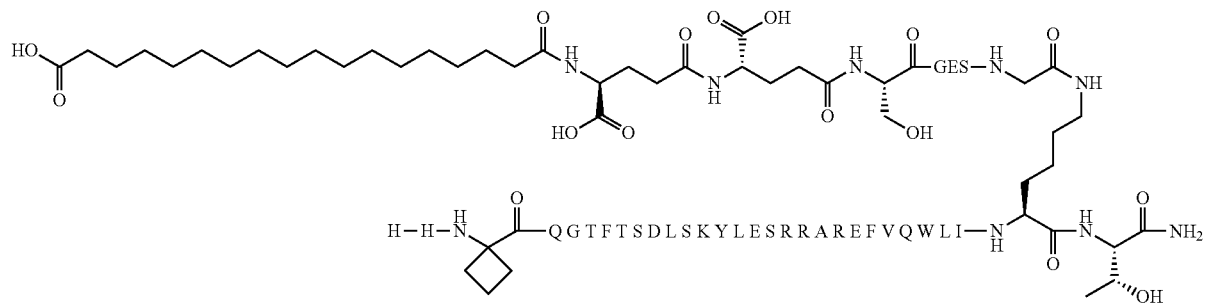

UPLC02v01: Rt=7.9 min
LCMS01v01: Rt=2.0 min; m/3=1490; m/4=1117; m/5=894

Example 17

$N^{\varepsilon 28}$-[(4S)-4-carboxy-4-[[(4S)-4-carboxy-4-[[2-[2[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Glu15,Arg20,Glu21,Ile27,Lys28]-Glucagon amide Chem. 17 (SEQ ID NO: 19):

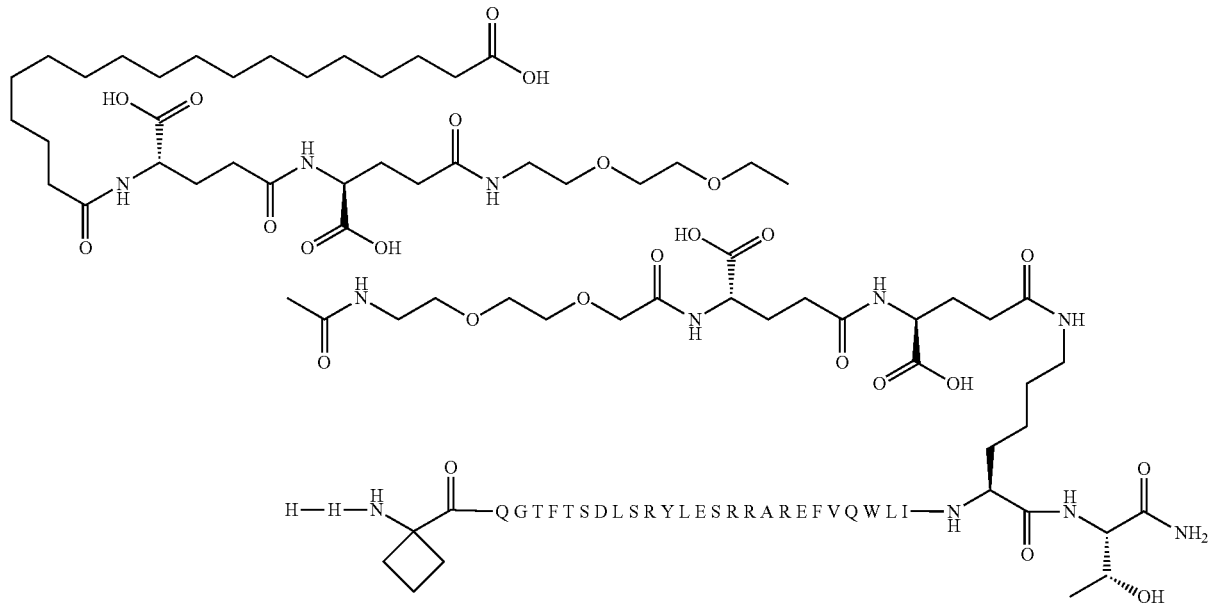

UPLC02v01: Rt=8.0 min
LCMS01v01: Rt=2.1 min; m/3=1542; m/4=1157; m/5=926

Example 18

N^ε28-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Acb2,Leu10,Glu15,Arg20,Glu21,Ile27,Lys28]-Glucagon amide Chem. 18 (SEQ ID NO: 20):

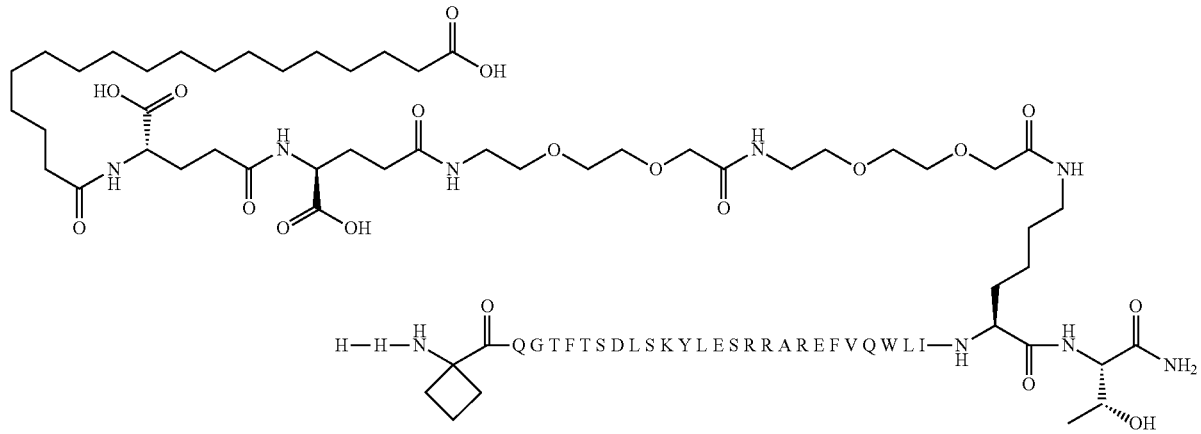

UPLC02v01: Rt=8.1 min
LCMS01v01: Rt=2.0 min; m/3=1447; m/4=1086; m/5=869

Example 19

N^ε28-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Val10,Glu15,Arg20,Glu21,Ile27,Lys28]-Glucagon amide Chem. 19 (SEQ ID NO: 21):

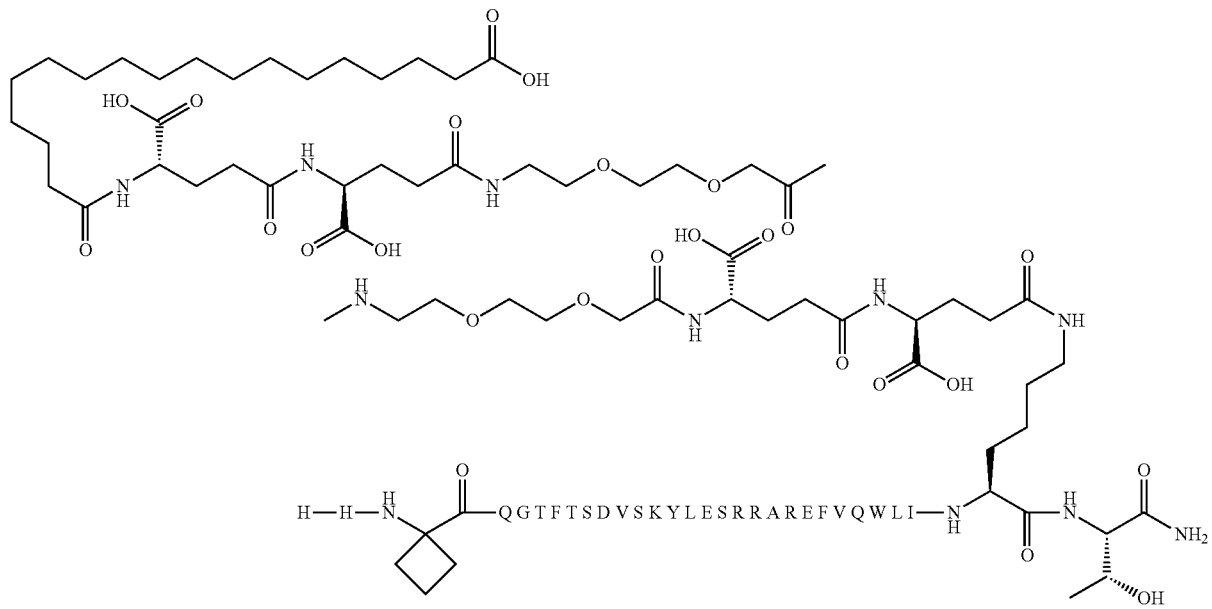

UPLC02v01: Rt=7.9 min
LCMS01v01: Rt=2.0 min; m/3=1528; m/4=1147; m/5=917

Example 20

N$^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Lys29]-Glucagon amide Chem. 20 (SEQ ID NO: 22):

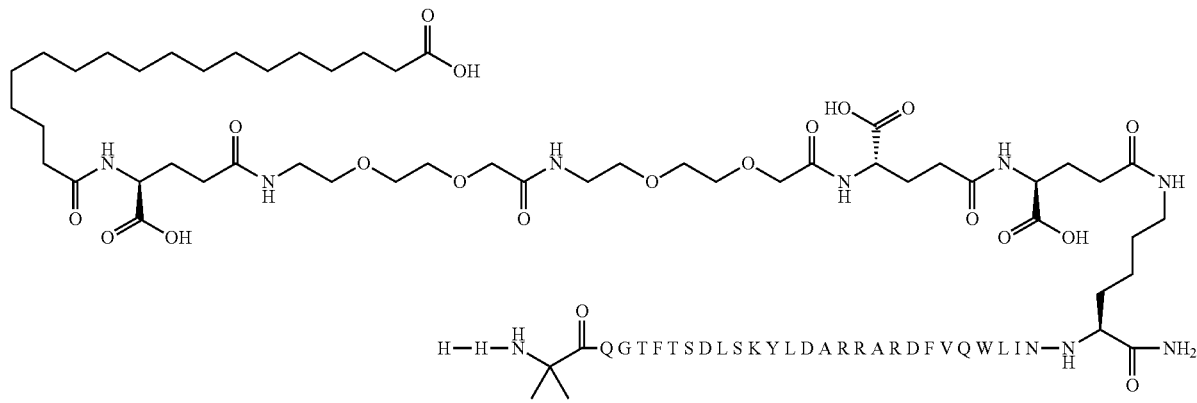

UPLC02v01: Rt=8.0 min
LCMS01v01: Rt=2.2 min; m/3=1476; m/4=1107; m/5=886

Example 21

N$^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Lys29]-Glucagon amide Chem. 21 (SEQ ID NO: 23):

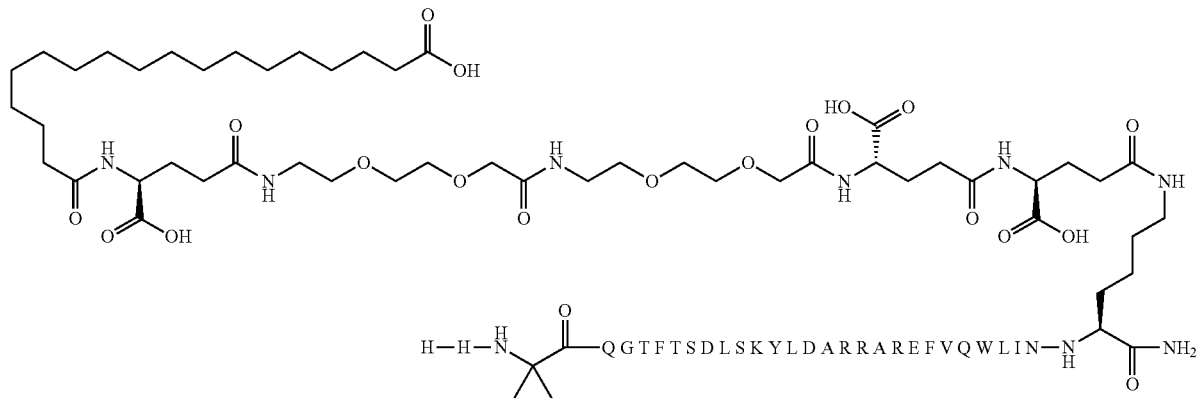

UPLC02v01: Rt=8.0 min
LCMS01v01: Rt=2.1 min; m/3=1480; m/4=1111; m/5=889

Example 22

$N^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Lys29]-Glucagon amide Chem. 22 (SEQ ID NO: 24):

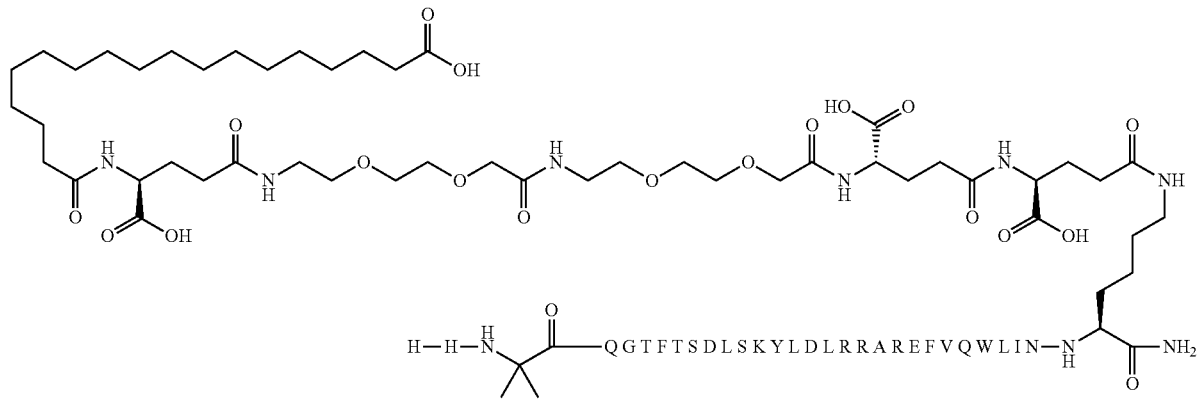

UPLC02v01: Rt=8.3 min
LCMS01v01: Rt=2.2 min; m/3=1494; m/4=1121; m/5=897

Example 23

$N^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Lys29]-Glucagon amide Chem. 23 (SEQ ID NO: 25):

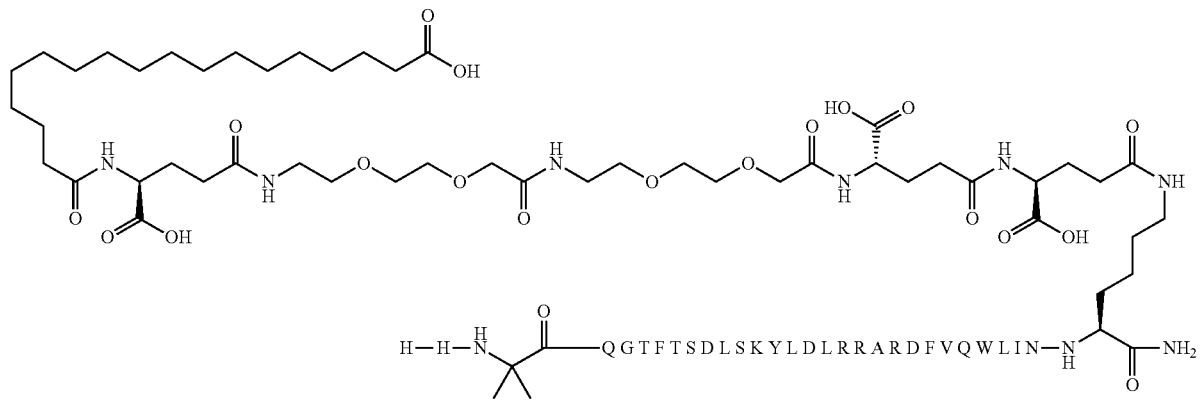

UPLC02v01: Rt=8.2 min
LCMS01v01: Rt=2.2 min; m/3=1490; m/4=1118; m/5=894

Example 24

N$^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Lys29]-Glucagon amide Chem. 24 (SEQ ID NO: 26):

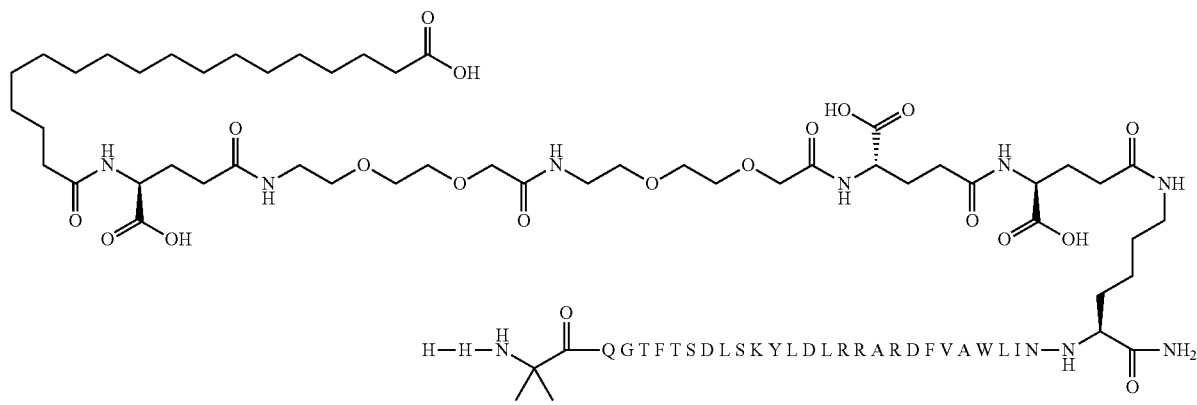

UPLC02v01: Rt=7.9 min
LCMS01v01: Rt=2.1 min; m/3=1473; m/4=1105; m/5=884

Example 25

N$^{\varepsilon 28}$-[(4S)-4-carboxy-4-[[(4S)-4-carboxy-4-[[2-[2-[2-[[2-[2-[2-[[(4S)-4- carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Ile27,Lys28]-Glucagon amide Chem. 25 (SEQ ID NO: 27):

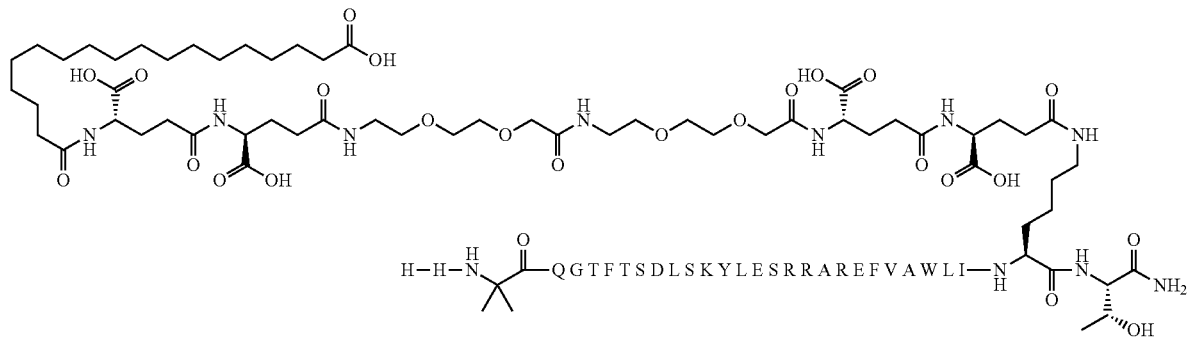

UPLC02v01: Rt=7.9 min
LCMS01v01: Rt=2.0 min; m/1=4586; m/3=1529; m/4=1147; m/5=918

Example 26

N^ε28-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Ile10,Glu15,Arg20,Glu21,Ile27,Lys28]-Glucagon amide Chem. 26 (SEQ ID NO: 28):

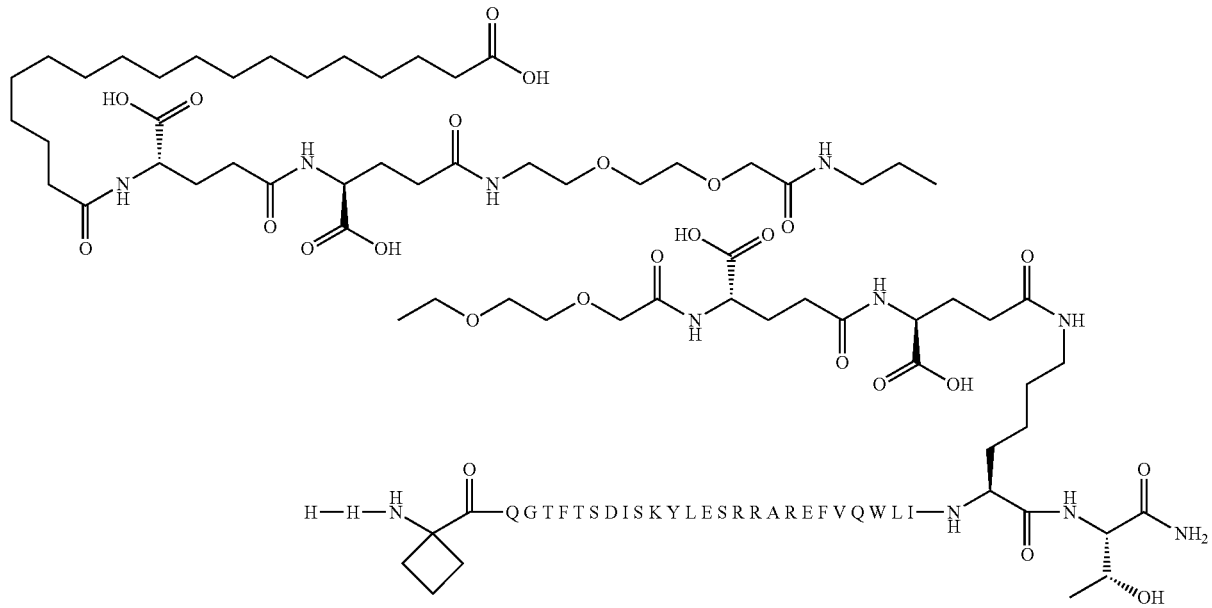

UPLC02v01: Rt=7.9 min
LCMS01v01: Rt=2.1 min; m/3=1533; m/4=1150; m/5=920

Example 27

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Ser28,Lys29]-Glucagon amide Chem. 27 (SEQ ID NO: 29):

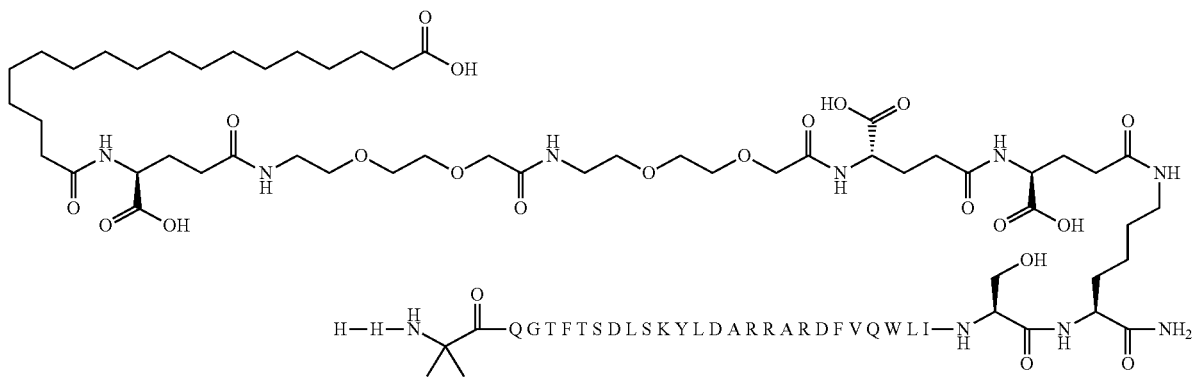

UPLC02v01: Rt=8.2 min
LCMS01v01: Rt=2.2 min; m/z=4398; m/3=1466; m/4=1100; m/5=880

Example 28

N^ε29-[(4S)-4-carboxy-4-[[(4S)-4-carboxy-4-[[2-[2-[2-[[2-[2-[2-[[(4S)-4-carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Ser28,Lys29]-Glucagon amide Chem. 28 (SEQ ID NO: 30):

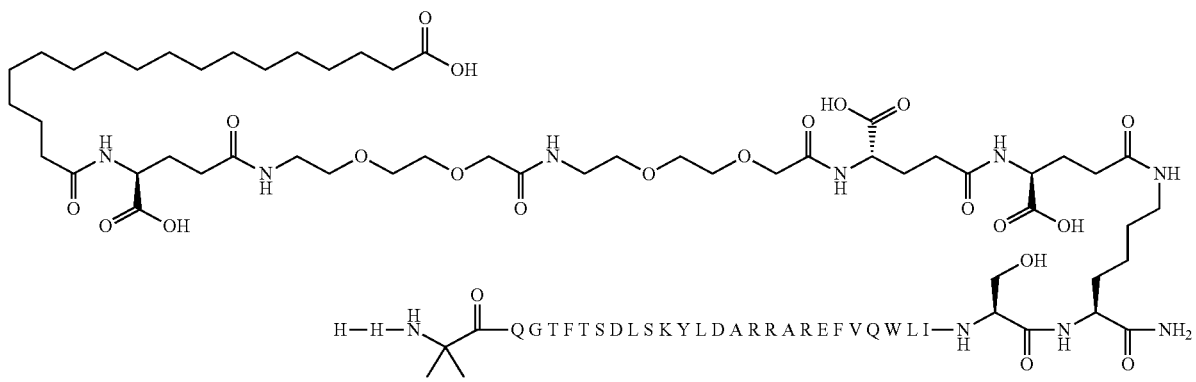

UPLC02v01: Rt=8.0 min
LCMS01v01: Rt=2.2 min; m/3=1472; m/4=1104; m/5=884

Example 29

N^ε29-[(4S)-4-carboxy-4-[[(4S)-4-carboxy-4-[[2-[2-[2-[[2-[2-[2-[[(4S)-4-carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Ser28,Lys29]-Glucagon amide Chem. 29 (SEQ ID NO: 31):

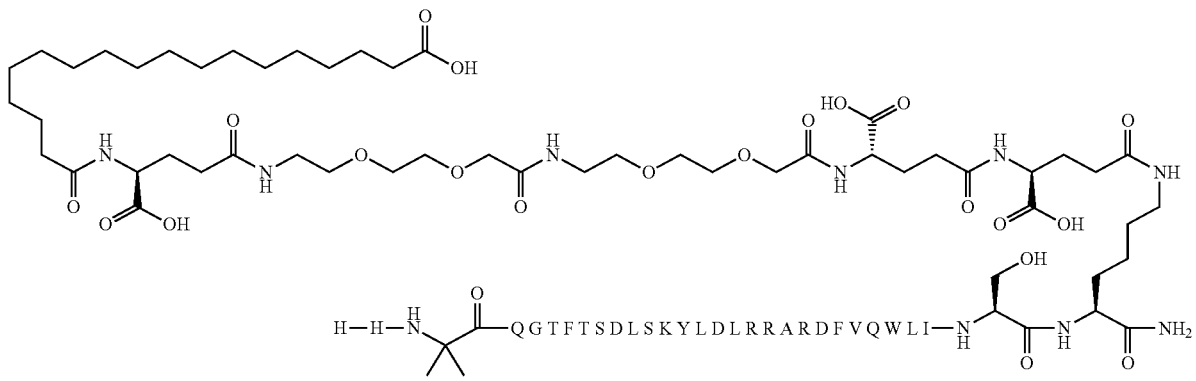

UPLC02v01: Rt=8.3 min
LCMS01v01: Rt=2.3 min; m/3=1481; m/4=1111; m/5=889

Example 30

N$^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Ser28,Lys29]-Glucagon amide Chem. 30 (SEQ ID NO: 32):

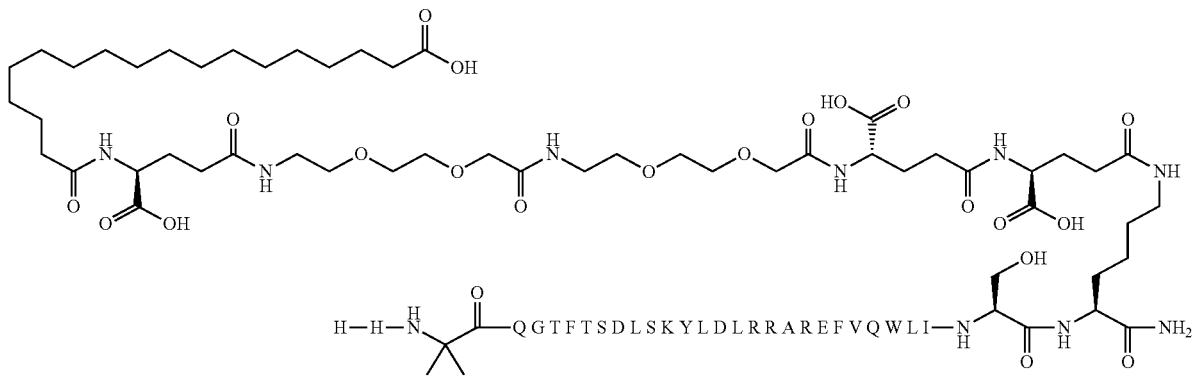

UPLC02v01: Rt=8.3 min
LCMS01v01: Rt=2.3 min; m/3=1485; m/4=1114; m/5=892

Example 31

N$^{\varepsilon 29}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Ser28,Lys29]-Glucagon amide Chem. 31 (SEQ ID NO: 33):

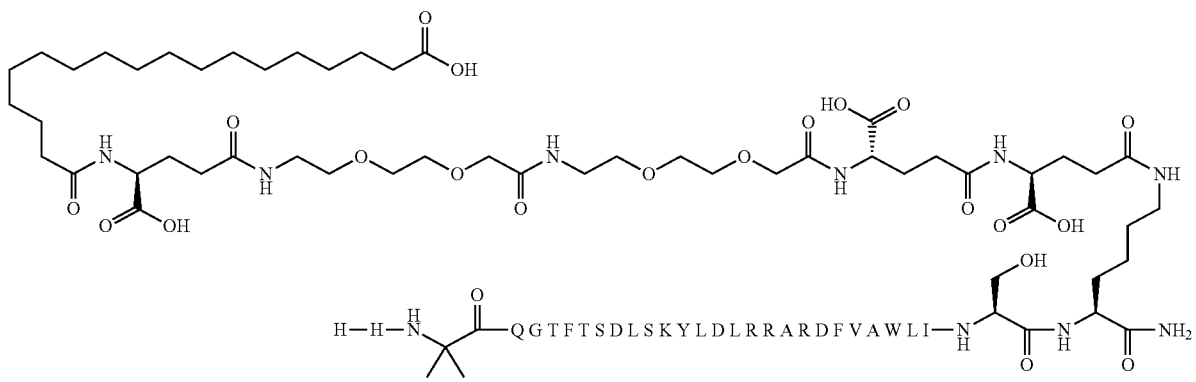

UPLC02v01: Rt=8.3 min
LCMS01v01: Rt=2.3 min; m/4=1097; m/5=877

Example 32

$N^{\varepsilon 28}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Ala16,Arg20,Ala24,Ile27, Lys28]-Glucagon amide Chem. 32 (SEQ ID NO: 34):

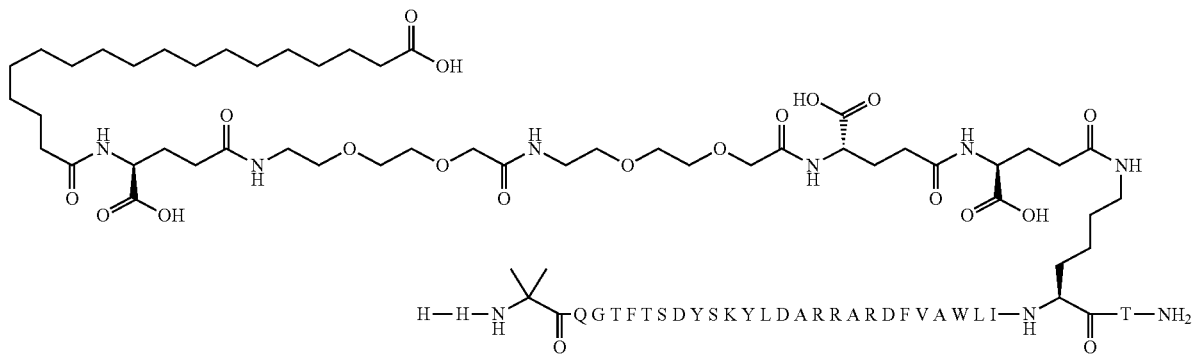

UPLC02v01: Rt=8.1 min
LCMS01v01: Rt=2.2 min; m/3=1469; m/4=1102; m/5=882

Example 33

$N^{\varepsilon 28}$-[(4S)-4-carboxy-4-[[(4S)-4-carboxy-4-[[2-[2-[2-[[2-[2-[2-[[(4S)-4- carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Leu16,Arg20,Ala24,Ile27, Lys28]-Glucagon amide Chem. 33 (SEQ ID NO: 35):

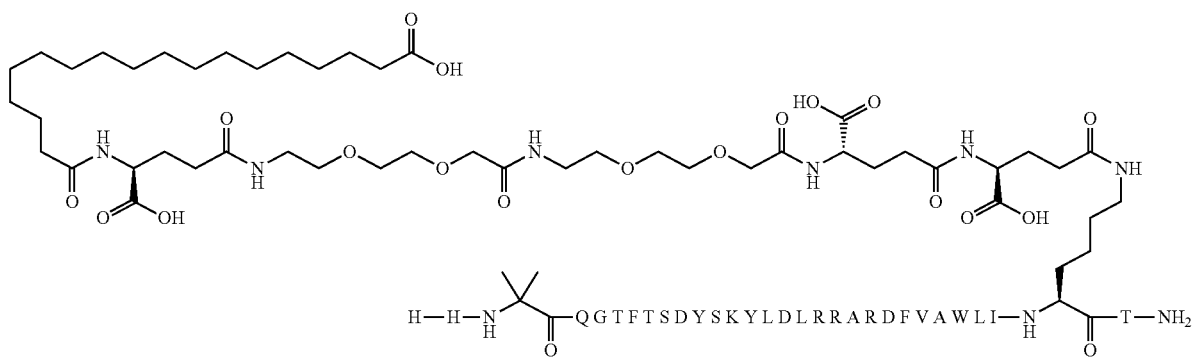

UPLC02v01: Rt=8.3 min
LCMS01v01: Rt=2.2 min; m/3=1483; m/4=1112; m/5=890

Example 34

$N^{\varepsilon 28}$-[(4S)-4-carboxy-4-[[(4S)-4-carboxy-4-[[2-[2-[2-[[2-[2-[2-[[(4S)-4-carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Lys28]-Glucagon amide Chem. 34 (SEQ ID NO: 36):

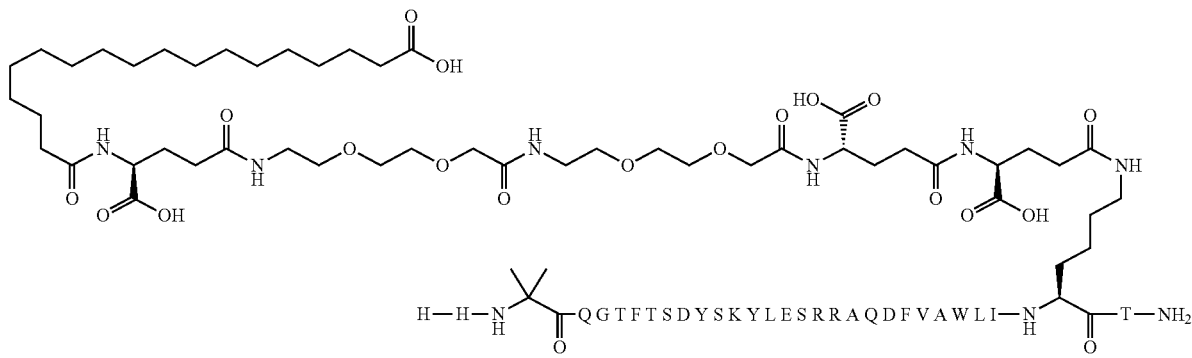

UPLC02v01: Rt=8.2 min
LCMS01v01: Rt=2.3 min; m/3=1469; m/4=1103

Example 35

$N^{\varepsilon 29}$-[(4S)-4-carboxy-4-[[(4S)-4-carboxy-4-[[2-[2-[2-[[2-[2-[2-[[(4S)-4-carboxy-4-(17-carboxyhepta-decanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Ser28,Lys29]-Glucagon amide Chem. 35 (SEQ ID NO: 37):

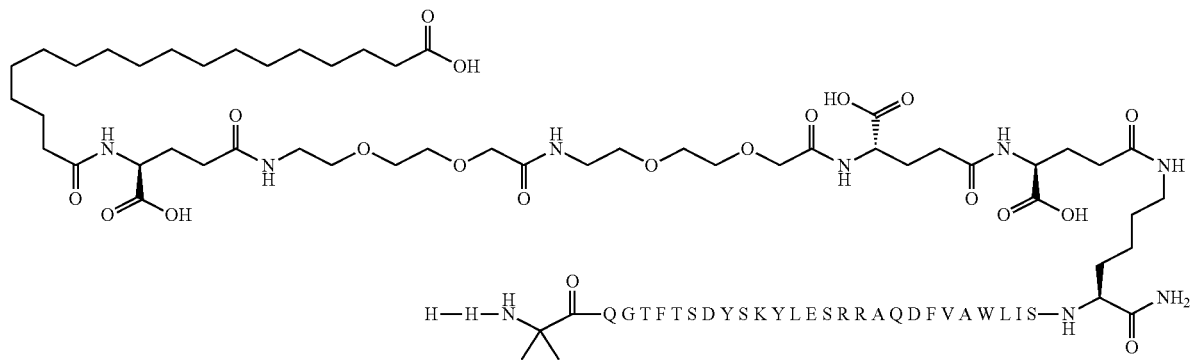

UPLC02v01: Rt=8.2 min
LCMS01v01: Rt=2.4; m/3=1465; m/4=1099

Example 36

$N^{\varepsilon 28}$-[(4S)-4-carboxy-4-[[2-[2-[2-[[(4S)-4-carboxy-4-[[2-[2-[2-[[(4S)-4- carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Acb2,Arg12,Glu15,Arg20,Ile27,Lys28]-Glucagon amide Chem. 36 (SEQ ID NO: 38):

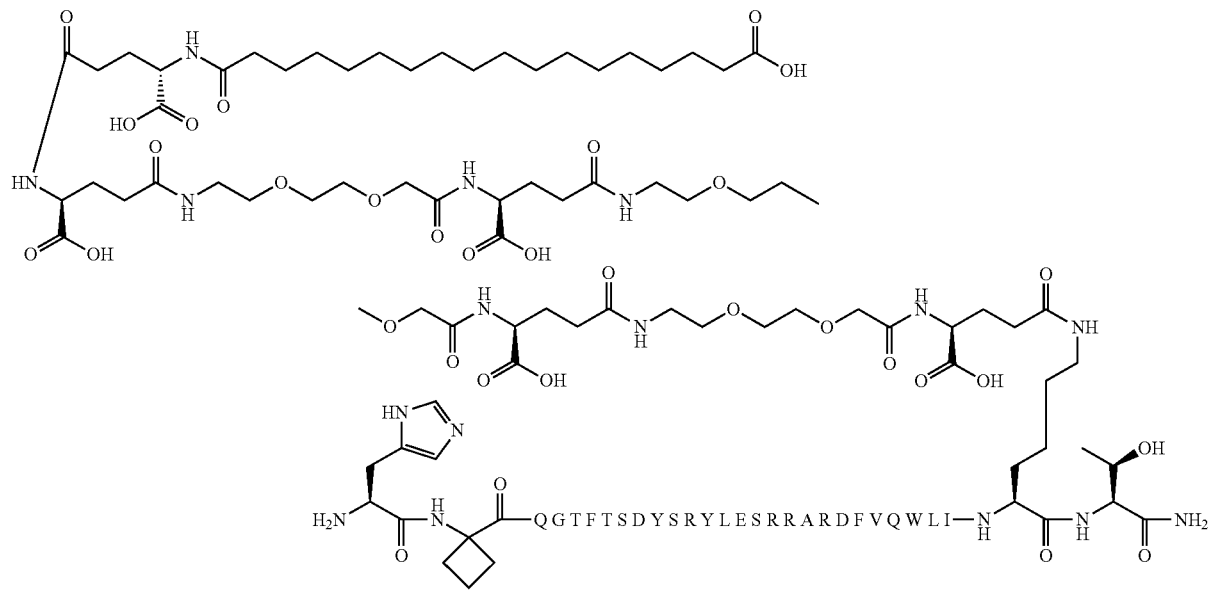

UPLC02v01: Rt=7.8 min
LCMS01v01: Rt=1.9; m/3=1646; m/4=1235; m/5=988

Example 37

$N^{28}$-[(4S)-4-carboxy-4-[[2-[2-[2-[[(4S)-4-carboxy-4-[[2-[2-[2-[[(4S)-4- carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Aib2,Arg12,Glu15,Arg20,Ile27,Lys28]-Glucagon amide Chem. 37 (SEQ ID NO: 39):

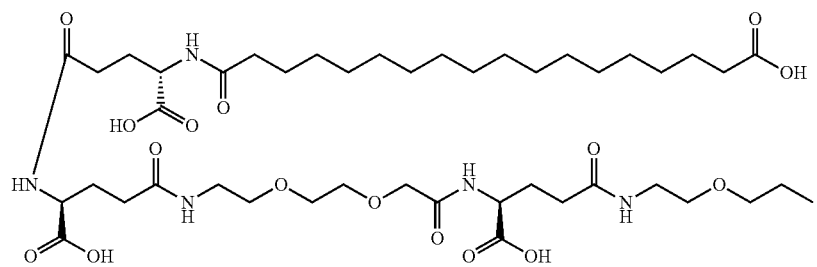

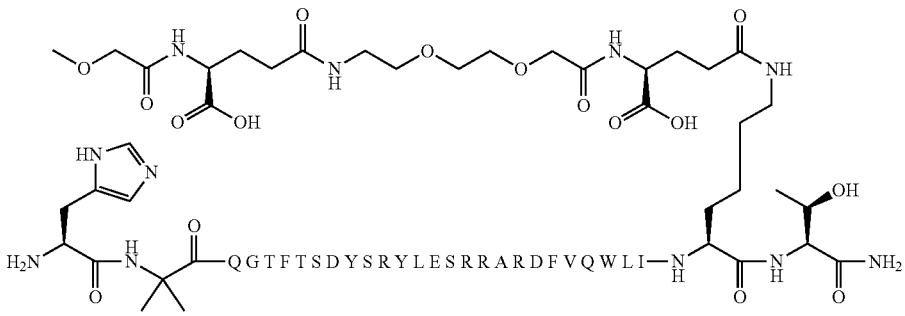
UPLC02v01: Rt=7.8 min
LCMS01v01: Rt=1.9 min; m/3=1641; m/4=1231; m/5=985
Example 38
N$^{\varepsilon 28}$-[(4S)-4-carboxy-4-[[2-[2-[2-[[2-[2-[2-[[(4S)-4-carboxy-4-[[(4S)-4- carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Acb2,Leu10,Glu15,Glu21,Ile27,Lys28]-Glucagon amide
Chem. 38 (SEQ ID NO: 40):
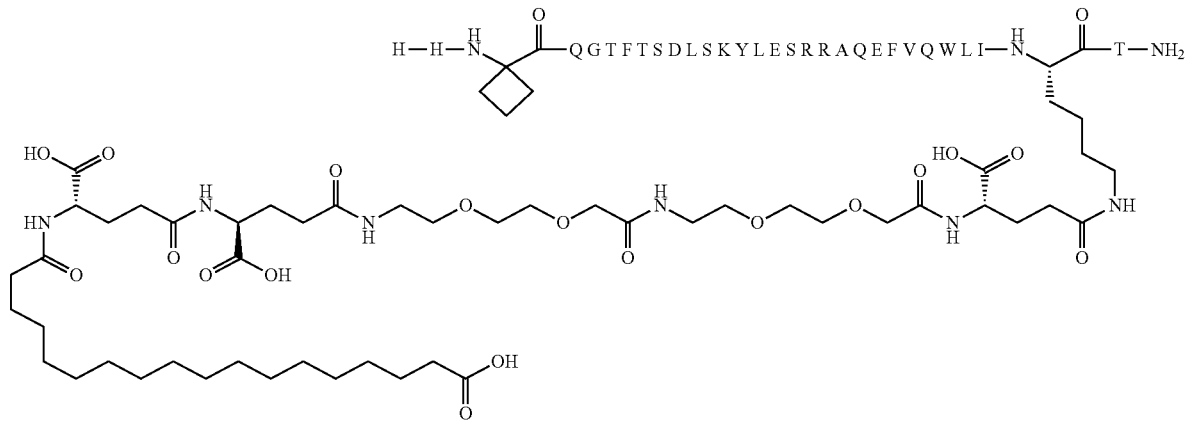

UPLC02v01: Rt=8.2 min
LCMS13v01: Rt=2.2 min; m/3=1480; m/4=1111

Example 39

N$^{\varepsilon 28}$-[(4S)-4-carboxy-4-[[2-[2-[2-[[2-[2-[2-[[(4S)-4-carboxy-4-[[(4S)-4- carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Val10,Ala16,Ile27,Lys28]-Glucagon amide Chem. 39 (SEQ ID NO: 41):

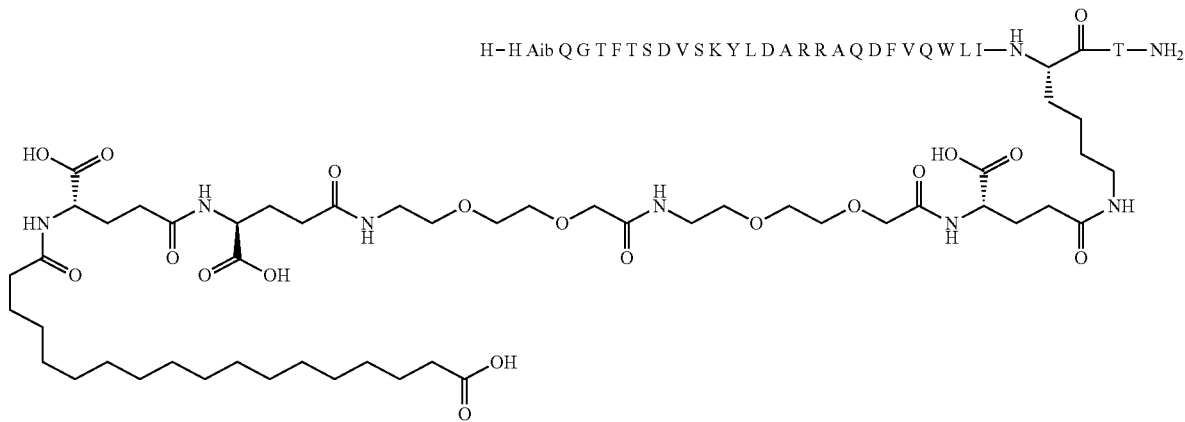

UPLC02v01: Rt=8.9 min
LCMS13v01: Rt=2.2 min; m/3=1458; m/4=1093

Example 40

N$^{\varepsilon 28}$-[(4S)-4-carboxy-4-[[2-[2-[2-[[2-[2-[2-[[(4S)-4-carboxy-4-[[(4S)-4- carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Val16,Ile27,Lys28]-Glucagon amide Chem. 40 (SEQ ID NO: 42):

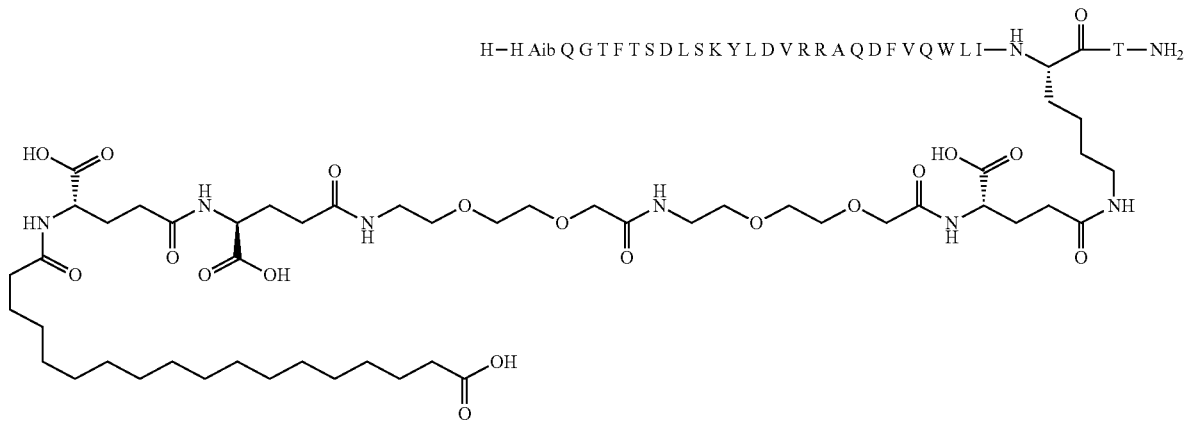

UPLC02v01: Rt=8.8 min
LCMS13v01: Rt=2.3 min; m/3=11044; m/4=1471

Assay (I): GLP-1 and Glucagon Receptor Potency

The purpose of this example was to test the activity or potency, of the glucagon derivatives of the invention, in vitro. The in vitro potency is the measure of human GLP-1 receptor (GLP-1R) or glucagon receptor (glucagonR) activation, respectively, in a whole cell assay.

Principle

In vitro potency was determined by measuring the response of human GLP-1 or glucagon receptor, respectively, in a reporter gene assay. The assay was performed in a stably transfected BHK cell line that expresses either the human GLP-1 receptor or the human glucagon receptor and contains the DNA for the cAMP response element (CRE) coupled to a promoter and the gene for firefly luciferase (CRE luciferase). When the human GLP-1 or glucagon receptor, respectively, was activated it resulted in the production of cAMP, which in turn resulted in the luciferase protein being expressed. When assay incubation was completed, the luciferase substrate (luciferin) was added and the enzyme converted luciferin to oxyluciferin and produces bioluminescence. The luminescence was measured as the readout for the assay.

(a) GLP-1 Receptor Activation

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% CO2 in DMEM medium with 10% FBS, 1×GlutaMAX, 1 mg/ml G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay medium. For 96-well plates the suspension was made to give a final concentration of 5×10EE3 cells/well.

Materials

The following chemicals were used in the assay: Pluronic F-68 (10%) (Gibco 2404), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757). Assay Medium consisted of DMEM w/o phenol red, 10 mM Hepes, 1× GlutaMAX, 2% Ovalbumin and 0.2% Pluronic F-68.

Procedure

Cell stocks were thawed in a 37° C. water bath. Cells were washed three times in PBS. The cells were counted and adjusted to 5×10EE3 cells/50 µl (1×10EE5 cells/ml) in Assay Medium. A 50 µl aliquot of cells was transferred to each well in the assay plate. Stocks of the test compounds and reference compounds were diluted to a concentration of 0.2 µM in Assay Medium. Compounds were diluted 10-fold to give the following concentrations: 2×10EE-6 M, 2×10EE-7 M, 2×10EE-8 M; 2×10EE-9 M, 2×10EE-10 M, 2×10EE-11 M, 2×10EE-12 M and 2×10EE-13 M. For each compound a blank assay medium control was also included.

A 50 µl aliquot of compound or blank was transferred from the dilution plate to the assay plate. Compounds were tested at the following final concentrations: 1×10EE-6 M, 1×10EE-7 M, 1×10EE-8 M; 1×10EE-9 M, 1×10EE-10 M, 1×10EE-11 M and 1×10EE-12 M and 1×10EE-13 M.

The assay plate was incubated for 3 h in a 5% CO2 incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Perkin Elmer TopCount NXT instrument.

Calculations

The data from the TopCount instrument was transferred to GraphPad Prism software. The software performed a non-linear regression (log(agonist) vs response-Variable slope (four parameter)). EC50 values were calculated by the software and reported in pM.

(b) Glucagon Receptor Activation

Cell Culture and Preparation

The cells used in this assay (clone pLJ6'-4-25) were BHK cells with BHK570 as a parent cell line expressing the CRE luciferase gene (clone BHK/KZ10-20-48) and were established by further transfection with the human glucagon receptor (clone pLJ6' in pHZ-1 vector).

The cells were cultured at 5% CO2 in DMEM medium with 10% FBS, 1×GlutaMAX, 1 mg/ml G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay medium. For 96-well plates the suspension was made to give a final concentration of 5×10EE3 cells/well.

Materials

The following chemicals were used in the assay: Pluronic F-68 (10%) (Gibco 2404), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757). Assay Medium consisted of DMEM w/o phenol red, 10 mM Hepes, 1× GlutaMAX, 2% Ovalbumin and 0.2% Pluronic F-68.

Procedure

Cell stocks were thawed in a 37° C. water bath. Cells were washed three times in PBS. The cells were counted and adjusted to 5×10EE3 cells/50 µl (1×10EE5 cells/ml) in Assay Medium. A 50 µl aliquot of cells was transferred to each well in the assay plate.

Stocks of the test compounds and reference compounds were diluted to a concentration of 0.2 µM in Assay Medium. Compounds were diluted 10-fold to give the following concentrations: 2×10EE-6 M, 2×10EE-7 M, 2×10EE-8 M; 2×10EE-9 M, 2×10EE-10 M, 2×10EE-11 M, 2×10EE-12 M and 2×10EE-13 M. For each compound a blank assay medium control was also included.

A 50 µl aliquot of compound or blank was transferred from the dilution plate to the assay plate. Compounds were tested at the following final concentrations: 1×10EE-6 M, 1×10EE-7 M, 1×10EE-8 M; 1×10EE-9 M, 1×10EE-10 M, 1×10EE-11 M and 1×10EE-12 M and 1×10EE-13 M.

The assay plate was incubated for 3 h in a 5% CO2 incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Perkin Elmer TopCount NXT instrument.

Calculations

The data from the TopCount instrument was transferred to GraphPad Prism software. The software performed a non-linear regression (log(agonist) vs response-Variable slope (four parameter)). EC50 values were calculated by the software and reported in pM.

Assay (II): GLP-1 and Glucagon Receptor Binding

The purpose of this assay is to test the in vitro receptor binding activity of the glucagon derivatives of the invention.

(a) GLP-1 Receptor Binding

The GLP-1 receptor (GLP-1R) binding is a measure of affinity of a compound for the human GLP-1 receptor.

Principle

The receptor binding of each compound to the human GLP-1 receptor was measured in a displacement binding assay. In this type of assay a labelled ligand (in this case 125I-GLP-1) is bound to the receptor. Each derivative was added in a series of concentrations to isolated membranes containing the human GLP-1 receptor and displacement of the labelled ligand was monitored. The receptor binding was reported as the concentration at which half of the labelled ligand was displaced from the receptor, the IC50 value.

In order to test the binding of the derivatives to albumin, the assay may be performed in a very low concentration of serum albumin (max. 0.001% final assay concentration) as well as in the presence of a (considerably) higher concentration of serum albumin (2.0% final assay concentration). An increase of the IC50 value, in the presence of serum albumin indicates an affinity to serum albumin and represents a method to predict a protracted pharmacokinetic profile of the test substance in animal models.

Materials

The following chemicals were used in the assay: DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, MgCl2 (Merck 1.05832.1000), Tween 20 (Amresco 0850C335), SPA particles (wheat germ agglutinin (WGA) SPA beads, Perkin Elmer RPNQ0001), [125I]-GLP-1]-(7-36)NH2 (produced in-house), OptiPlate™-96 (Perkin Elmer).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM MgCl2, 0.005% Tween 20 and pH was adjusted to 7.4.

Cell Culture and Membrane Preparation

The cells used in this assay (clone FCW467-12A) were BHK cells with BHKTS13 as a parent cell line. The cells express the human GLP-1 receptor.

The cells were grown at 5% CO2 in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay, 50 µl of the assay buffer was added to each well of an assay plate.
2. Test compounds were serially diluted to give the following concentrations: 8×10EE-7 M, 8×10EE-8 M, 8×10EE-9 M, 8×10EE-10 M, 8×10EE-11 M, 8×10EE-12 M and 8×10EE-13 M. Twenty-five µl were added to appropriate wells in the assay plate.
3. Cell membrane aliquots were thawed and diluted to their working concentration. Fifty µl were added to each well in the assay plate.
4. WGA SPA beads were suspended in assay buffer at 20 mg/ml. The suspension was diluted to 10 mg/ml in assay buffer just prior to addition to the assay plate. Fifty µl were added to each well in the assay plate.
5. The incubation was started by adding 25 µl of 480 µM solution of [125I]-GLP-1]-(7-36)NH2 to each well of the assay plate. A 25 µl aliquot was reserved for measuring total counts/well.
6. The assay plate was incubated for 2 h at 30° C.
7. The assay plate was centrifuged for 10 min.
8. The assay plate was read in a Perkin Elmer TopCount NXT instrument.

Calculations

The data from the TopCount instrument were transferred to GraphPad Prism software. The software averaged the values for the replicates and performed a non-linear regression. IC50 values were calculated by the software and reported in nM.

(b) Glucagon Receptor Binding

The glucagon receptor (glucagonR) binding activity is a measure of affinity of a derivative for the human glucagon receptor.

Principle

The receptor binding of each compound to the human glucagon receptor was measured in a displacement binding assay. In this type of assay a labelled ligand (in this case 125I-glucagon) is bound to the receptor. Each derivative was added in a series of concentrations to isolated membranes containing the human glucagon receptor and displacement of the labelled ligand is monitored. The receptor binding was reported as the concentration at which half of the labelled ligand is displaced from the receptor, the IC50 value.

In order to test the binding of the derivatives to albumin, the assay may be performed in a very low concentration of serum albumin (max. 0.001% final assay concentration) as well as in the presence of a higher concentration of serum albumin (0.2% final assay concentration). An increase of the IC50 value, in the presence of serum albumin indicates an affinity to serum albumin and represents a method to predict a protracted pharmacokinetic profile of the test substance in animal models.

Materials

The following chemicals were used in the assay: DMEM w Glutamax (Gibco 61965-026), Pen/strep (Invitrogen 15140-122), G418 (Invitrogen 10131-027), Versene (Gibco 15040), 1 M Hepes (Gibco 15630), PBS (Invitrogen 14190-094), fetal calf serum (Invitrogen 16140-071), MgCl2 (Merck 1.05832.1000), EDTA (Invitrogen 15575-038), CaCl2 (Sigma, C5080), Tween 20 (Amresco 0850C335), ovalbumin (Sigma A5503), SPA particles (wheat germ agglutinin (WGA) SPA beads, Perkin Elmer RPNQ0001), [125I]-glucagon (produced in-house), OptiPlate™-96 (Packard 6005290).

HME buffer consisted of 25 mM HEPES, 2 mM MgCl2 and 1 mM EDTA, and pH was adjusted to 7.4. Assay buffer consisted of 50 mM HEPES supplemented with 5 mM MgCl2, 1 mM CaCl2, 0.02% Tween 20 and 0.1% Ovalbumin, and pH was adjusted to 7.4.

Cell Culture and Membrane Preparation

The cells used in this assay (clone BHK hGCGR A3*25) were BHK cells stable transfected with an expression plasmid containing the cDNA encoding the human glucagon receptor.

The cells were grown at 5% $CO_2$ in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. Lyse the cells by adding approx. 5 ml HME buffer, mix by pipetting and snap freeze in liquid nitrogen. Thaw quickly and add HME buffer to 10 ml. The cell pellet was homogenised with an ULTRA-THURRAX dispersing instrument for 20-30 seconds. The homogenate was centrifuged at 20.000× G, 4° C. for 10 minutes. The pellet was resuspended (homogenised) in 1-2 ml HME buffer. The protein concentration was determined. The membranes were aliquoted and snapfrozen in liquid nitrogen and stored at minus 80° C.

Procedure

1. For the receptor binding assay, 50 µl of the assay buffer was added to each well of an assay plate.
2. Test compounds were serially diluted to give the following concentrations: 8×10EE-7 M, 8×10EE-8 M, 8×10EE-9 M, 8×10EE-10 M, 8×10EE-11 M, 8×10EE-12 M and 8×10EE-13 M. Twenty-five µl were added to appropriate wells in the assay plate.
3. Cell membrane aliquots were thawed and diluted to their working concentration. Fifty µl were added to each well in the assay plate.
4. WGA SPA beads were suspended in assay buffer at 20 mg/ml. The suspension was diluted to 10 mg/ml in assay buffer just prior to addition to the assay plate. Fifty µl were added to each well in the assay plate.
5. The incubation was started by adding 25 µl of 480 µM solution of [125I]-glucagon to each well of the assay plate. A 25 µl aliquot was reserved for measuring total counts/well.
6. The assay plate was incubated for 2 h at 25° C.
7. The assay plate was centrifuged for 10 min at 1500 rpm.
8. The assay plate was read in a Perkin Elmer TopCount NXT instrument.

Calculations

The data from the TopCount instrument were transferred to GraphPad Prism software. The software averaged the values for the replicates and performed a non-linear regression.

Assay (III): ThT Fibrillation Assay for the Assessment of Physical Stability of Peptide Formulations The purpose of this assay is to assess the physical stability of the glucagon derivatives of the invention in aqueous solutions.

Low physical stability of a peptide may lead to amyloid fibril formation, which is observed as well-ordered, thread-like macromolecular structures in the sample, which eventually may lead to gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Here, as indicated in FIG. 1, F is the ThT fluorescence at the time t. The constant t0 is the time needed to reach 50% of maximum fluorescence. The two important parameters describing fibril formation are the lag-time calculated by $t0-2\tau$ and the apparent rate constant kapp $1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Samples were prepared freshly before each assay. Each sample composition is described in the legends. The pH of the sample was adjusted to the desired value using appropriate amounts of concentrated NaOH and HCl. Thioflavin T was added to the samples from a stock solution in $H_2O$ to a final concentration of 1 µM.

Sample aliquots of 200 µl (250 µM of the glucagon derivative in 10 mM HEPES buffer, pH 7.5) were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation at given temperature, shaking and measurement of the ThT fluorescence emission were done in a Fluoroskan Ascent FL fluorescence platereader (Thermo Labsystems). The temperature was adjusted to 37° C. The plate was incubated with orbital shaking adjusted to 960 rpm with an amplitude of 1 mm. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

After completion of the ThT assay the four or eight replica of each sample was pooled and centrifuged at 20000 rpm for 30 minutes at 18° C. The supernatant was filtered through a 0.22 µm filter and an aliquot was transferred to a HPLC vial.

The concentration of peptide in the initial sample and in the filtered supernatant was determined by reverse phase HPLC using an appropriate standard as reference. The percentage fraction the concentration of the filtered sample constituted of the initial sample concentration was reported as the recovery.

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, the lag time before fibrillation may be assessed by visual inspection of the curve identifying the time point at which ThT fluorescence increases significantly above the background level.

Assay (IV): Pharmacokinetic Profile in Mice

The purpose of this assay is to assess the pharmocokinetic profiles of the glucagon derivatives of the invention in mice.

The pharmacokinetic profile of glucagon derivatives may be tested in normal male c57/BL6 mice (approximately body weight: 30 grams), n=12 with for example 3 mice represented at each time point (for example: t=0.25, 0.5, 1, 3, 6, 10, 24, 30 and 48 hours). The test compound may be dosed as a single subcutaneous dose of 10 nmol/kg.

The plasma levels of the glucagon derivatives may be determined using an ELISA/LOCI assay or LCMS. Pharmacokinetic calculations such as half-life ($T_{1/2}$) maximum concentration ($C_{max}$) and time for maximum concentration ($T_{max}$) of the compounds may be determined using the PC based software, Phoenix (WinNonLin version 6.3 from Pharsight, Certara).

Assay (V): Chemical Stability Assessment

The purpose of this assay is to assess the chemical stability of the glucagon derivatives of the present invention in aqueous solutions.

Chemical stability of glucagon derivatives may be investigated by RP-UPLC separation and UV detection. Lyophilized samples are dissolved in a 8 mM Phosphate buffer pH 8.6, followed by adjustment to pH 7.3. using HCl to a final concentration of 333 μM. Samples are incubated for 14 days at 5° C. and 37° C. followed by RP-UPLC analysis. Purity is defined as the area percentage of the main peak in relation to the total area of all integrated peaks in each chromatogram. Purity loss after 14 days at 37° C. is determined as the difference in purity between the samples incubated at 5° C. and 37° C., divided by the purity of the sample after incubation for 14 days at 5° C.

RP-UPLC analysis is performed using a Waters BEH130 2.1 mm×150 mm, 1.7 μm column operated at 50° C. and a flow rate of 0.4 mL/min using a mobile phase system consisting of A: 0.05% TFA in MQ-water B: 0.05% TFA in Acetonitrile. UV-detection is performed at 215 nm. The typical gradient profile used for most of the samples is shown below in Table 1.

TABLE 1

Typical gradient profile used for RP-UPLC analysis

| Time (min) | % B |
|---|---|
| Injection | 20 |
| 30 | 60 |
| 31 | 99 |
| 37 | 99 |
| 39 | 20 |
| 40 | 20 |
| 45 | 20 |

For some individual derivatives eluting at substantially different retention times compared with the majority of derivatives, some adjustments to the gradient profile are made to better enable purity assessment comparison across samples.

Example 42: Data on Receptor Potency and Binding and Physical Stability of Glucagon Derivatives GLP-1 and glucagon receptor potency (EC50) and binding (IC50) as well as physical stability were determined for glucagon derivatives of the invention according to the methods described in Assay (I), (II) and (III) herein. Assay (I) and (II) were carried out without presence of serum albumin. Assay (III) was carried out at pH 7.5. The results are shown in Table 2.

TABLE 2

EC50 and IC50 values on the human GLP-1 and glucagon receptors and physical stability of glucagon derivatives assessed in the ThT assay.

| Glucagon derivative | GLP-1R EC50 (pM) [Assay (I)(a)] | GLP-1R IC50 (nM) [Assay (II)(a)] | GlucagonR EC50 (pM), [Assay (I)(b)] | GlucagonR IC50 (nM) [Assay (II)(b)] | ThT Assay Lag time (h) [Assay (III), pH 7.5] | ThT Assay Recovery (%), [Assay (III), pH 7.5] |
|---|---|---|---|---|---|---|
| Chem. 1 | 3.5 | .9 | 17.5 | 11.3 | 45.0 | 108.0 |
| Chem. 2 | 2.0 | .3 | 10.0 | 7.5 | 33.0 | 4.0 |
| Chem. 3 | 2.0 | .1 | 245.0 | 31.6 | 45.0 | 100.0 |
| Chem. 4 | 3.0 | .1 | 12.0 | 3.9 | 26.0 | 16.0 |
| Chem. 5 | 5.5 | .1 | 29.0 | 6.7 | 45.0 | 100.0 |
| Chem. 6 | 5.0 | .1 | 14.0 | 3.7 | 34.0 | 71.0 |
| Chem. 7 | 2.0 | .3 | 32.0 | 6.0 | 45.0 | 107.0 |
| Chem. 8 | 7.0 | .1 | 517.0 | 27.6 | 45.0 | 104.0 |
| Chem. 9 | 10.0 | .5 | 44.0 | 17.3 | 45.0 | 105.0 |
| Chem. 10 | 3.0 | .1 | 748.0 | 42.4 | 45.0 | 100.0 |
| Chem. 11 | 8.0 | .5 | 428.0 | 52.0 | 45.0 | 104.0 |
| Chem. 12 | 29.0 | 2.8 | 108.0 | 95.9 | 45.0 | 104.0 |
| Chem. 13 | 4.0 | .1 | 23.0 | 1.8 | | |
| Chem. 14 | 2.0 | .1 | 9.0 | 6.4 | 45.0 | 106.0 |
| Chem. 15 | 4.0 | .0 | 7.0 | 1.7 | 45.0 | 104.0 |
| Chem. 16 | 5.0 | .0 | 13.0 | 2.7 | 16.0 | 5.0 |
| Chem. 17 | 4.0 | .1 | 45.0 | 4.3 | 12.3 | 9.0 |
| Chem. 18 | 4.0 | .1 | 32.0 | 11.1 | 5.0 | .0 |
| Chem. 19 | 6.0 | .0 | 37.0 | 2.5 | 45.0 | 100.0 |
| Chem. 20 | 4.0 | .1 | 70.0 | 13.6 | 45.0 | 100.0 |
| Chem. 21 | 3.0 | .1 | 31.0 | 8.7 | 45.0 | 100.0 |
| Chem. 22 | | .3 | | 67.3 | 45.0 | 92.0 |
| Chem. 23 | | .3 | | 83.2 | 45.0 | 100.0 |
| Chem. 24 | 3.0 | .4 | 55.0 | 14.0 | 45.0 | 100.0 |
| Chem. 25 | 2.0 | .1 | 52.0 | 11.2 | 23.0 | 86.0 |
| Chem. 26 | 2.0 | .4 | 42.0 | 10.1 | 45.0 | 105.0 |

TABLE 2-continued

EC50 and IC50 values on the human GLP-1 and glucagon receptors and physical stability of glucagon derivatives assessed in the ThT assay.

| Glucagon derivative | GLP-1R EC50 (pM) [Assay (I)(a)] | GLP-1R IC50 (nM) [Assay (II)(a)] | GlucagonR EC50 (pM), [Assay (I)(b)] | GlucagonR IC50 (nM) [Assay (II)(b)] | ThT Assay Lag time (h) [Assay (III), pH 7.5] | ThT Assay Recovery (%), [Assay (III), pH 7.5] |
|---|---|---|---|---|---|---|
| Chem. 27 | 3.0 | .2 | 66.0 | 19.1 | 45.0 | 100.0 |
| Chem. 28 | 3.0 | .2 | 36.0 | 8.6 | 45.0 | 100.0 |
| Chem. 29 |  | 1.0 |  | 64.7 | 45.0 | 100.0 |
| Chem. 30 |  | .9 |  | 71.2 | 45.0 | 100.0 |
| Chem. 31 |  | 1.1 |  | 144.0 | 45.0 | 100.0 |
| Chem. 32 | 2.0 | .3 | 7.0 | .9 | 45.0 | 100.0 |
| Chem. 33 | 7.0 | 2.3 | 8.0 | 6.9 | 45.0 | 100.0 |
| Chem. 34 | 3.0 | 2.2 | 66.0 | 7.0 | 45.0 | 100.0 |
| Chem. 35 |  | 2.2 |  | 60 | 45.0 | 100.0 |
| Chem. 36 | 4.0 | 1.5 | 22.0 | 6.5 | 3.7 | 46.0 |
| Chem. 37 | 4.0 | 1.5 | 98.0 | 6.6 | 6.3 | 96.0 |
| Chem. 38 | 2.0 | .3 | 12.0 | 2.7 | 45.0 | 100.0 |
| Chem. 39 | 1.0 | .1 | 24.0 | 4.6 | 45.0 | 90.0 |
| Chem. 40 | 3.0 | 1.2 | 30.0 | 7.1 | 45.0 | 111.0 |

The results in Table 2 show that the glucagon derivatives are GLP-1/glucagon receptor co-agonists with preference for the GLP-1 receptor. In addition, the results show that most glucagon derivatives show very high physical stability assessed by the ThT fibrillation assay.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A glucagon derivative comprising an amino acid sequence of Formula I (SEQ ID NO:2):

X1-X2-X3-Gly-Thr-Phe-Thr-Ser-Asp-X10-Ser-X12-Tyr-Leu-X15-X16-X17-X18-Ala-X20-X21-Phe-Val-X24-Trp-Leu-Ile-X28-X29-X30     (I)

wherein

X1 represents His or Imp;
X2 represents Aib or Acb;
X3 represents Gln or His;
X10 represents Tyr, Leu, Ile or Val;
X12 represents Lys or Arg;
X15 represents Asp or Glu;
X16 represents Ser, Ala, Leu, Thr, Glu, Aib, Ile, Val or Lys;
X17 represents Arg, Lys or Gln;
X18 represents Arg, Ala or Lys;
X20 represents Gln, Arg or Lys;
X21 represents Asp, Glu or Lys;
X24 represents Gln, Ala, Arg, Glu or Lys;
X28 represents Asn, Ser, Thr, Gln, Ala, Gly, Glu or Lys;
X29 represents Thr, Gly, Ser, Gln, Ala, Glu or Lys; and
X30 is absent or represents Lys;

wherein said amino acid sequence of Formula I comprises a lysine residue at one or more of positions 12, 16, 17, 18, 20, 21, 24, 28, 29, and 30; and wherein said glucagon derivative comprises a substituent comprising a lipophilic moiety and at least three negatively charged moieties, wherein one of said negatively charged moieties is at a distal end of the lipophilic moiety relative to the point of attachment between the lipophilic moiety and the amino acid sequence, and wherein said substituent is attached at the epsilon position of a lysine residue in one of the amino acid positions 16, 17, 18, 20, 21, 24, 28, 29 or 30;

and wherein said glucagon derivative is a C-terminal amide;

or a pharmaceutically acceptable salt thereof.

2. The glucagon derivative according to claim 1, wherein said glucagon derivative is a GLP-1/glucagon receptor co-agonist.

3. The glucagon derivative according to claim 1, wherein said substituent comprises three, four or five negatively charged moieties.

4. The glucagon derivative according to claim 1, wherein said substituent comprising a lipophilic moiety and at least three negatively charged moieties is a substituent represented by Formula II:

Z1-Z2-Z3-Z4-Z5-Z6-Z7-Z8-Z9-Z10-     (II)

wherein,

Z1 represents a structure according to the Formula IIa:

(IIa)

wherein n is 6-20;

the symbol * represents the attachment point to the nitrogen of the neighbouring group; and Z2-Z3-Z4-Z5-Z6-Z7-Z8-Z9-Z10- represents a linker, wherein each of Z2 to Z10 individually are represented by any one of the following amino acid residues: Glu, gamma-Glu (gGlu), Gly, Ser, Ala, Thr and/or Ado; or one or more of residues Z2 to Z10 are absent; provided, however, that at least two of residues Z2 to Z10 are present;

wherein Z1-Z2-Z3-Z4-Z5-Z6-Z7-Z8-Z9-Z10- together contains at least three negatively charged moieties; and wherein said substituent is attached at the epsilon position of a Lys in the amino acid sequence of Formula I.

5. The glucagon derivative according to claim 4, wherein Z1 represents a fatty di-acid of Formula IIa;

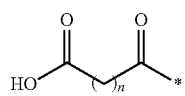

(IIa)

wherein n represents an integer in the range of from 12 to 18.

6. The glucagon derivative according to claim 1, wherein said substituent is attached at the epsilon position of a lysine residue at one of positions 24, 28 or 29.

7. The glucagon derivative according to claim 1, wherein said amino acid sequence of Formula I has 3-15 amino acid residue modifications as compared to human glucagon (SEQ ID NO: 1).

8. The glucagon derivative according to claim 4, wherein $Z^2$-$Z^3$-$Z^4$-$Z^5$-$Z^6$-$Z^7$-$Z^8$-$Z^9$-$Z^{10}$- represents a linker selected from the group consisting of gGlu-Ado-gGlu-;

gGlu-Ado-2xgGlu- (SEQ ID NO:51);

gGlu-2xAdo-2xgGlu- (SEQ ID NO:52);

2xgGlu-;

2xgGlu-Ado-;

2xgGlu-Ado-gGlu- (SEQ ID NO:53);

2xgGlu-Ado-gGlu-Ado- (SEQ ID NO:54);

2xgGlu-Ado-2xgGlu- (SEQ ID NO:55);

2xgGlu-2xAdo- (SEQ ID NO:56);

2xgGlu-2xAdo-gGlu- (SEQ ID NO:57);

2xgGlu-2xAdo-2xgGlu- (SEQ ID NO:58);

2xgGlu-Ser-Gly-Glu-Ser- (SEQ ID NO:49);

2xgGlu-Ser-Gly-Glu-Ser-Gly- (SEQ ID NO:50);

3xgGlu-;

3xgGlu-Ado- (SEQ ID NO:61);

3xgGlu-2xAdo- (SEQ ID NO:59); and

2xgGlu-Ado-gGlu-Ado-gGlu-Ado-gGlu- (SEQ ID NO:60).

9. The glucagon derivative according to claim 1, wherein $X^1$ represents His or Imp;

$X^3$ represents Gln;

$X^{10}$ represents Tyr, Leu, Ile or Val;

$X^{16}$ represents Ser, Ala, Leu or Val;

$X^{17}$ represents Arg or Lys;

$X^{18}$ represents Arg;

$X^{20}$ represents Gln or Arg;

$X^{21}$ represents Asp or Glu;

$X^{24}$ represents Gln, Ala or Lys;

$X^{28}$ represents Asn, Ser or Lys;

$X^{29}$ represents Thr or Lys; and $X^{30}$ is absent;

and wherein said substituent is attached at the epsilon position of a lysine residue in one of the amino acid positions 24, 28 and 29.

10. The glucagon derivative according to claim 1, wherein $X^{24}$ represents Gln or Ala;

$X^{28}$ represents Asn or Ser;

$X^{29}$ represents Lys; and $X^{30}$ is absent;

and wherein said substituent is attached at the epsilon position of a lysine residue in position 29.

11. The glucagon derivative according to claim 1, wherein $X^{24}$ represents Gln or Ala;

$X^{28}$ represents Lys;

$X^{29}$ represents Thr; and $X^{30}$ is absent;

and wherein said substituent is attached at the epsilon position of a lysine residue in position 28.

12. The glucagon derivative according to claim 1, wherein $X^{24}$ represents Lys;

$X^{28}$ represents Asn or Ser;

$X^{29}$ represents Thr; and $X^{30}$ is absent;

and wherein said substituent is attached at the epsilon position of a lysine residue in position 24.

13. The glucagon derivative according to claim 1, wherein said glucagon derivative is selected from the group consisting of:

N$^{\epsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Arg20,Lys24,Ile27,Ser28]-Glucagon amide
Chem 1 (SEQ ID NO: 3):

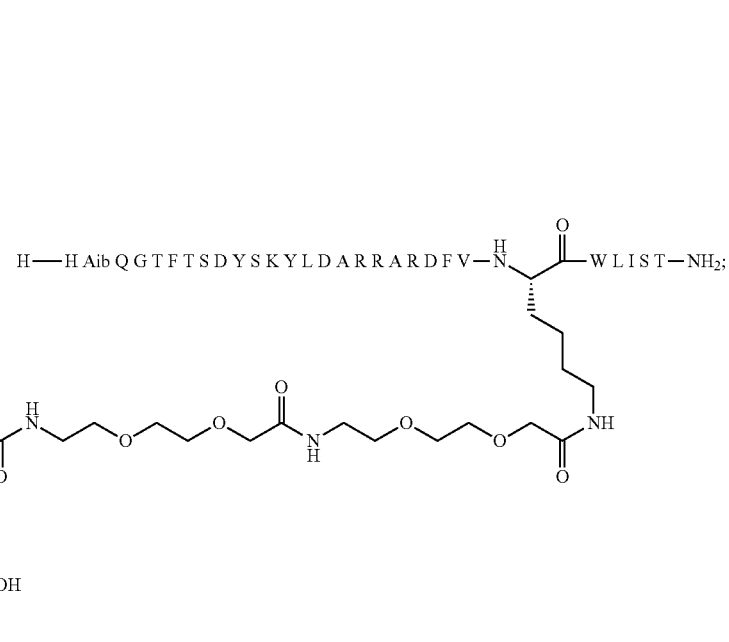

N$^{\epsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Lys17,Arg20,Glu21,Lys24,Ile27, Ser28]-Glucagon amide
Chem 2 (SEQ ID NO: 4):

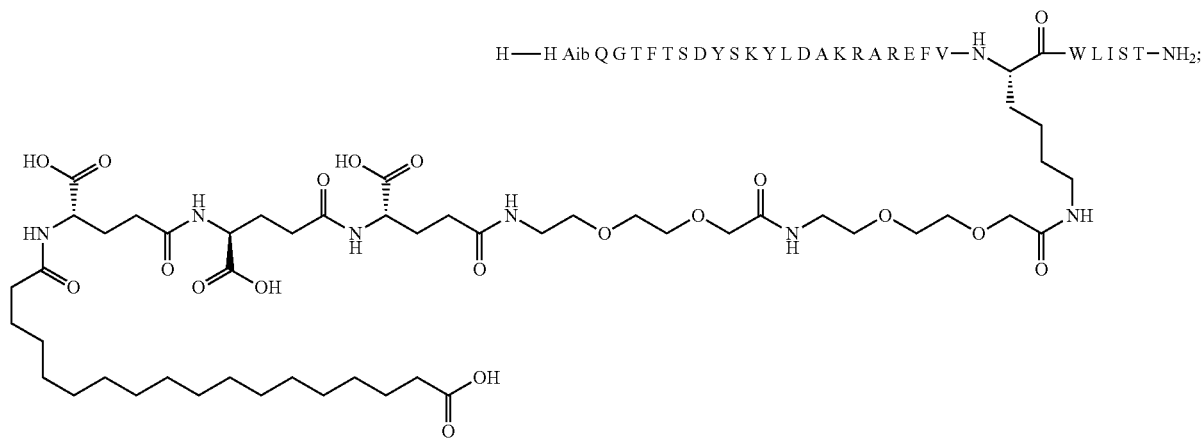

N^{ε28}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Arg20,Ile27,Lys28]-Glucagon amide
Chem 3 (SEQ ID NO: 5):

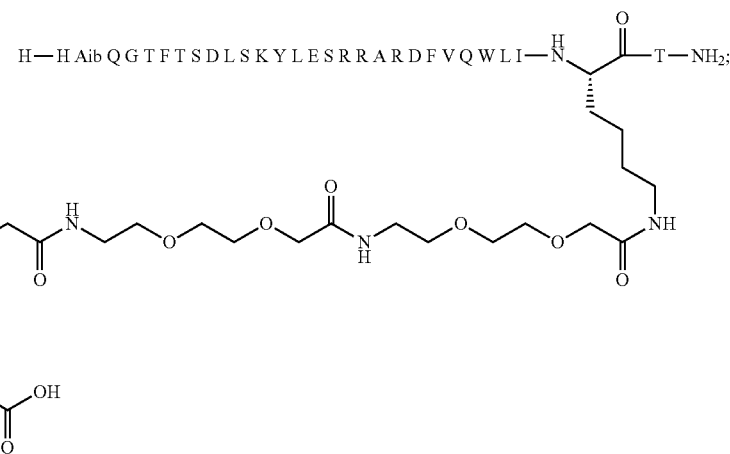

N^{ε24}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Ala16,Arg20,Glu21,Lys24,Ile27,Ser28]-Glucagon amide
Chem 4 (SEQ ID NO: 6):

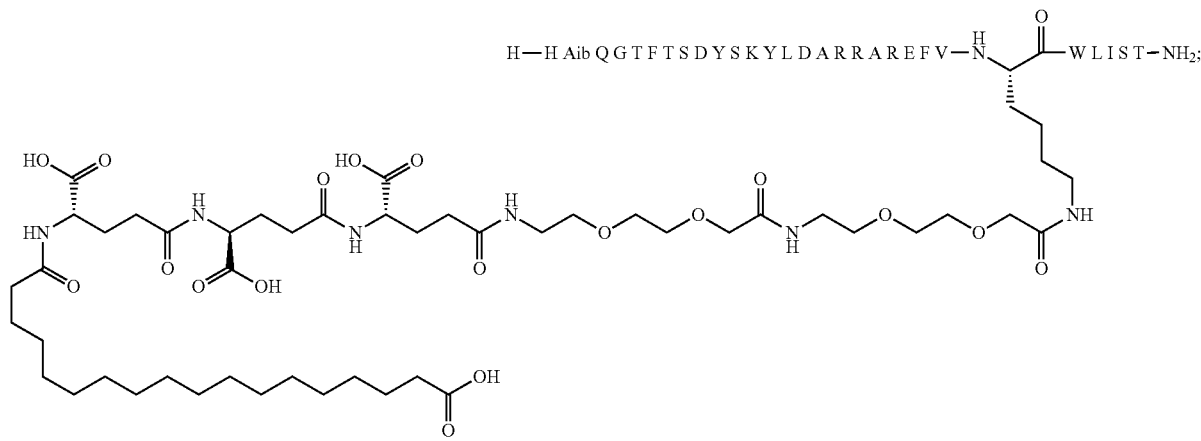

N^{ε28}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Ala16,Arg20,Ile27,Lys28]-Glucagon amide Chem 5 (SEQ ID NO: 7):

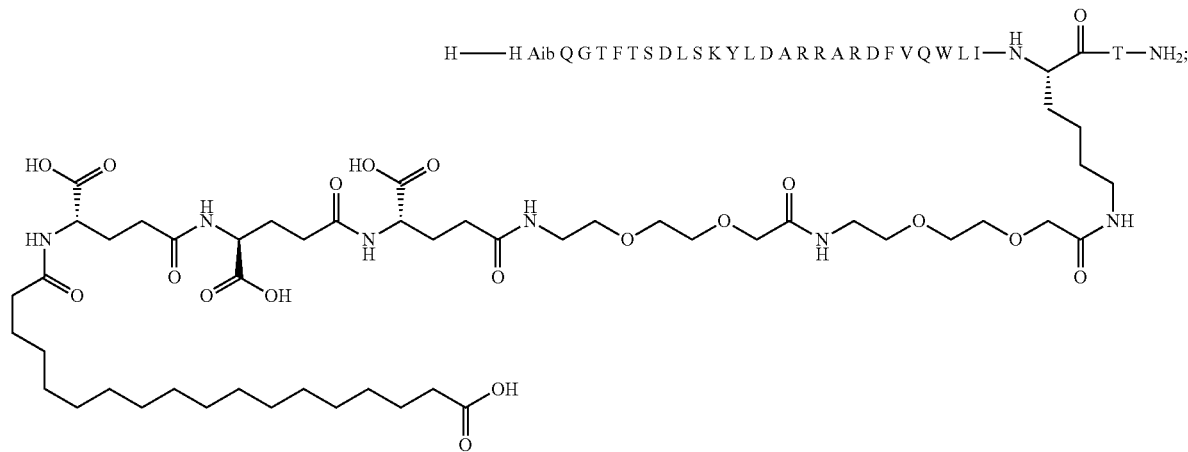

N$^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu1,Ala16,Arg20,Glu21,Ile27,Lys28]-Glucagon amide Chem 6 (SEQ ID NO: 8):

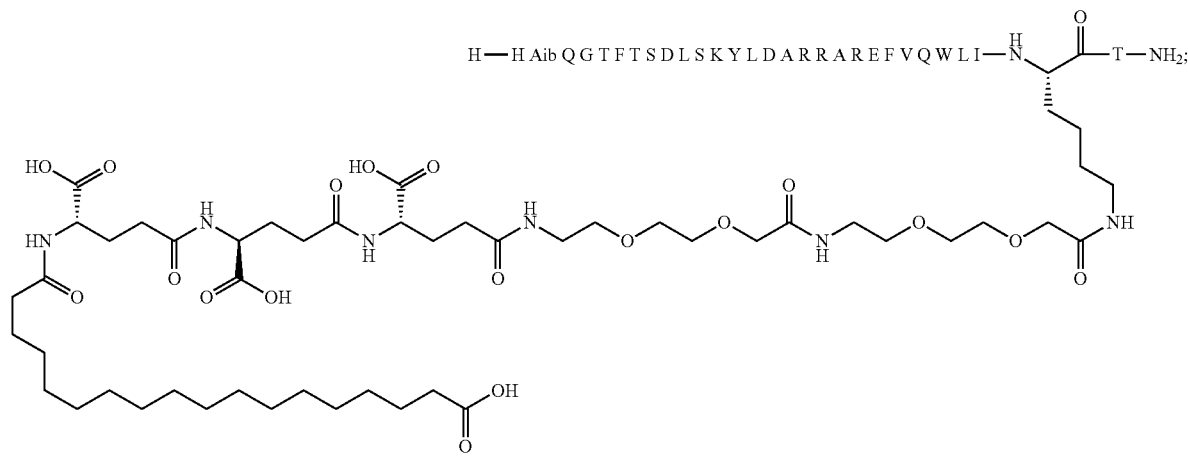

N$^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu0,Ala16,Ile27,Lys28]-Glucagon amide Chem 7 (SEQ ID NO: 9):

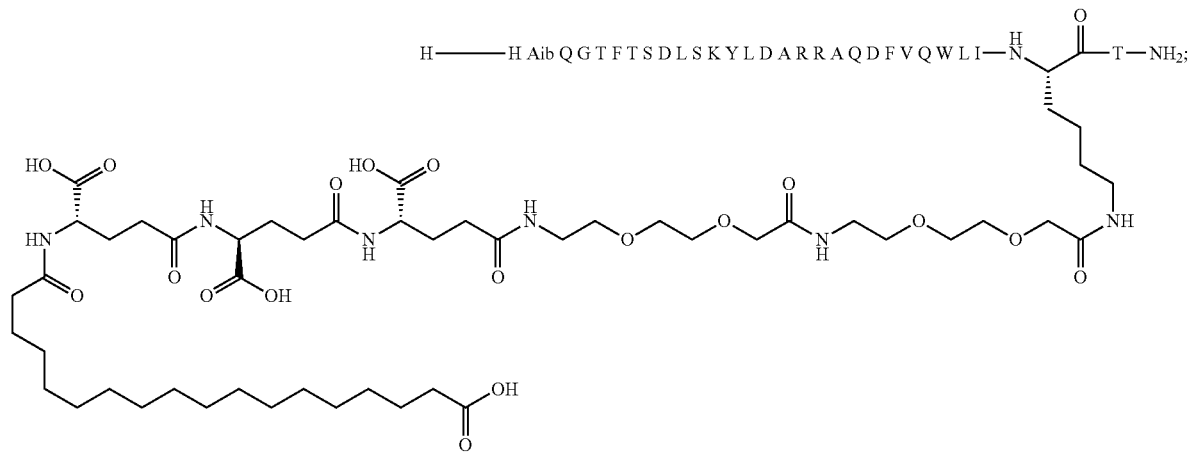

N$^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Ile27,Lys28]-Glucagon amide Chem 8 (SEQ ID NO: 10):

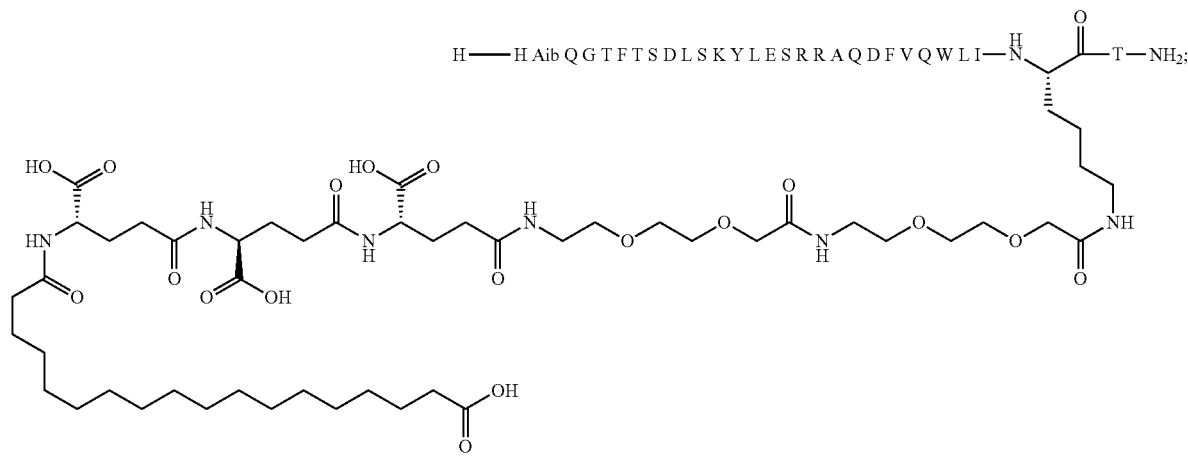

N$^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu1,Leu16,Ile27,Lys28]-Glucagon amide Chem 9 (SEQ ID NO: 11):

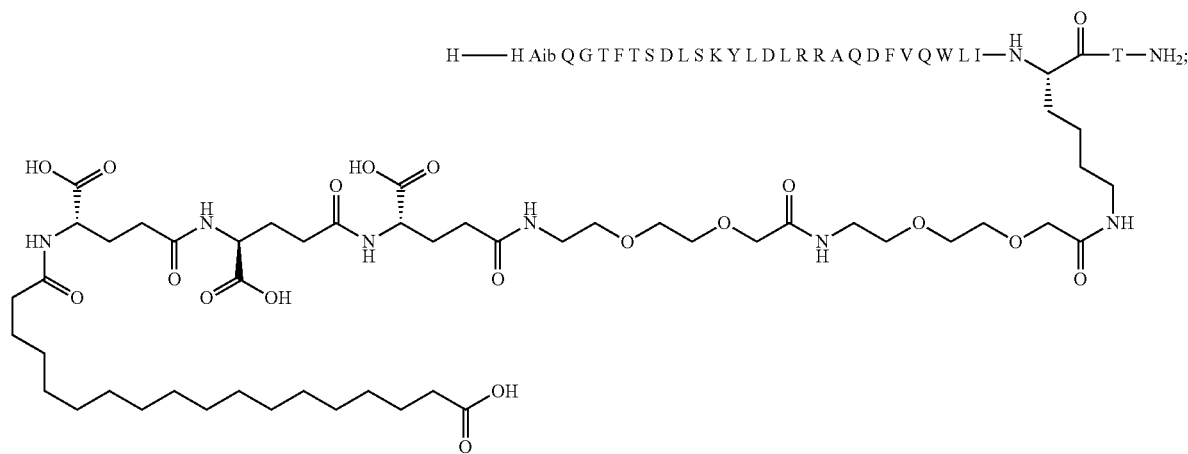

$N^{\varepsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Glu15,Ile27,Lys28]-Glucagon amide Chem 10 (SEQ ID NO: 12):

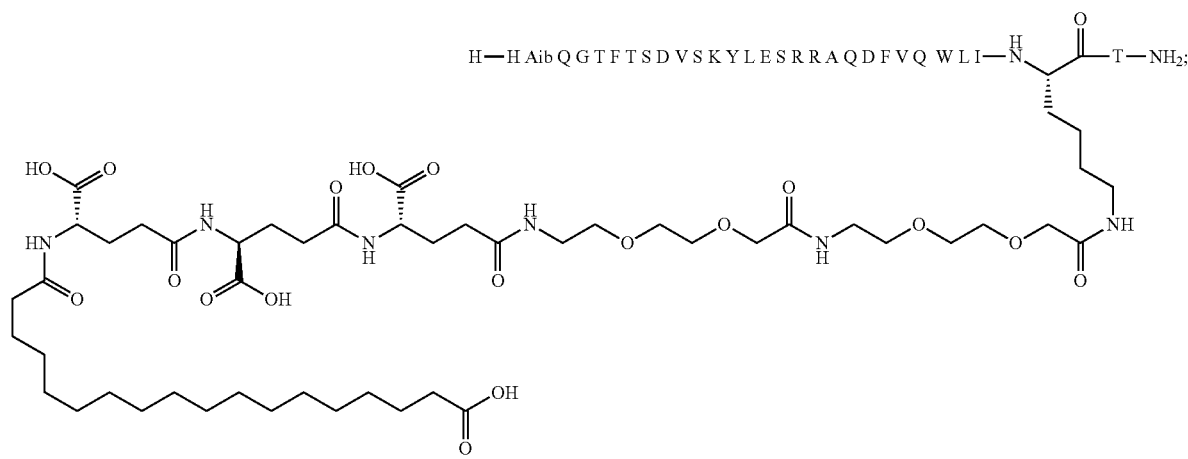

$N^{\varepsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2, Glu15,Arg20,Lys24,Ile27,Ser28]-Glucagon amide Chem 11 (SEQ ID NO: 13):

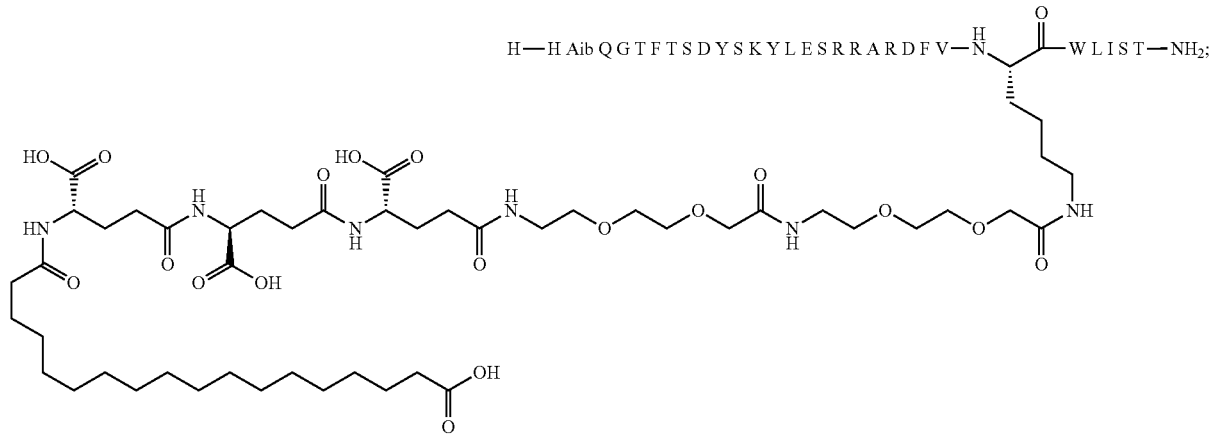

N^{ε24}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu16,Arg20,Lys24,Ile27,Ser28]-Glucagon amide Chem 12 (SEQ ID NO: 14):

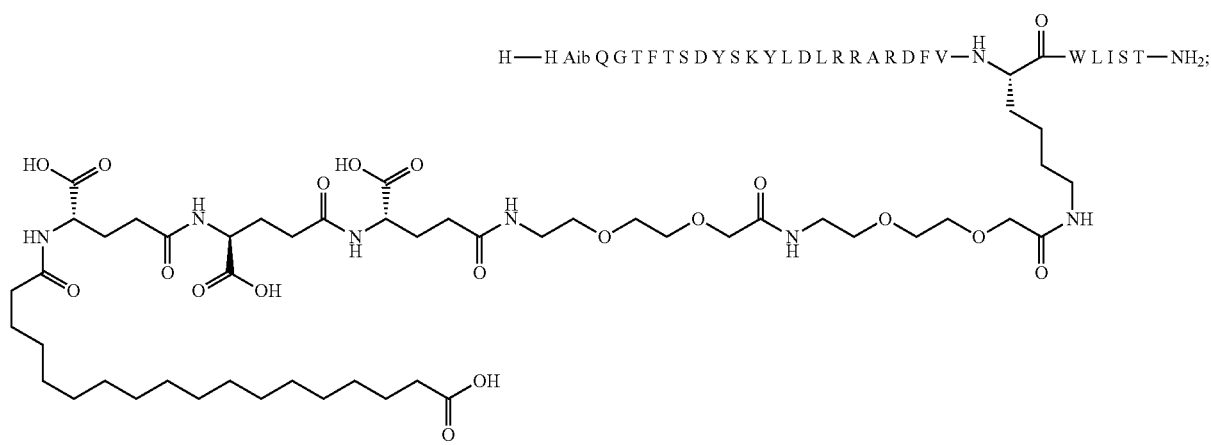

N^{ε28}-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Ile27,Lys28]-Glucagon amide Chem 13 (SEQ ID NO: 15):
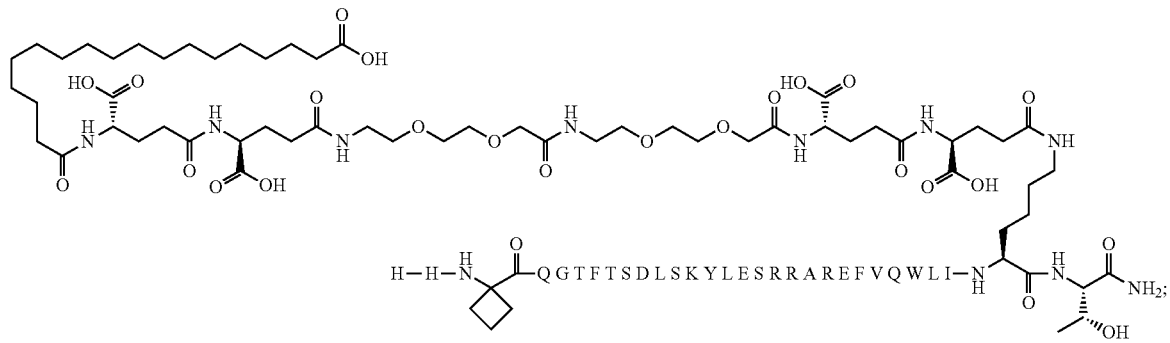
N$^{\varepsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Ala16,Arg20,Ile27,Lys28]-Glucagon amide
Chem 14 (SEQ ID NO: 16):
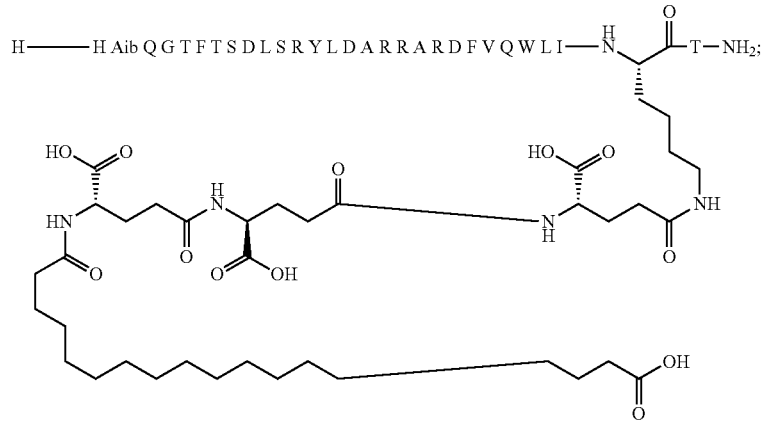
N$^{\varepsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Ala16,Arg20,Ile27,Lys28]-Glucagon amide
Chem 15 (SEQ ID NO: 17):
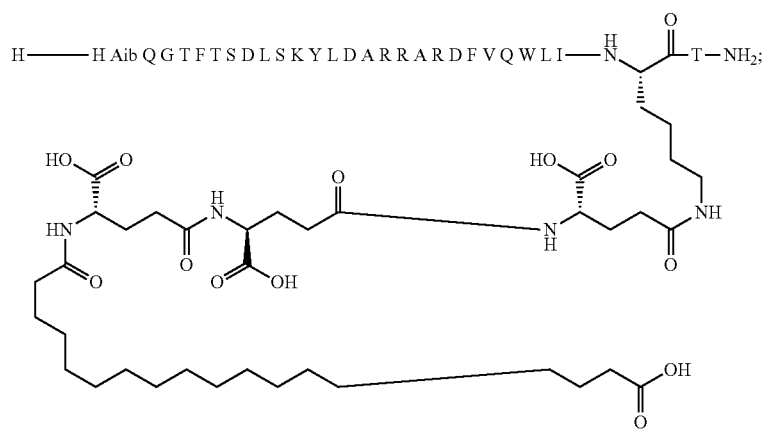

N^{ε28}-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl] amino]butanoyl]amino]-3-hydroxypropanoyl]amino]acetyl]amino]butanoyl]amino]-3-hydroxypropanoyl]amino]acetyl]-[Acb2, Leu10,Glu15,Arg20,Glu21,Ile27,Lys28]-Glucagon amide Chem 16 (SEQ ID NO: 18):

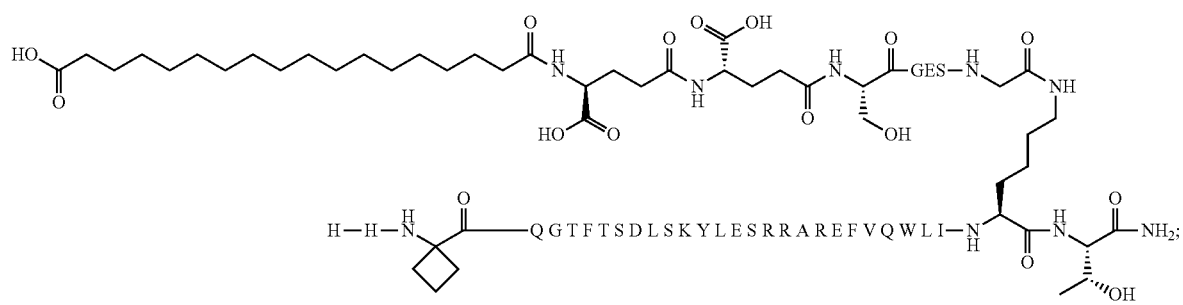

N^{ε28}-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Glu15,Arg20,Glu21,Ile27,Lys28]-Glucagon amide Chem 17 (SEQ ID NO: 19):

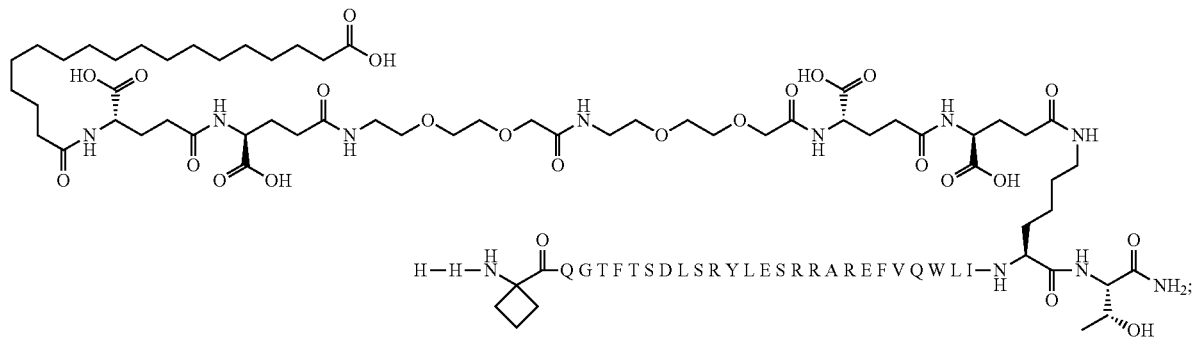

$N^{e28}$-[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Acb2,Leu10,Glu15,Arg20,Glu21,Ile27,Lys28]-Glucagon amide
Chem 18 (SEQ ID NO: 20):

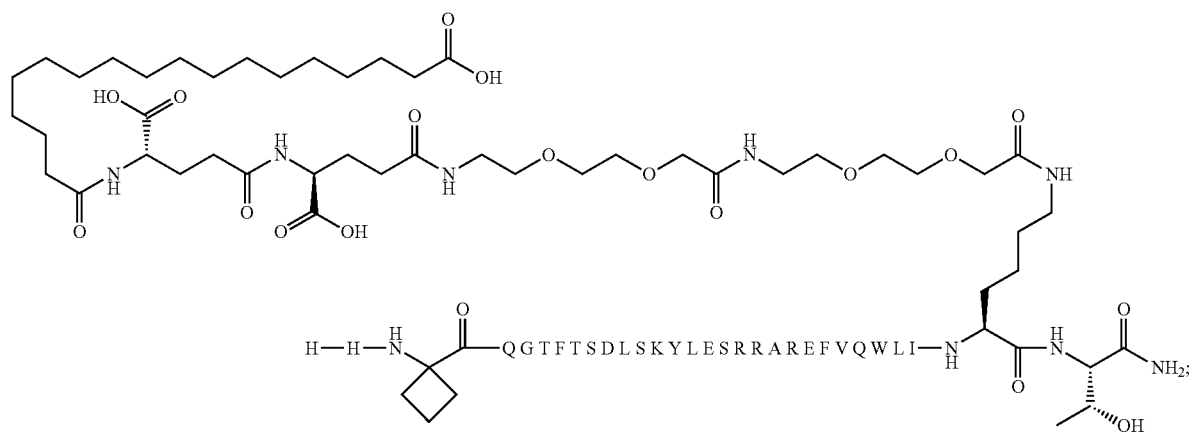

$N^{e28}$[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Val10,Glu15,Arg20,Glu21,Ile27,Lys28]-Glucagon amide
Chem 19 (SEQ ID NO: 21):

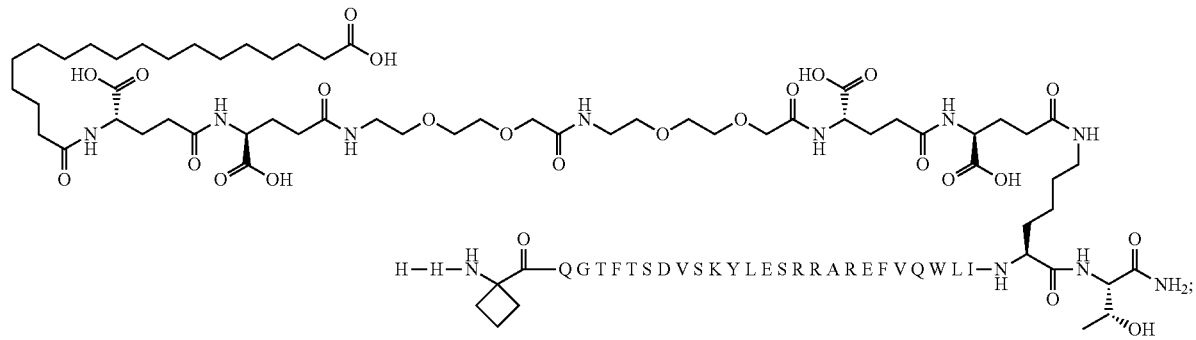

$N^{e29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Lys29]-Glucagon amide Chem 20 (SEQ ID NO: 22):

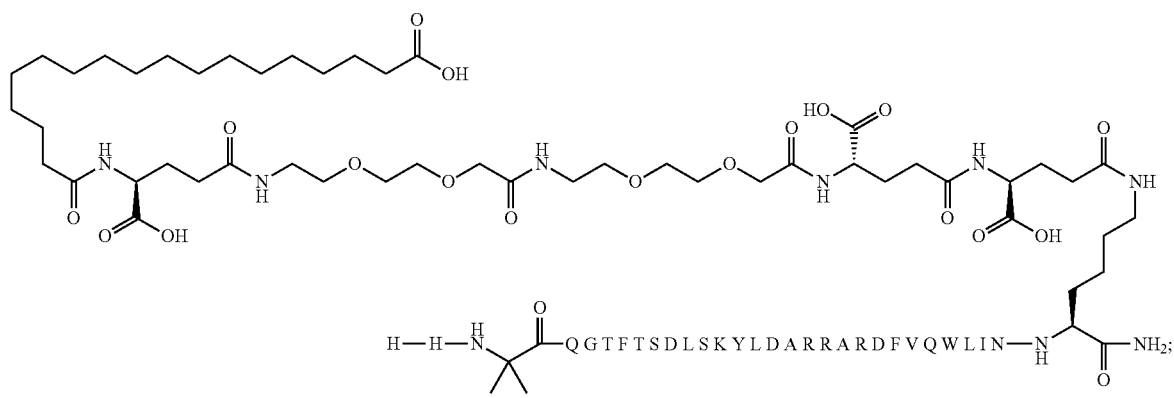

N$^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Lys29]-Glucagon amide Chem 21 (SEQ ID NO: 23):

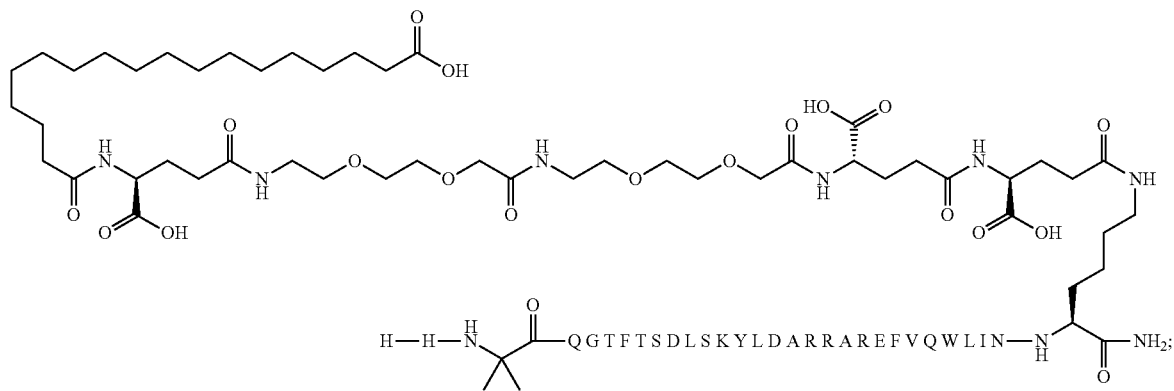

N$^{\varepsilon 29}$-[(4S)-4-carboxy-4-[[(4 S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Lys29]-Glucagon amide Chem 22 (SEQ ID NO: 24):

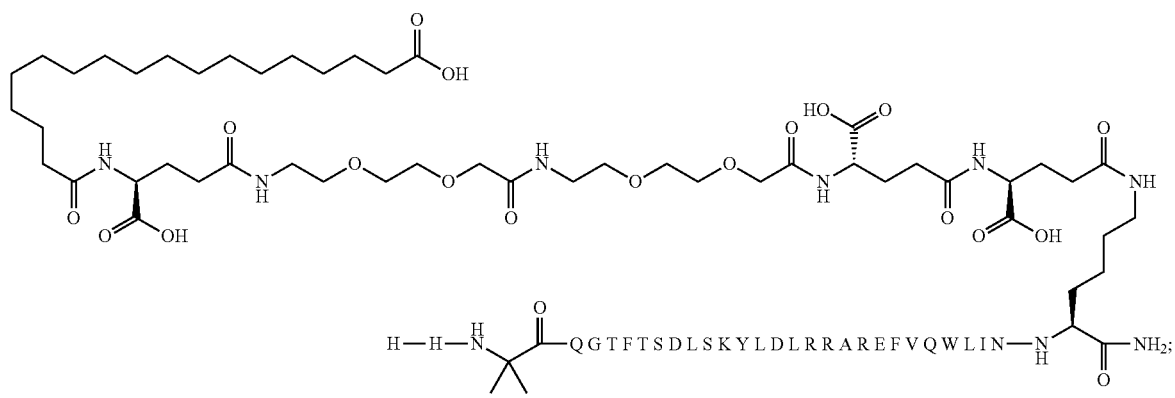

N$^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ile27,Lys29]-Glucagon amide Chem 23 (SEQ ID NO: 25):

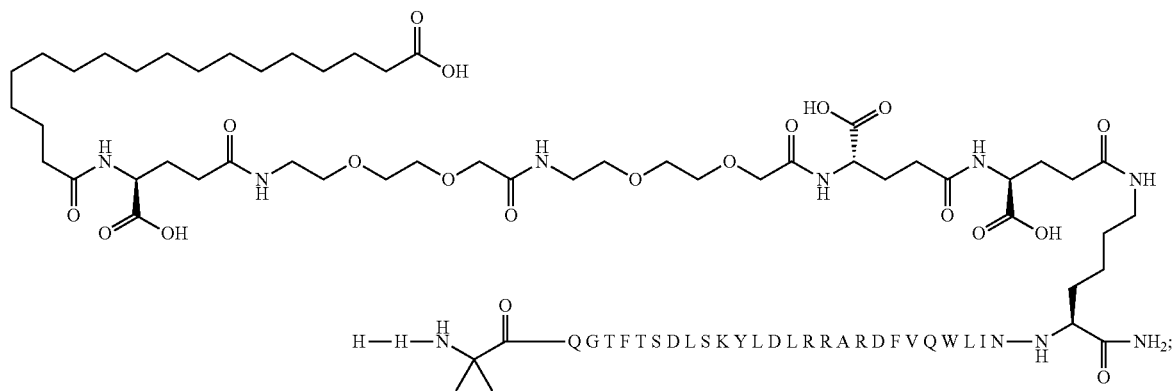

N$^{\varepsilon 29}$-[(4 S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Lys29]-Glucagon amide Chem 24 (SEQ ID NO: 26):

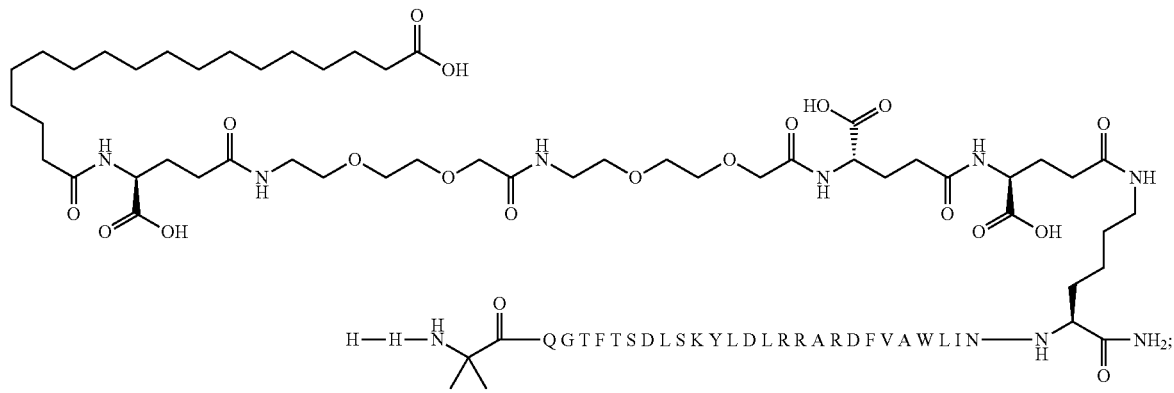

N^{ε28}-[(4 S)-4-carboxy-4-[[(4 S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Ile27,Lys28]-Glucagon amide Chem 25 (SEQ ID NO: 27):

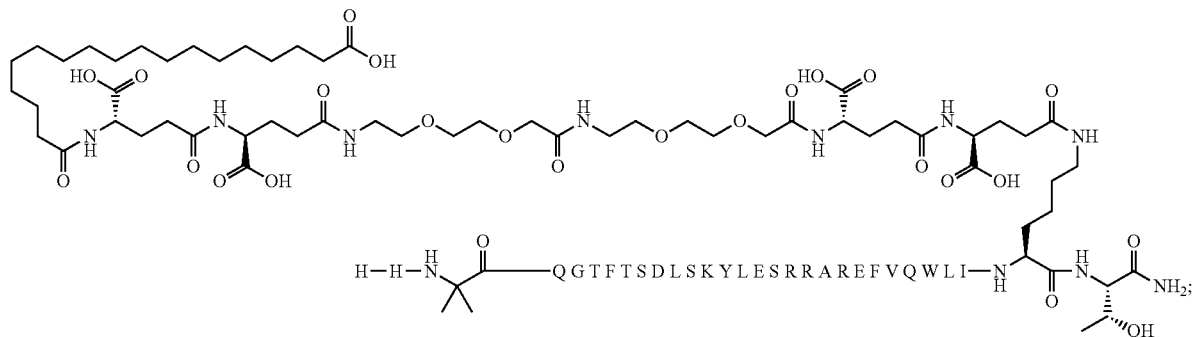

N^{ε28}-[(4S)-4-carboxy-4-[[(4S)-4-carboxy-4-[[2-[2-[2-[[2-[2-[2-2[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Ile10,Glu15,Arg20,Glu21,Ile27,Lys28]-Glucagon amide Chem 26 (SEQ ID NO: 28):

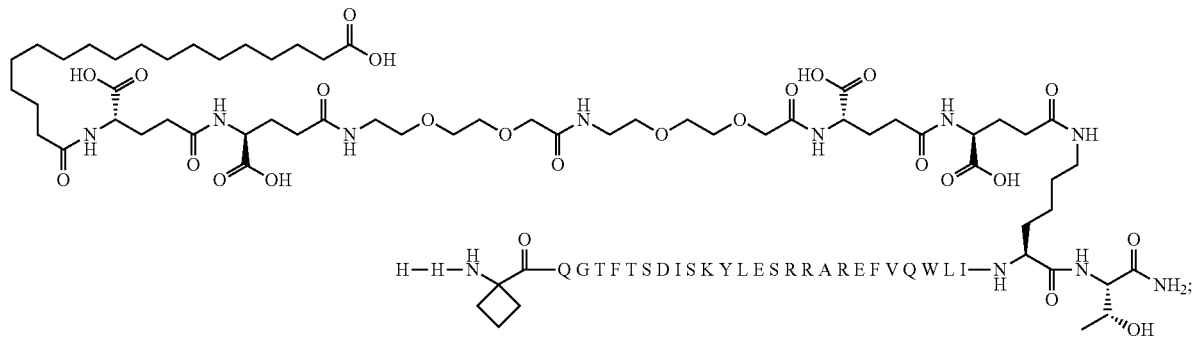

N^ε29-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Ile27,Ser28,Lys29]-Glucagon amide Chem 27 (SEQ ID NO: 29):

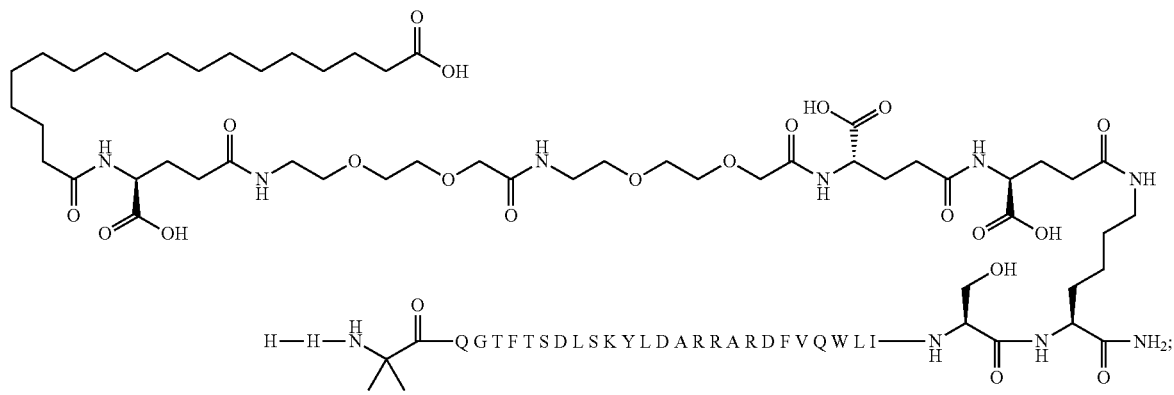

N^ε29-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Ile27,Ser28,Lys29]-Glucagon amide Chem 28 (SEQ ID NO: 30):

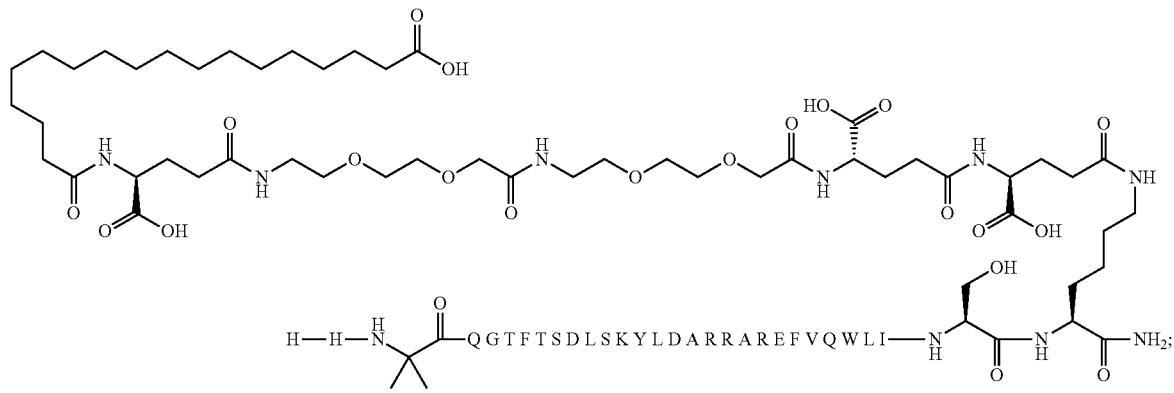

N^{e29}-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu0,Leu6,Arg20,Ile27, Ser28, Lys29]-Glucagon amide
Chem 29 (SEQ ID NO: 31):

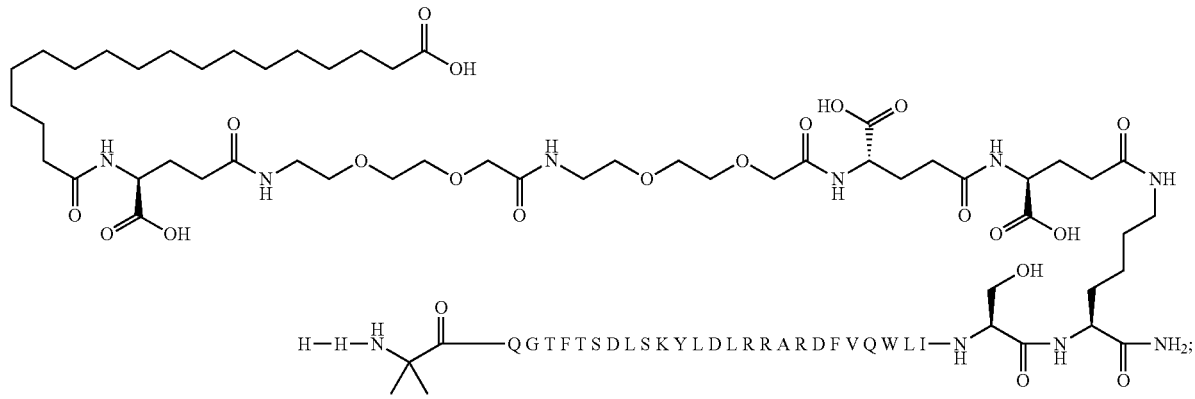

N^{e29}-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Glu21,Ile27,Ser28,Lys29]-Glucagon amide
Chem 30 (SEQ ID NO: 32):

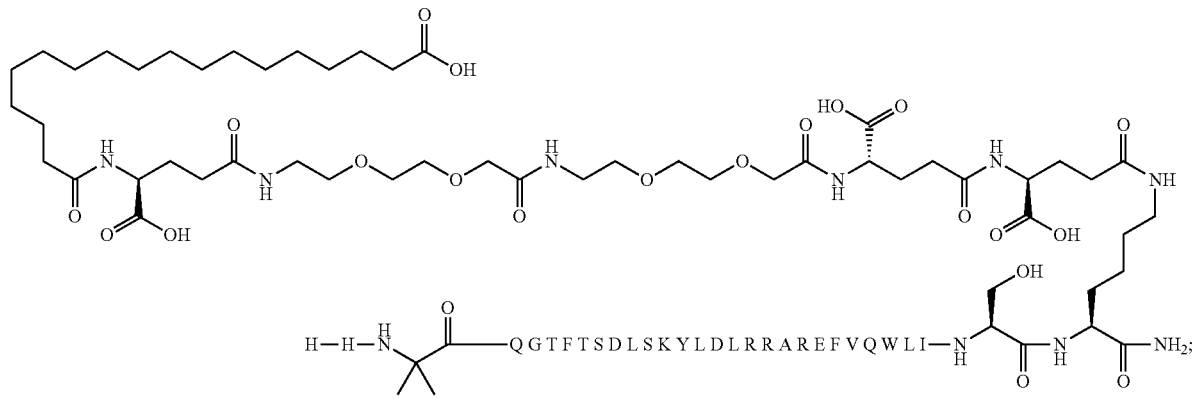

N^{e29}-[(4 S)-4-carboy-4-[[(4 S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Arg20,Ala24,Ile27,Ser28,Lys29]-Glucagon amide Chem 31 (SEQ ID NO: 33):

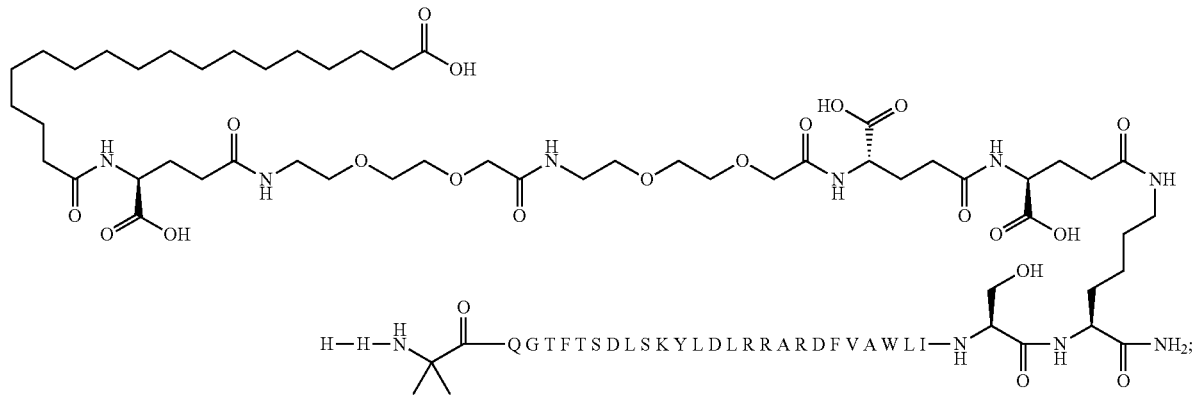

N^{ε28}-[(4S)-4-carboxy-4-[[(4 S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl] amino]ethoxy]ethoxy]acetyl]amino]butanoyl]amino] butanoyl]-[Aib2,Ala16,Arg20,Ala24,Ile27,Lys28]-Glucagon amide Chem 32 (SEQ ID NO: 34):

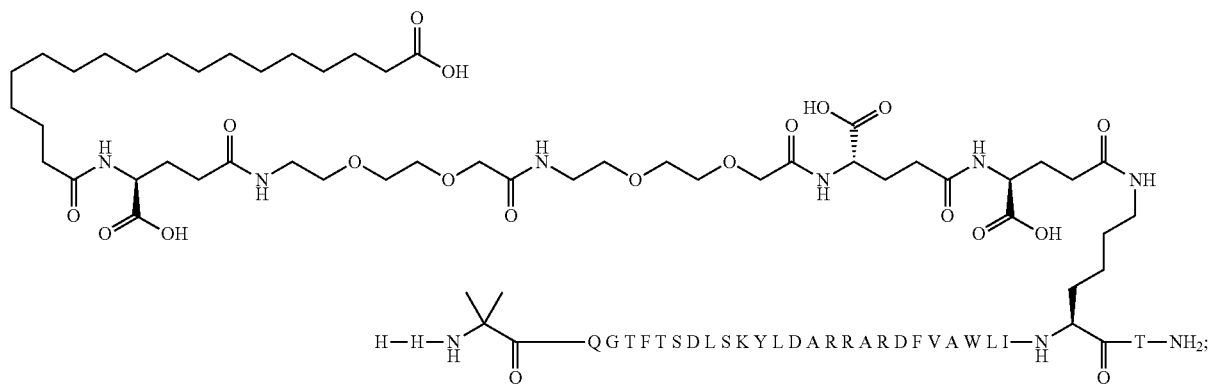

N^{ε28}-[(4S)-4-carboxy-4-[[(4S)-4-carboxy-4-[[2-[2-[2-[[2-[2-[2-[[(4S)-4- carboxy-4-(17-carboxyheptade-canoylamino)butanoyl]amino]ethoxy]ethoxy]acetyl] amino]ethoxy]ethoxy]acetyl]amino]butanoyl]amino] butanoyl]-[Aib2,Leu16,Arg20,Ala24,Ile27,Lys28]-Glucagon amide Chem 33 (SEQ ID NO: 35):

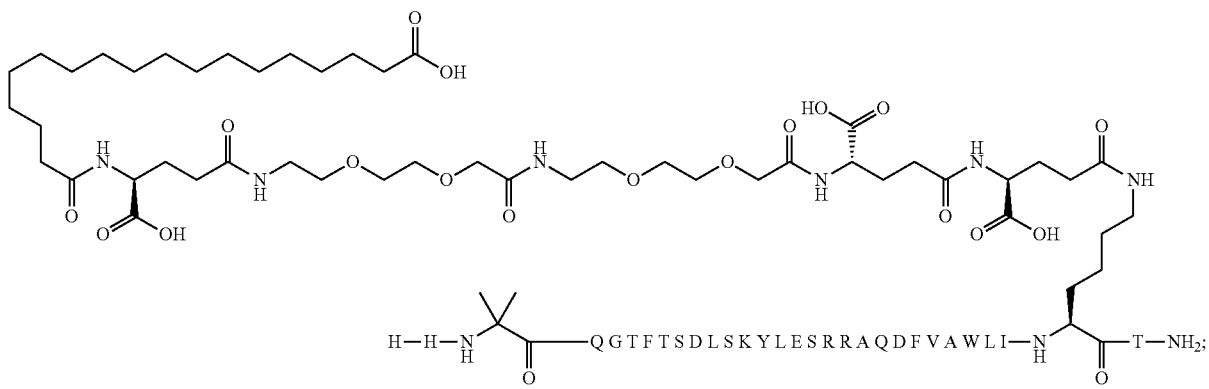

$N^{\varepsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Lys28]-Glucagon amide Chem 34 (SEQ ID NO: 36):

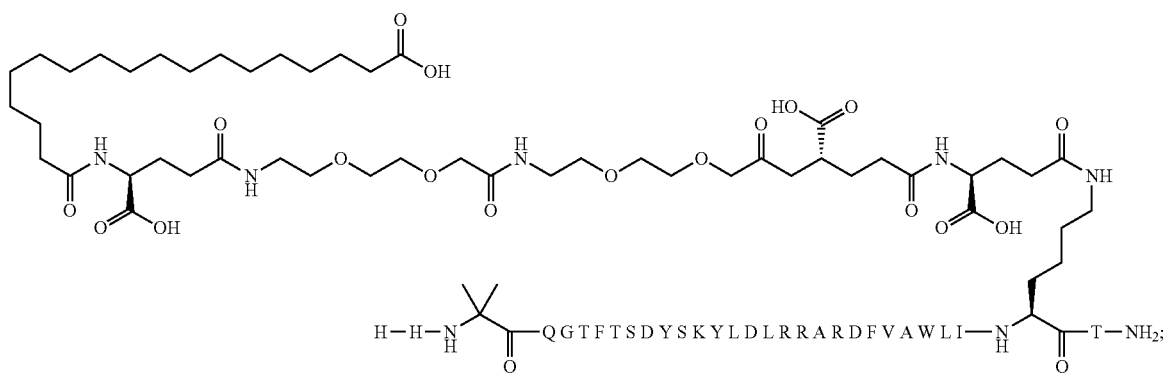

$N^{\varepsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Glu15,Ala24,Ile27,Ser28,Lys29]-Glucagon amide Chem 35 (SEQ ID NO: 37):

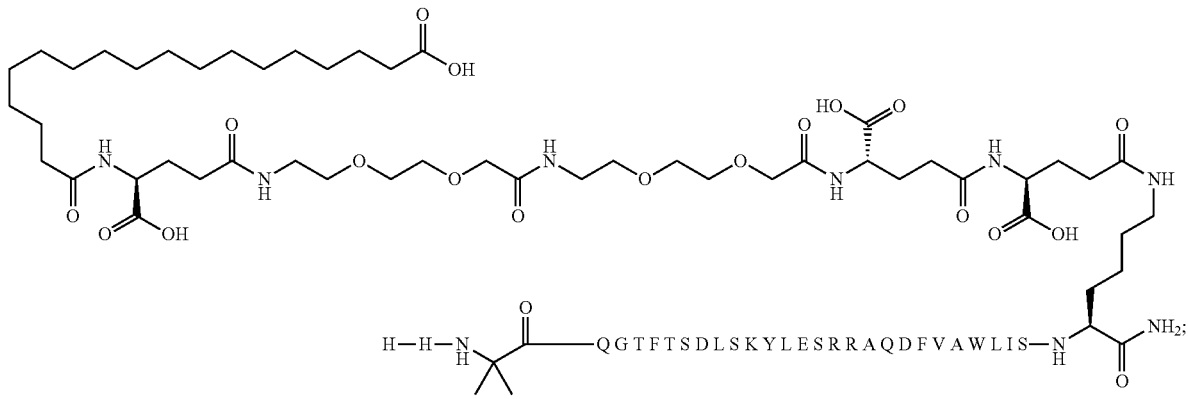

N^ε28-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Acb2,Arg12,Glu15,Arg20,Ile27,Lys28]-Glucagon amide Chem 36 (SEQ ID NO: 38):

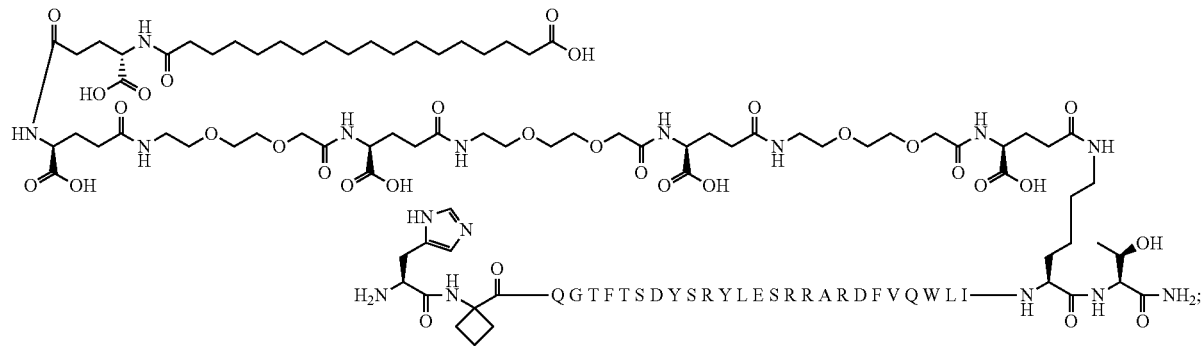

N^ε28-[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]ethoxy]ethoxy]acetyl]amino]butanoyl]amino]ethoxy]ethoxy]acetyl]amino]butanoyl]-[Aib2,Arg12,Glu15,Arg20,Ile27,Lys28]-Glucagon amide Chem 37 (SEQ ID NO: 39):

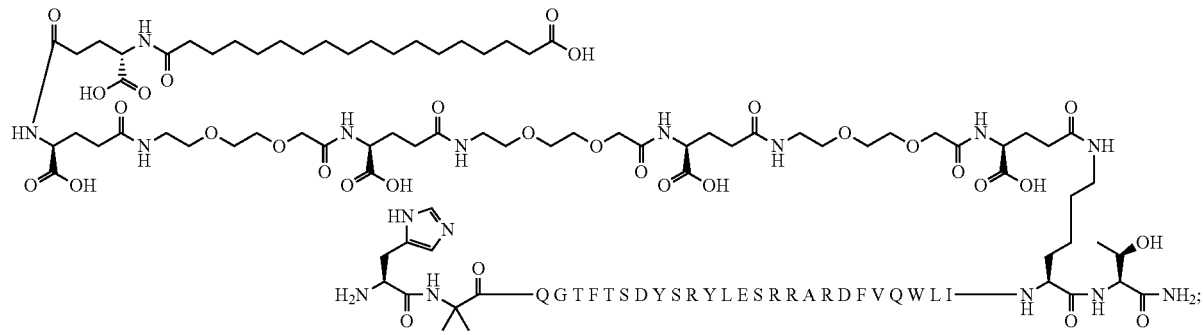

N^ε28-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Acb2,Leu10,Glu15,Glu21,Ile27,Lys28]-Glucagon amide Chem 38 (SEQ ID NO: 40):

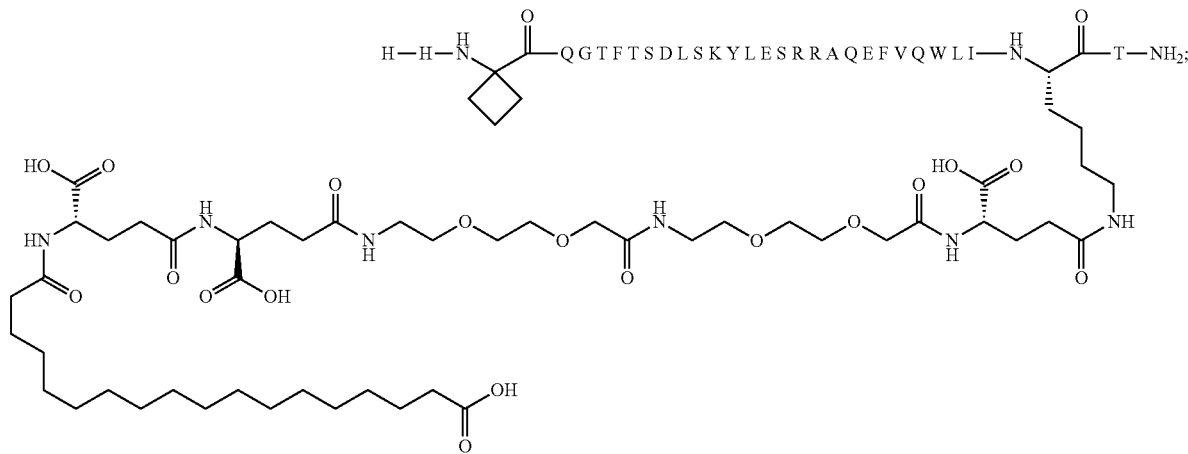

N$^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Val10,Ala16,Ile27,Lys28]-Glucagon amide Chem 39 (SEQ ID NO: 41):

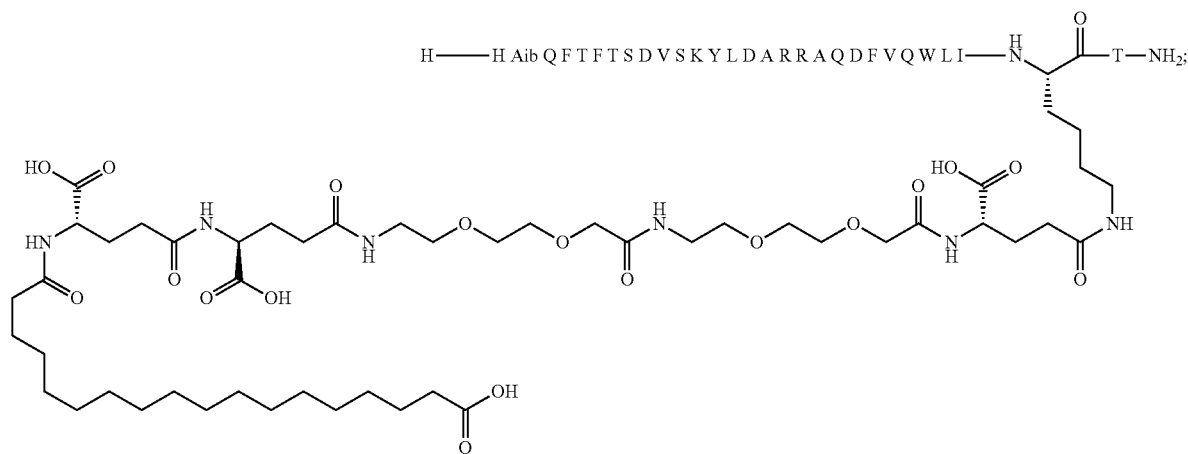

and N$^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Val16,Ile27,Lys28]-Glucagon amide Chem 40 (SEQ ID NO: 42):

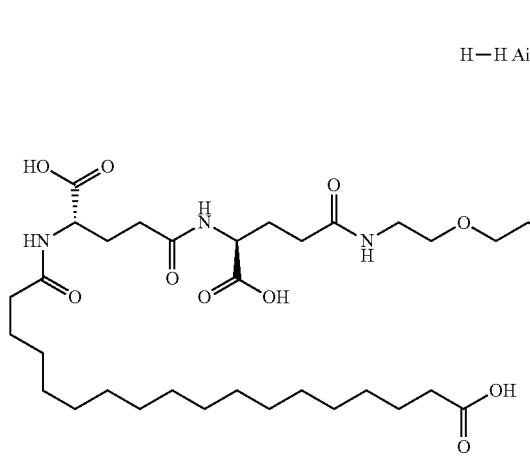

14. A pharmaceutical composition comprising the glucagon derivative according to claim 1 and one or more additional therapeutically active compounds.

15. A pharmaceutical composition comprising the glucagon derivative as defined in claim 1 and one or more pharmaceutically acceptable excipients.

16. A method for treating obesity, comprising administering the glucagon derivative according to claim 1 to a subject in need thereof.

17. The method according to claim 16, further comprising administering the glucagon derivative in combination with one or more additional therapeutically active compounds.

18. A method for treating obesity, comprising administering the glucagon derivative according to claim 13 to a subject in need thereof.

19. The method according to claim 18, further comprising administering the glucagon derivative in combination with one or more additional therapeutically active compounds.

* * * * *

SEQUENCE LISTING

```
<160> NUMBER OF SEQ ID NOS: 61

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (1)..(1)
<223> OTHER INFORMATION: His or Imp
<220> FEATURE:
<221> NAME/KEY: MISC_FEATURE
<222> LOCATION: (2)..(2)
<223> OTHER INFORMATION: Aib or Acb
<220> FEATURE:
<221> NAME/KEY: MISC_FEATURE
<222> LOCATION: (3)..(3)
<223> OTHER INFORMATION: Gln or His
```

```
<220> FEATURE:
<221> NAME/KEY: MISC_FEATURE
<222> LOCATION: (10)..(10)
<223> OTHER INFORMATION: Tyr, Leu, Ile or Val
<220> FEATURE:
<221> NAME/KEY: MISC_FEATURE
<222> LOCATION: (12)..(12)
<223> OTHER INFORMATION: Lys or Arg
<220> FEATURE:
<221> NAME/KEY: MISC_FEATURE
<222> LOCATION: (15)..(15)
<223> OTHER INFORMATION: Asp or Glu
<220> FEATURE:
<221> NAME/KEY: MISC_FEATURE
<222> LOCATION: (16)..(16)
<223> OTHER INFORMATION: Ser, Ala, Leu, Thr, Glu, Aib, Ile, Val or Lys
<220> FEATURE:
<221> NAME/KEY: MISC_FEATURE
<222> LOCATION: (17)..(17)
<223> OTHER INFORMATION: Arg, Lys or Gln
<220> FEATURE:
<221> NAME/KEY: MISC_FEATURE
<222> LOCATION: (18)..(18)
<223> OTHER INFORMATION: Arg, Ala or Lys
<220> FEATURE:
<221> NAME/KEY: MISC_FEATURE
<222> LOCATION: (20)..(20)
<223> OTHER INFORMATION: Gln, Arg or Lys
<220> FEATURE:
<221> NAME/KEY: MISC_FEATURE
<222> LOCATION: (21)..(21)
<223> OTHER INFORMATION: Asp, Glu or Lys
<220> FEATURE:
<221> NAME/KEY: MISC_FEATURE
<222> LOCATION: (24)..(24)
<223> OTHER INFORMATION: Gln, Ala, Arg, Glu or Lys
<220> FEATURE:
<221> NAME/KEY: MISC_FEATURE
<222> LOCATION: (28)..(28)
<223> OTHER INFORMATION: Asn, Ser, Thr, Gln, Ala, Gly, Glu or Lys
<220> FEATURE:
<221> NAME/KEY: MISC_FEATURE
<222> LOCATION: (29)..(29)
<223> OTHER INFORMATION: Thr, Gly, Ser, Gln, Ala, Glu or Lys
<220> FEATURE:
<221> NAME/KEY: MISC_FEATURE
<222> LOCATION: (30)..(30)
<223> OTHER INFORMATION: this residue is absent or represents Lys

<400> SEQUENCE: 2

Xaa Xaa Xaa Gly Thr Phe Thr Ser Asp Xaa Ser Xaa Tyr Leu Xaa Xaa
1               5                   10                  15

Xaa Xaa Ala Xaa Xaa Phe Val Xaa Trp Leu Ile Xaa Xaa Xaa
            20                  25                  30

<210> SEQ ID NO 3
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 3

His Xaa Gln Gly Thr Phe Thr Ser Asp Tyr Ser Lys Tyr Leu Asp Ala
1               5                   10                  15
```

Arg Arg Ala Arg Asp Phe Val Lys Trp Leu Ile Ser Thr
            20                  25

<210> SEQ ID NO 4
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 4

His Xaa Gln Gly Thr Phe Thr Ser Asp Tyr Ser Lys Tyr Leu Asp Ala
1               5                   10                  15

Lys Arg Ala Arg Glu Phe Val Lys Trp Leu Ile Ser Thr
            20                  25

<210> SEQ ID NO 5
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 5

His Xaa Gln Gly Thr Phe Thr Ser Asp Leu Ser Lys Tyr Leu Glu Ser
1               5                   10                  15

Arg Arg Ala Arg Asp Phe Val Gln Trp Leu Ile Lys Thr
            20                  25

<210> SEQ ID NO 6
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 6

His Xaa Gln Gly Thr Phe Thr Ser Asp Tyr Ser Lys Tyr Leu Asp Ala
1               5                   10                  15

Arg Arg Ala Arg Glu Phe Val Lys Trp Leu Ile Ser Thr
            20                  25

```
<210> SEQ ID NO 7
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 7

His Xaa Gln Gly Thr Phe Thr Ser Asp Leu Ser Lys Tyr Leu Asp Ala
1               5                   10                  15

Arg Arg Ala Arg Asp Phe Val Gln Trp Leu Ile Lys Thr
            20                  25

<210> SEQ ID NO 8
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 8

His Xaa Gln Gly Thr Phe Thr Ser Asp Leu Ser Lys Tyr Leu Asp Ala
1               5                   10                  15

Arg Arg Ala Arg Glu Phe Val Gln Trp Leu Ile Lys Thr
            20                  25

<210> SEQ ID NO 9
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 9

His Xaa Gln Gly Thr Phe Thr Ser Asp Leu Ser Lys Tyr Leu Asp Ala
1               5                   10                  15

Arg Arg Ala Gln Asp Phe Val Gln Trp Leu Ile Lys Thr
            20                  25

<210> SEQ ID NO 10
<211> LENGTH: 29
<212> TYPE: PRT
<213> ORGANISM: artificial
```

```
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 10

His Xaa Gln Gly Thr Phe Thr Ser Asp Leu Ser Lys Tyr Leu Glu Ser
1               5                   10                  15

Arg Arg Ala Gln Asp Phe Val Gln Trp Leu Ile Lys Thr
            20                  25

<210> SEQ ID NO 11
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 11

His Xaa Gln Gly Thr Phe Thr Ser Asp Leu Ser Lys Tyr Leu Asp Leu
1               5                   10                  15

Arg Arg Ala Gln Asp Phe Val Gln Trp Leu Ile Lys Thr
            20                  25

<210> SEQ ID NO 12
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: misc
<222> LOCATION: (2)..(2)
<223> OTHER INFORMATION: Aib
<220> FEATURE:
<221> NAME/KEY: misc
<222> LOCATION: (29)..(29)
<223> OTHER INFORMATION: C-terminal amide

<400> SEQUENCE: 12

His Xaa Gln Gly Thr Phe Thr Ser Asp Val Ser Lys Tyr Leu Glu Ser
1               5                   10                  15

Arg Arg Ala Gln Asp Phe Val Gln Trp Leu Ile Lys Thr
            20                  25

<210> SEQ ID NO 13
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
```

```
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 13

His Xaa Gln Gly Thr Phe Thr Ser Asp Tyr Ser Lys Tyr Leu Glu Ser
1               5                   10                  15

Arg Arg Ala Arg Asp Phe Val Lys Trp Leu Ile Ser Thr
            20                  25

<210> SEQ ID NO 14
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 14

His Xaa Gln Gly Thr Phe Thr Ser Asp Tyr Ser Lys Tyr Leu Asp Leu
1               5                   10                  15

Arg Arg Ala Arg Asp Phe Val Lys Trp Leu Ile Ser Thr
            20                  25

<210> SEQ ID NO 15
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide

<400> SEQUENCE: 15

His Xaa Gln Gly Thr Phe Thr Ser Asp Leu Ser Lys Tyr Leu Glu Ser
1               5                   10                  15

Arg Arg Ala Arg Glu Phe Val Gln Trp Leu Ile Lys Thr
            20                  25

<210> SEQ ID NO 16
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
```

```
<221> NAME/KEY: MISC_FEATURE
<222> LOCATION: (29)..(29)
<223> OTHER INFORMATION: C-terminal amide

<400> SEQUENCE: 16

His Xaa Gln Gly Thr Phe Thr Ser Asp Leu Ser Arg Tyr Leu Asp Ala
1               5                   10                  15

Arg Arg Ala Arg Asp Phe Val Gln Trp Leu Ile Lys Thr
            20                  25

<210> SEQ ID NO 17
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 17

His Xaa Gln Gly Thr Phe Thr Ser Asp Leu Ser Lys Tyr Leu Asp Ala
1               5                   10                  15

Arg Arg Ala Arg Asp Phe Val Gln Trp Leu Ile Lys Thr
            20                  25

<210> SEQ ID NO 18
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide

<400> SEQUENCE: 18

His Xaa Gln Gly Thr Phe Thr Ser Asp Leu Ser Lys Tyr Leu Glu Ser
1               5                   10                  15

Arg Arg Ala Arg Glu Phe Val Gln Trp Leu Ile Lys Thr
            20                  25

<210> SEQ ID NO 19
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide
```

<400> SEQUENCE: 19

His Xaa Gln Gly Thr Phe Thr Ser Asp Leu Ser Arg Tyr Leu Glu Ser
1               5                   10                  15

Arg Arg Ala Arg Glu Phe Val Gln Trp Leu Ile Lys Thr
            20                  25

<210> SEQ ID NO 20
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide

<400> SEQUENCE: 20

His Xaa Gln Gly Thr Phe Thr Ser Asp Leu Ser Lys Tyr Leu Glu Ser
1               5                   10                  15

Arg Arg Ala Arg Glu Phe Val Gln Trp Leu Ile Lys Thr
            20                  25

<210> SEQ ID NO 21
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide

<400> SEQUENCE: 21

His Xaa Gln Gly Thr Phe Thr Ser Asp Val Ser Lys Tyr Leu Glu Ser
1               5                   10                  15

Arg Arg Ala Arg Glu Phe Val Gln Trp Leu Ile Lys Thr
            20                  25

<210> SEQ ID NO 22
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 22

His Xaa Gln Gly Thr Phe Thr Ser Asp Leu Ser Lys Tyr Leu Asp Ala
1               5                   10                  15

Arg Arg Ala Arg Asp Phe Val Gln Trp Leu Ile Asn Lys
            20                  25

<210> SEQ ID NO 23
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 23

His Xaa Gln Gly Thr Phe Thr Ser Asp Leu Ser Lys Tyr Leu Asp Ala
1               5                   10                  15

Arg Arg Ala Arg Glu Phe Val Gln Trp Leu Ile Asn Lys
            20                  25

<210> SEQ ID NO 24
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 24

His Xaa Gln Gly Thr Phe Thr Ser Asp Leu Ser Lys Tyr Leu Asp Leu
1               5                   10                  15

Arg Arg Ala Arg Glu Phe Val Gln Trp Leu Ile Asn Lys
            20                  25

<210> SEQ ID NO 25
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 25

His Xaa Gln Gly Thr Phe Thr Ser Asp Leu Ser Lys Tyr Leu Asp Leu
1               5                   10                  15

Arg Arg Ala Arg Asp Phe Val Gln Trp Leu Ile Asn Lys
            20                  25

```
<210> SEQ ID NO 26
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 26

His Xaa Gln Gly Thr Phe Thr Ser Asp Leu Ser Lys Tyr Leu Asp Leu
1               5                   10                  15

Arg Arg Ala Arg Asp Phe Val Ala Trp Leu Ile Asn Lys
            20                  25

<210> SEQ ID NO 27
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 27

His Xaa Gln Gly Thr Phe Thr Ser Asp Leu Ser Lys Tyr Leu Glu Ser
1               5                   10                  15

Arg Arg Ala Arg Glu Phe Val Gln Trp Leu Ile Lys Thr
            20                  25

<210> SEQ ID NO 28
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide

<400> SEQUENCE: 28

His Xaa Gln Gly Thr Phe Thr Ser Asp Ile Ser Lys Tyr Leu Glu Ser
1               5                   10                  15

Arg Arg Ala Arg Glu Phe Val Gln Trp Leu Ile Lys Thr
            20                  25

<210> SEQ ID NO 29
<211> LENGTH: 29
<212> TYPE: PRT
```

```
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 29

His Xaa Gln Gly Thr Phe Thr Ser Asp Leu Ser Lys Tyr Leu Asp Ala
1               5                   10                  15

Arg Arg Ala Arg Asp Phe Val Gln Trp Leu Ile Ser Lys
            20                  25

<210> SEQ ID NO 30
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: misc
<222> LOCATION: (2)..(2)
<223> OTHER INFORMATION: Aib
<220> FEATURE:
<221> NAME/KEY: misc
<222> LOCATION: (29)..(29)
<223> OTHER INFORMATION: C-terminal amide

<400> SEQUENCE: 30

His Xaa Gln Gly Thr Phe Thr Ser Asp Leu Ser Lys Tyr Leu Asp Ala
1               5                   10                  15

Arg Arg Ala Arg Glu Phe Val Gln Trp Leu Ile Ser Lys
            20                  25

<210> SEQ ID NO 31
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 31

His Xaa Gln Gly Thr Phe Thr Ser Asp Leu Ser Lys Tyr Leu Asp Leu
1               5                   10                  15

Arg Arg Ala Arg Asp Phe Val Gln Trp Leu Ile Ser Lys
            20                  25

<210> SEQ ID NO 32
<211> LENGTH: 29
<212> TYPE: PRT
<213> ORGANISM: artificial
<220> FEATURE:
<223> OTHER INFORMATION: Artificial amino acid sequence based on human
      glucagon
```

```
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 32

His Xaa Gln Gly Thr Phe Thr Ser Asp Leu Ser Lys Tyr Leu Asp Leu
1               5                   10                  15

Arg Arg Ala Arg Glu Phe Val Gln Trp Leu Ile Ser Lys
            20                  25

<210> SEQ ID NO 33
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 33

His Xaa Gln Gly Thr Phe Thr Ser Asp Leu Ser Lys Tyr Leu Asp Leu
1               5                   10                  15

Arg Arg Ala Arg Asp Phe Val Ala Trp Leu Ile Ser Lys
            20                  25

<210> SEQ ID NO 34
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 34

His Xaa Gln Gly Thr Phe Thr Ser Asp Tyr Ser Lys Tyr Leu Asp Ala
1               5                   10                  15

Arg Arg Ala Arg Asp Phe Val Ala Trp Leu Ile Lys Thr
            20                  25

<210> SEQ ID NO 35
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
```

```
<220> FEATURE:
<221> NAME/KEY: MISC_FEATURE
<222> LOCATION: (29)..(29)
<223> OTHER INFORMATION: C-terminal amide

<400> SEQUENCE: 35

His Xaa Gln Gly Thr Phe Thr Ser Asp Tyr Ser Lys Tyr Leu Asp Leu
1               5                   10                  15

Arg Arg Ala Arg Asp Phe Val Ala Trp Leu Ile Lys Thr
            20                  25

<210> SEQ ID NO 36
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 36

His Xaa Gln Gly Thr Phe Thr Ser Asp Tyr Ser Lys Tyr Leu Glu Ser
1               5                   10                  15

Arg Arg Ala Gln Asp Phe Val Ala Trp Leu Ile Lys Thr
            20                  25

<210> SEQ ID NO 37
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 37

His Xaa Gln Gly Thr Phe Thr Ser Asp Tyr Ser Lys Tyr Leu Glu Ser
1               5                   10                  15

Arg Arg Ala Gln Asp Phe Val Ala Trp Leu Ile Ser Lys
            20                  25

<210> SEQ ID NO 38
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide
```

<400> SEQUENCE: 38

His Xaa Gln Gly Thr Phe Thr Ser Asp Tyr Ser Arg Tyr Leu Glu Ser
1               5                   10                  15

Arg Arg Ala Arg Asp Phe Val Gln Trp Leu Ile Lys Thr
            20                  25

<210> SEQ ID NO 39
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 39

His Xaa Gln Gly Thr Phe Thr Ser Asp Tyr Ser Arg Tyr Leu Glu Ser
1               5                   10                  15

Arg Arg Ala Arg Asp Phe Val Gln Trp Leu Ile Lys Thr
            20                  25

<210> SEQ ID NO 40
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Acb
<220> FEATURE:
<221> NAME/KEY: MISC_FEATURE
<222> LOCATION: (29)..(29)
<223> OTHER INFORMATION: C-terminal amide

<400> SEQUENCE: 40

His Xaa Gln Gly Thr Phe Thr Ser Asp Leu Ser Lys Tyr Leu Glu Ser
1               5                   10                  15

Arg Arg Ala Gln Glu Phe Val Gln Trp Leu Ile Lys Thr
            20                  25

<210> SEQ ID NO 41
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 41

His Xaa Gln Gly Thr Phe Thr Ser Asp Val Ser Lys Tyr Leu Asp Ala

```
                  1               5                  10                  15
Arg Arg Ala Gln Asp Phe Val Gln Trp Leu Ile Lys Thr
            20                  25

<210> SEQ ID NO 42
<211> LENGTH: 29
<212> TYPE: PRT
<213> ORGANISM: artificial
<220> FEATURE:
<223> OTHER INFORMATION: Artificial amino acid sequence based on human
      glucagon
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: C-terminal amide

<400> SEQUENCE: 42

His Xaa Gln Gly Thr Phe Thr Ser Asp Leu Ser Lys Tyr Leu Asp Val
1               5                  10                  15
Arg Arg Ala Gln Asp Phe Val Gln Trp Leu Ile Lys Thr
            20                  25

<210> SEQ ID NO 43
<211> LENGTH: 31
<212> TYPE: PRT
<213> ORGANISM: artificial
<220> FEATURE:
<223> OTHER INFORMATION: Artificial amino acid sequence based on human
      GLP-1
<220> FEATURE:
<221> NAME/KEY: MISC_FEATURE
<222> LOCATION: (20)..(20)
<223> OTHER INFORMATION: Acylation at epsilon amino group

<400> SEQUENCE: 43

His Ala Glu Gly Thr Phe Thr Ser Asp Val Ser Ser Tyr Leu Glu Gly
1               5                  10                  15
Gln Ala Ala Lys Glu Phe Ile Ala Trp Leu Val Arg Gly Arg Gly
            20                  25                  30

<210> SEQ ID NO 44
<211> LENGTH: 31
<212> TYPE: PRT
<213> ORGANISM: artificial
<220> FEATURE:
<223> OTHER INFORMATION: Artificial amino acid sequence based on human
      GLP-1
<220> FEATURE:
<221> NAME/KEY: MISC_FEATURE
<222> LOCATION: (1)..(1)
<223> OTHER INFORMATION: DesaminoHis
<220> FEATURE:
<221> NAME/KEY: MISC_FEATURE
<222> LOCATION: (31)..(31)
<223> OTHER INFORMATION: Acylation at epsilon amino group

<400> SEQUENCE: 44

His Ala Glu Gly Thr Phe Thr Ser Asp Val Ser Ser Tyr Leu Glu Glu
1               5                  10                  15
Gln Ala Ala Arg Glu Phe Ile Ala Trp Leu Val Arg Gly Arg Lys
            20                  25                  30

<210> SEQ ID NO 45
<211> LENGTH: 31
```

```
<212> TYPE: PRT
<213> ORGANISM: artificial
<220> FEATURE:
<223> OTHER INFORMATION: Artificial amino acid sequence based on human
      GLP-1
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Acylation at epsilon amino group

<400> SEQUENCE: 45

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 46
<211> LENGTH: 31
<212> TYPE: PRT
<213> ORGANISM: artificial
<220> FEATURE:
<223> OTHER INFORMATION: Artificial amino acid sequence based on human
      GLP-1
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Aib
<220> FEATURE:
<221> NAME/KEY: MISC_FEATURE
<222> LOCATION: (29)..(29)
<223> OTHER INFORMATION: Aib
<220> FEATURE:
<221> NAME/KEY: MISC_FEATURE
<222> LOCATION: (31)..(31)
<223> OTHER INFORMATION: Acylation at epsilon amino group

<400> SEQUENCE: 46

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Xaa Arg Lys
            20                  25                  30

<210> SEQ ID NO 47
<211> LENGTH: 22
<212> TYPE: PRT
<213> ORGANISM: Artificial Sequence
<220> FEATURE:
<223> OTHER INFORMATION: Artificial amino acid sequence based on human
      insulin
<220> FEATURE:
<221> NAME/KEY: DISULFID
<222> LOCATION: (7)..(7)
<223> OTHER INFORMATION: Disulfide bond between this residue and the
      residue in position 12 of SEQ ID NO 47
<220> FEATURE:
<221> NAME/KEY: DISULFID
<222> LOCATION: (8)..(8)
<223> OTHER INFORMATION: Disulfide bond between this residue and the
      residue in position 7 of SEQ ID NO 48
<220> FEATURE:
<221> NAME/KEY: DISULFID
<222> LOCATION: (12)..(12)
<223> OTHER INFORMATION: Disulfide bond between this residue and the
      residue in position 7 of SEQ ID NO 47
<220> FEATURE:
```

```
<221> NAME/KEY: DISULFID
<222> LOCATION: (21)..(21)
<223> OTHER INFORMATION: Disulfide bond between this residue and the
      residue in position 19 of SEQ ID NO 48

<400> SEQUENCE: 47

Gly Ile Val Glu Glu Gln Cys Cys Thr Ser Ile Cys Ser Leu Tyr Gln
1               5                   10                  15

Leu Glu Asn Tyr Cys Asn
            20

<210> SEQ ID NO 48
<211> LENGTH: 29
<212> TYPE: PRT
<213> ORGANISM: artificial
<220> FEATURE:
<223> OTHER INFORMATION: Artificial amino acid sequence based on human
      insulin
<220> FEATURE:
<221> NAME/KEY: DISULFID
<222> LOCATION: (7)..(7)
<223> OTHER INFORMATION: Disulfide bond between this residue and the
      residue in position 7 of SEQ ID NO 47
<220> FEATURE:
<221> NAME/KEY: DISULFID
<222> LOCATION: (19)..(19)
<223> OTHER INFORMATION: Disulfide bond between this residue and the
      residue in position 21 of SEQ ID NO 47
<220> FEATURE:
<221> NAME/KEY: MISC_FEATURE
<222> LOCATION: (29)..(29)
<223> OTHER INFORMATION: Acylation at epsilon amino group

<400> SEQUENCE: 48

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 49
<211> LENGTH: 6
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu

<400> SEQUENCE: 49

Xaa Xaa Ser Gly Glu Ser
1               5

<210> SEQ ID NO 50
<211> LENGTH: 7
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
```

```
<223> OTHER INFORMATION: X is gGlu

<400> SEQUENCE: 50

Xaa Xaa Ser Gly Glu Ser Gly
1               5

<210> SEQ ID NO 51
<211> LENGTH: 4
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is Ado
<220> FEATURE:
<221> NAME/KEY: MISC_FEATURE
<222> LOCATION: (3)..(3)
<223> OTHER INFORMATION: X is gGlu
<220> FEATURE:
<221> NAME/KEY: MISC_FEATURE
<222> LOCATION: (4)..(4)
<223> OTHER INFORMATION: X is gGlu

<400> SEQUENCE: 51

Xaa Xaa Xaa Xaa
1

<210> SEQ ID NO 52
<211> LENGTH: 5
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is Ado
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is gGlu
<220> FEATURE:
<221> NAME/KEY: MISC_FEATURE
<222> LOCATION: (5)..(5)
<223> OTHER INFORMATION: X is gGlu

<400> SEQUENCE: 52

Xaa Xaa Xaa Xaa Xaa
1               5

<210> SEQ ID NO 53
<211> LENGTH: 4
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
```

```
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is gGlu

<400> SEQUENCE: 53

Xaa Xaa Xaa Xaa
1

<210> SEQ ID NO 54
<211> LENGTH: 5
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is gGlu
<220> FEATURE:
<221> NAME/KEY: MISC_FEATURE
<222> LOCATION: (5)..(5)
<223> OTHER INFORMATION: X is Ado

<400> SEQUENCE: 54

Xaa Xaa Xaa Xaa Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is gGlu
<220> FEATURE:
<221> NAME/KEY: MISC_FEATURE
<222> LOCATION: (5)..(5)
<223> OTHER INFORMATION: X is gGlu
```

-continued

<400> SEQUENCE: 55

Xaa Xaa Xaa Xaa Xaa
1               5

<210> SEQ ID NO 56
<211> LENGTH: 4
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is Ado

<400> SEQUENCE: 56

Xaa Xaa Xaa Xaa
1

<210> SEQ ID NO 57
<211> LENGTH: 5
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is Ado
<220> FEATURE:
<221> NAME/KEY: MISC_FEATURE
<222> LOCATION: (5)..(5)
<223> OTHER INFORMATION: X is gGlu

<400> SEQUENCE: 57

Xaa Xaa Xaa Xaa Xaa
1               5

<210> SEQ ID NO 58
<211> LENGTH: 6
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu

```
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
<221> NAME/KEY: MISC_FEATURE
<222> LOCATION: (4)..(4)
<223> OTHER INFORMATION: X is Ado
<220> FEATURE:
<221> NAME/KEY: MISC_FEATURE
<222> LOCATION: (5)..(5)
<223> OTHER INFORMATION: X is gGlu
<220> FEATURE:
<221> NAME/KEY: MISC_FEATURE
<222> LOCATION: (6)..(6)
<223> OTHER INFORMATION: X is gGlu

<400> SEQUENCE: 58

Xaa Xaa Xaa Xaa Xaa Xaa
1               5

<210> SEQ ID NO 59
<211> LENGTH: 5
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is gGlu
<220> FEATURE:
<221> NAME/KEY: MISC_FEATURE
<222> LOCATION: (4)..(4)
<223> OTHER INFORMATION: X is Ado
<220> FEATURE:
<221> NAME/KEY: MISC_FEATURE
<222> LOCATION: (5)..(5)
<223> OTHER INFORMATION: X is Ado

<400> SEQUENCE: 59

Xaa Xaa Xaa Xaa Xaa
1               5

<210> SEQ ID NO 60
<211> LENGTH: 8
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is Ado
<220> FEATURE:
```

```
<221> NAME/KEY: MISC_FEATURE
<222> LOCATION: (4)..(4)
<223> OTHER INFORMATION: X is gGlu
<220> FEATURE:
<221> NAME/KEY: MISC_FEATURE
<222> LOCATION: (5)..(5)
<223> OTHER INFORMATION: X is Ado
<220> FEATURE:
<221> NAME/KEY: MISC_FEATURE
<222> LOCATION: (6)..(6)
<223> OTHER INFORMATION: X is gGlu
<220> FEATURE:
<221> NAME/KEY: MISC_FEATURE
<222> LOCATION: (7)..(7)
<223> OTHER INFORMATION: X is Ado
<220> FEATURE:
<221> NAME/KEY: MISC_FEATURE
<222> LOCATION: (8)..(8)
<223> OTHER INFORMATION: X is gGlu

<400> SEQUENCE: 60

Xaa Xaa Xaa Xaa Xaa Xaa Xaa Xaa
1               5

<210> SEQ ID NO 61
<211> LENGTH: 4
<212> TYPE: PRT
<213> ORGANISM: Artificial Sequence
<220> FEATURE:
<223> OTHER INFORMATION: artificial
<220> FEATURE:
<221> NAME/KEY: MISC_FEATURE
<222> LOCATION: (1)..(1)
<223> OTHER INFORMATION: X is gGlu
<220> FEATURE:
<221> NAME/KEY: MISC_FEATURE
<222> LOCATION: (2)..(2)
<223> OTHER INFORMATION: X is gGlu
<220> FEATURE:
<221> NAME/KEY: MISC_FEATURE
<222> LOCATION: (3)..(3)
<223> OTHER INFORMATION: X is gGlu
<220> FEATURE:
<221> NAME/KEY: MISC_FEATURE
<222> LOCATION: (4)..(4)
<223> OTHER INFORMATION: X is Ado

<400> SEQUENCE: 61

Xaa Xaa Xaa Xaa
1
```